United States Patent
Tobis

(10) Patent No.: US 10,433,963 B2
(45) Date of Patent: Oct. 8, 2019

(54) TISSUE ANCHOR AND DELIVERY TOOL

(71) Applicant: 4TECH INC., Waltham, MA (US)

(72) Inventor: Idan Tobis, Beth Hashmonai (IL)

(73) Assignee: 4TECH INC., Waltham, MA (US)

( * ) Notice: Subject to any disclaimer, the term of this patent is extended or adjusted under 35 U.S.C. 154(b) by 67 days.

(21) Appl. No.: 15/436,174

(22) Filed: Feb. 17, 2017

(65) Prior Publication Data

US 2017/0156719 A1 Jun. 8, 2017

Related U.S. Application Data

(63) Continuation of application No. 15/056,417, filed on Feb. 29, 2016, now abandoned, which is a
(Continued)

(51) Int. Cl.
*A61F 2/24* (2006.01)
*A61B 17/04* (2006.01)
(Continued)

(52) U.S. Cl.
CPC ........ *A61F 2/2457* (2013.01); *A61B 17/0401* (2013.01); *A61B 17/0469* (2013.01);
(Continued)

(58) Field of Classification Search
CPC ............ A61F 2/2457; A61F 2002/0072; A61F 2/2466; A61F 2002/249; A61F 2/2427;
(Continued)

(56) References Cited

U.S. PATENT DOCUMENTS

| 3,874,388 A | 4/1975 | King et al. |
| 4,214,349 A | 7/1980 | Munch |

(Continued)

FOREIGN PATENT DOCUMENTS

| DE | 102007043830 | 4/2009 |
| EP | 1568326 | 8/2005 |

(Continued)

OTHER PUBLICATIONS

An International Search Report and a Written Opinion both dated Dec. 6, 2013, which issued during the prosecution of Applicant's PCT/IL2013/050470.
(Continued)

*Primary Examiner* — Seema Mathew
(74) *Attorney, Agent, or Firm* — UltimatEdge IP Law Group, P.C.; Dean G. Stathakis; Vito A. Canuso, III

(57) ABSTRACT

A torque-delivering cable is provided, which includes a first coupling. The torque-delivering cable and the first coupling are shaped so as to collectively define a first passage therethrough. A tissue anchor is further provided, which includes a tissue-engaging element and a second coupling, which second coupling is shaped so as to define a second passage therethrough. The first and the second couplings are interlockingly coupleable to each other. An elongate longitudinal locking element is additionally provided, which is shaped so as to define a sharp tip, and which (a) when reversibly disposed in the first and the second passages, maintains coupling together of the first and the second couplings, and (b) when withdrawn from the second passage, allows decoupling of the first and the second coupling from each another.

11 Claims, 61 Drawing Sheets

Related U.S. Application Data continuation of application No. 14/143,355, filed on Dec. 30, 2013, now Pat. No. 9,307,980, which is a continuation-in-part of application No. 13/553,081, filed on Jul. 19, 2012, now Pat. No. 9,241,702.

(51) Int. Cl.

| | | |
|---|---|---|
| *A61B 17/064* | (2006.01) | |
| *A61B 17/068* | (2006.01) | |
| *A61F 2/915* | (2013.01) | |
| *A61F 2/95* | (2013.01) | |
| *A61B 17/06* | (2006.01) | |
| *A61B 17/00* | (2006.01) | |

(52) U.S. Cl.
CPC .......... *A61B 17/064* (2013.01); *A61B 17/068* (2013.01); *A61B 17/06166* (2013.01); *A61F 2/246* (2013.01); *A61F 2/2466* (2013.01); *A61F 2/2487* (2013.01); *A61F 2/915* (2013.01); *A61F 2/95* (2013.01); *A61B 2017/00243* (2013.01); *A61B 2017/048* (2013.01); *A61B 2017/0409* (2013.01); *A61B 2017/0412* (2013.01); *A61B 2017/0414* (2013.01); *A61B 2017/0441* (2013.01); *A61B 2017/0443* (2013.01); *A61B 2017/0464* (2013.01); *A61B 2017/0488* (2013.01); *A61B 2017/0496* (2013.01); *A61B 2017/0649* (2013.01); *A61F 2/2445* (2013.01); *A61F 2/2451* (2013.01); *A61F 2002/9511* (2013.01); *A61F 2220/0008* (2013.01); *A61F 2230/0013* (2013.01); *A61F 2230/0054* (2013.01)

(58) Field of Classification Search
CPC ...... A61B 2017/0435; A61B 2017/044; A61B 2017/0453; A61B 2017/0443; A61B 2017/0445; A61B 2017/06171; A61B 2002/701

See application file for complete search history.

(56) References Cited

U.S. PATENT DOCUMENTS

| | | |
|---|---|---|
| 4,405,313 A | 9/1983 | Sisley et al. |
| 4,423,525 A | 1/1984 | Vallana |
| 4,444,207 A | 4/1984 | Robicsek |
| 4,493,329 A | 1/1985 | Crawford et al. |
| 4,532,926 A | 8/1985 | O'Holla |
| 4,548,202 A | 10/1985 | Duncan |
| 4,602,911 A | 7/1986 | Ahmadi et al. |
| 4,625,727 A | 12/1986 | Leiboff |
| 4,712,549 A | 12/1987 | Peters et al. |
| 4,741,336 A | 5/1988 | Failla et al. |
| 4,778,468 A | 10/1988 | Hunt et al. |
| 4,808,157 A | 2/1989 | Coombs |
| 4,853,986 A | 8/1989 | Allen |
| 5,108,420 A | 4/1992 | Marks |
| 5,330,521 A | 7/1994 | Cohen |
| 5,336,233 A | 8/1994 | Chen |
| 5,350,399 A | 9/1994 | Erlebacher et al. |
| 5,450,860 A | 9/1995 | O'Connor |
| 5,473,812 A | 12/1995 | Morris et al. |
| 5,474,518 A | 12/1995 | Farrer-Velazquez |
| 5,702,343 A | 12/1997 | Alferness et al. |
| 5,776,178 A | 7/1998 | Pohndorf et al. |
| 5,792,400 A | 8/1998 | Talja et al. |
| 5,843,120 A | 12/1998 | Israel |
| 5,843,164 A | 12/1998 | Frantzen et al. |
| 5,904,697 A | 5/1999 | Gifford et al. |
| 5,948,000 A | 9/1999 | Larsen et al. |
| 5,957,953 A | 9/1999 | DiPoto et al. |
| 5,961,440 A | 10/1999 | Schweich, Jr. et al. |
| 6,010,113 A | 1/2000 | Rotering |
| 6,024,756 A | 2/2000 | Huebsch et al. |
| 6,027,523 A | 2/2000 | Schmieding |
| 6,045,497 A | 4/2000 | Schweich, Jr. et al. |
| 6,050,936 A | 4/2000 | Schweich, Jr. et al. |
| 6,077,214 A | 6/2000 | Mortier et al. |
| 6,183,512 B1 | 2/2001 | Howanec et al. |
| 6,193,734 B1 | 2/2001 | Bolduc et al. |
| 6,206,913 B1 | 3/2001 | Yencho et al. |
| 6,210,432 B1 | 4/2001 | Solem et al. |
| 6,231,516 B1 | 5/2001 | Keilman et al. |
| 6,260,552 B1 | 7/2001 | Mortier et al. |
| 6,298,272 B1 | 10/2001 | Peterfeso et al. |
| 6,299,635 B1 | 10/2001 | Frantzen |
| 6,332,893 B1 | 12/2001 | Mortier et al. |
| 6,338,738 B1 | 1/2002 | Bellotti et al. |
| 6,358,247 B1 * | 3/2002 | Altman ............ A61B 18/1492 606/41 |
| 6,402,780 B2 | 6/2002 | Williamson, IV et al. |
| 6,402,781 B1 | 6/2002 | Langberg et al. |
| 6,406,420 B1 | 6/2002 | McCarthy et al. |
| 6,461,336 B1 | 10/2002 | Larre |
| 6,533,810 B2 | 3/2003 | Hankh et al. |
| 6,537,198 B1 | 3/2003 | Vidlund et al. |
| 6,537,314 B2 | 3/2003 | Langberg et al. |
| 6,575,976 B2 | 6/2003 | Grafton |
| 6,585,766 B1 | 7/2003 | Huynh et al. |
| 6,602,288 B1 | 8/2003 | Cosgrove et al. |
| 6,613,062 B1 | 9/2003 | Leckrone et al. |
| 6,613,078 B1 | 9/2003 | Barone |
| 6,613,079 B1 | 9/2003 | Wolinsky |
| 6,616,684 B1 | 9/2003 | Vidlund et al. |
| 6,619,291 B2 | 9/2003 | Hlavka et al. |
| 6,622,730 B2 | 9/2003 | Ekvall et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,641,597 B2 | 11/2003 | Burkhart et al. |
| 6,645,193 B2 | 11/2003 | Mangosong |
| 6,669,687 B1 | 12/2003 | Saadat |
| 6,695,768 B1 | 2/2004 | Levine et al. |
| 6,702,846 B2 | 3/2004 | Mikus |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,730,118 B2 | 5/2004 | Spenser et al. |
| 6,743,198 B1 | 6/2004 | Tihon |
| 6,746,472 B2 | 6/2004 | Frazier et al. |
| 6,764,510 B2 | 7/2004 | Vidlund et al. |
| 6,776,754 B1 | 8/2004 | Wilk |
| 6,797,001 B2 | 9/2004 | Mathis |
| 6,810,882 B2 | 11/2004 | Langberg et al. |
| 6,884,250 B2 | 4/2005 | Monassevitch |
| 6,890,295 B2 | 5/2005 | Michels et al. |
| 6,893,459 B1 | 5/2005 | Macoviak |
| 6,908,478 B2 | 6/2005 | Alfemess et al. |
| 6,929,660 B1 | 8/2005 | Ainsworth et al. |
| 6,989,028 B2 | 1/2006 | Lashinski et al. |
| 6,997,951 B2 | 2/2006 | Solem et al. |
| 7,011,682 B2 | 3/2006 | Lashinski et al. |
| 7,018,406 B2 | 3/2006 | Seguin et al. |
| 7,018,408 B2 | 3/2006 | Bailey et al. |
| 7,037,290 B2 | 5/2006 | Gardeski et al. |
| 7,041,097 B1 | 5/2006 | Webler |
| 7,044,967 B1 | 5/2006 | Solem et al. |
| 7,056,333 B2 | 6/2006 | Walshe |
| 7,063,711 B1 | 6/2006 | Loshakove et al. |
| 7,077,861 B2 | 7/2006 | Spence |
| 7,083,628 B2 | 8/2006 | Bachman |
| 7,087,064 B1 | 8/2006 | Hyde |
| 7,094,244 B2 | 8/2006 | Schreck |
| 7,101,395 B2 | 9/2006 | Tremulis et al. |
| 7,101,396 B2 | 9/2006 | Artof et al. |
| 7,112,219 B2 | 9/2006 | Vidlund et al. |
| 7,125,421 B2 | 10/2006 | Tremulis et al. |
| 7,144,363 B2 | 12/2006 | Pai et al. |
| 7,159,593 B2 | 1/2007 | McCarthy et al. |

(56) References Cited

U.S. PATENT DOCUMENTS

| | | |
|---|---|---|
| 7,166,127 B2 | 1/2007 | Spence et al. |
| 7,169,187 B2 | 1/2007 | Datta |
| 7,175,625 B2 | 2/2007 | Culbert |
| 7,179,282 B2 | 2/2007 | Alferness et al. |
| 7,186,262 B2 | 3/2007 | Saadat |
| 7,189,199 B2 | 3/2007 | McCarthy et al. |
| 7,192,442 B2 | 3/2007 | Solem et al. |
| 7,192,443 B2 | 3/2007 | Solem et al. |
| 7,198,646 B2 | 4/2007 | Figulla et al. |
| 7,201,772 B2 | 4/2007 | Schwammenthal |
| 7,211,107 B2 | 5/2007 | Bruckheime et al. |
| 7,211,110 B2 | 5/2007 | Rowe et al. |
| 7,241,257 B1 | 7/2007 | Ainsworth et al. |
| 7,247,134 B2 | 7/2007 | Vidlund et al. |
| 7,258,697 B1 | 8/2007 | Cox et al. |
| 7,291,168 B2 | 11/2007 | Macoviak et al. |
| 7,309,328 B2 | 12/2007 | Kaplan et al. |
| 7,311,697 B2 | 12/2007 | Osborne |
| 7,311,728 B2 | 12/2007 | Solem et al. |
| 7,316,706 B2 | 1/2008 | Bloom et al. |
| 7,316,710 B1 | 1/2008 | Cheng et al. |
| 7,329,279 B2 | 2/2008 | Haug et al. |
| 7,331,972 B1 | 2/2008 | Cox |
| 7,335,213 B1 | 2/2008 | Hyde et al. |
| 7,338,506 B2 | 3/2008 | Caro |
| 7,351,256 B2 | 4/2008 | Hojeibane |
| 7,371,244 B2 | 5/2008 | Chatlynne et al. |
| 7,374,573 B2 | 5/2008 | Gabbay |
| 7,381,210 B2 | 6/2008 | Zarbatany et al. |
| 7,381,220 B2 | 6/2008 | Macoviak et al. |
| 7,390,329 B2 | 6/2008 | Westra et al. |
| 7,431,692 B2 | 10/2008 | Zollinger et al. |
| 7,431,726 B2 | 10/2008 | Spence et al. |
| 7,485,143 B2 | 2/2009 | Webler et al. |
| 7,500,989 B2 | 3/2009 | Solem et al. |
| 7,503,931 B2 | 3/2009 | Kowalsky et al. |
| 7,510,575 B2 | 3/2009 | Spenser et al. |
| 7,527,646 B2 | 5/2009 | Randert et al. |
| 7,530,995 B2 | 5/2009 | Quijano et al. |
| 7,547,321 B2 | 6/2009 | Silvestri et al. |
| 7,549,983 B2 | 6/2009 | Roue et al. |
| 7,597,703 B2 | 10/2009 | Sater |
| 7,608,102 B2 | 10/2009 | Adams et al. |
| 7,618,449 B2 | 11/2009 | Tremulis et al. |
| 7,628,797 B2 | 12/2009 | Tieu et al. |
| 7,632,303 B1 | 12/2009 | Stalker et al. |
| 7,637,946 B2 | 12/2009 | Solem et al. |
| 7,666,204 B2 | 2/2010 | Thornton et al. |
| 7,695,512 B2 | 4/2010 | Lashinski et al. |
| 7,704,277 B2 | 4/2010 | Zakay et al. |
| 7,722,523 B2 | 5/2010 | Mortier et al. |
| 7,758,521 B2 | 7/2010 | Morris et al. |
| 7,758,632 B2 | 7/2010 | Hojeibane et al. |
| 7,766,816 B2 | 8/2010 | Chin et al. |
| 7,771,467 B2 | 8/2010 | Svensson |
| 7,780,726 B2 | 8/2010 | Seguin |
| 7,785,366 B2 | 8/2010 | Maurer et al. |
| 7,803,187 B2 | 9/2010 | Hauser |
| 7,806,910 B2 | 10/2010 | Anderson |
| 7,837,727 B2 | 11/2010 | Goetz et al. |
| 7,841,502 B2 | 11/2010 | Walberg et al. |
| 7,857,846 B2 | 12/2010 | Alferness et al. |
| 7,871,433 B2 | 1/2011 | Lattouf |
| 7,883,539 B2 | 2/2011 | Schweich, Jr. et al. |
| 7,892,214 B2 | 2/2011 | Kagan |
| 7,930,016 B1 | 4/2011 | Saadat |
| 7,942,927 B2 | 5/2011 | Kaye et al. |
| 7,947,207 B2 | 5/2011 | Mcniven et al. |
| 7,972,378 B2 | 7/2011 | Tabor et al. |
| 7,991,484 B1 | 8/2011 | Sengupta et al. |
| 7,992,567 B2 | 8/2011 | Hirotsuka |
| 7,993,368 B2 | 8/2011 | Gambale et al. |
| 7,993,397 B2 | 8/2011 | Lashinski et al. |
| 8,010,207 B2 | 8/2011 | Smits et al. |
| 8,025,495 B2 | 9/2011 | Hardert et al. |
| 8,029,518 B2 | 10/2011 | Goldfarb et al. |
| 8,052,592 B2 | 11/2011 | Goldfarb et al. |
| 8,075,616 B2 | 12/2011 | Solem et al. |
| 8,092,517 B2 | 1/2012 | Kalmann et al. |
| 8,092,520 B2 | 1/2012 | Quadri |
| 8,092,525 B2 | 1/2012 | Eliasen et al. |
| 8,100,820 B2 | 1/2012 | Hauser et al. |
| 8,108,054 B2 | 1/2012 | Helland |
| 8,109,996 B2 | 2/2012 | Stacchino et al. |
| 8,137,381 B2 | 3/2012 | Foerster et al. |
| 8,142,493 B2 | 3/2012 | Spence et al. |
| 8,142,495 B2 | 3/2012 | Hasenkam et al. |
| 8,147,542 B2 | 4/2012 | Maisano et al. |
| 8,157,810 B2 | 4/2012 | Case et al. |
| 8,172,898 B2 | 5/2012 | Alferness et al. |
| 8,197,441 B2 | 6/2012 | Webler et al. |
| 8,202,281 B2 | 6/2012 | Voss |
| 8,202,315 B2 | 6/2012 | Hlavka et al. |
| 8,216,302 B2 | 7/2012 | Wilson et al. |
| 8,226,707 B2 | 7/2012 | White |
| 8,236,013 B2 | 8/2012 | Chu |
| 8,236,049 B2 | 8/2012 | Rowe et al. |
| 8,252,005 B2 | 8/2012 | Findlay et al. |
| 8,262,567 B2 | 9/2012 | Sharp et al. |
| 8,262,724 B2 | 9/2012 | Seguin et al. |
| 8,262,725 B2 | 9/2012 | Subramanian |
| 8,267,981 B2 | 9/2012 | Boock et al. |
| 8,313,497 B2 | 11/2012 | Walberg et al. |
| 8,313,498 B2 | 11/2012 | Pantages et al. |
| 8,323,312 B2 | 12/2012 | Clark |
| 8,323,335 B2 | 12/2012 | Rowe et al. |
| 8,332,051 B2 | 12/2012 | Sommer et al. |
| 8,361,088 B2 | 1/2013 | McIntosh |
| 8,382,829 B1 | 2/2013 | Call et al. |
| 8,394,008 B2 | 3/2013 | Annest et al. |
| 8,398,672 B2 | 3/2013 | Kleshinski et al. |
| 8,409,273 B2 | 4/2013 | Thornton et al. |
| 8,419,753 B2 | 4/2013 | Stafford |
| 8,430,893 B2 | 4/2013 | Ma |
| 8,449,606 B2 | 5/2013 | Eliasen et al. |
| 8,460,368 B2 | 6/2013 | Taylor et al. |
| 8,460,371 B2 | 6/2013 | Hlavka et al. |
| 8,475,525 B2 | 7/2013 | Maisano et al. |
| 8,480,691 B2 | 7/2013 | Dana et al. |
| 8,480,730 B2 | 7/2013 | Maurer et al. |
| 8,523,881 B2 | 9/2013 | Cabiri et al. |
| 8,524,132 B2 | 9/2013 | Von Oepen et al. |
| 8,529,621 B2 | 9/2013 | Alfieri et al. |
| 8,545,553 B2 | 10/2013 | Zipory et al. |
| 8,568,475 B2 | 10/2013 | Nguyen et al. |
| 8,568,476 B2 | 10/2013 | Rao et al. |
| 8,591,460 B2 | 11/2013 | Wilson et al. |
| 8,597,347 B2 | 12/2013 | Maurer et al. |
| 8,628,569 B2 | 1/2014 | Benichou et al. |
| 8,628,571 B1 | 1/2014 | Hacohen |
| 8,663,248 B2 | 3/2014 | Zung et al. |
| 8,685,080 B2 | 4/2014 | White |
| 8,685,083 B2 | 4/2014 | Perier et al. |
| 8,721,588 B2 | 5/2014 | Echarri et al. |
| 8,728,097 B1 | 5/2014 | Sugimoto et al. |
| 8,747,463 B2 | 6/2014 | Fogarty et al. |
| 8,753,357 B2 | 6/2014 | Roorda et al. |
| 8,753,373 B2 | 6/2014 | Chau et al. |
| 8,758,402 B2 | 6/2014 | Jenson et al. |
| 8,778,017 B2 | 7/2014 | Eliasen et al. |
| 8,784,481 B2 | 7/2014 | Alkhatib et al. |
| 8,790,394 B2 | 7/2014 | Miller et al. |
| 8,795,356 B2 | 8/2014 | Quadri et al. |
| 8,808,366 B2 | 8/2014 | Braido et al. |
| 8,808,368 B2 | 8/2014 | Maisano et al. |
| 8,845,723 B2 | 9/2014 | Spence et al. |
| 8,852,270 B2 | 10/2014 | Maurer et al. |
| 8,852,272 B2 | 10/2014 | Gross et al. |
| 8,858,594 B2 | 10/2014 | Clark |
| 8,858,623 B2 | 10/2014 | Miller et al. |
| 8,864,822 B2 | 10/2014 | Spence et al. |
| 8,870,949 B2 | 10/2014 | Rowe |
| 8,870,950 B2 | 10/2014 | Hacohen |
| 8,893,947 B2 | 11/2014 | Reynolds et al. |

(56) References Cited

U.S. PATENT DOCUMENTS

| | | |
|---|---|---|
| 8,911,461 B2 | 12/2014 | Traynor et al. |
| 8,926,691 B2 | 1/2015 | Chau et al. |
| 8,945,177 B2 | 2/2015 | Dell et al. |
| 8,945,211 B2 | 2/2015 | Sugimoto |
| 8,951,285 B2 | 2/2015 | Sugimoto et al. |
| 8,961,594 B2 | 2/2015 | Maisano et al. |
| 8,961,595 B2 | 2/2015 | Alkhatib |
| 8,961,596 B2 | 2/2015 | Maisano et al. |
| 8,968,335 B2 | 3/2015 | Robinson et al. |
| 8,968,336 B2 | 3/2015 | Conklin et al. |
| 8,968,395 B2 | 3/2015 | Hauser et al. |
| 8,979,750 B2 | 3/2015 | Van Bladel et al. |
| 8,979,922 B2 | 3/2015 | Jayasinghe et al. |
| 8,979,923 B2 | 3/2015 | Spence et al. |
| 9,005,273 B2 | 4/2015 | Salahieh et al. |
| 9,011,468 B2 | 4/2015 | Ketai et al. |
| 9,017,347 B2 | 4/2015 | Oba et al. |
| 9,034,032 B2 | 5/2015 | McLean et al. |
| 9,034,033 B2 | 5/2015 | McLean et al. |
| 9,078,652 B2 | 7/2015 | Conklin et al. |
| 9,084,676 B2 | 7/2015 | Chau et al. |
| 9,107,749 B2 | 8/2015 | Bobo et al. |
| 9,131,939 B1 | 9/2015 | Call et al. |
| 9,138,335 B2 | 9/2015 | Cartledge et al. |
| 9,180,005 B1 | 11/2015 | Lashinski et al. |
| 9,192,471 B2 | 11/2015 | Bolling |
| 9,211,115 B2 | 12/2015 | Annest et al. |
| 9,211,203 B2 | 12/2015 | Pike et al. |
| 9,241,702 B2 | 1/2016 | Maisano et al. |
| 9,241,706 B2 | 1/2016 | Paraschac et al. |
| 9,259,218 B2 | 2/2016 | Robinson |
| 9,259,317 B2 | 2/2016 | Wilson et al. |
| 9,282,965 B2 | 3/2016 | Kokish |
| 9,289,282 B2 | 3/2016 | Olson et al. |
| 9,289,297 B2 | 3/2016 | Wilson et al. |
| 9,301,749 B2 | 4/2016 | Rowe et al. |
| 9,307,980 B2 | 4/2016 | Gilmore et al. |
| 9,314,242 B2 | 4/2016 | Bachman |
| 9,326,870 B2 | 5/2016 | Berglund et al. |
| 9,339,293 B2 | 5/2016 | Morgan |
| 9,358,111 B2 | 6/2016 | Spence et al. |
| 9,408,607 B2 | 8/2016 | Cartledge et al. |
| 9,474,605 B2 | 10/2016 | Rowe et al. |
| 9,662,212 B2 | 5/2017 | Van Bladel et al. |
| 9,675,338 B2 | 6/2017 | Shanley et al. |
| 2001/0018611 A1 | 8/2001 | Solem et al. |
| 2002/0013571 A1 | 1/2002 | Goldfarb et al. |
| 2002/0032481 A1 | 5/2002 | Gabbay |
| 2002/0082625 A1 | 6/2002 | Huxel et al. |
| 2002/0107564 A1 | 8/2002 | Cox et al. |
| 2002/0151961 A1 | 10/2002 | Lashinski et al. |
| 2002/0156517 A1 | 10/2002 | Perouse |
| 2002/0177904 A1 | 11/2002 | Huxel et al. |
| 2003/0033003 A1 | 2/2003 | Harrison et al. |
| 2003/0057156 A1 | 3/2003 | Peterson et al. |
| 2003/0083742 A1 | 5/2003 | Spence et al. |
| 2003/0093096 A1 | 5/2003 | McGuckin, Jr. et al. |
| 2003/0167071 A1 | 9/2003 | Martin et al. |
| 2003/0229350 A1 | 12/2003 | Kay |
| 2003/0236568 A1 | 12/2003 | Hojeibane et al. |
| 2004/0049207 A1* | 3/2004 | Goldfarb ............ A61M 25/0136 606/139 |
| 2004/0117009 A1 | 6/2004 | Cali et al. |
| 2004/0133274 A1 | 7/2004 | Webler et al. |
| 2004/0158314 A1 | 8/2004 | Hogendijk |
| 2004/0172046 A1 | 9/2004 | Hlavka et al. |
| 2004/0181287 A1 | 9/2004 | Gellman |
| 2004/0186566 A1 | 9/2004 | Hindrichs et al. |
| 2004/0193092 A1 | 9/2004 | Deal |
| 2004/0236419 A1 | 11/2004 | Milo |
| 2004/0260389 A1 | 12/2004 | Case et al. |
| 2005/0004668 A1 | 1/2005 | Aklog et al. |
| 2005/0016560 A1 | 1/2005 | Voughlohn |
| 2005/0021085 A1 | 1/2005 | Abrams et al. |
| 2005/0055089 A1 | 3/2005 | Macoviak et al. |
| 2005/0059984 A1 | 3/2005 | Chanduszko et al. |
| 2005/0059997 A1 | 3/2005 | Bauman et al. |
| 2005/0075713 A1 | 4/2005 | Biancucci et al. |
| 2005/0075723 A1 | 4/2005 | Schroeder et al. |
| 2005/0080483 A1 | 4/2005 | Solem et al. |
| 2005/0090827 A1 | 4/2005 | Gedebou |
| 2005/0096666 A1 | 5/2005 | Gordon et al. |
| 2005/0107812 A1 | 5/2005 | Starksen et al. |
| 2005/0107871 A1 | 5/2005 | Realyvasquez et al. |
| 2005/0113900 A1 | 5/2005 | Shiroff et al. |
| 2005/0125077 A1 | 6/2005 | Harmon et al. |
| 2005/0137688 A1 | 6/2005 | Salahieh et al. |
| 2005/0137695 A1 | 6/2005 | Salahieh et al. |
| 2005/0143770 A1 | 6/2005 | Carter et al. |
| 2005/0149182 A1 | 7/2005 | Alferness et al. |
| 2005/0154448 A1 | 7/2005 | Cully et al. |
| 2005/0165466 A1* | 7/2005 | Morris ............ A61B 17/00234 607/116 |
| 2005/0177180 A1 | 8/2005 | Kaganov et al. |
| 2005/0177224 A1 | 8/2005 | Fogarty et al. |
| 2005/0177228 A1 | 8/2005 | Solem |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222488 A1 | 10/2005 | Chang et al. |
| 2005/0222665 A1 | 10/2005 | Arayani |
| 2005/0228422 A1 | 10/2005 | Machold et al. |
| 2005/0251208 A1 | 11/2005 | Elmer et al. |
| 2005/0256532 A1 | 11/2005 | Nayak et al. |
| 2005/0273138 A1 | 12/2005 | To et al. |
| 2005/0283246 A1 | 12/2005 | Cauthen et al. |
| 2006/0004442 A1 | 1/2006 | Spenser et al. |
| 2006/0020326 A9 | 1/2006 | Bolduc et al. |
| 2006/0020327 A1 | 1/2006 | Lashinski et al. |
| 2006/0052821 A1 | 3/2006 | Abbot et al. |
| 2006/0079736 A1 | 4/2006 | Chin et al. |
| 2006/0089671 A1* | 4/2006 | Goldfarb ............ A61B 17/122 606/215 |
| 2006/0106278 A1 | 5/2006 | Machold et al. |
| 2006/0106279 A1 | 5/2006 | Machold et al. |
| 2006/0106420 A1 | 5/2006 | Dolan et al. |
| 2006/0106423 A1 | 5/2006 | Weisel et al. |
| 2006/0129166 A1 | 6/2006 | Lavelle |
| 2006/0161265 A1 | 7/2006 | Levine et al. |
| 2006/0173524 A1 | 8/2006 | Salahieh et al. |
| 2006/0178700 A1 | 8/2006 | Quinn |
| 2006/0200199 A1 | 9/2006 | Bonutti et al. |
| 2006/0206201 A1 | 9/2006 | Garcia et al. |
| 2006/0229708 A1 | 10/2006 | Powell et al. |
| 2006/0241745 A1 | 10/2006 | Solem |
| 2006/0241748 A1 | 10/2006 | Lee et al. |
| 2006/0252984 A1 | 11/2006 | Randert et al. |
| 2006/0259135 A1 | 11/2006 | Navia et al. |
| 2006/0259137 A1 | 11/2006 | Artof et al. |
| 2006/0265042 A1 | 11/2006 | Catanese et al. |
| 2006/0276871 A1 | 12/2006 | Lamson et al. |
| 2006/0282161 A1 | 12/2006 | Huynh et al. |
| 2007/0016287 A1 | 1/2007 | Cartledge |
| 2007/0016288 A1 | 1/2007 | Gurskis |
| 2007/0021781 A1 | 1/2007 | Jervis et al. |
| 2007/0032787 A1 | 2/2007 | Hassett et al. |
| 2007/0032796 A1 | 2/2007 | Chin-Chen et al. |
| 2007/0032820 A1 | 2/2007 | Chin-Chen et al. |
| 2007/0038221 A1 | 2/2007 | Fine et al. |
| 2007/0038296 A1 | 2/2007 | Navia |
| 2007/0049942 A1 | 3/2007 | Hindrichs et al. |
| 2007/0049970 A1 | 3/2007 | Belef et al. |
| 2007/0049971 A1 | 3/2007 | Chin et al. |
| 2007/0051377 A1 | 3/2007 | Douk et al. |
| 2007/0055340 A1 | 3/2007 | Pryor |
| 2007/0060895 A1 | 3/2007 | Sibbitt et al. |
| 2007/0060989 A1 | 3/2007 | Deem et al. |
| 2007/0061010 A1 | 3/2007 | Hauser et al. |
| 2007/0066863 A1 | 3/2007 | Rafiee et al. |
| 2007/0083168 A1 | 4/2007 | Whiting et al. |
| 2007/0093869 A1 | 4/2007 | Bloom et al. |
| 2007/0100427 A1 | 5/2007 | Perouse |
| 2007/0112425 A1 | 5/2007 | Schaller et al. |
| 2007/0118151 A1 | 5/2007 | Davidson |

(56) References Cited

U.S. PATENT DOCUMENTS

| | | |
|---|---|---|
| 2007/0123936 A1 | 5/2007 | Goldin et al. |
| 2007/0162107 A1 | 7/2007 | Haug et al. |
| 2007/0168013 A1 | 7/2007 | Douglas |
| 2007/0185532 A1 | 8/2007 | Stone et al. |
| 2007/0198082 A1 | 8/2007 | Kapadia et al. |
| 2007/0203391 A1 | 8/2007 | Bloom et al. |
| 2007/0208389 A1 | 9/2007 | Amundson et al. |
| 2007/0219558 A1 | 9/2007 | Deutsch |
| 2007/0250160 A1 | 10/2007 | Rafiee |
| 2007/0265658 A1 | 11/2007 | Nelson et al. |
| 2007/0265700 A1 | 11/2007 | Eliasen et al. |
| 2007/0270943 A1 | 11/2007 | Solem et al. |
| 2007/0276437 A1 | 11/2007 | Call et al. |
| 2007/0276467 A1 | 11/2007 | Kalmann |
| 2007/0282375 A1 | 12/2007 | Hindrichs et al. |
| 2007/0282429 A1 | 12/2007 | Hauser et al. |
| 2007/0288086 A1 | 12/2007 | Kalmann et al. |
| 2007/0288089 A1 | 12/2007 | Gurskis et al. |
| 2008/0003539 A1 | 1/2008 | Lundgren |
| 2008/0015617 A1 | 1/2008 | Harari et al. |
| 2008/0027268 A1 | 1/2008 | Buckner et al. |
| 2008/0027446 A1 | 1/2008 | Stone et al. |
| 2008/0027483 A1 | 1/2008 | Cartledge |
| 2008/0033475 A1 | 2/2008 | Meng |
| 2008/0035160 A1 | 2/2008 | Woodson et al. |
| 2008/0039845 A1 | 2/2008 | Bonutti et al. |
| 2008/0058866 A1 | 3/2008 | Young et al. |
| 2008/0077231 A1 | 3/2008 | Heringes et al. |
| 2008/0091264 A1 | 4/2008 | Machold et al. |
| 2008/0097595 A1 | 4/2008 | Gabbay |
| 2008/0125861 A1 | 5/2008 | Webler et al. |
| 2008/0140116 A1 | 6/2008 | Bonutti |
| 2008/0140188 A1 | 6/2008 | Randert et al. |
| 2008/0167714 A1 | 7/2008 | St. Goar |
| 2008/0190989 A1 | 8/2008 | Crews et al. |
| 2008/0262598 A1 | 10/2008 | Elmaleh |
| 2008/0262609 A1 | 10/2008 | Gross et al. |
| 2008/0275469 A1 | 11/2008 | Fanton et al. |
| 2008/0281411 A1 | 11/2008 | Berreklouw et al. |
| 2008/0288044 A1 | 11/2008 | Osborne |
| 2008/0288062 A1 | 11/2008 | Andrieu et al. |
| 2008/0300629 A1 | 12/2008 | Surti |
| 2009/0005863 A1 | 1/2009 | Goetz et al. |
| 2009/0043382 A1 | 2/2009 | Maurer et al. |
| 2009/0048668 A1 | 2/2009 | Wilson et al. |
| 2009/0082828 A1 | 3/2009 | Ostroff |
| 2009/0082847 A1 | 3/2009 | Zacharias et al. |
| 2009/0084386 A1 | 4/2009 | McClellan et al. |
| 2009/0099647 A1 | 4/2009 | Glimsdale et al. |
| 2009/0099649 A1 | 4/2009 | Chobotov et al. |
| 2009/0112052 A1 | 4/2009 | Lund et al. |
| 2009/0118776 A1 | 5/2009 | Kelsch et al. |
| 2009/0131849 A1 | 5/2009 | Maurer et al. |
| 2009/0132033 A1 | 5/2009 | Maurer et al. |
| 2009/0143808 A1 | 6/2009 | Houser |
| 2009/0149872 A1 | 6/2009 | Gross et al. |
| 2009/0171439 A1 | 7/2009 | Nissl |
| 2009/0216265 A1 | 8/2009 | DeVries |
| 2009/0240326 A1 | 9/2009 | Wilson et al. |
| 2009/0254103 A1 | 10/2009 | Deutsch et al. |
| 2009/0259307 A1 | 10/2009 | Gross et al. |
| 2009/0264991 A1 | 10/2009 | Paul et al. |
| 2009/0264995 A1 | 10/2009 | Subramanian |
| 2009/0276040 A1 | 11/2009 | Rowe et al. |
| 2009/0287304 A1 | 11/2009 | Dahlgren et al. |
| 2009/0306622 A1 | 12/2009 | Machold et al. |
| 2009/0326648 A1 | 12/2009 | Machold et al. |
| 2010/0022948 A1 | 1/2010 | Wilson et al. |
| 2010/0023117 A1 | 1/2010 | Yoganathan et al. |
| 2010/0023118 A1 | 1/2010 | Medlock et al. |
| 2010/0029071 A1 | 2/2010 | Russell et al. |
| 2010/0030329 A1 | 2/2010 | Frater |
| 2010/0049293 A1 | 2/2010 | Zukowski et al. |
| 2010/0063520 A1 | 3/2010 | Bilotti |
| 2010/0063542 A1 | 3/2010 | Van der Burg et al. |
| 2010/0063586 A1 | 3/2010 | Hasenkam et al. |
| 2010/0121349 A1 | 5/2010 | Meier et al. |
| 2010/0121434 A1 | 5/2010 | Paul et al. |
| 2010/0121435 A1 | 5/2010 | Subramanian et al. |
| 2010/0130992 A1 | 5/2010 | Machold et al. |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168791 A1 | 7/2010 | Kassab |
| 2010/0174358 A1 | 7/2010 | Rabkin |
| 2010/0185278 A1 | 7/2010 | Schankereli |
| 2010/0204662 A1 | 8/2010 | Orlov et al. |
| 2010/0211166 A1 | 8/2010 | Miller et al. |
| 2010/0217309 A1 | 8/2010 | Hansen et al. |
| 2010/0217382 A1 | 8/2010 | Chau et al. |
| 2010/0228269 A1 | 9/2010 | Garrison et al. |
| 2010/0234935 A1 | 9/2010 | Bashiri |
| 2010/0249908 A1 | 9/2010 | Chau et al. |
| 2010/0249920 A1 | 9/2010 | Bolling et al. |
| 2010/0256743 A1 | 10/2010 | Hinchliffe et al. |
| 2010/0264192 A1 | 10/2010 | Marczyk |
| 2010/0268204 A1 | 10/2010 | Tieu et al. |
| 2010/0280603 A1 | 11/2010 | Maisano et al. |
| 2010/0280604 A1* | 11/2010 | Zipory ............. A61B 17/0401 623/2.11 |
| 2010/0280605 A1 | 11/2010 | Hammer et al. |
| 2010/0286628 A1 | 11/2010 | Gross |
| 2010/0286767 A1 | 11/2010 | Zipory et al. |
| 2010/0298930 A1 | 11/2010 | Orlov |
| 2010/0324598 A1 | 12/2010 | Anderson |
| 2010/0324668 A1 | 12/2010 | Maurer et al. |
| 2010/0331854 A1 | 12/2010 | Greenberg et al. |
| 2011/0009818 A1 | 1/2011 | Goff |
| 2011/0011917 A1 | 1/2011 | Loulmet |
| 2011/0022164 A1 | 1/2011 | Quinn et al. |
| 2011/0029066 A1 | 2/2011 | Gilad |
| 2011/0029071 A1 | 2/2011 | Zlotnick et al. |
| 2011/0035000 A1 | 2/2011 | Nieminen et al. |
| 2011/0040366 A1 | 2/2011 | Goetz et al. |
| 2011/0071626 A1 | 3/2011 | Wright et al. |
| 2011/0077733 A1 | 3/2011 | Solem |
| 2011/0082538 A1 | 4/2011 | Dahlgren et al. |
| 2011/0087146 A1 | 4/2011 | Ryan et al. |
| 2011/0092990 A1* | 4/2011 | Gambale ............. A61B 17/0469 606/144 |
| 2011/0092993 A1 | 4/2011 | Jacobs |
| 2011/0093002 A1 | 4/2011 | Rucker et al. |
| 2011/0098732 A1 | 4/2011 | Jacobs |
| 2011/0106245 A1 | 5/2011 | Miller et al. |
| 2011/0106247 A1 | 5/2011 | Miller et al. |
| 2011/0112619 A1 | 5/2011 | Foster et al. |
| 2011/0112632 A1 | 5/2011 | Chau et al. |
| 2011/0137397 A1 | 6/2011 | Chau et al. |
| 2011/0152998 A1 | 6/2011 | Berez et al. |
| 2011/0166636 A1 | 7/2011 | Rowe |
| 2011/0184510 A1 | 7/2011 | Maisano |
| 2011/0190879 A1 | 8/2011 | Bobo et al. |
| 2011/0208283 A1 | 8/2011 | Rust et al. |
| 2011/0224785 A1 | 9/2011 | Hacohen |
| 2011/0238088 A1 | 9/2011 | Bolduc et al. |
| 2011/0238112 A1 | 9/2011 | Kim et al. |
| 2011/0251678 A1 | 10/2011 | Eidenschink |
| 2011/0264208 A1 | 10/2011 | Duffy et al. |
| 2011/0301698 A1 | 12/2011 | Miller et al. |
| 2012/0016343 A1 | 1/2012 | Gill |
| 2012/0022633 A1 | 1/2012 | Olson et al. |
| 2012/0022639 A1 | 1/2012 | Hacohen et al. |
| 2012/0022640 A1 | 1/2012 | Gross et al. |
| 2012/0143320 A1 | 1/2012 | Eliasen et al. |
| 2012/0029628 A1 | 2/2012 | Rowe |
| 2012/0035712 A1 | 2/2012 | Maisano |
| 2012/0083806 A1 | 4/2012 | Goertzen |
| 2012/0123531 A1 | 5/2012 | Tsukashima et al. |
| 2012/0130374 A1 | 5/2012 | Bouduban et al. |
| 2012/0130421 A1 | 5/2012 | Hafez et al. |
| 2012/0158021 A1 | 6/2012 | Morrill |
| 2012/0158053 A1 | 6/2012 | Paulos |
| 2012/0179244 A1 | 7/2012 | Schankereli et al. |

(56) References Cited

U.S. PATENT DOCUMENTS

| | | |
|---|---|---|
| 2012/0215236 A1 | 8/2012 | Matsunaga et al. |
| 2012/0222969 A1 | 9/2012 | Osborne et al. |
| 2012/0226349 A1 | 9/2012 | Tuval et al. |
| 2012/0232373 A1 | 9/2012 | Hallander et al. |
| 2012/0245604 A1 | 9/2012 | Tegzes |
| 2012/0283757 A1 | 11/2012 | Miller et al. |
| 2012/0296349 A1 | 11/2012 | Smith et al. |
| 2012/0310328 A1 | 12/2012 | Olson et al. |
| 2013/0018459 A1 | 1/2013 | Maisano et al. |
| 2013/0030522 A1 | 1/2013 | Rowe et al. |
| 2013/0041459 A1 | 2/2013 | Wilson et al. |
| 2013/0046373 A1 | 2/2013 | Cartledge et al. |
| 2013/0053951 A1 | 2/2013 | Baliarda |
| 2013/0079873 A1 | 3/2013 | Migliazza et al. |
| 2013/0085529 A1 | 4/2013 | Housman |
| 2013/0096664 A1 | 4/2013 | Goetz et al. |
| 2013/0096672 A1 | 4/2013 | Reich et al. |
| 2013/0110230 A1 | 5/2013 | Solem |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0190863 A1 | 7/2013 | Call et al. |
| 2013/0281760 A1 | 10/2013 | Farnan et al. |
| 2013/0296925 A1 | 11/2013 | Chanduszko et al. |
| 2013/0325110 A1 | 12/2013 | Khalil et al. |
| 2013/0331930 A1 | 12/2013 | Rowe et al. |
| 2014/0005778 A1 | 1/2014 | Buchbinder et al. |
| 2014/0018911 A1 | 1/2014 | Zhou et al. |
| 2014/0031864 A1 | 1/2014 | Jafari et al. |
| 2014/0031928 A1 | 1/2014 | Murphy et al. |
| 2014/0058405 A1 | 2/2014 | Foster |
| 2014/0066693 A1 | 3/2014 | Goldfarb et al. |
| 2014/0067054 A1 | 3/2014 | Chau et al. |
| 2014/0100604 A1 | 4/2014 | Litvack et al. |
| 2014/0114390 A1 | 4/2014 | Tobis et al. |
| 2014/0121763 A1 | 5/2014 | Duffy et al. |
| 2014/0142689 A1 | 5/2014 | De Canniere et al. |
| 2014/0163690 A1 | 6/2014 | White |
| 2014/0200657 A1 | 7/2014 | Maurer et al. |
| 2014/0207231 A1 | 7/2014 | Hacohen et al. |
| 2014/0214159 A1 | 7/2014 | Vidlund et al. |
| 2014/0243894 A1 | 8/2014 | Groothuis et al. |
| 2014/0257475 A1 | 9/2014 | Gross et al. |
| 2014/0275757 A1 | 9/2014 | Goodwin et al. |
| 2014/0277390 A1 | 9/2014 | Ratz et al. |
| 2014/0277427 A1 | 9/2014 | Ratz et al. |
| 2014/0288639 A1 | 9/2014 | Gainor |
| 2014/0296962 A1 | 10/2014 | Cartledge et al. |
| 2014/0309730 A1 | 10/2014 | Alon et al. |
| 2014/0324164 A1 | 10/2014 | Gross et al. |
| 2014/0358224 A1 | 12/2014 | Tegels et al. |
| 2014/0371843 A1 | 12/2014 | Wilson et al. |
| 2014/0379006 A1 | 12/2014 | Sutherland et al. |
| 2014/0379074 A1 | 12/2014 | Spence et al. |
| 2014/0379076 A1 | 12/2014 | Vidlund et al. |
| 2015/0018940 A1 | 1/2015 | Quill et al. |
| 2015/0045879 A1 | 2/2015 | Longoria et al. |
| 2015/0051698 A1 | 2/2015 | Baliarda et al. |
| 2015/0066082 A1 | 3/2015 | Moshe et al. |
| 2015/0066138 A1 | 3/2015 | Alexander et al. |
| 2015/0073545 A1 | 3/2015 | Braido |
| 2015/0094800 A1 | 4/2015 | Chawla |
| 2015/0094802 A1 | 4/2015 | Buchbinder et al. |
| 2015/0100116 A1 | 4/2015 | Mohl et al. |
| 2015/0119936 A1 | 4/2015 | Gilmore et al. |
| 2015/0127097 A1 | 5/2015 | Neumann et al. |
| 2015/0142049 A1 | 5/2015 | Delgado et al. |
| 2015/0142103 A1 | 5/2015 | Vidlund |
| 2015/0142105 A1 | 5/2015 | Bolling et al. |
| 2015/0157329 A1 | 6/2015 | Rudakov et al. |
| 2015/0182336 A1 | 7/2015 | Zipory et al. |
| 2015/0196693 A1 | 7/2015 | Lin |
| 2015/0223934 A1 | 8/2015 | Vidlund et al. |
| 2015/0250590 A1 | 9/2015 | Gries et al. |
| 2015/0272730 A1 | 10/2015 | Melnick et al. |
| 2015/0320414 A1 | 11/2015 | Conklin et al. |
| 2015/0351909 A1 | 12/2015 | Bobo et al. |
| 2015/0366666 A1 | 12/2015 | Khairkhahan et al. |
| 2016/0022417 A1 | 1/2016 | Karapetian et al. |
| 2016/0022422 A1 | 1/2016 | Annest et al. |
| 2016/0038285 A1 | 2/2016 | Glenn et al. |
| 2016/0081829 A1 | 3/2016 | Rowe |
| 2016/0120672 A1 | 5/2016 | Martin et al. |
| 2016/0128689 A1 | 5/2016 | Sutherland et al. |
| 2016/0157862 A1 | 6/2016 | Hernandez et al. |
| 2016/0174964 A1 | 6/2016 | Tobis |
| 2016/0174979 A1 | 6/2016 | Wei |
| 2016/0228246 A1 | 8/2016 | Zimmerman |
| 2016/0228252 A1 | 8/2016 | Keidar |
| 2016/0235526 A1 | 8/2016 | Lashinski et al. |
| 2016/0242762 A1 | 8/2016 | Gilmore et al. |
| 2016/0256269 A1 | 9/2016 | Cahalane et al. |
| 2016/0262741 A1 | 9/2016 | Gilmore et al. |
| 2016/0270776 A1 | 9/2016 | Miraki et al. |
| 2016/0270916 A1 | 9/2016 | Cahalane et al. |
| 2016/0287383 A1 | 10/2016 | Rowe |
| 2016/0287387 A1 | 10/2016 | Wei |
| 2017/0100250 A1* | 4/2017 | Marsot .................. A61F 2/2454 |
| 2017/0156731 A1* | 6/2017 | Mark .................. A61B 17/122 |
| 2018/0133454 A1* | 5/2018 | von Oepen .......... A61F 2/2436 |
| 2018/0289478 A1 | 10/2018 | Quill |

FOREIGN PATENT DOCUMENTS

| | | |
|---|---|---|
| EP | 1759663 | 3/2007 |
| EP | 1 836 971 | 9/2007 |
| EP | 1 968 491 | 7/2010 |
| EP | 2399549 | 3/2014 |
| WO | 1992/005093 | 4/1992 |
| WO | 1993015791 A1 | 8/1993 |
| WO | 1997/041778 | 11/1997 |
| WO | 2000/28923 | 5/2000 |
| WO | 2001/010306 | 2/2001 |
| WO | 2002/062236 | 8/2002 |
| WO | 2003/000331 | 1/2003 |
| WO | 2004/030569 | 4/2004 |
| WO | 2004/069055 | 8/2004 |
| WO | 2004/082538 | 9/2004 |
| WO | 2004/112585 | 12/2004 |
| WO | 2005/018507 | 3/2005 |
| WO | 2005/021063 | 3/2005 |
| WO | 2005/058206 | 6/2005 |
| WO | 2005/082288 | 9/2005 |
| WO | 2005/102194 | 11/2005 |
| WO | 2006/019498 | 2/2006 |
| WO | 2006/034062 | 3/2006 |
| WO | 2006/097931 | 9/2006 |
| WO | 2006/105008 | 10/2006 |
| WO | 2006/105009 | 10/2006 |
| WO | 2007/038786 | 4/2007 |
| WO | 2007/080595 | 7/2007 |
| WO | 2007/135101 | 11/2007 |
| WO | 2007/140309 | 12/2007 |
| WO | 2008/065044 | 6/2008 |
| WO | 2008/068756 | 6/2008 |
| WO | 2009/039400 | 3/2009 |
| WO | 2009/101617 | 8/2009 |
| WO | 2010/004546 | 1/2010 |
| WO | 2010/008549 | 1/2010 |
| WO | 2010/071494 | 6/2010 |
| WO | 2010/073246 | 7/2010 |
| WO | 2010/099032 | 9/2010 |
| WO | 2010/108079 | 9/2010 |
| WO | 2010/128502 | 11/2010 |
| WO | 2010/128503 | 11/2010 |
| WO | 2011/014496 | 2/2011 |
| WO | 2011/034973 | 3/2011 |
| WO | 2011/037891 | 3/2011 |
| WO | 2011/051942 | 5/2011 |
| WO | 2011/089601 | 7/2011 |
| WO | 2011/097355 | 8/2011 |
| WO | 2011/143263 | 11/2011 |
| WO | 2011/153408 | 12/2011 |
| WO | 2012/127309 | 9/2012 |

(56) References Cited

FOREIGN PATENT DOCUMENTS

| | | |
|---|---|---|
| WO | 2013/003228 | 1/2013 |
| WO | 2013/011502 | 1/2013 |
| WO | 2013/028145 | 2/2013 |
| WO | 2013/078497 | 6/2013 |
| WO | 2013/179295 | 12/2013 |
| WO | 2014/043527 | 3/2014 |
| WO | 2014/064694 | 5/2014 |
| WO | 2014/087402 | 6/2014 |
| WO | 2014/108903 | 7/2014 |
| WO | 2014/141239 | 9/2014 |
| WO | 2015/015497 | 2/2015 |
| WO | 2015/063580 | 5/2015 |
| WO | 2015/193728 | 12/2015 |
| WO | 2016/011275 | 1/2016 |
| WO | 2016/087934 | 6/2016 |
| WO | 2016/189391 | 12/2016 |

OTHER PUBLICATIONS

An Interview Summary dated Oct. 24, 2012, which issued during the prosecution of U.S. Appl. No. 12/692,061.
Alfieri et al., "An effective technique to correct anterior mitral leaflet prolapse," J Card Surg 14(6):468-470 (1999).
An Interview Summary dated Dec. 5, 2016, which issued during the prosecution of U.S. Appl. No. 13/574,088.
Alfieri et al., "Novel suture device for beating heart mitral leaflet approximation," Annals of Thoracic Surgery 74:1488 1493 (2002).
Alfieri et al., "The double orifice technique in mitral valve repair: a simple solution for complex problems," Journal of Thoracic Cardiovascular Surgery 122:674-681 (2001).
Amplatzer Cardiac Plug Brochure (English pages), AGA Medical Corporation, Plymouth, MN Copyright 2008-2011, downloaded Jan. 11, 2011.
Beale BS, "Surgical Repair of Collateral Ligament Injuries," presented at 63rd CVMA Convention, Halifax, Nova Scotia, Canada, Jul. 6-9, 2011.
Dentistry Today, "Implant Direct" product information page, Jun. 1, 2011, downloaded Dec. 10, 2012 from http://dentistrytoday.com/top25implant-i/5558-implant-direct.
Maisano et al., "The double-orifice technique as a standardized approach to treat mitral regurgitation due to severe myxomatous disease: surgical technique," European Journal of Cardio-thoracic Surgery 17 (2000) 201-205.
Shikhar Agarwal et al., "Interventional Cardiology Perspective of Functional Tricuspid Regurgitation," Circulatoin: Cardiovascular Interventions, pp. 565-573; Dec. 2009; vol. 2, Issue 6.
Smith & Nephew MINITAC™ 2.0 Suture Anchor Product Description, downloaded on Dec. 9, 2012 from http://global.smith-nephew.com/us/MINITAC_TI_2_SUTURE_ANCHR_3127.htm.
Second Notice of Allowance dated May 10, 2013, which issued during the prosecution of U.S. Appl. No. 12/692,061.
An Office Action dated Mar. 23, 2017, which issued during the prosecution of U.S. Appl. No. 13/574,088.
An Office Action dated Jul. 6, 2012, which issued during the prosecution of U.S. Appl. No. 12/692,061.
A Notice of Allowance dated Mar. 6, 2013, which issued during the prosecution of U.S. Appl. No. 12/692,061.
An International Search Report and a Written Opinion both dated May 19, 2011, which issued during the prosecution of Applicant's PCT/IL11/00064.
An International Search Report and a Written Opinion both dated Jan. 22, 2013, which issued during the prosecution of Applicant's PCT/IL2012/000282.
An Office Action dated Dec 5, 2013, which issued during the prosecution of U.S. Appl. No. 13/485,145.
An International Search Report and a Written Opinion both dated Mar. 17, 2014, which issued during the prosecution of Applicant's PCT/IL2013/050937.
Invitation to pay additional fees in PCT/IL2014/050027 dated Apr. 4, 2014.
An International Search Report and a Written Opinion both dated May 28, 2014, which issued during the prosecution of Applicant's PCT/IL2014/050027.
U.S. Appl. No. 60/902,146, filed Feb. 16, 2007.
European Search Report dated Apr. 10, 2015, which issued during the prosecution of Applicant's European App No. 11734451.5.
European Search Report dated May 15, 2015, which issued during the prosecution of Applicant's European App No. 12814417.7.
An Office Action dated Sep. 14, 2015, which issued during the prosecution of U.S. Appl. No. 13/553,081.
An English Translation of an Office Action dated Jun. 30, 2015 which issued during the prosecution of Chinese Patent Application No. 201180015301.6.
An English Translation of an Office Action dated Jul. 7, 2015 which issued during the prosecution of Japanese Patent Application No. 2012-549463.
An Office Action dated Oct. 7, 2015, which issued during the prosecution of U.S. Appl. No. 13/574,088.
Invitation to Pay Additional Fees dated Apr. 20, 2015, which issued during the prosecution of Applicant's PCT/IB2014/002351.
An International Search Report and a Written Opinion both dated Jun. 10, 2015, which issued during the prosecution of Applicant's PCT/IB2014/002351.
An Office Action dated Feb. 2, 2015, which issued during the prosecution of U.S. Appl. No. 14/143,355.
An English Translation of an Office Action dated Feb. 10, 2015 which issued during the prosecution of Chinese Patent Application No. 201180015301.6.
An Office Action dated Feb. 25, 2015, which issued during the prosecution of U.S. Appl. No. 13/574,088.
Notice of Allowance dated Sep. 24, 2015, which issued during the prosecution of U.S. Appl. No. 14/143,355.
Notice of Allowance dated Dec. 4, 2015, which issued during the prosecution of U.S. Appl. No. 14/143,355.
An Office Action dated Jul. 7, 2014, which issued during the prosecution of U.S. Appl. No. 13/485,145.
An Office Action dated Jun. 30, 2014 which issued Chinese Patent Application No. 201180015301.6.
An Office Action dated Sep. 25, 2014, which issued during the prosecution of U.S. Appl. No. 13/485,145.
An Office Action dated Oct. 28, 2014,which issued Japanese Patent Application No. 2012-549463.
Notice of Allowance dated Dec. 9, 2014, which issued during the prosecution of U.S. Appl. No. 13/485,145.
An International Search Report and a Written Opinion both dated Jun. 30, 2014, which issued during the prosecution of Applicant's PCT/IL2014/050233.
An International Search Report and a Written Opinion both dated Jan. 8 2016, 2014, which issued during the prosecution of Applicant's PCT/IB2015/001196.
Invitation to pay additional fees in PCT/IB2015/001196 dated Oct. 26, 2015.
Notice of Allowance dated Dec. 4, 2014, which issued during the prosecution of U.S. Appl. No. 13/188,175.
An Office Action dated Nov. 25, 2014, which issued during the prosecution of U.S. Appl. No. 13/553,081.
An Office Action dated Apr. 18, 2016, which issued during the prosecution of U.S. Appl. No. 14/584,286.
Spinal & Epidural Needles—downloaded on Feb. 18, 2016 from http://www.cothon.net/Anestesia_Obstetrica/Neuroaxial_needles.html.
An Office Action dated May 11, 2016, which issued during the prosecution of U.S. Appl. No. 13/574,088.
An International Search Report and a Written Opinion both dated Apr. 15, 2016, 2014, which issued during the prosecution of Applicant's PCT/IB2015/002354.
An Office Action dated Jan. 19, 2017, which issued during the prosecution of Chinese Patent Application No. 2014800131345.
An English Translation of an Office Action dated Jun. 23, 2016 which issued during the prosecution of Chinese Patent Application No. 201480028044.3. (the relevant part only).

(56) References Cited

OTHER PUBLICATIONS

An International Search Report and a Written Opinion both dated Dec. 8, 2016, which issued during the prosecution of Applicant's PCT/IB2016/000840.

Notice of Allowance dated Sep. 5, 2016, which issued during the prosecution of Chinese Application No. 2014800280443. (with Translation).

An Office Action dated Sep. 14, 2016, which issued during the prosecution of U.S. Appl. No. 13/574,088.

Invitation to pay additional fees in PCT/IB2016/000840 dated Oct. 13, 2016.

An Office Action dated Jan. 12, 2017, which issued during the prosecution of U.S. Appl. No. 15/264,250.

An Office Action dated Apr. 6, 2017, which issued during the prosecution of U.S. Appl. No. 14/759,768.

An Office Action dated Feb. 21, 2017, which issued during the prosecution of Japanese Patent Application No. 2016-097937.

An Office Action dated Jun. 19, 2017, which issued during the prosecution of U.S. Appl. No. 15/123,157.

* cited by examiner

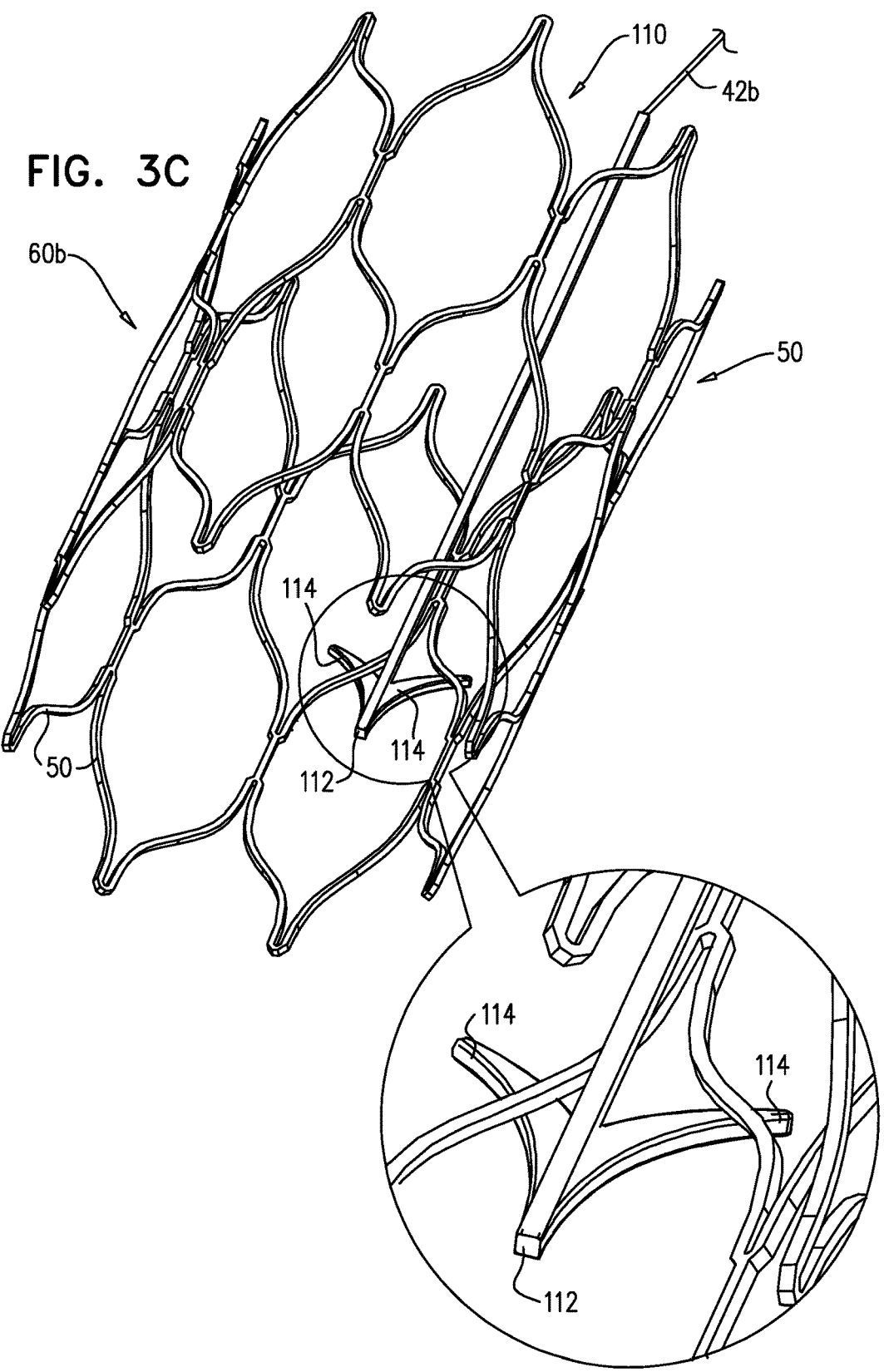

SECTION A-A

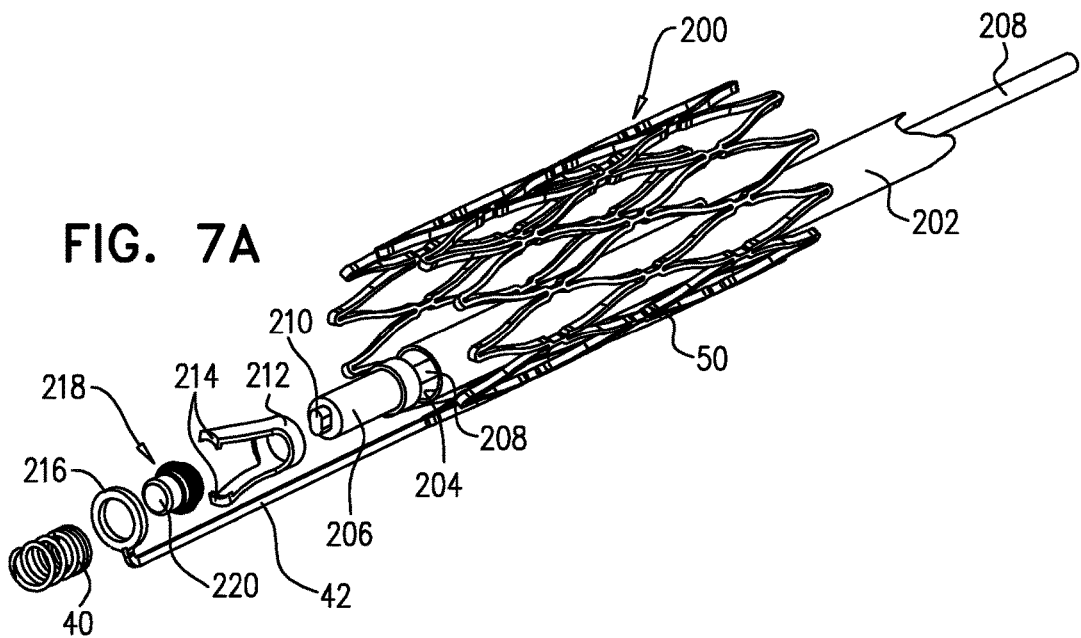
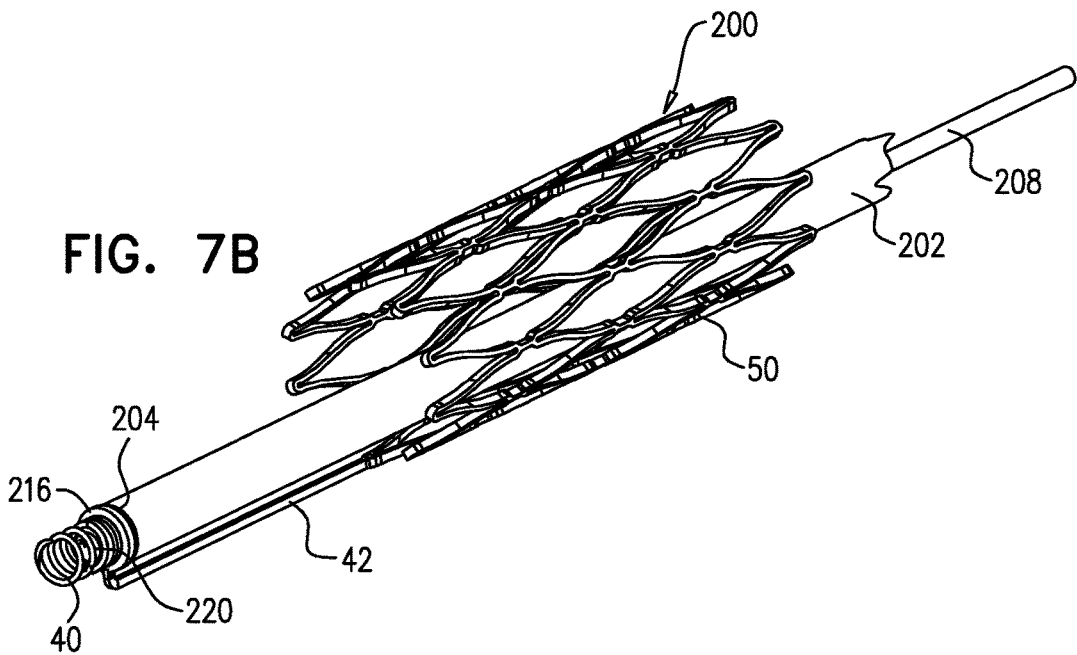

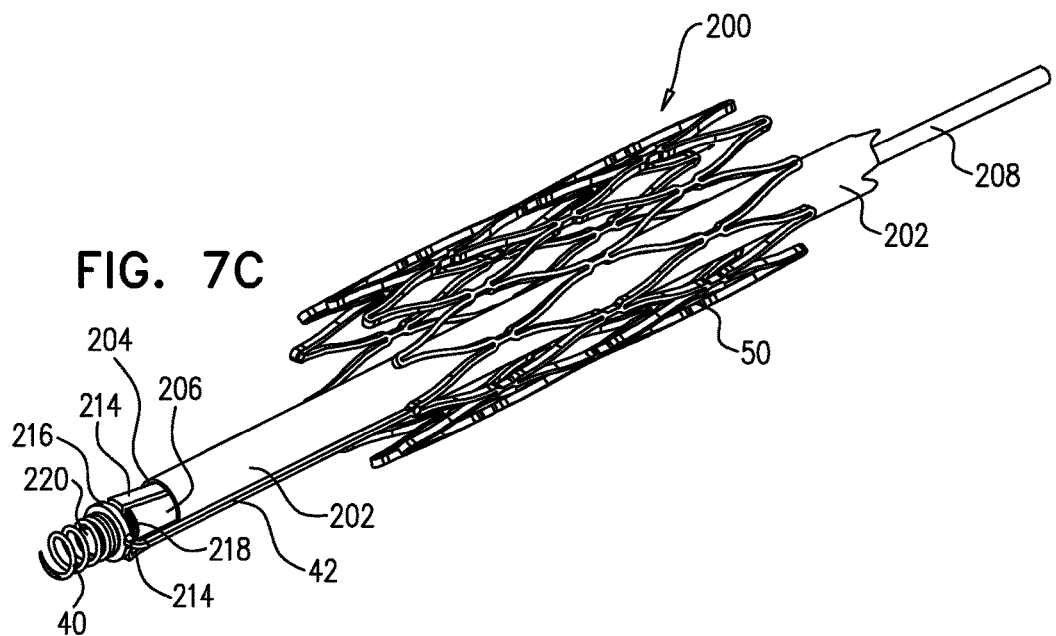
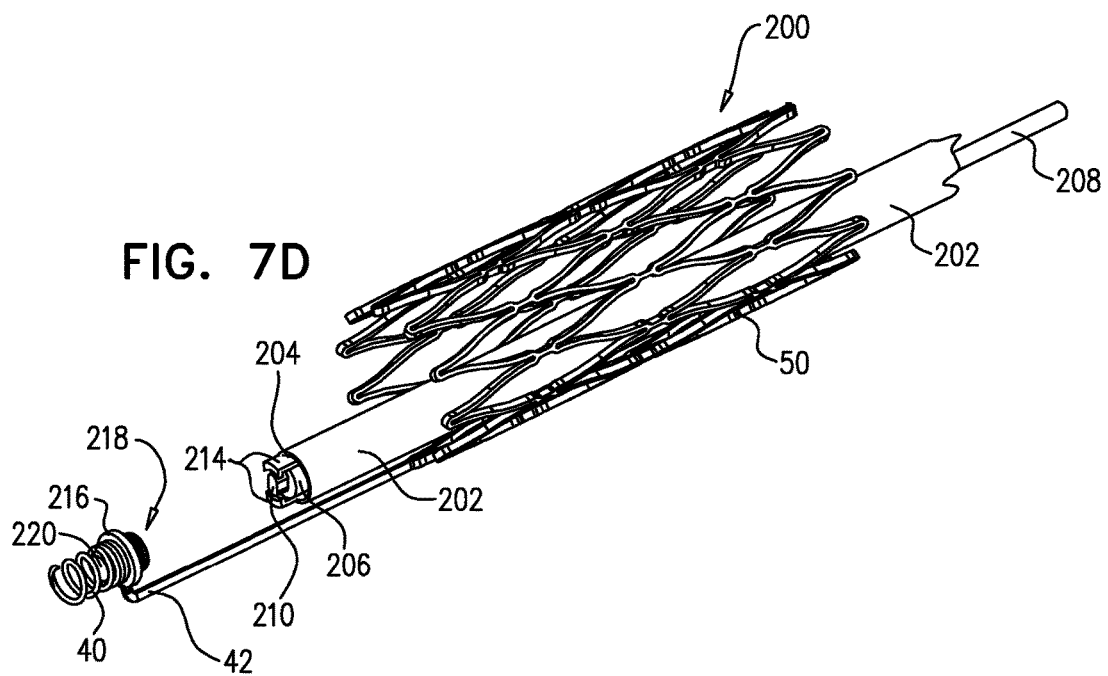

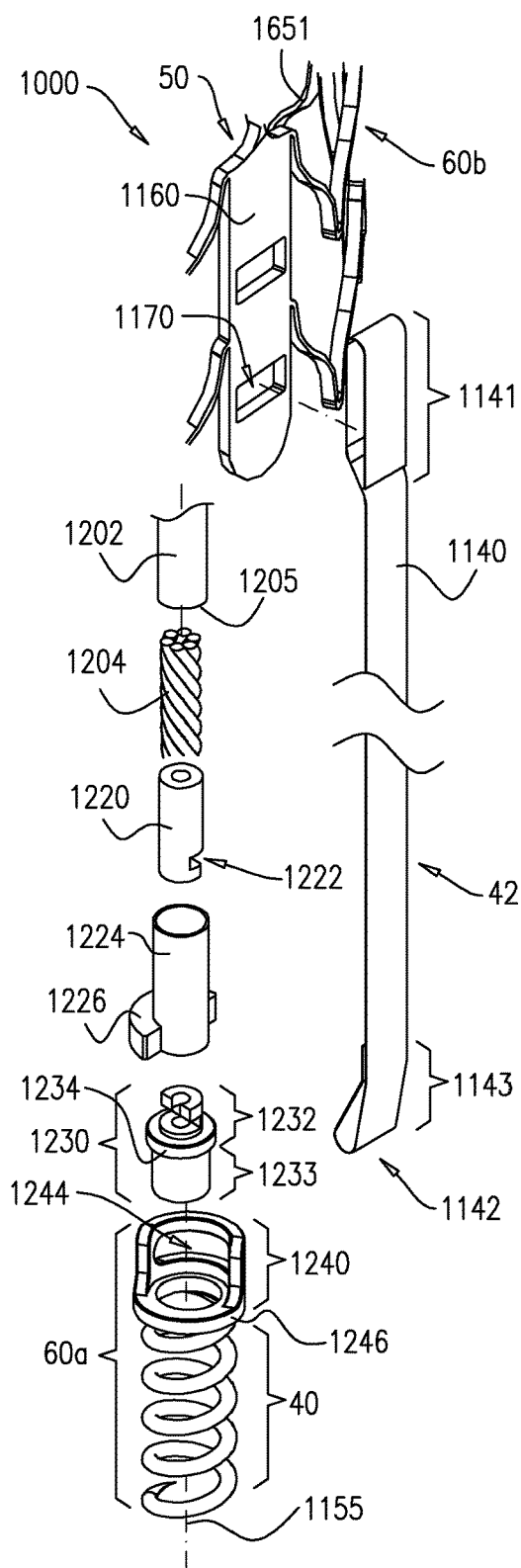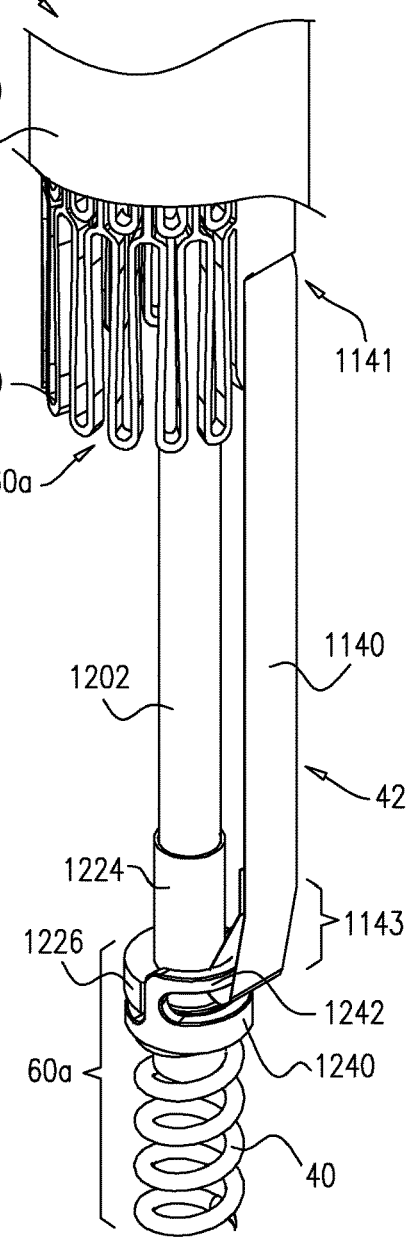

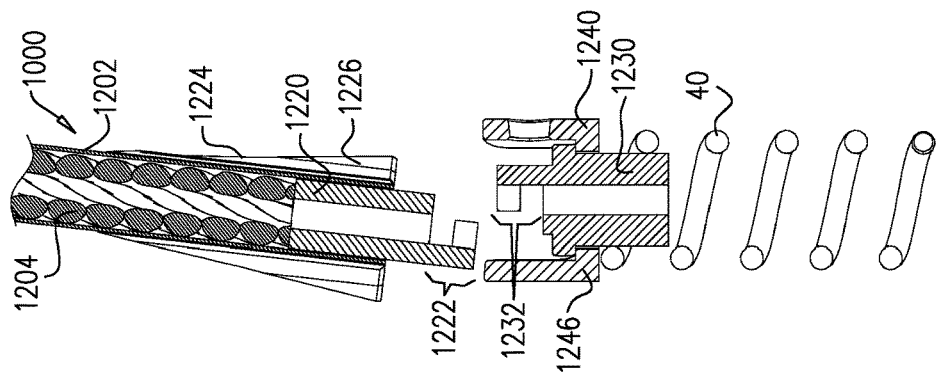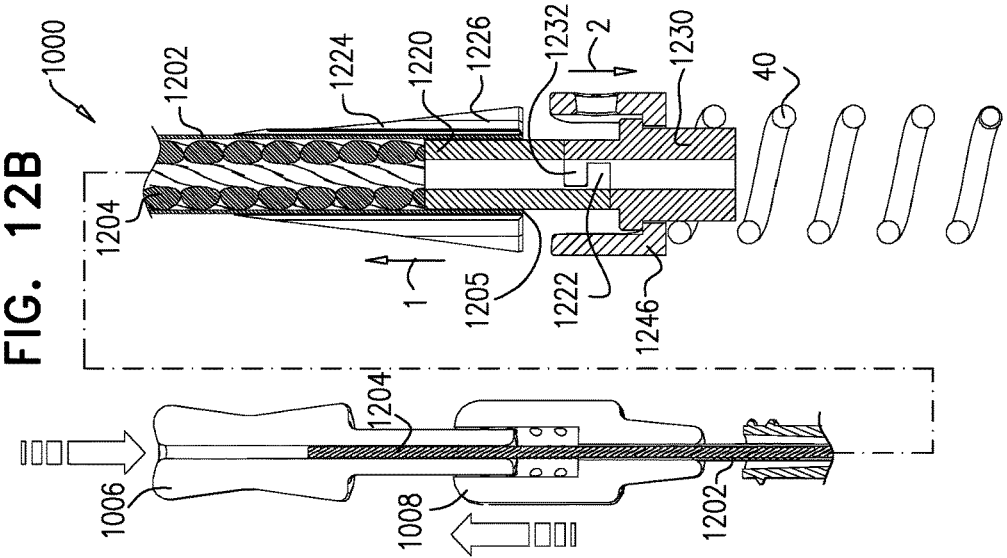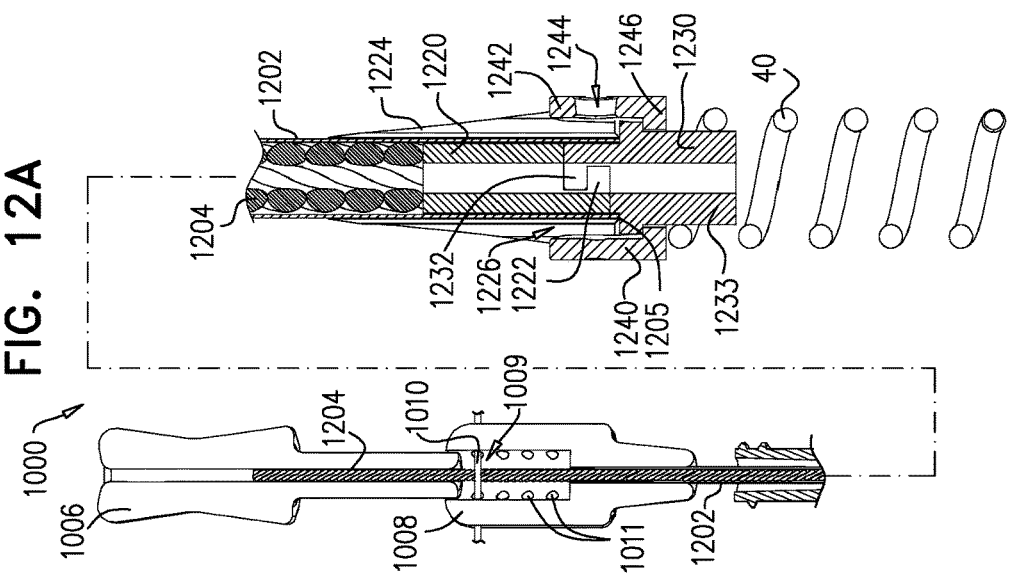

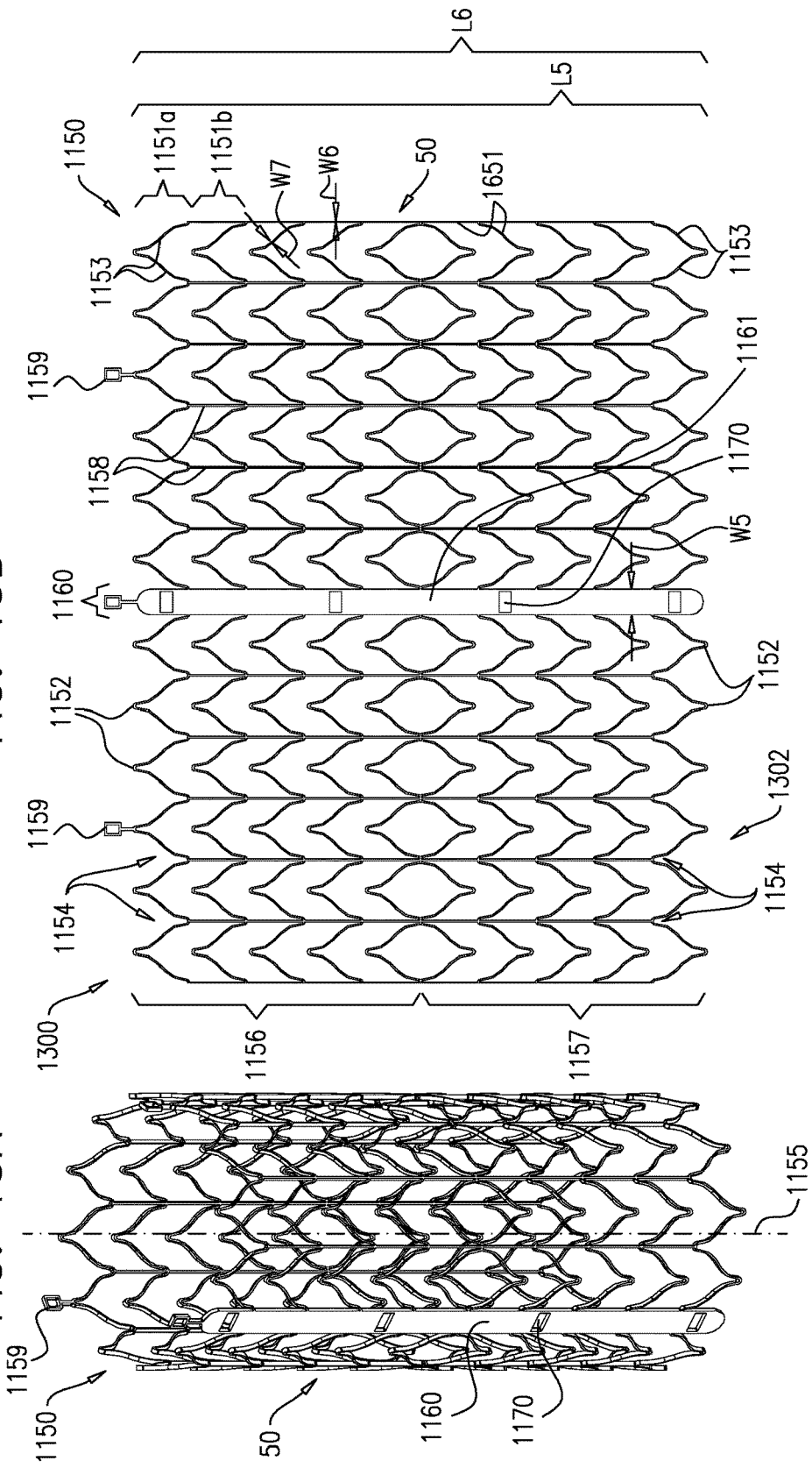

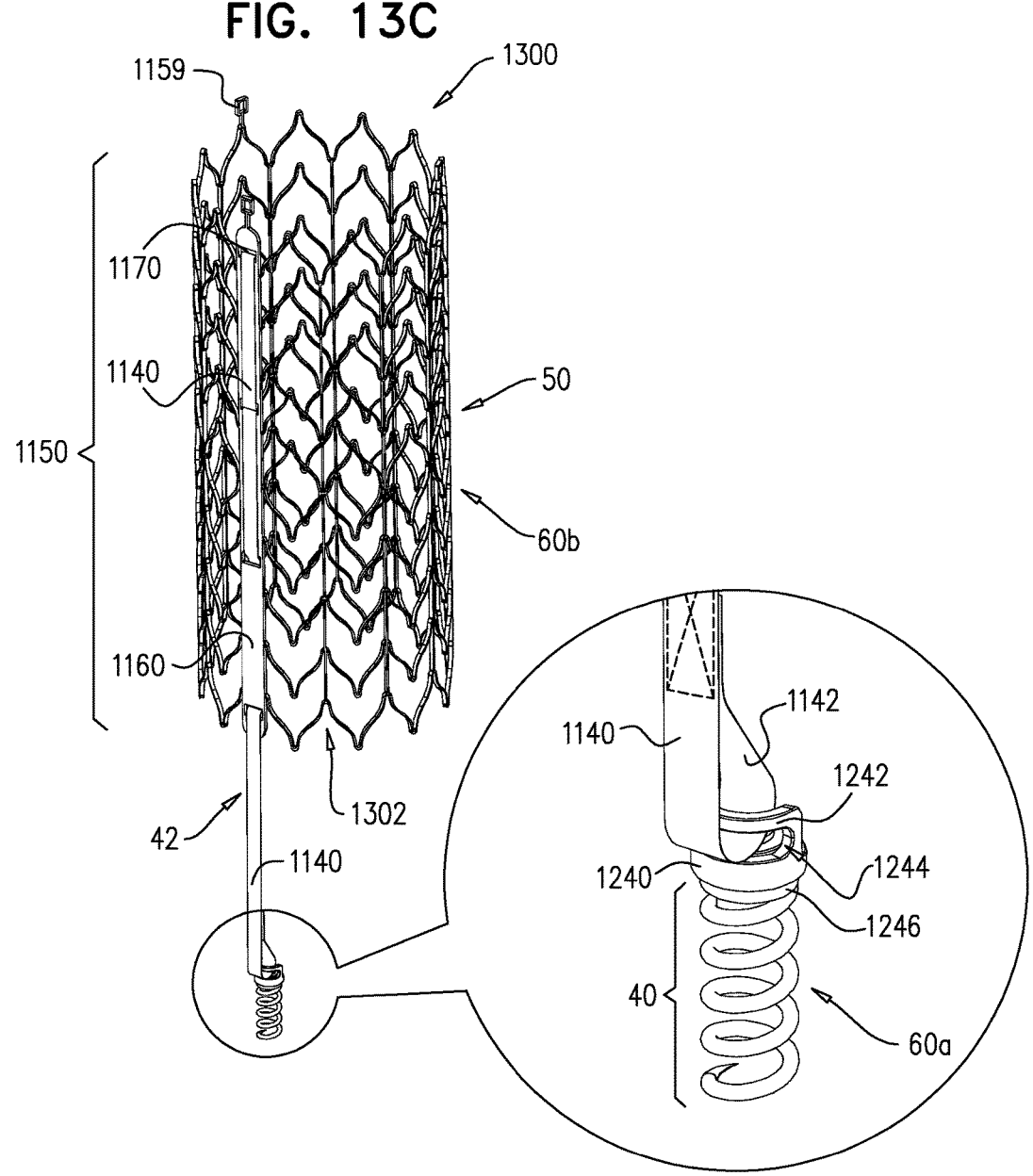

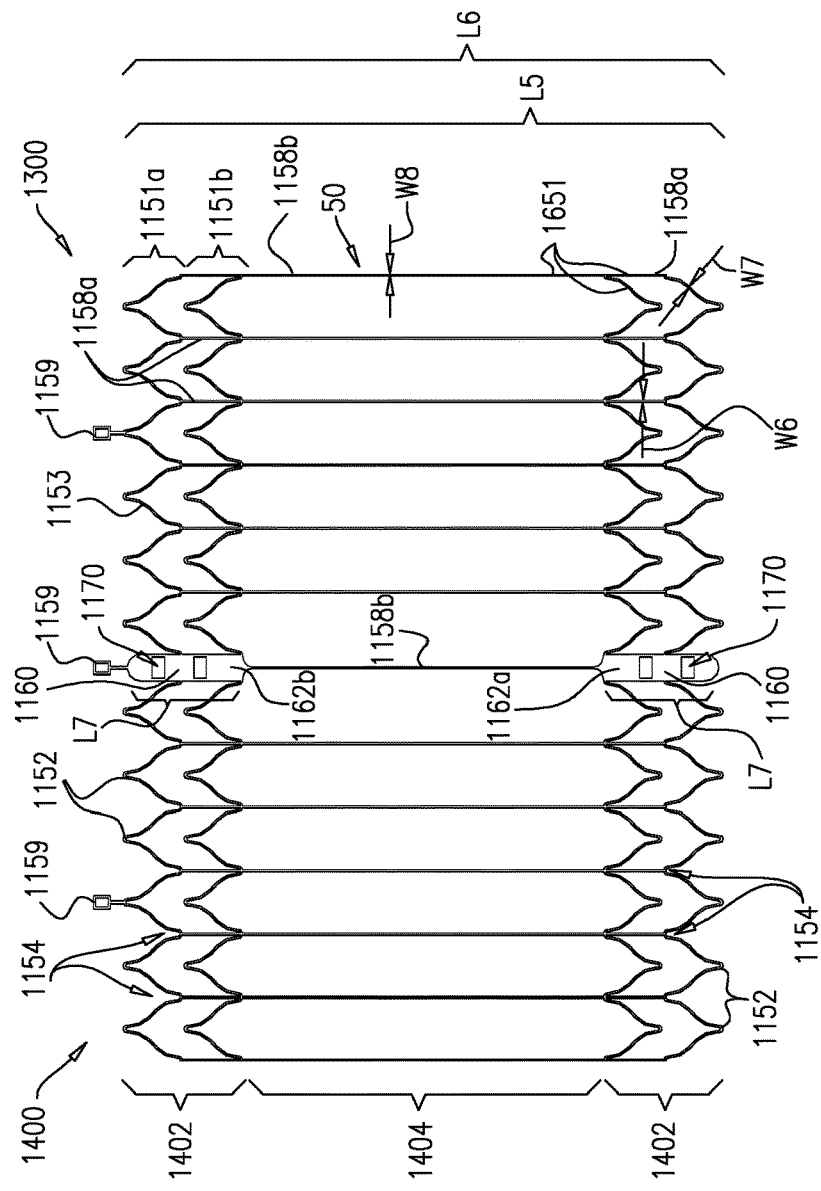
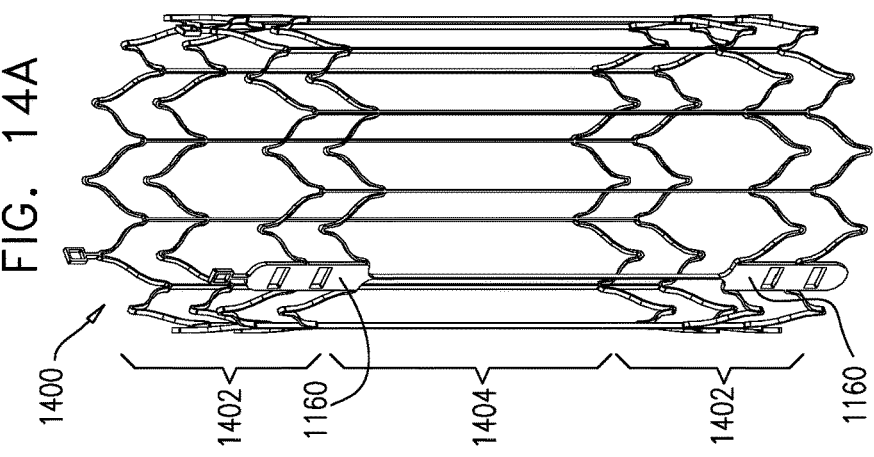
FIG. 14B
FIG. 14A

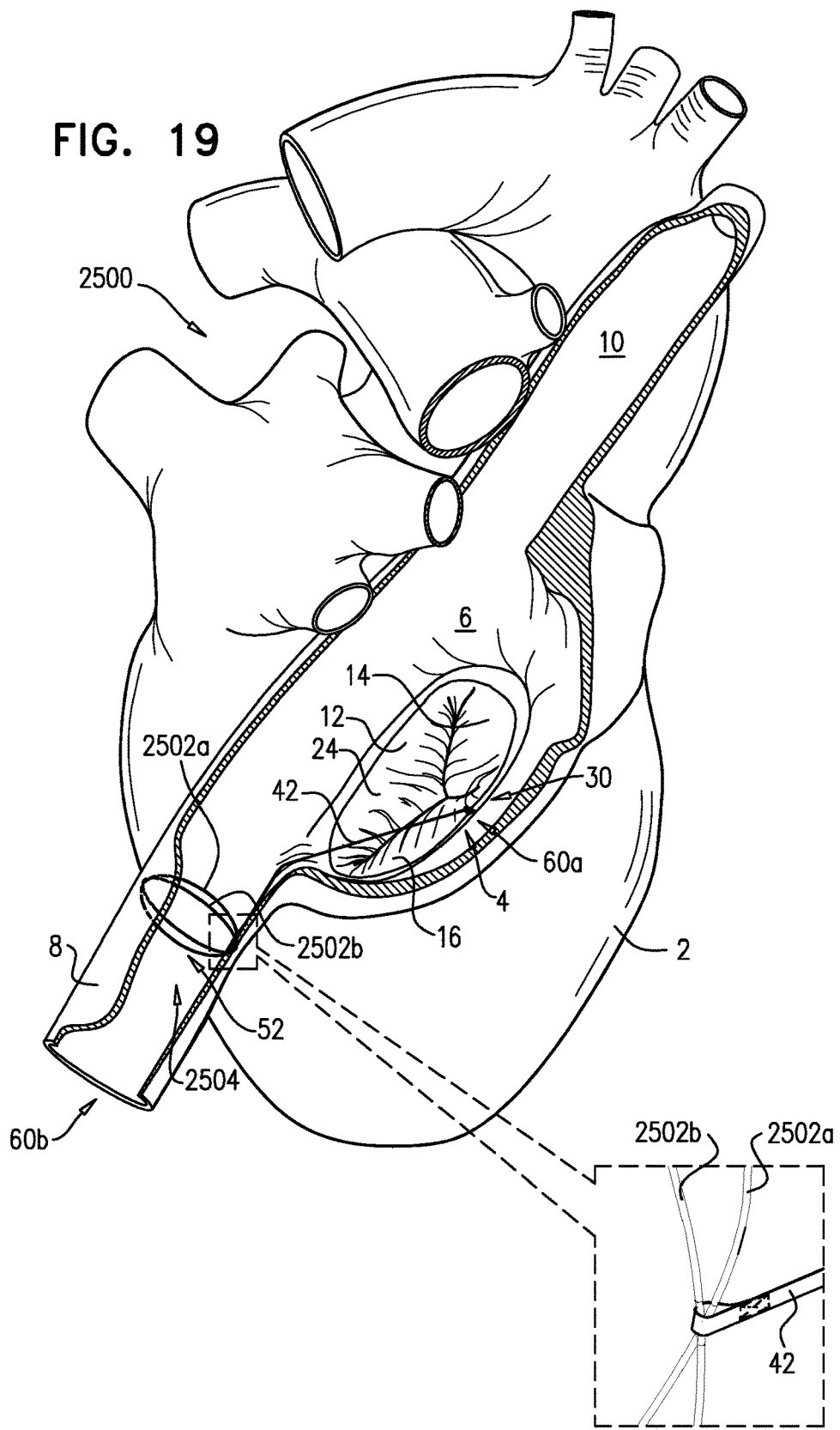

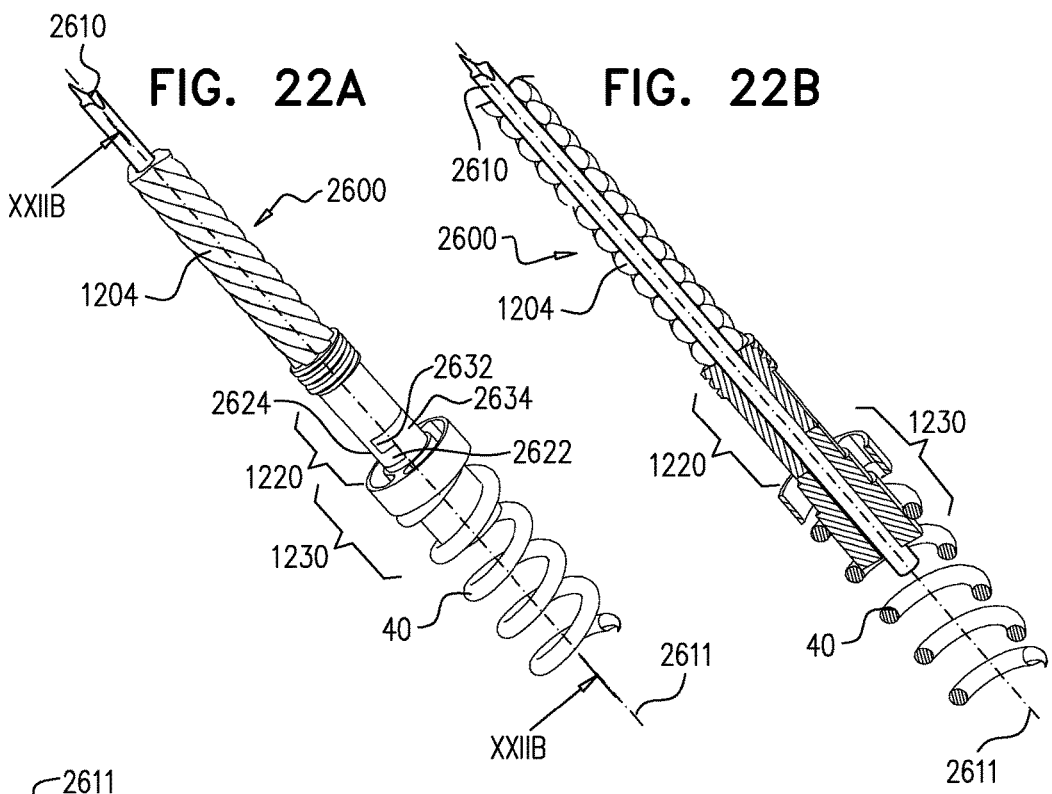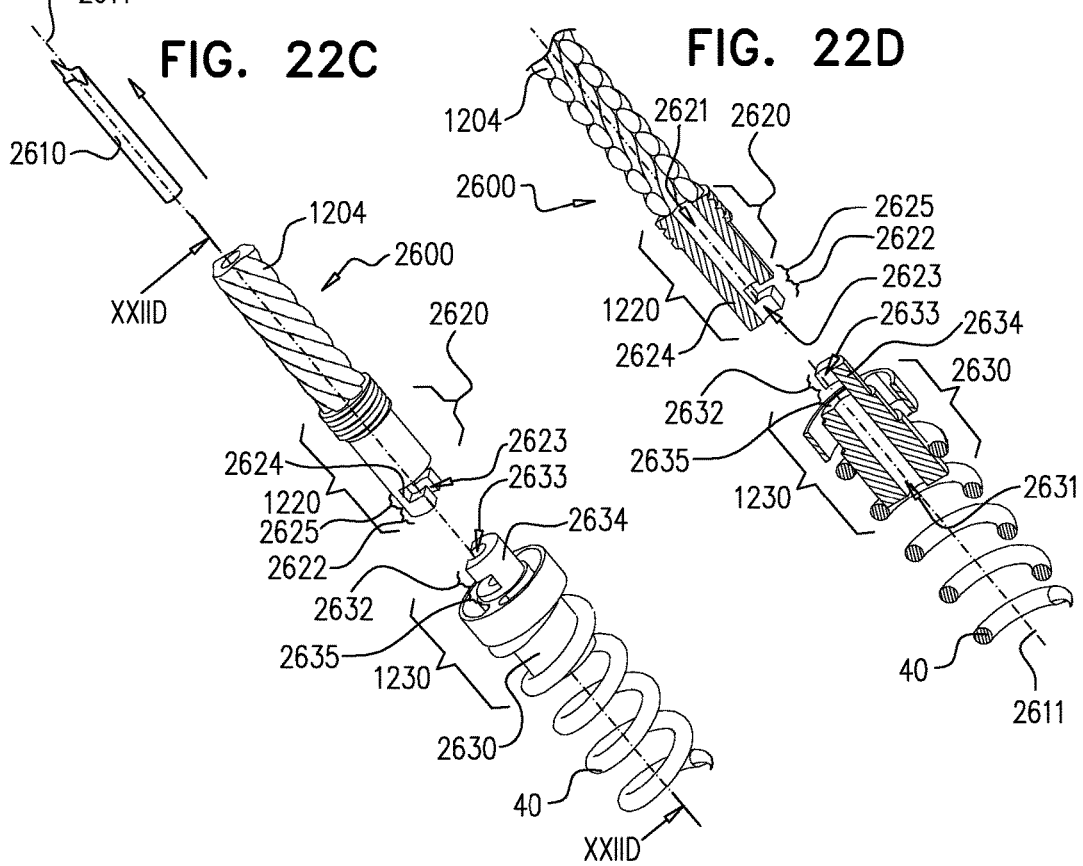

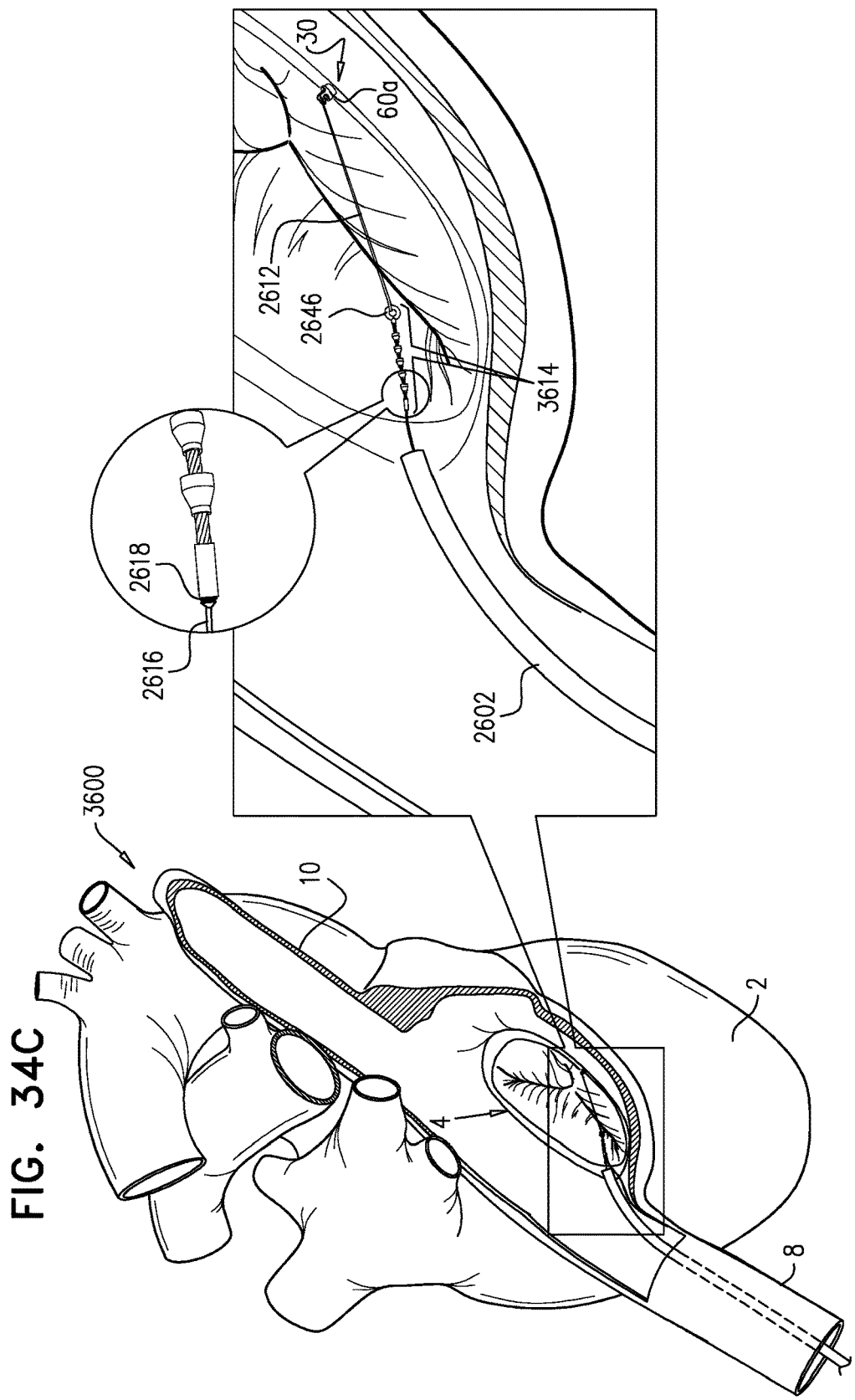

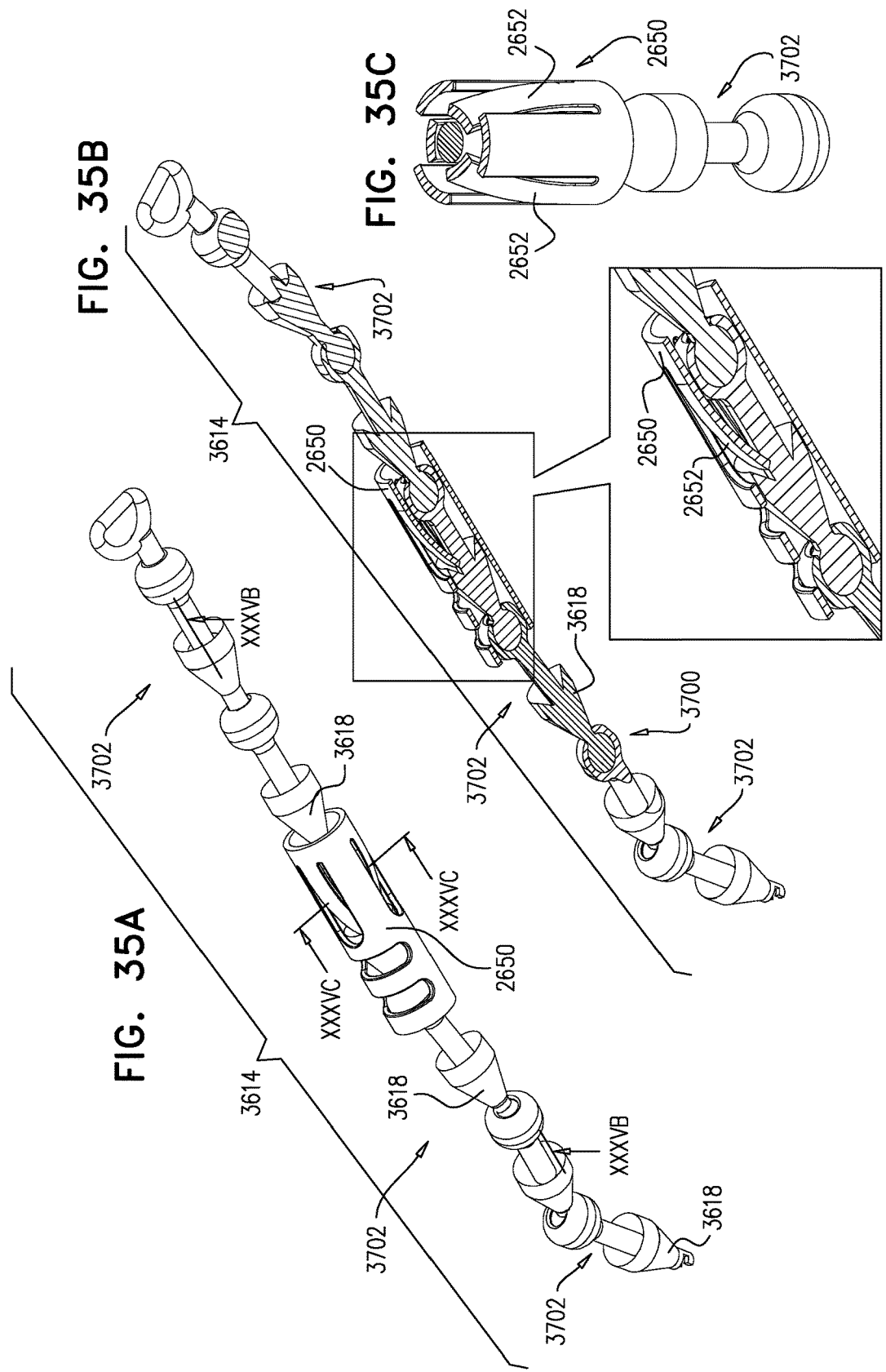

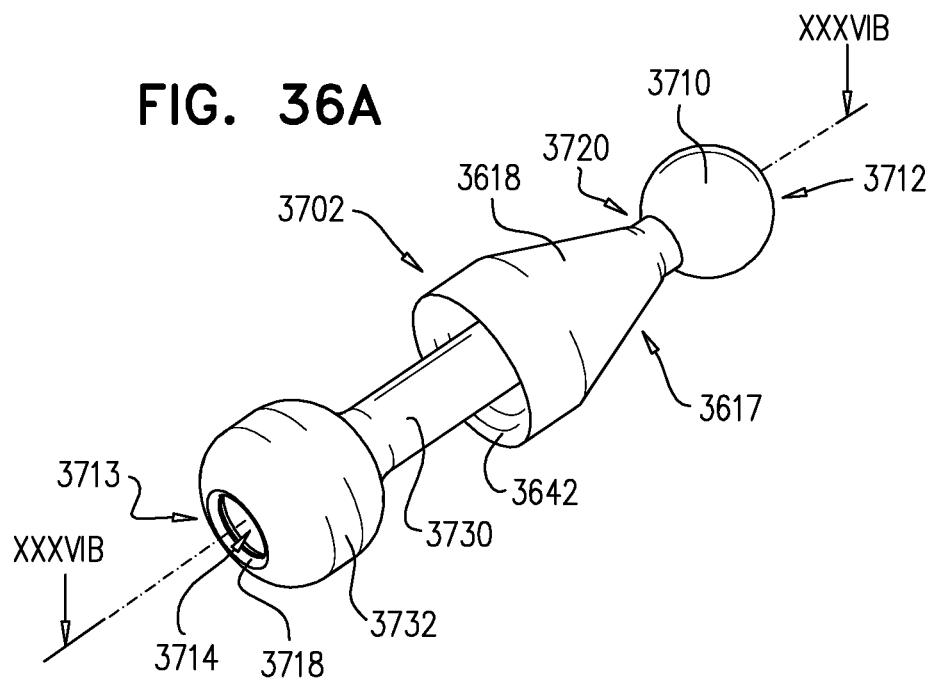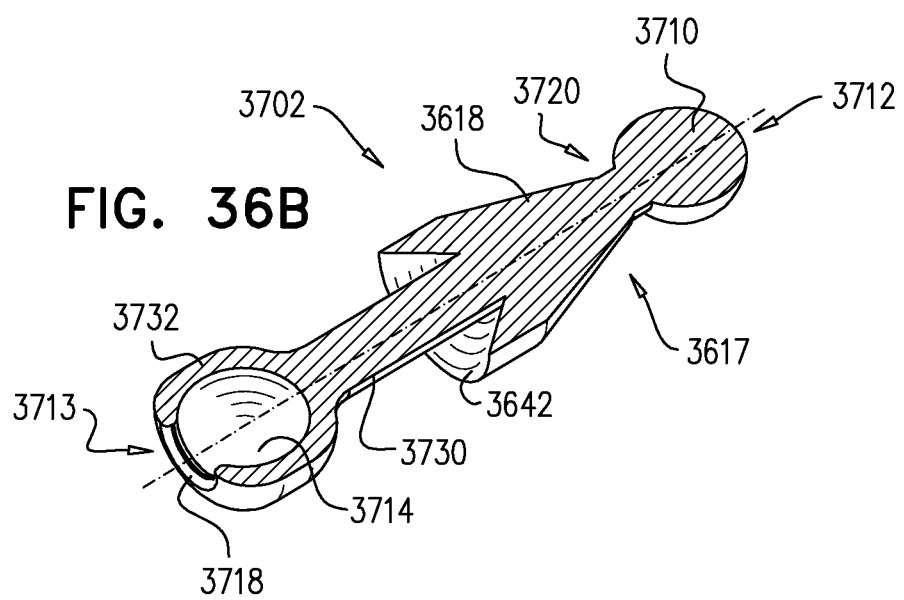

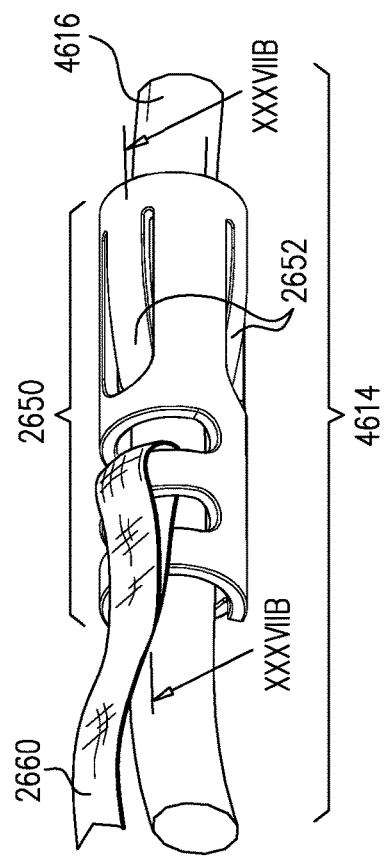
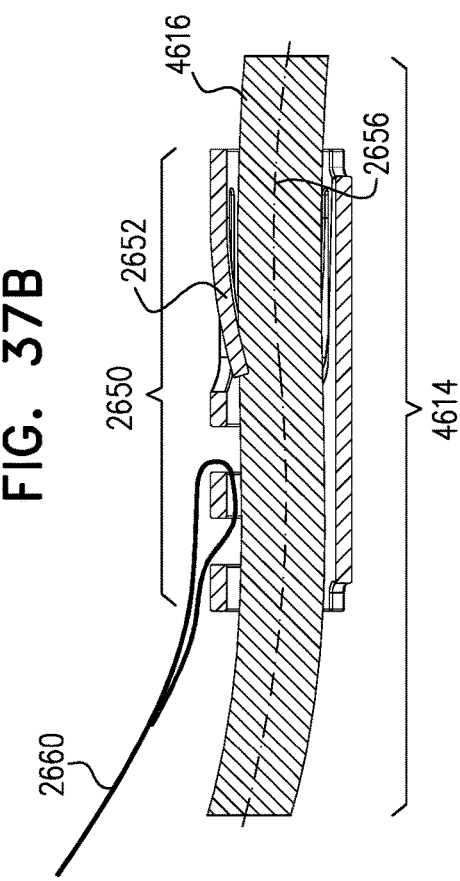

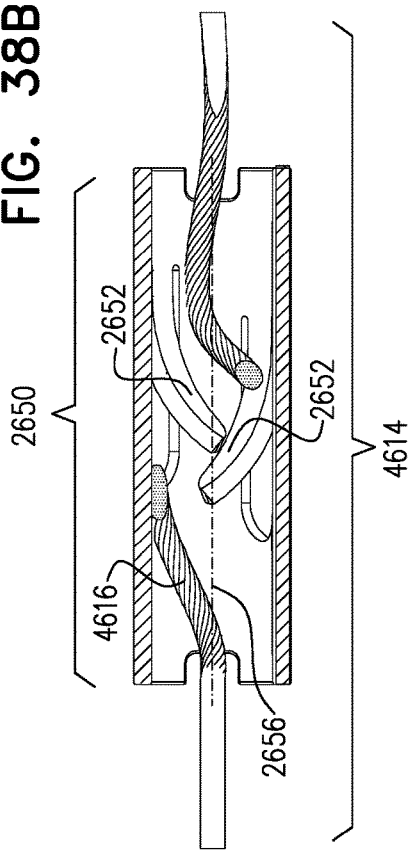
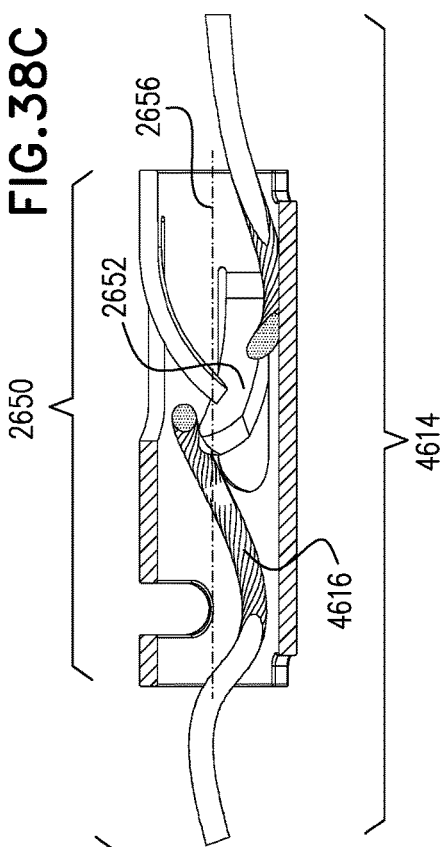
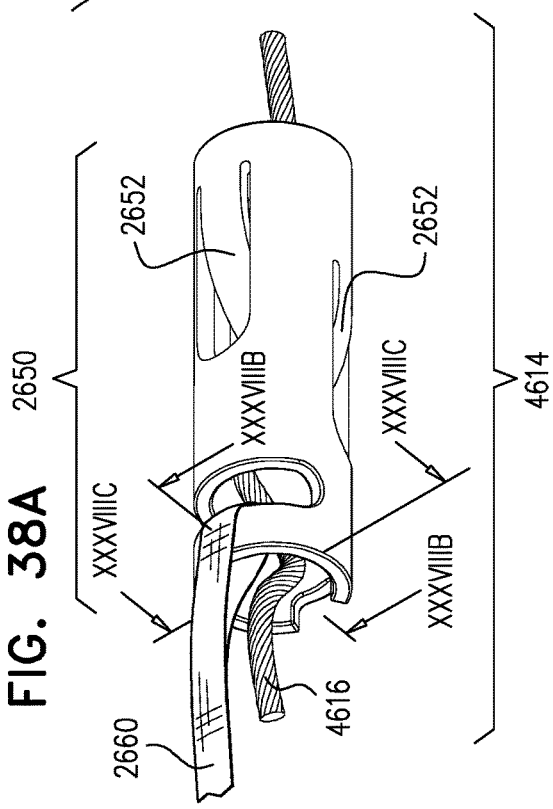
FIG. 38A
FIG. 38B
FIG. 38C

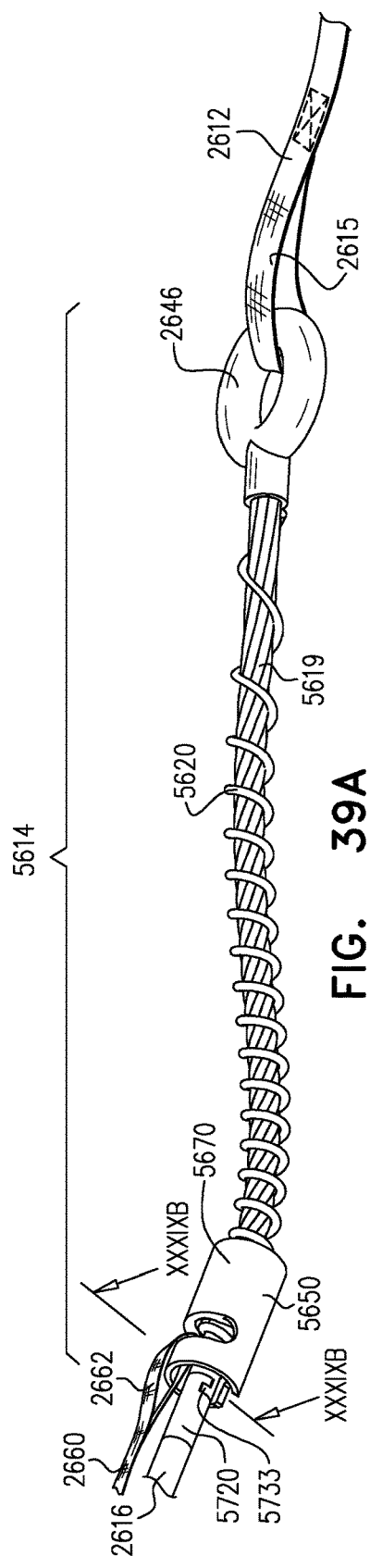
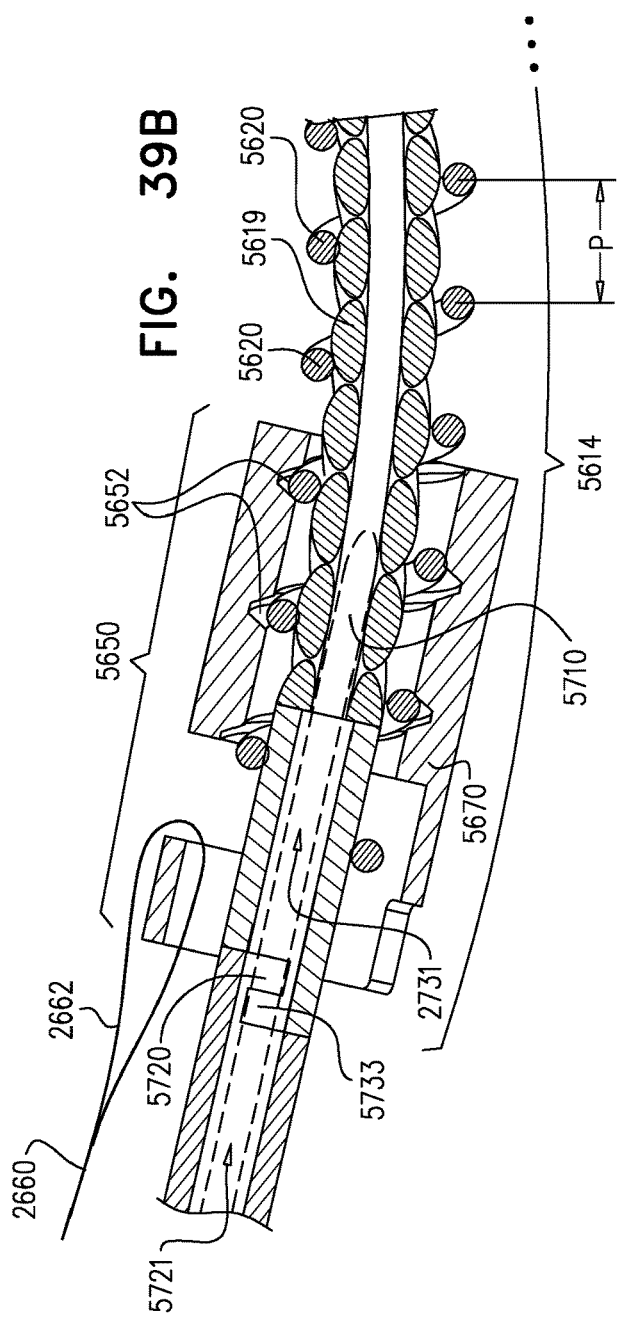
FIG. 39A
FIG. 39B

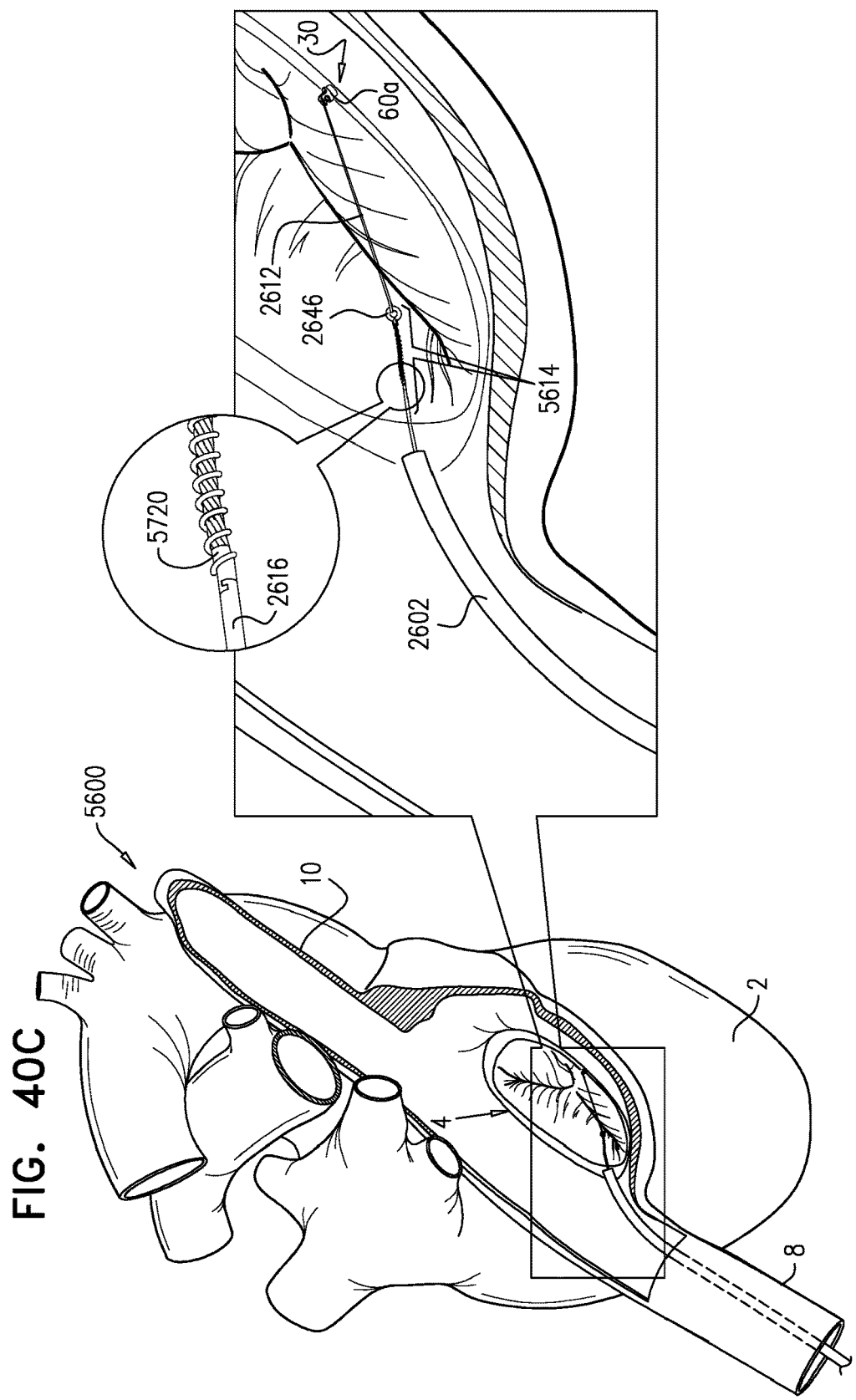

TISSUE ANCHOR AND DELIVERY TOOL

CROSS-REFERENCES TO RELATED APPLICATIONS

The present application is a continuation of U.S. patent application Ser. No. 15/056,417, filed Feb. 29, 2016, now abandoned, which is a continuation of U.S. patent application Ser. No. 14/143,355, filed Dec. 30, 2013, now U.S. Pat. No. 9,307,980, which is a continuation-in-part of U.S. patent application Ser. No. 13/553,081, filed Jul. 19, 2012, now U.S. Pat. No. 9,241,702.

All of the above-mentioned applications are incorporated herein by reference.

FIELD OF THE APPLICATION

Some applications of the present invention relate in general to valve repair. More specifically, some applications of the present invention relate to repair of a tricuspid valve of a patient.

BACKGROUND OF THE APPLICATION

Functional tricuspid regurgitation (FTR) is governed by several pathophysiologic abnormalities such as tricuspid valve annular dilatation, annular shape, pulmonary hypertension, left or right ventricle dysfunction, right ventricle geometry, and leaflet tethering. Treatment options for FTR are primarily surgical. The current prevalence of moderate-to-severe tricuspid regurgitation is estimated to be 1.6 million in the United States. Of these, only 8,000 patients undergo tricuspid valve surgeries annually, most of them in conjunction with left heart valve surgeries.

SUMMARY OF APPLICATIONS

In some applications of the present invention, techniques are provided for percutaneously repairing an atrioventricular valve of a patient using tension. Typically, the techniques facilitate reducing of atrioventricular valve regurgitation by altering the geometry of the atrioventricular valve and/or by altering the geometry of the wall of the right or left atria of the heart of the patient. In some applications of the present invention, a first tissue-engaging element is implanted at a first implantation site in a vicinity of the atrioventricular valve. A second tissue-engaging element is implanted at a second implantation site in a second portion of tissue that is upstream of the atrioventricular valve (e.g., in a blood vessel that empties into an atrium). Each tissue-engaging element is coupled to respective first and second longitudinal members, which are coupled together using first and second longitudinal-member-coupling elements.

In some applications of the present invention, the second tissue-engaging element is implanted after the first and the second longitudinal members are coupled together. For some of these applications, the second longitudinal member, as it is extended by pulling on the second tissue-engaging element, pulls on and applies tension to the first longitudinal member. Responsively, a distance between the leaflets of the atrioventricular valve is adjusted prior to implanting the second tissue-engaging element. Alternatively or additionally, following implantation of both the first and second tissue-engaging elements, the distance between the leaflets of the tricuspid valve is adjusted by pulling the first and the second longitudinal members that connect the first and second tissue-engaging elements or by pulling at least one of the tissue-engaging elements. For some applications, the first and second longitudinal members are coupled at least in part to an adjusting mechanism, and the first and second longitudinal members are pulled or relaxed responsively to actuation of the adjusting mechanism. In some applications, first delivery tool is provided which facilitates implantation of the first tissue-engaging element. A second delivery tool is provided which facilitates coupling of the first and the second longitudinal members together, and, for some applications, also facilitates implantation of the second tissue-engaging element or vice versa.

In some applications of the present invention, the first and the second longitudinal members are coupled together using a ratchet mechanism, which allows percutaneous and remote (through a catheter) insertion, coupling, and linear tensioning of the longitudinal members. The ratchet mechanism comprises a male first longitudinal-member-coupling element and a female second longitudinal-member-coupling element. The two longitudinal-member-coupling elements are typically separately inserted and manipulated in the body, using two separate delivery tools. For these applications, after implanting the second tissue-engaging element, the operator couples the first and the second longitudinal-member-coupling elements together, and then tensions the first and the second longitudinal members by ratcheting the first and the second longitudinal members closer together.

In some applications of the present invention, the male first longitudinal-member-coupling element comprises a flexible chain of interconnected links, which are shaped so as to define respective male couplings. For some applications, each of the male couplings is shaped so as to define a conical feature. For some applications, the female second longitudinal-member-coupling element comprises a hollow cylinder with several internal tabs, biased to flex toward a longitudinal axis of the cylinder. The tabs, which may be considered to function as pawls, allow advancement of male couplings in a single direction (during tensioning), while inhibiting (e.g., preventing) advancement of the male couplings in the opposite direction (i.e., inhibiting relaxing).

For some applications, a flexible longitudinal guide member is removably coupled to a proximal end of the male first longitudinal-member-coupling element. Using the above-mentioned second delivery tool, the operator slides the female second flexible-longitudinal-member-coupling element along the guide member in order to couple the female second flexible-longitudinal-member-coupling element to the male first flexible-longitudinal-member-coupling element. In order to allow such sliding, the female second flexible-longitudinal-member-coupling element is typically shaped so as to define a lumen therethrough, through which the guide member passes. A leading (proximal-most) one of the male couplings may help direct the female second flexible-longitudinal-member-coupling element onto the male first flexible-longitudinal-member-coupling element. The guide member and the second delivery tool thus allow the operator to remotely and percutaneously control the coupling and tensioning of the first and the second flexible-longitudinal-member-coupling elements, including remotely and percutaneously inserting the leading (proximal-most) male coupling into the female hollow cylinder. The guide member is subsequently decoupled from the male first flexible-longitudinal-member-coupling element and removed from the body.

For other applications, the male first flexible-longitudinal-member-coupling element comprises a cable, to which the male couplings are fixed at respective, different longitudinal sites. The cable is flexible, allowing free bending but not twisting. The male couplings may include conical features.

For still other applications, the ratchet mechanism is not mechanically-based, but instead friction-based. The ratchet mechanism comprises the female second longitudinal-member-coupling element, but does not comprise any male couplings. Instead, the first longitudinal-member-coupling element comprises a flexible cable. The female second longitudinal-member-coupling element comprises a hollow cylinder with several internal tabs, biased to flex toward a longitudinal axis of the cylinder. The tabs, which may be considered to function as pawls, apply more friction to the cable in the direction of loosening (relaxing) than in the direction of tightening (tensioning). For some applications, the tabs are arranged in a cascading pattern.

In some applications of the present invention, a threaded mechanism, rather than the ratchet mechanism, is used to couple the first and the second longitudinal members. The threaded mechanism allows percutaneous and remote (through a catheter) insertion, coupling, and both linear tensioning and relaxing of the longitudinal members. The threaded mechanism comprises a male first flexible-longitudinal-member-coupling element and a female second flexible-longitudinal-member-coupling element. The male first flexible-longitudinal-member-coupling element comprises a flexible and substantially non-twistable cable, and a wire that is helically wound around the cable. The female second flexible-longitudinal-member-coupling element part comprises a hollow cylinder shaped so as to define an internal thread shaped and sized so as to correspond with the helically-wound wire, so as to couple together the first and second flexible-longitudinal-member-coupling elements. Rotation of the male first flexible-longitudinal-member-coupling element with respect to the female second flexible-longitudinal-member-coupling element in a first direction tightens the threaded coupling therebetween, thereby tensioning the longitudinal members. Rotation in the opposite direction loosens the coupling, thereby relaxing the longitudinal members.

The techniques described herein for providing an adjustable connection between the first and the second longitudinal members may allow fine-tuning of the tension by the operator, both during and after implantation of both tissue-engaging elements, and even after formation of neointima on the tissue-engaging elements. These techniques also allow separate delivery of the tissue-engaging elements, using two separate delivery tools. Such separate delivery simplifies the procedure for the operator as well as allowing approaches via two or more different blood vessels, such as transfemoral, transjugular, transradial, and/or or transapical approaches, which may provide simpler access to the anchoring point.

In some applications of the present invention, a first tissue-engaging element is implanted in a first portion of tissue that is upstream of the tricuspid valve. A second tissue-engaging element is then implanted in a second portion of tissue that is upstream of the tricuspid valve. For some applications, a distance between the leaflets of the tricuspid valve is adjusted by pulling on and applying tension to the longitudinal member responsively to pulling on the second tissue-engaging element prior to implanting the second tissue-engaging element. Alternatively or additionally, following implantation of both the first and second tissue-engaging elements, the distance between the leaflets of the tricuspid valve is adjusted by pulling a longitudinal member that connects the first and second tissue-engaging elements or by pulling at least one of the tissue-engaging elements. For some applications, the longitudinal member is coupled at least in part to an adjusting mechanism, and the longitudinal member is pulled or relaxed responsively to actuation of the adjusting mechanism. In some applications, a delivery tool is provided which facilitates implantation of the first and second tissue-engaging elements.

For some applications, techniques described herein are used to repair the tricuspid valve. It is to be noted, however, that the scope of the present invention includes use of techniques described herein to repair the mitral valve of the patient, mutatis mutandis.

In some applications of the present invention, techniques are provided to achieve bicuspidization of the tricuspid valve. For such applications, the anterior leaflet and the septal leaflet are typically drawn together to enhance coaptation.

For some applications, the first tissue-engaging element comprises a tissue anchor (e.g., a helical tissue anchor) which is implanted in a portion of tissue surrounding an annulus of the tricuspid valve (e.g., an anterior-posterior commissure). Typically, the second tissue-engaging element comprises a stent which is expanded in a portion of a blood vessel of a patient, e.g., the superior vena cava, the inferior vena cava, coronary sinus, or a hepatic vein, e.g., the left hepatic vein, the right hepatic vein, or the middle hepatic vein. During the adjusting of the distance between the first and second tissue-engaging elements, the operator monitors a parameter indicative of regurgitation of the tricuspid valve. Responsively to the pulling of the longitudinal element(s), the geometry of the right atrium is altered, thereby drawing together the leaflets of the tricuspid valve.

For some applications of the present invention, the first tissue-engaging element comprises a second stent which is expanded in a portion of a second blood vessel of the patient, e.g., the superior vena cava, the inferior vena cava, the coronary sinus, or a hepatic vein, e.g., the left hepatic vein, the right hepatic vein, and the middle hepatic vein.

For some applications, a plurality of second tissue-engaging elements are provided (such as two or three), which are implanted in respective portions of cardiac tissue in a vicinity of the heart valve. For some applications, a longitudinal member is (a) directly coupled to the first tissue-engaging element, (b) directly coupled to one of the second tissue-engaging elements, and (c) indirectly coupled to two others of the second tissue-engaging elements by a longitudinal sub-member.

For still other applications of the present invention, both the first and second tissue-engaging elements comprise respective first and second tissue anchors. Each tissue anchor punctures a respective portion of cardiac tissue of the patient and is implanted at least in part in the respective portion of cardiac tissue. The tensioning element couples the first and second tissue anchors and is adjusted following implantation of the first and second tissue anchors by pulling or relaxing the tensioning element.

For some applications of the present invention, a torque-delivering tool is provided for rotating a tissue anchor, so as to drive the anchor into tissue. The torque-delivering tool comprises a torque-delivering cable, a distal end of which comprises a first coupling that is configured to removably engage a second coupling coupled to the anchor in a controlled manner, such that rotation of the torque-delivering cable rotates the anchor. For some applications, the apparatus further comprises an anti-entanglement device which prevents entanglement of the flexible longitudinal member during rotation of the anchor.

For some applications, the stents described hereinabove comprise a plurality of interconnected superelastic metallic struts. For some applications, the stents described herein comprise a force-distributing element providing means to connect the stent to the flexible member and distribute tension applied from the flexible member to the stent along a longitudinal length of the stent.

There is therefore provided, in accordance with an application of the present invention, apparatus including:

first and second tissue-engaging elements:

first and second flexible longitudinal members, coupled at respective first end portions thereof to the first and the second tissue-engaging elements, respectively:

a first flexible-longitudinal-member-coupling element coupled to a second end portion of the first flexible longitudinal member, wherein the first and the second end portions of the first flexible longitudinal member are disposed at opposite longitudinal ends of the first flexible longitudinal member;

a second flexible-longitudinal-member-coupling element coupled to a second end portion of the second flexible longitudinal member, wherein the first and the second end portions of the second flexible longitudinal member are disposed at opposite longitudinal ends of the second flexible longitudinal member; and a flexible longitudinal guide member reversibly coupled to the first flexible-longitudinal-member-coupling element, wherein the first and second flexible-longitudinal-member-coupling elements are configured to be couplable together to couple together the first and the second flexible longitudinal elements.

For some applications, the first tissue-engaging element includes a helical tissue anchor. For some applications, the apparatus further includes a torque-delivering tool configured to screw the helical tissue anchor into tissue of a patient.

For some applications, the second tissue-engaging element includes a radially-expandable stent configured to be implanted in a blood vessel selected from the group consisting of: an inferior vena cava, a superior vena cava, and a coronary sinus.

For some applications, the first tissue-engaging element includes a helical tissue anchor, and the second tissue-engaging element includes a radially-expandable stent configured to be implanted in a blood vessel selected from the group consisting of: an inferior vena cava, a superior vena cava, and a coronary sinus.

For some applications, the second flexible-longitudinal-member-coupling element is shaped so as to define a lumen therethrough, and is configured to slide along the flexible longitudinal guide member when the flexible longitudinal guide member passes through the lumen.

For some applications, the second flexible-longitudinal-member-coupling element is shaped so as to define a coupling interface that is not coaxial with the second flexible-longitudinal-member-coupling element, and the second flexible longitudinal member is fixed to the coupling interface.

For some applications, a proximal end of the first flexible-longitudinal-member-coupling element is shaped so as to define a threaded coupling, and the flexible longitudinal guide member is shaped so as to define a screw that is reversibly coupled to the threaded coupling.

For some applications, the flexible longitudinal guide member is reversibly coupled to the first flexible-longitudinal-member-coupling element by being looped through a portion of the first flexible-longitudinal-member-coupling element.

For some applications, the apparatus further includes a snare couplable to the flexible longitudinal guide member so as to facilitate extraction of a portion of the flexible longitudinal guide member to outside a body of a patient.

For any of the applications described above, the apparatus may further include:

a first delivery tool, which (a) includes a first catheter tube, and (b) is configured to deliver the first tissue-engaging element, the first flexible longitudinal member, the first flexible-longitudinal-member-coupling element, and the flexible longitudinal guide member; and a second delivery tool, which (a) includes a second catheter tube, and (b) is configured to deliver the second flexible longitudinal member and the second flexible-longitudinal-member-coupling element, and to couple the second flexible-longitudinal-member-coupling element to the first flexible-longitudinal-member-coupling element.

For some applications, the second delivery tool is configured to deliver the second flexible longitudinal member and the second flexible-longitudinal-member-coupling element after deployment of the second tissue-engaging element.

For some applications, the second tissue-engaging element includes a radially-expandable stent configured to be implanted in a blood vessel selected from the group consisting of: an inferior vena cava, and a superior vena cava; and the second delivery tool is configured and sized to pass through the stent when the stent is in a radially-expanded state.

For some applications, the second delivery tool further includes an advancement tube, which is advanceable through a lumen of the second catheter tube, and is configured to couple the second flexible-longitudinal-member-coupling element to the first flexible-longitudinal-member-coupling element.

For any of the applications described above:

the first flexible-longitudinal-member-coupling element may include a plurality of male couplings, disposed along the first flexible-longitudinal-member-coupling element at respective, different longitudinal sites, and the second flexible-longitudinal-member-coupling element may include a female coupling configured to receive the male couplings, allow advancement of the male couplings through the female coupling in a first direction, and restrict advancement of the male couplings through the female coupling in a second direction opposite the first direction.

For some applications, the male couplings have respective conical features.

For some applications:

the female coupling (a) includes a hollow cylinder configured to receive the male couplings, and (b) is shaped so as to define one or more tabs biased to flex toward a central longitudinal axis of the cylinder, the male couplings are shaped so as to define respective protrusions, and the protrusions and the one or more tabs are shaped and sized to allow the advancement of the first flexible-longitudinal-member-coupling element through the hollow cylinder in the first direction, and to restrict the advancement of the first flexible-longitudinal-member-coupling element in the second direction.

For some applications, each of the male couplings is shaped so as to define one or more internal ridges, which are configured to engage the one or more tabs when the tabs enter one of the male couplings.

For some applications, the first flexible-longitudinal-member-coupling element includes a flexible chain of interconnected links, which are shaped so as to define the male couplings, respectively. For some applications, the male couplings have respective conical features. For some applications, the links are shaped so as to define respective spherical heads and spherical receptacles, which are shaped and sized so as to couplingly receive the spherical head of an adjacent one of the links.

For some applications, the first flexible-longitudinal-member-coupling element includes a flexible cable to which the male couplings are fixed at the respective, different longitudinal sites. For some applications, the male couplings have respective conical features. For some applications, the flexible cable is substantially not twistable.

For some applications, the protrusions are shaped so as to define respective edges, and the one or more tabs are configured to flex toward the longitudinal axis after the advancement of the edges of the male couplings beyond the one or more edges, so as to restrict advancement of the male couplings with respect to the one or more tabs in the second direction.

For any of the applications described above,
the first flexible-longitudinal-member-coupling element may include:
a cable, which is configured to be flexible and substantially not twistable; and
a wire, which is helically wound around and fixed to the cable, and
the second flexible-longitudinal-member-coupling element may include a female coupling, which (a) includes a hollow cylinder configured to receive the flexible-longitudinal-member-coupling element, and (b) is shaped so as to define an internal thread shaped and sized so as to correspond with the helically-wound wire.

For some applications, the wire is helically wound around the cable at an average pitch equal to between one and four times a diameter of the cable. Alternatively or additionally, for some applications, the wire is welded to the cable.

For any of the applications described above,
the first flexible-longitudinal-member-coupling element may include a flexible cable,
the second flexible-longitudinal-member-coupling element may include a female coupling, which (a) includes a hollow cylinder configured to receive the cable, and (b) is shaped so as to define one or more tabs biased to flex toward a central longitudinal axis of the cylinder, and
the cable and the one or more tabs may be shaped and sized to allow advancement of the first flexible-longitudinal-member-coupling element through the hollow cylinder in a first direction, and to restrict, by friction, advancement of the first flexible-longitudinal-member-coupling element in a second direction opposite the first direction.

For some applications, the male coupling is shaped so as to define one or more internal ridges, which are configured to engage the one or more tabs when the tabs enter the male coupling.

For any of the applications described above, the first flexible-longitudinal-member-coupling element includes a male coupling, and the second flexible-longitudinal-member-coupling element includes a female coupling configured to receive the male coupling.

For some applications:
the female coupling (a) includes a hollow cylinder configured to receive the male coupling, (b) is shaped so as to define one or more tabs biased to flex toward a central longitudinal axis of the cylinder,
the male coupling is shaped so as to provide one or more protrusions, and
the male coupling and the one or more tabs are sized and shaped to (a) allow advancement of the male coupling with respect to the one or more tabs in a first direction, by pushing the one or more tabs away from the longitudinal axis, and (b) restrict advancement of the male coupling with respect to the one or more tabs in a second direction opposite the first direction.

For some applications, the one or more protrusions are shaped so as to define a shelf, and the one or more tabs are configured to flex toward the longitudinal axis after the advancement of the shelf of the male coupling beyond the one or more tabs, so as to restrict advancement of the male coupling with respect to the one or more tabs in the second direction.

For some applications:
the female coupling includes a structural element including one or more walls shaped so as to define an opening,
the male coupling includes one or more radially-displaceable arms, and
the one or more radially-displaceable arms are:
compressible by the walls during advancement of the one or more radially-displaceable arms through the opening, and
following advancement of the one or more radially-displaceable arms through opening, expandable to a first dimension that is larger than a second dimension of the opening so as to lock the male coupling to the female coupling.

For some applications:
the female coupling includes a structural element including one or more walls shaped so as to define an opening,
the male coupling includes one or more radially-displaceable arms, and
the one or more radially-displaceable arms are:
compressible by the walls during advancement of the one or more radially-displaceable arms through the opening, and
following advancement of the one or more radially-displaceable arms through opening, expandable to a position in which at least a portion of an outer surface of the one or more arms is beyond and above the one or more walls.

For some applications:
the female coupling includes a structural element including one or more walls shaped so as to define one or more shelves,
the male coupling includes one or more radially-displaceable legs, and
the one or more radially-displaceable legs are:
compressible by the walls during advancement of the one or more radially-displaceable legs along the one or more shelves, and
following the advancement of the one or more radially-displaceable legs beyond the one or more shelves in a first advancement direction, expandable to lock the male coupling to the female coupling, and
following expanding of the one or more radially-displaceable legs, the one or more shelves of the female coupling restrict advancement of the one or more radially-displaceable legs in a second advancement direction opposite the first advancement direction.

For some applications, the one or more walls of the female coupling element are shaped so as to define at least one groove, and the male coupling element is shaped so as to define at least one protrusion shaped so as to fit within the at least one groove.

For some applications, the female coupling includes a structural element shaped so as to define a curved groove, and the male coupling includes a projection advanceable within the curved groove so as to lock the male coupling to the female coupling.

There is further provided, in accordance with an application of the present invention, apparatus including:

first and second tissue-engaging elements:

first and second flexible longitudinal members, coupled at respective first end portions thereof to the first and the second tissue-engaging elements, respectively:

a first flexible-longitudinal-member-coupling element, which (a) is coupled to a second end portion of the first flexible longitudinal member, and (b) includes (i) a cable, which is configured to be flexible and substantially not twistable; and (ii) a wire, which is helically wound around and fixed to the cable, wherein the first and the second end portions of the first flexible longitudinal member are disposed at opposite longitudinal ends of the first flexible longitudinal member;

a second flexible-longitudinal-member-coupling element, which (a) is coupled to a second end portion of the second flexible longitudinal member, and (b) includes a female coupling, which (i) includes a hollow cylinder configured to receive the first flexible-longitudinal-member-coupling element, and (ii) is shaped so as to define an internal thread shaped and sized so as to correspond with the helically-wound wire, so as to couple together the first and the second flexible-longitudinal-member-coupling elements, wherein the first and the second end portions of the second flexible longitudinal member are disposed at opposite longitudinal ends of the second flexible longitudinal member; and a flexible longitudinal guide member reversibly coupled to the first flexible-longitudinal-member-coupling element.

For some applications, the wire is helically wound around the cable at an average pitch equal to between one and four times a diameter of the cable. Alternatively or additionally, for some applications, the wire is welded to the cable.

For some applications, the hollow cylinder of the female coupling is shaped so as to define a lumen therethrough, and is configured to slide along the flexible longitudinal guide member when the flexible longitudinal guide member passes through the lumen.

For some applications, the second flexible-longitudinal-member-coupling element is shaped so as to define a coupling interface that is not coaxial with the second flexible-longitudinal-member-coupling element, and the second flexible longitudinal member is fixed to the coupling interface.

For any of the applications described above, the apparatus may further include:

a first delivery tool, which includes a first catheter tube, and which is configured to deliver the first tissue-engaging element, the first flexible longitudinal member, the first flexible-longitudinal-member-coupling element, and the flexible longitudinal guide member; and a second delivery tool, which includes a second catheter tube, and which is configured to deliver the second flexible longitudinal member and the second flexible-longitudinal-member-coupling element, and to couple the second flexible-longitudinal-member-coupling element to the first flexible-longitudinal-member-coupling element.

For some applications, the second delivery tool is configured to deliver the second flexible longitudinal member and the second flexible-longitudinal-member-coupling element after deployment of the second tissue-engaging element.

For some applications, the second tissue-engaging element includes a radially-expandable stent configured to be implanted in a blood vessel selected from the group consisting of: an inferior vena cava, and a superior vena cava; and the second delivery tool is configured and sized to pass through the stent when the stent is in a radially-expanded state.

For some applications, the second delivery tool further includes a rotation-stabilization tube, which is advanceable over the flexible longitudinal guide member and through a lumen of the second catheter tube, and is configured to reversibly engage and rotationally lock with the second flexible-longitudinal-member-coupling element.

There is still further provided, in accordance with an application of the present invention, a method including:

implanting, in tissue of an atrium of a patient, a first tissue-engaging element, to which a first end portion of a first flexible longitudinal member is coupled, while a flexible longitudinal guide member is reversibly coupled to a first flexible-longitudinal-member-coupling element that is coupled to a second end portion of the first flexible longitudinal element, wherein the first and the second end portions of the first flexible longitudinal member are disposed at opposite longitudinal ends of the first flexible longitudinal member;

advancing, over the flexible longitudinal guide member, toward the atrium, a second flexible-longitudinal-member-coupling element coupled to a second end portion of a second flexible longitudinal member, wherein a second tissue-engaging element is coupled to a first end portion of the second flexible longitudinal member, and the first and the second end portions of the second flexible longitudinal member are disposed at opposite longitudinal ends of the second flexible longitudinal member;

coupling together the first and the second flexible-longitudinal-member-coupling elements; and implanting the second tissue-engaging element upstream of the atrium.

For some applications, coupling together the first and the second flexible-longitudinal-member-coupling elements includes performing one or both of the group of actions consisting of: pulling the flexible longitudinal guide member, and pushing the second flexible-longitudinal-member-coupling element.

For some applications, implanting the first tissue-engaging element includes implanting the first tissue-engaging element in tissue selected from the group consisting of: tissue of an annulus of an atrioventricular valve, and tissue of a wall of the atrium adjacent the atrioventricular valve. For some applications, the first tissue-engaging element includes a helical tissue anchor, and implanting the first tissue-engaging element includes implanting the helical tissue anchor in the tissue of the atrium. For some applications, implanting the helical tissue anchor includes screwing the helical tissue anchor into the tissue of the atrium using a torque-delivering tool.

For some applications, the second tissue-engaging element includes a radially-expandable stent, and implanting the second tissue-engaging element including expanding the radially-expandable in a blood vessel of the patient selected from the group consisting of: an inferior vena cava, and a superior vena cava.

For some applications:

the first tissue-engaging element includes a helical tissue anchor, and the second tissue-engaging element includes a radially-expandable stent, implanting the first tissue-engaging element includes implanting the helical tissue anchor in tissue selected from the group consisting of: tissue of an annulus of an atrioventricular valve, and tissue of a wall of the atrium adjacent the atrioventricular valve, and implanting the second tissue-engaging element including expanding the radially-expandable in a blood vessel of the patient selected from the group consisting of: an inferior vena cava, a superior vena cava, and a coronary sinus.

For some applications, the method further includes facilitating repair of an atrioventricular valve of the patient by applying tension to the second flexible longitudinal member. For some applications, facilitating repair includes remodeling the atrioventricular valve by drawing together leaflets of the valve by applying tension to the second flexible longitudinal member.

For some applications, the method further includes decoupling the flexible longitudinal guide member from the first flexible-longitudinal-member-coupling element, after coupling together the first and the second flexible-longitudinal-member-coupling elements. For some applications:

a proximal end of the first flexible-longitudinal-member-coupling element is shaped so as to define a threaded coupling, the flexible longitudinal guide member is shaped so as to define a screw that is reversibly coupled to the threaded coupling, and decoupling includes unscrewing the flexible longitudinal guide member from the first flexible-longitudinal-member-coupling element.

For some applications, the flexible longitudinal guide member is reversibly coupled to the first flexible-longitudinal-member-coupling element by being looped through a portion of the first flexible-longitudinal-member-coupling element, and decoupling includes releasing a first end of the flexible longitudinal guide member, and unlooping the flexible longitudinal guide member from the first flexible-longitudinal-member-coupling element by pulling a second end of the flexible longitudinal guide member.

For some applications, implanting the second tissue-engaging element includes implanting the second tissue-engaging element after coupling together the first and the second flexible-longitudinal-member-coupling elements.

For some applications, implanting the second tissue-engaging element includes implanting the second tissue-engaging element before coupling together the first and the second flexible-longitudinal-member-coupling elements.

For some applications:

the first flexible-longitudinal-member-coupling element includes a plurality of male couplings, disposed along the first flexible-longitudinal-member-coupling element at respective, different longitudinal sites, the second flexible-longitudinal-member-coupling element includes a female coupling configured to receive the male couplings, allow advancement of the male couplings through the female coupling in a first direction, and restrict advancement of the male couplings through the female coupling in a second direction opposite the first direction, and coupling together the first and the second flexible-longitudinal-member-coupling elements includes tensioning the first and the second flexible longitudinal members by pulling one or more of the male couplings into the female coupling, by performing one or both of the group of actions consisting of: pulling the flexible longitudinal guide member, and pushing the second flexible-longitudinal-member-coupling element.

For some applications, the male couplings have respective conical features.

For some applications:

the female coupling (a) includes a hollow cylinder configured to receive the male couplings, and (b) is shaped so as to define one or more tabs biased to flex toward a central longitudinal axis of the cylinder, the male couplings are shaped so as to define respective protrusions, the protrusions and the one or more tabs are shaped and sized to allow the advancement of the first flexible-longitudinal-member-coupling element through the cylinder in the first direction, and to restrict the advancement of the first flexible-longitudinal-member-coupling element in the second direction, and coupling together the first and the second flexible-longitudinal-member-coupling elements includes tensioning the first and the second flexible longitudinal members by pulling one or more of the protrusions through the hollow cylinder, by performing one or both of the group of actions consisting of: pulling the flexible longitudinal guide member, and pushing the second flexible-longitudinal-member-coupling element.

For some applications, each of the male couplings is shaped so as to define one or more internal ridges, which are configured to engage the one or more tabs when the tabs enter one of the male couplings.

For some applications, the first flexible-longitudinal-member-coupling element includes a flexible chain of interconnected links, which are shaped so as to define the male couplings, respectively. For some applications, the male couplings have respective conical features. For some applications, the links are shaped so as to define respective spherical heads and spherical receptacles, which are shaped and sized so as to couplingly receive the spherical head of an adjacent one of the links.

For some applications, the first flexible-longitudinal-member-coupling element includes a flexible cable to which the male couplings are fixed at the respective, different longitudinal sites. For some applications, the male couplings have respective conical features. For some applications, the flexible cable is substantially not twistable.

For some applications:

the first flexible-longitudinal-member-coupling element includes (a) a cable, which is configured to be flexible and substantially not twistable; and (b) a wire, which is helically wound around and fixed to the cable, the second flexible-longitudinal-member-coupling element includes a female coupling, which (a) includes a cylinder configured to receive the flexible-longitudinal-member-coupling element, and (b) is shaped so as to define an internal thread shaped and sized so as to correspond with the helically-wound wire, and coupling together the first and the second flexible-longitudinal-member-coupling elements includes tensioning the first and the second flexible longitudinal members by rotating the cable with respect to the female coupling.

For some applications, the wire is helically wound around the cable at an average pitch equal to between one and four times a diameter of the cable.

For some applications, rotating the cable with respect to the female coupling includes rotating the flexible longitudinal guide member. For some applications, rotating the cable with respect to the female coupling includes: advancing a rotation-stabilization tube over the flexible longitudinal guide member; reversibly engaging and rotationally locking the rotation-stabilization tube with the second flexible-longitudinal-member-coupling element; and while holding the rotation-stabilization tube rotationally stationary, rotating the flexible longitudinal guide member.

For some applications:

the first flexible-longitudinal-member-coupling element includes a flexible cable, the second flexible-longitudinal-member-coupling element includes a female coupling, which (a) includes a cylinder configured to receive the cable, and (b) is shaped so as to define one or more tabs biased to flex toward a central longitudinal axis of the cylinder, the cable and the one or more tabs are shaped and sized to allow advancement of the first flexible-longitudinal-member-coupling element through the cylinder in a first direction, and to restrict, by friction, advancement of the first flexible-longitudinal-member-coupling element in a second direction opposite the first direction, and coupling together the first and the second flexible-longitudinal-member-coupling elements includes tensioning the first and the second flexible longitudinal members by performing one or both of the group of actions consisting of: pulling the flexible longitudinal guide member, and pushing the second flexible-longitudinal-member-coupling element.

For some applications:

the second tissue-engaging element includes a radially-expandable stent, implanting the second tissue-engaging element including expanding the radially-expandable in a blood vessel of the patient selected from the group consisting of: an inferior vena cava, and a superior vena cava, and advancing the second flexible-longitudinal-member-coupling element includes advancing the second flexible-longitudinal-member-coupling element through the radially-expanded stent.

For some applications, the second flexible-longitudinal-member-coupling element is shaped so as to define a lumen therethrough, and advancing includes sliding the second flexible-longitudinal-member-coupling element along the flexible longitudinal guide member while the flexible longitudinal guide member passes through the lumen.

For some applications, the second flexible-longitudinal-member-coupling element is shaped so as to define a coupling interface that is not coaxial with the second flexible-longitudinal-member-coupling element, and the second flexible longitudinal member is fixed to the coupling interface.

For some applications, the method further includes extracting of a portion of the flexible longitudinal guide member to outside a body of the patient by snaring the flexible longitudinal guide member. For some applications:

implanting the first tissue-engaging element includes advancing the first tissue-engaging element, the first flexible longitudinal member, and the first flexible-longitudinal-member-coupling element into the atrium via a vein selected from the group of veins consisting of: a superior vena cava, and an inferior vena cava, advancing the second tissue-engaging element includes advancing the second tissue-engaging element, the second flexible longitudinal member, and the second flexible-longitudinal-member-coupling element into the atrium via the other vein of the group of veins, and extracting includes extracting of the portion of the flexible longitudinal guide member to outside the body via the other vein of the group of veins.

For some applications, the method further includes:

implanting the first tissue-engaging element including using a first delivery tool, which includes a first catheter tube, to deliver the first tissue-engaging element, the first flexible longitudinal member, the first flexible-longitudinal-member-coupling element, and the flexible longitudinal guide member, and advancing the second flexible-longitudinal-member-coupling element and coupling together the first and the second flexible-longitudinal-member-coupling elements includes using a second delivery tool, which includes a second catheter tube, to deliver the second flexible longitudinal member and the second flexible-longitudinal-member-coupling element, and to couple the second flexible-longitudinal-member-coupling element to the first flexible-longitudinal-member-coupling element.

For some applications:

the second tissue-engaging element includes a radially-expandable stent, implanting the second tissue-engaging element including expanding the radially-expandable in a blood vessel of the patient selected from the group consisting of: an inferior vena cava, and a superior vena cava, and using the second delivery tool includes passing a portion of the second delivery tool through the radially-expanded stent.

For some applications, the second delivery tool further includes an advancement tube, and coupling together the first and the second flexible-longitudinal-member-coupling elements includes advancing the advancement tube through a lumen of the second catheter tube, and using the advancement tube to couple the second flexible-longitudinal-member-coupling element to the first flexible-longitudinal-member-coupling element.

For some applications:

the first flexible-longitudinal-member-coupling element includes a male coupling.

the second flexible-longitudinal-member-coupling element includes a female coupling configured to receive the male coupling, and coupling together the first and the second flexible-longitudinal-member-coupling elements includes coupling the male and the female couplings together.

For some applications:

the female coupling (a) includes a cylinder configured to receive the male coupling, (b) is shaped so as to define one or more tabs biased to flex toward a central longitudinal axis of the cylinder, the male coupling is shaped so as to provide one or more protrusions, and the male coupling and the one or more tabs are sized and shaped to (a) allow advancement of the male coupling with respect to the one or more tabs in a first direction, by pushing the one or more tabs away from the longitudinal axis, and (b) restrict advancement of the male coupling with respect to the one or more tabs in a second direction opposite the first direction.

For some applications, the male coupling is shaped so as to define one or more internal ridges, which are configured to engage the one or more tabs when the tabs enter the male coupling.

For some applications, the one or more protrusions are shaped so as to define a shelf, and the one or more tabs are configured to flex toward the longitudinal axis after the advancement of the shelf of the male coupling beyond the one or more tabs, so as to restrict advancement of the male coupling with respect to the one or more tabs in the second direction.

For some applications:

the female coupling includes a structural element including one or more walls shaped so as to define an opening, the male coupling includes one or more radially-displaceable arms, and the one or more radially-displaceable arms are:

compressible by the walls during advancement of the one or more radially-displaceable arms through the opening, and following advancement of the one or more radially-displaceable arms through opening, expandable to a first dimension that is larger than a second dimension of the opening so as to lock the male coupling to the female coupling.

For some applications:

the female coupling includes a structural element including one or more walls shaped so as to define an opening.

the male coupling includes one or more radially-displaceable arms, and the one or more radially-displaceable arms are:

compressible by the walls during advancement of the one or more radially-displaceable arms through the opening, and following advancement of the one or more radially-displaceable arms through opening, expandable to a position in which at least a portion of an outer surface of the one or more arms is beyond and above the one or more walls.

For some applications:

the female coupling includes a structural element including one or more walls shaped so as to define one or more shelves, the male coupling includes one or more radially-displaceable legs, and the one or more radially-displaceable legs are:

compressible by the walls during advancement of the one or more radially-displaceable legs along the one or more shelves, and following the advancement of the one or more radially-displaceable legs beyond the one or more shelves in a first advancement direction, expandable to lock the male coupling to the female coupling, and following expanding of the one or more radially-displaceable legs, the one or more shelves of the female coupling restrict advancement of the one or more radially-displaceable legs in a second advancement direction opposite the first advancement direction.

For some applications, the one or more walls of the female coupling element are shaped so as to define at least one groove, and the male coupling element is shaped so as to define at least one protrusion shaped so as to fit within the at least one groove.

For some applications, the female coupling includes a structural element shaped so as to define a curved groove, and the male coupling includes a projection advanceable within the curved groove so as to lock the male coupling to the female coupling.

There is additionally provided, in accordance with an application of the present invention, apparatus including:

a stent;

a longitudinal member, which has a distal end that includes an annular loop that extends laterally from the longitudinal member; and a tissue anchor, which is coupled to the annular loop, such that the anchor can rotate with respect to the annular loop, the longitudinal member, and the stent.

There is also provided, in accordance with some applications of the present invention, apparatus, including:

a radially-expandable percutaneous implant:

a tissue anchor having a central longitudinal axis;

a connecting element shaped so as to provide an annular loop surrounding a proximal portion of the tissue anchor in a manner which enables rotation of the anchor about the central longitudinal axis when surrounded by the annular loop; and a flexible longitudinal member coupled at a first portion thereof to at least a portion of the percutaneous implant and at a second portion to the connecting element, the annular loop of the connecting element facilitating rotation of the tissue anchor about the central longitudinal axis such that the anchor can rotate about the central longitudinal axis with respect to the annular loop, the flexible longitudinal member, and the percutaneous implant.

In some applications of the present invention, the longitudinal member includes a plurality of fibers.

In some applications of the present invention, the plurality of fibers are arranged such that the longitudinal member has a length of between 10 mm and 300 mm, a width of between 1 and 4 mm, and a thickness of between 1 and 2 mm.

In some applications of the present invention, the plurality of fibers are arranged such that the longitudinal member has a length of between 20 mm and 80 mm, a width of between 1 and 4 mm, and a thickness of between 1 and 2 mm.

In some applications of the present invention, the plurality of fibers are interwoven so as to form a fabric.

In some applications of the present invention, the apparatus includes:

a tube, which is sized to pass through a lumen defined by the percutaneous implant, the tube having at least one tube lumen, and a torque-delivering tool configured for slidable passage through the tube, the torque-delivering tool is configured to be removably coupled to the tissue anchor, such that rotation of the torque-delivering tool rotates the tissue anchor.

In some applications of the present invention, the apparatus includes a sheath configured to surround the percutaneous implant such that the percutaneous implant is maintained in a crimped state when the sheath surrounds the implant, and the sheath is slidable with respect to the tube in order to expose the implant from within the sheath.

In some applications of the present invention, the apparatus includes a secondary tube through which a guidewire may be passed, the secondary tube being configured to be disposed alongside the tube surrounding the torque-delivering tool, the guidewire being configured to facilitate guiding of the apparatus through vasculature of a patient.

In some applications of the present invention:

the connecting element is shaped so as to define a flexible-longitudinal-member-coupler at a proximal portion thereof that is proximal to the annular loop, the flexible-longitudinal-member-coupler is coupled to the second portion of the flexible longitudinal member, and the torque-delivering tool passes alongside the flexible longitudinal member in a manner which restricts entanglement of the flexible longitudinal member during rotation of the torque-delivering tool to rotate the anchor.

In some applications of the present invention, the apparatus includes an anti-entanglement device coupled to the tube at a distal portion thereof, the anti-entanglement device is configured to restrict entanglement of the flexible longitudinal member during (1) rotation of the torque-delivering tool to rotate the anchor, and (2) rotation of the anchor with respect to the surrounding annular loop of the connecting element.

In some applications of the present invention, the anti-entanglement device is configured to be disposed adjacently to the flexible-longitudinal-member-coupler in a manner which restricts entanglement of the flexible longitudinal member during rotation of the torque-delivering tool to rotate the anchor.

In some applications of the present invention, the apparatus includes:
the torque-delivering tool includes a first coupling at a distal end thereof, and
the apparatus further includes an adapter head coupled to the tissue anchor at a proximal end of the tissue anchor, the adapter head including a second coupling reversibly couplable to the first coupling in a manner which:
(1) couples the tissue anchor to the torque-delivering tool when the first and second couplings are coupled together, and
(2) decouples the tissue anchor from the torque-delivering tool when the first and second couplings are not coupled together.

In some applications of the present invention, the first coupling includes a male coupling, the second coupling includes a female coupling, and the first and second couplings are couplable together by being matingly engaged.

In some applications of the present invention, when the distal end of the tool is surrounded by the tube, the first and second couplings are disposed within the tube and are engaged, and the tool is slidable within the tube so as to expose the distal end of the tool and the first and second couplings from within the tube in order to facilitate disengaging of the couplings.

In some applications of the present invention, the apparatus includes a proximal handle portion coupled to a proximal portion of the tube, the handle portion including:
a holder having a recess, the holder being coupled to a proximal portion of the tube, and
an anchor-deployment actuator including a proximal knob and a distal protrusion slidable within the recess of the holder, wherein:
the anchor-deployment actuator is coupled to a proximal portion of the torque-delivering tool,
the torque-delivering tool is slidable within the tube,
the anchor-deployment actuator is rotatable to rotate the torque-delivering tool and the anchor, and
during a pushed state of the anchor-deployment actuator, the protrusion slides distally within the recess of the holder, and responsively, the torque-delivering tool is pushed distally to expose the first and second couplings from within the tube and disengage the first and second couplings.

In some applications of the present invention, the apparatus includes a safety coupled to the holder configured to prevent unwanted sliding distally of the protrusion of the anchor-deployment actuator within the recess of the holder.

In some applications of the present invention, at least a proximal portion of the tissue anchor is shaped so as to define an opening and a passage therethrough, and the adapter head is shaped so as to define a distal protrusion sized so as to fit within the passage, thereby coupling the adapter head to the tissue anchor.

In some applications of the present invention:
a portion of the adapter head that is between the distal protrusion and the second coupling is shaped so as to define a longest dimension at a first cross-sectional plane that is perpendicular to the central axis of the tissue anchor,
the annular loop of the connecting element is shaped so as to define a longest dimension a second cross-sectional plane that is perpendicular to the central axis of the tissue anchor, and
the proximal portion of the adapter head is disposed coaxially proximally to the annular loop along the longitudinal axis in a manner which restricts decoupling of the connecting element from the tissue anchor.

In some applications of the present invention, the percutaneous implant is shaped so as to define a tension-distributing element, and the first portion of the flexible longitudinal element is coupled to the percutaneous implant via the tension-distributing element.

In some applications of the present invention, the tension-distributing element and the percutaneous implant are fabricated from a single unit.

In some applications of the present invention, the tension-distributing element is configured to distribute tension applied by the flexible longitudinal member along a longitudinal length of the percutaneous implant.

In some applications of the present invention, the tension-distributing element has a width of between 1 and 4 mm.

In some applications of the present invention, the percutaneous implant includes a stent including a plurality of struts, and a width of a widest strut is between 100 and 500 micron, and a width of the tension-distributing element is between 1 and 4 mm.

In some applications of the present invention, the percutaneous implant includes an endoluminal implant including a stent including a plurality of struts, and a width of the tension-distributing element is at least 13 times a width of a widest strut of the stent.

In some applications of the present invention, a longitudinal length of the tension-distributing element is at least 15% of the longitudinal length of the percutaneous implant.

In some applications of the present invention, the longitudinal length of the percutaneous implant is between 20 and 120 mm, and the longitudinal length of the tension-distributing element is between 10 and 120 mm.

In some applications of the present invention, the percutaneous implant includes an endoluminal implant including a stent.

In some applications of the present invention, a first section of the stent includes two or more coaxial annular ring portions, each ring portion shaped so as to define a plurality of peaks and valleys, and the first section includes a plurality of interconnectors configured to connect the two or more annular ring portions.

In some applications of the present invention:
the two or more coaxial annular ring portions include first and second annular ring portions that are in phase, and
each one of the plurality of interconnectors is disposed vertically between a respective valley of the first and second ring portions.

In some applications of the present invention:
the stent is configured to assume a compressed state within a sheath and an expanded state when exposed from within the sheath by retracting the sheath in a distal-to-proximal direction,
each one of the valleys of the first annular ring portion is connected by a respective interconnector to a respective valley of the second annular ring portion, and
each one of the peaks points in a distal direction in a manner in which, following expansion of the first and second annular ring portions from within a sheath, the first and second annular ring portions are compressible and retrievable into the sheath when the sheath is advanced in a proximal-to-distal direction.

In some applications of the present invention, the stent is shaped so as to define a first section configured, in a radially-expanded state of the stent, to exert a stronger radial force on surrounding tissue than a second section of the stent.

In some applications of the present invention, the first and second portions are each shaped so as to define respective wire structures, each wire structure including a respective plurality of wire segments, and each wire segment of the second portion has a length greater than a length of a respective wire segment of the first portion.

In some applications of the present invention, the first and second portions are each shaped so as to define respective wire structures, each wire structure including a respective plurality of wire segments, and each wire segment of the first portion has a thickness greater than a thickness of a respective wire segment of the second portion.

In some applications of the present invention, each wire segment of the first portion has a thickness of between 50 and 1000 micron, and each wire segment of the second portion has a thickness of between 50 and 1000 micron.

In some applications of the present invention, the first section includes two or more coaxial annular ring portions, each ring portion shaped so as to define a plurality of peak and valleys, and the first section includes a plurality of interconnectors configured to connect the two or more annular ring portions.

In some applications of the present invention:

the two or more coaxial annular ring portions include first and second annular ring portions that are in phase, and each one of the plurality of interconnectors is disposed vertically between a respective valley of the first and second ring portions.

In some applications of the present invention:

the stent is configured to assume a compressed state within a sheath and an expanded state when exposed from within the sheath by retracting the sheath in a distal-to-proximal direction, each one of the valleys of the first annular ring portion is connected by a respective interconnector to a respective valley of the second annular ring portion, and each one of the peaks points in a distal direction in a manner in which, following expansion of the first and second annular ring portions from within a sheath, the first and second annular ring portions are compressible and retrievable into the sheath when the sheath is advanced in a proximal-to-distal direction.

In some applications of the present invention, the second section includes a plurality of vertical elements extending from the first portion.

In some applications of the present invention, the vertical elements each have a length of between 10 and 80 mm.

In some applications of the present invention, the stent is shaped so as to define a third portion configured, in the radially-expanded state of the stent, to exert a stronger radial force on surrounding tissue than the second section of the stent.

There is further provided, in accordance with some applications of the present invention, a method, including:

providing (a) a radially-expandable percutaneous implant, (b) tissue anchor having a central longitudinal axis, (c) a connecting element shaped so as to provide an annular loop surrounding a proximal portion of the tissue anchor in a manner which enables rotation of the anchor about the central longitudinal axis when surrounded by the annular ring, and (d) a flexible longitudinal member, which has a first portion that is coupled to at least a portion of the percutaneous implant and a second portion that is coupled to the connecting element;

positioning the percutaneous implant in a blood vessel of a patient;

coupling the tissue anchor to tissue in a vicinity of a heart valve of the patient by rotating the anchor with respect to the annular loop, the longitudinal member, and the percutaneous implant; and after coupling the tissue anchor to the tissue, deploying the percutaneous implant such that the implant expands and is implanted in the blood vessel at an implantation site.

In some applications of the present invention, the method includes, after coupling the tissue anchor to the tissue and before deploying the percutaneous implant, pulling the anchor toward the implantation site.

In some applications of the present invention, the blood vessel is selected from the group of blood vessels consisting of: a superior vena cava, an inferior vena cava, a coronary sinus, and a hepatic vein.

In some applications of the present invention, rotating includes rotating the anchor using a tube, which passes through a lumen defined by the stent, and which is removably coupled to the tissue anchor.

There is additionally provided, in accordance with some applications of the present invention, a method, including:

providing (a) a radially-expandable percutaneous implant, (b) tissue anchor having a central longitudinal axis, (c) a connecting element shaped so as to provide an annular loop surrounding a proximal portion of the tissue anchor in a manner which enables rotation of the anchor about the central longitudinal axis when surrounded by the annular ring, and (d) a flexible longitudinal member, which has a first portion that is coupled to at least a portion of the percutaneous implant and a second portion that is coupled to the connecting element; and rotating the anchor with respect to the annular loop, the longitudinal member, and the percutaneous implant while restricting rotation of the flexible longitudinal member.

There is yet additionally provided, in accordance with some applications of the present invention, apparatus including:

a radially-expandable percutaneous implant shaped so as to define a tension-distributing element; and a flexible longitudinal member coupled at a first portion thereof to at least a portion of the percutaneous implant via the tension-distributing element, and the tension-distributing element is configured to distribute tension applied by the flexible longitudinal member along a longitudinal length of the percutaneous implant.

In some applications of the present invention, the apparatus includes a tissue anchor coupled to the flexible longitudinal member at a second portion thereof, the tissue anchor, and the flexible longitudinal member being configured to apply tension to the tension-distributing element.

In some applications of the present invention, the tension-distributing element and the percutaneous implant are fabricated from a single unit.

In some applications of the present invention, the tension-distributing element has a width of between 1 and 4 mm.

In some applications of the present invention, the percutaneous implant includes a stent including a plurality of struts, and a width of a widest strut is between 100 and 500 micron and a width of the tension-distributing element is between 1 and 4 mm.

In some applications of the present invention, the percutaneous implant includes a stent including a plurality of struts, and a width of the tension-distributing element is at least 13 times a width of a widest strut of the stent.

In some applications of the present invention, a longitudinal length of the tension-distributing element is at least 15% of the longitudinal length of the percutaneous implant.

In some applications of the present invention, the longitudinal length of the percutaneous implant is between 20 and 120 mm, and the longitudinal length of the tension-distributing element is between 10 and 120 mm.

In some applications of the present invention, the percutaneous implant includes an endoluminal implant including a stent.

In some applications of the present invention, a first section of the stent includes two or more coaxial annular ring portions, each ring portion shaped so as to define a plurality of peaks and valleys, and the first section includes a plurality of interconnectors configured to connect the two or more annular ring portions.

In some applications of the present invention:
the two or more coaxial annular ring portions include first and second annular ring portions that are in phase, and
each one of the plurality of interconnectors is disposed vertically between a respective valley of the first and second ring portions.

In some applications of the present invention:
the stent is configured to assume a compressed state within a sheath and an expanded state when exposed from within the sheath by retracting the sheath in a distal-to-proximal direction,
each one of the valleys of the first annular ring portion is connected by a respective interconnector to a respective valley of the second annular ring portion, and
each one of the peaks points in a distal direction in a manner in which, following expansion of the first and second annular ring portions from within a sheath, the first and second annular ring portions are compressible and retrievable into the sheath when the sheath is advanced in a proximal-to-distal direction.

In some applications of the present invention, the stent is shaped so as to define a first section configured to exert a stronger radial force on surrounding tissue than a second section of the stent.

In some applications of the present invention, the first and second portions are each shaped so as to define respective wire structures, each wire structure including a respective plurality of wire segments, each wire segment of the second portion has a length greater than a length of a respective wire segment of the first portion.

In some applications of the present invention, the first and second portions are each shaped so as to define respective wire structures, each wire structure including a respective plurality of wire segments, each wire segment of the first portion has a thickness greater than a thickness of a respective wire segment of the second portion.

In some applications of the present invention, each wire segment of the first portion has a thickness of between 100 and 1000 micron, and each wire segment of the second portion has a thickness of between 100 and 1000 micron.

In some applications of the present invention, the first section includes two or more coaxial annular ring portions, each ring portion shaped so as to define a plurality of peak and valleys, and the first section includes a plurality of interconnectors configured to connect the two or more annular ring portions.

In some applications of the present invention:
the two or more coaxial annular ring portions include first and second annular ring portions that are in phase, and
each one of the plurality of interconnectors is disposed vertically between a respective valley of the first and second ring portions.

In some applications of the present invention:
the stent is configured to assume a compressed state within a sheath and an expanded state when exposed from within the sheath by retracting the sheath in a distal-to-proximal direction,
each one of the valleys of the first annular ring portion is connected by a respective interconnector to a respective valley of the second annular ring portion, and
each one of the peaks points in a distal direction in a manner in which, following expansion of the first and second annular ring portions from within a sheath, the first and second annular ring portions are compressible and retrievable into the sheath when the sheath is advanced in a proximal-to-distal direction.

In some applications of the present invention, the second section includes a plurality of vertical elements extending from the first portion.

In some applications of the present invention, the vertical elements each have a length of between 10 and 60 mm.

In some applications of the present invention, the stent is shaped so as to define a third portion configured to exert a stronger radial force on surrounding tissue than the second section of the stent.

There is also provided, in accordance with some applications of the present invention, apparatus, including:
a first radially-expandable percutaneous implant including a plurality of mechanical structural elements arranged so as to assume a first tubular structure, the first radially-expandable percutaneous implant, in a radially-expanded state thereof, having a lumen having an inner diameter;
a flexible longitudinal member coupled at a first portion thereof to at least a portion of the first radially-expandable percutaneous implant, the flexible longitudinal member being configured to apply tension to the first radially-expandable percutaneous implant; and
a second radially-expandable percutaneous implant positionable within the lumen of the first radially-expandable percutaneous implant, the second radially-expandable percutaneous implant:
including a plurality of mechanical structural elements arranged so as to assume a second tubular structure,
being shaped so as to define a plurality of tissue-engaging elements configured to engage tissue of a patient in a radially-expanded state of the second radially-expandable percutaneous implant,
in the radially-expanded state thereof, being configured to:
  excluding the plurality of tissue-engaging elements, assume an outer diameter of the second radially-expandable percutaneous implant that is at least as large as the inner diameter of the first radially-expandable percutaneous implant in the radially-expanded state of the first radially-expandable percutaneous implant, and
  provide anchoring of the first radially-expandable percutaneous implant in the radially-expanded state, to tissue of the patient by facilitating engaging of the plurality of tissue-engaging elements with the tissue of the patient in the radially-expanded state of the second radially-expandable percutaneous implant.

In some applications of the present invention, the apparatus includes a tissue anchor coupled to the flexible longitudinal member at a second portion thereof, the tissue anchor, and the flexible longitudinal member being configured to apply tension to the tension-distributing element.

In some applications of the present invention, the plurality of tissue-engaging elements include a plurality of barbs.

In some applications of the present invention, in the radially-expanded state of the second radially-expandable percutaneous implant, the second radially-expandable percutaneous implant pushes radially against the first radially-expandable percutaneous implant.

There is further provided, in accordance with some applications of the present invention, a method, including:

positioning a first radially-expandable percutaneous implant in a blood vessel of a patient, the first radially-expandable percutaneous implant including a plurality of mechanical struts arranged so as to assume a first tubular structure, the first radially-expandable percutaneous implant, in a radially-expanded state thereof, having a lumen having an inner diameter;

applying tension to the first radially-expandable percutaneous implant;

while tension is applied to the first radially-expandable percutaneous implant, expanding the first radially-expandable percutaneous implant in the blood vessel in a manner in which the first radially-expandable percutaneous implant exerts a radial force on the blood vessel; and anchoring the first radially-expandable percutaneous implant to the blood vessel by expanding a second radially-expandable percutaneous implant within the lumen of the first radially-expandable percutaneous implant, the second radially-expandable percutaneous implant including a plurality of mechanical struts arranged so as to assume a second tubular structure, and by the expanding, engaging a plurality of tissue-engaging elements of the second radially-expandable percutaneous implant with tissue of the blood vessel.

In some applications of the present invention, expanding the second radially-expandable percutaneous implant includes expanding the second radially-expandable percutaneous implant in a manner in which the second radially-expandable percutaneous implant, excluding the plurality of tissue-engaging elements, assumes an outer diameter that is at least as large as the inner diameter of the first radially-expandable percutaneous implant in the radially-expanded state of the first radially-expandable percutaneous implant.

In some applications of the present invention, prior to expanding the second radially-expandable percutaneous implant, allowing migration within the blood vessel of the first radially-expandable percutaneous implant.

In some applications of the present invention, engaging the plurality of tissue-engaging elements of the second radially-expandable percutaneous implant with tissue of the blood vessel includes preventing migration of the first radially-expandable implant within the blood vessel.

There is additionally provided, in accordance with some applications of the present invention, apparatus, including:

a first tissue-engaging element:

a first flexible longitudinal member coupled at a first end portion thereof to at least a portion of the first tissue-engaging element;

a first flexible-longitudinal-member-coupling element coupled to the first flexible longitudinal member at a second end portion of the first flexible longitudinal member:

a second tissue-engaging element;

a second flexible longitudinal member coupled at a first end portion thereof to at least a portion of the second tissue-engaging element; and a second flexible-longitudinal-member-coupling element coupled to the second flexible longitudinal member at a second end portion of the second flexible longitudinal member, the first and second flexible-longitudinal-member-coupling elements being couplable to couple together the first and second flexible longitudinal elements.

In some applications of the present invention, at least a portion of the first tissue-engaging element is shaped so as to define a loop, and the first end portion of the first flexible longitudinal member is configured to be looped at least in part around the loop of the first tissue-engaging element.

In some applications of the present invention, the apparatus includes a connecting element coupled to the first tissue-engaging element, the connecting element shaped so as to provide an annular loop surrounding a proximal portion of the first tissue-engaging element in a manner which enables rotation of the anchor about the central longitudinal axis when surrounded by the annular loop, wherein the annular loop of the connecting element facilitates rotation of the first tissue-engaging element about a central longitudinal axis of the first tissue-engaging element such that the first tissue-engaging element can rotate about the central longitudinal axis with respect to the annular loop and the first flexible longitudinal member.

In some applications of the present invention, the apparatus includes a flexible-longitudinal-member-adjustment mechanism coupled to a flexible longitudinal member selected from the group consisting of: the first flexible longitudinal member and the second flexible longitudinal member, and the flexible-longitudinal-member-adjustment mechanism is configured to adjust a length of the selected flexible longitudinal member.

In some applications of the present invention, the flexible-longitudinal-member-adjustment mechanism includes a spool configured to adjust a length of the selected flexible longitudinal member by winding a portion of the selected flexible longitudinal member around the spool.

In some applications of the present invention, the first tissue-engaging element includes a tissue anchor configured to penetrate tissue of an annulus of an atrioventricular valve of a patient.

In some applications of the present invention, the second tissue-engaging element includes a radially-expandable percutaneous implant configured to engage tissue of the patient upstream of the atrioventricular valve.

In some applications of the present invention, the radially-expandable percutaneous implant includes a stent configured for placement within a blood vessel that empties into an atrium of a heart of the patient.

In some applications of the present invention, the tissue anchor includes a helical tissue anchor, and the apparatus further includes a torque-delivering tool configured to corkscrew the helical tissue anchor into tissue of a patient.

In some applications of the present invention, the apparatus includes a connecting element shaped to define an annular loop surrounding a proximal portion of the tissue anchor, in a manner which enables rotation of the anchor about a longitudinal axis of the tissue anchor, when surrounded by the annular loop, and with respect to the first flexible longitudinal member.

In some applications of the present invention:

the apparatus further includes a first coupling element coupled to the first tissue-engaging element, the first coupling element having a first-coupling-element longitudinal axis and shaped so as to define:

a first-coupling-element main body portion shaped so as to define a first-coupling-element-main-body passage, a first-coupling-element secondary body portion coaxial with the first-coupling-element main body portion, the first-coupling element secondary body portion shaped so as to define a first-coupling-element-secondary-body-portion passage coaxial with the first-coupling-element-main-body passage; and a connecting element connecting the first-coupling-element secondary body portion to the first-coupling-element main body portion, the first coupling element is shaped so as to define a first-coupling-element space between the first-coupling-element main body portion and the first-coupling-element secondary body portion, the apparatus further includes a second coupling element having a second-coupling-element longitudinal axis and shaped so as to define:

a second-coupling-element main body portion shaped so as to define second-coupling-element-main-body passage, a second-coupling-element secondary body portion coaxial with the main body portion, the second-coupling-element secondary body portion shaped so as to define a second-coupling-element-secondary-body-portion passage coaxial with the second-coupling-element-main-body passage, and a connecting element connecting the second-coupling-element secondary body portion to the second-coupling-element main body portion, the second coupling element is shaped so as to define a second-coupling-element space between the main body portion and the secondary body portion, and the first and second coupling elements are couplable together by fitting the first-coupling-element secondary body portion within the second-coupling-element space of the second coupling element, and by fitting the second-coupling-element secondary body portion within the first-coupling-element space of the first coupling element in a manner in which the first-coupling-element-main-body passage, the first-coupling-element-secondary-body-portion passage, the second-coupling-element-main-body passage, and the second-coupling-element-secondary-body-portion passage are aligned, and the apparatus further includes an elongate longitudinal element:

disposable within the first-coupling-element-main-body passage, the first-coupling-element-secondary-body-portion passage, the second-coupling-element-main-body passage, and the second-coupling-element-secondary-body-portion passage to maintain coupling of the first coupling element to the second coupling element, and removable from the first-coupling-element-main-body passage, the first-coupling-element-secondary-body-portion passage, the second-coupling-element-main-body passage, and the second-coupling-element-secondary-body-portion passage to facilitate decoupling of the first and second coupling elements.

In some applications of the present invention, the elongate longitudinal element includes a rod.

In some applications of the present invention, the first-coupling-element main body portion is shaped so as to define a cylinder.

In some applications of the present invention, the second-coupling-element main body portion is shaped so as to define a cylinder.

In some applications of the present invention, the first flexible-longitudinal-member-coupling element includes a male coupling, and the second flexible-longitudinal-member-coupling element includes a female coupling configured to receive the male coupling.

In some applications of the present invention, the female coupling is shaped so as to define one or more grooves, and the male coupling is shaped so as to provide one or more protrusions configured to fit within the one or more grooves of the female coupling.

In some applications of the present invention:

the female coupling includes a cylinder configured to receive the male coupling, the female coupling is shaped so as to define one or more tabs biased to flex toward a longitudinal axis of the cylinder, the male coupling is shaped so as to provide one or more protrusions defining a shelf, the male coupling advanceable with respect to the one or more tabs in a first direction to push the tab away from the longitudinal axis, and the one or more tabs are configured to flex toward the longitudinal axis after the advancement of the shelf of the male coupling beyond the one or more tabs to restrict advancement of the male coupling in a second direction.

In some applications of the present invention, the female coupling includes a structural element including one or more walls shaped so as to define an opening, the male coupling includes one or more radially-displaceable arms, and the one or more radially-displaceable arms are:

compressible by the walls during advancement of the one or more radially-displaceable arms through the opening, and following advancement of the one or more radially-displaceable arms through the opening, expandable to a first dimension that is larger than a second dimension of the opening so as to lock the male coupling to the female coupling.

In some applications of the present invention.

the female coupling includes a structural element including one or more walls shaped so as to define an opening, the male coupling includes one or more radially-displaceable arms, and the one or more radially-displaceable arms are:

compressible by the walls during advancement of the one or more radially-displaceable arms through the opening, and following advancement of the one or more radially-displaceable arms through opening, expandable to a position in which at least a portion of an outer surface of the one or more arms is beyond and above the one or more walls.

In some applications of the present invention, the female coupling includes a structural element including one or more walls shaped so as to define one or more shelves, the male coupling includes one or more radially-displaceable legs, the one or more radially-displaceable legs are:

compressible by the walls during advancement of the one or more radially-displaceable legs along the one or more shelves, and following the advancement of the one or more radially-displaceable legs beyond the one or more shelves in a first advancement direction, expandable to lock the male coupling to the female coupling, and following expanding of the one or more radially-displaceable legs, the one or more shelves of the female coupling restrict advancement of the one or more radially-displaceable legs in a second advancement direction.

In some applications of the present invention, the one or more walls of the female coupling element is shaped so as to define at least one groove, and the male coupling element is shaped so as to define at least one protrusion shaped so as to fit within the at least one groove.

In some applications of the present invention, the female coupling includes a structural element shaped so as to define a curved groove, and the male coupling includes a projection advanceable within the curved groove so as to lock the male coupling to the female coupling.

In some applications of the present invention, the apparatus further includes a flexible longitudinal guide member reversibly coupled to the first flexible-longitudinal-member-coupling element.

In some applications of the present invention, the flexible longitudinal guide member is reversibly coupled to the first flexible-longitudinal-member-coupling element by being looped through a portion of the first flexible-longitudinal-member-coupling element.

In some applications of the present invention:
the first flexible-longitudinal-member-coupling element is shaped so as to define a first coupling.
the flexible longitudinal guide member is reversibly coupled to the first flexible-longitudinal-member-coupling element via the first coupling, and
the flexible longitudinal guide member is configured to facilitate advancement of the second flexible-longitudinal-member-coupling element along the guide member and toward the first flexible-longitudinal-member-coupling element.

In some applications of the present invention, the apparatus includes a snare couplable to the flexible longitudinal guide member so as to facilitate extraction of a portion of the guide member outside a body of a patient.

In some applications of the present invention:
the first tissue-engaging element, the first flexible longitudinal member, and the first flexible-longitudinal-member-coupling element are advanceable within the body of that patient from a first site thereof,
the second tissue-engaging element, the second flexible longitudinal member, and the second flexible-longitudinal-member-coupling element are advanceable within the body of that patient from a second site thereof, and
the snare is configured to extend a portion of the flexible longitudinal guide member toward the second site.

In some applications of the present invention, the first coupling includes a threaded coupling, and the flexible longitudinal guide member is reversibly coupled to the first coupling by being screwed with respect to the threaded coupling.

In some applications of the present invention, the first coupling is shaped so as to define at least one shelf, and the apparatus further includes a longitudinal-guide-member-coupling element, and the longitudinal-guide-member-coupling element is:
coupled to the longitudinal guide member,
restricted from advancement in a first direction by the at least one shelf, and
displaceable with respect to the at least one shelf in response to a change in a spatial orientation of the longitudinal-guide-member-coupling element with respect to the at least one shelf, and allowed to advance in the first direction in order to decouple the longitudinal guide member from the first flexible-longitudinal-member-coupling element.

In some applications of the present invention:
the first flexible-longitudinal-member-coupling element has a first-coupling-element longitudinal axis and the first coupling is shaped so as to define:
a first-coupling-element main body portion shaped so as to define first-coupling-element-main-body passage;
a first-coupling-element secondary body portion coaxial with the main body portion, the first-coupling element secondary body portion shaped so as to define a first-coupling-element-secondary-body-portion passage coaxial with the first-coupling-element-main-body passage; and
a connecting element connecting the secondary body portion to the main body portion,
the first flexible-longitudinal-member-coupling element is shaped so as to define a first-coupling-element space between the main body portion and the secondary body portion,
the apparatus further includes a longitudinal-guide-member-coupling element having a longitudinal-guide-member-coupling element longitudinal axis and a second coupling, wherein the flexible longitudinal guide member coupled to the longitudinal-guide-member-coupling element, and is reversibly coupled to the first flexible-longitudinal-member-coupling element via the longitudinal-guide-member-coupling element, the second coupling being shaped so as to define:
a longitudinal-guide-member-coupling-element main body portion shaped so as to define second-coupling-element-main-body passage;
a longitudinal-guide-member-coupling-element secondary body portion coaxial with the main body portion, the longitudinal-guide-member-coupling-element secondary body portion shaped so as to define a longitudinal-guide-member-coupling element-secondary-body-portion passage coaxial with the longitudinal-guide-member-coupling-element-main-body passage; and
a connecting element connecting the longitudinal-guide-member-coupling-element secondary body portion to the longitudinal-guide-member-coupling-element main body portion,
the second coupling element is shaped so as to define a second-coupling-element space between the main body portion and the secondary body portion, and
the first and second couplings are couplable together by fitting the first-coupling-element secondary body portion within the longitudinal-guide-member-coupling-element space of the second coupling element, and by fitting the longitudinal-guide-member-coupling-element secondary body portion within the first-coupling-element space of the first coupling element in a manner in which the first-coupling-element-main-body passage, the first-coupling-element-secondary-body-portion passage, the longitudinal-guide-member-coupling-element-main-body passage, and the longitudinal-guide-member-coupling-element-secondary-body-portion passage are aligned.

In some applications of the present invention, the apparatus further includes an elongate longitudinal element:
disposable within the first-coupling-element-main-body passage, the first-coupling-element-secondary-body-portion passage, the longitudinal-guide-member-coupling-element-main-body passage, and the longitudinal-guide-member-coupling-element-secondary-body-portion passage to maintain coupling of the first and second couplings, and
removable from the first-coupling-element-main-body passage, the first-coupling-element-secondary-body-portion passage, the longitudinal-guide-member-coupling-elementmain-body passage, and the longitudinal-guide-member-coupling-element-secondary-body-portion passage to facilitate decoupling of the first and second couplings.

There is yet additionally provided, in accordance with some applications of the present invention a method, including:

implanting a first tissue-engaging element at a first implantation site in tissue of an atrioventricular valve of a patient;

extending from the first tissue-engaging element, a first flexible longitudinal member coupled at a first end portion thereof to at least a portion of the first tissue-engaging element, the first flexible longitudinal element being coupled at a second end portion thereof to a first flexible-longitudinal-member-coupling element:

advancing toward the valve of the patient a second tissue-engaging element coupled to a first end portion of a second flexible longitudinal member, the second flexible longitudinal member being coupled at a second end portion thereof to a second flexible-longitudinal-member-coupling element;

coupling together the first and second flexible-longitudinal-member-coupling elements;

facilitating repairing of the atrioventricular valve by pulling on the second tissue-engaging element, and responsively, pulling on the first and second flexible longitudinal members; and implanting the second tissue-engaging element at a second implantation site upstream of the atrioventricular valve.

In some applications of the present invention, facilitating repairing includes remodeling the atrioventricular valve by drawing together leaflets of the valve responsively to the pulling.

There is still yet additionally provided, in accordance with some applications of the present invention, apparatus including:

a first coupling element having a first-coupling-element longitudinal axis and shaped so as to define:
  a first-coupling-element main body portion shaped so as to define first-coupling-element-main-body passage;
  a first-coupling-element secondary body portion coaxial with the first-coupling-element main body portion, the first-coupling element secondary body portion shaped so as to define a first-coupling-element-secondary-body-portion passage coaxial with the first-coupling-element-main-body passage; and
  a first-coupling-element connecting element connecting the first-coupling-element secondary body portion to the first-coupling-element main body portion,
wherein the first coupling element is shaped so as to define a first-coupling-element space between the first-coupling-element main body portion and the first-coupling-element secondary body portion:
a second coupling element having a second-coupling-element longitudinal axis and shaped so as to define:
  a second-coupling-element main body portion shaped so as to define second-coupling-element-main-body passage;
  a second-coupling-element secondary body portion coaxial with the second-coupling-element main body portion, the second-coupling-element secondary body portion shaped so as to define a second-coupling-element-secondary-body-portion passage coaxial with the second-coupling-element-main-body passage; and
  a second-coupling-element connecting element connecting the second-coupling-element secondary body portion to the second-coupling-element main body portion, wherein:
  the second coupling element is shaped so as to define a second-coupling-element space between the second-coupling-element main body portion and the second-coupling-element secondary body portion, and
  the first and second coupling elements are couplable together by fitting the first-coupling-element secondary body portion within the second-coupling-element space of the second coupling element, and by fitting the second-coupling-element secondary body portion within the first-coupling-element space of the first coupling element in a manner in which the first-coupling-element-main-body passage, the first-coupling-element-secondary-body-portion passage, the second-coupling-element-main-body passage, and the second-coupling-element-secondary-body-portion passage are aligned; and
an elongate longitudinal element:
disposable within the first-coupling-element-main-body passage, the first-coupling-element-secondary-body-portion passage, the second-coupling-element-main-body passage, and the second-coupling-element-secondary-body-portion passage to maintain coupling of the first coupling element to the second coupling element, and
removable from the first-coupling-element-main-body passage, the first-coupling-element-secondary-body-portion passage, the second-coupling-element-main-body passage, and the second-coupling-element-secondary-body-portion passage to facilitate decoupling of the first and second coupling elements.

In some applications of the present invention, the elongate longitudinal element includes a rod.

In some applications of the present invention, the first-coupling-element main body portion is shaped so as to define a cylinder.

In some applications of the present invention, the second-coupling-element main body portion is shaped so as to define a cylinder.

In some applications of the present invention, the first coupling element is coupled to a tissue anchor and the second coupling element is coupled to a tissue-anchor-delivering tool.

In some applications of the present invention, the tissue anchor includes a helical tissue anchor, and the tissue-anchor-delivering tool includes a torque-delivering tool configured to corkscrew the helical tissue anchor into tissue of a patient.

In some applications of the present invention, the torque-delivering tool is coupled to the second coupling element.

In some applications of the present invention, the apparatus includes a connecting element shaped to define an annular loop surrounding a proximal portion of the first coupling element, in a manner which enables rotation of the anchor and the first coupling element about the first-coupling-element longitudinal axis, when surrounded by the annular loop.

In some applications of the present invention, the apparatus includes a flexible, longitudinal band coupled to the connecting element, and the tissue anchor and the first coupling element are configured to rotate with respect to the flexible, longitudinal band.

There is further provided, in accordance with some applications of the present invention, a method, including:
providing a first coupling element having a first-coupling-element longitudinal axis and shaped so as to define:

a first-coupling-element main body portion shaped so as to define first-coupling-element-main-body passage;

a first-coupling-element secondary body portion coaxial with the main body portion, the first-coupling element secondary body portion shaped so as to define a first-coupling-element-secondary-body-portion passage coaxial with the first-coupling-element-main-body passage; and a connecting element connecting the secondary body portion to the main body portion, wherein the first coupling element is shaped so as to define a first-coupling-element space between the main body portion and the secondary body portion:

providing a second coupling element having a second-coupling-element longitudinal axis and shaped so as to define:

a second-coupling-element main body portion shaped so as to define second-coupling-element-main-body passage;

a second-coupling-element secondary body portion coaxial with the main body portion, the second-coupling element secondary body portion shaped so as to define a second-coupling-element-secondary-body-portion passage coaxial with the second-coupling-element-main-body passage; and a connecting element connecting the secondary body portion to the main body portion, wherein the second coupling element is shaped so as to define a second-coupling-element space between the main body portion and the secondary body portion;

coupling together the first and second coupling elements are couplable together by fitting the first-coupling-element secondary body portion within the second-coupling-element space of the second coupling element, and by fitting the second-coupling-element secondary body portion within the first-coupling-element space of the first coupling element in a manner in which the first-coupling-element-main-body passage, the first-coupling-element-secondary-body-portion passage, the second-coupling-element-main-body passage, and the second-coupling-element-secondary-body-portion passage are aligned;

maintaining the coupling by inserting an elongate longitudinal element within the first-coupling-element-main-body passage, the first-coupling-element-secondary-body-portion passage, the second-coupling-element-main-body passage, and the second-coupling-element-secondary-body-portion passage to maintain coupling of the first coupling element to the second coupling element; and facilitating decoupling of the first and second coupling elements by removing the elongate longitudinal element.

In some applications of the present invention, the elongate longitudinal element includes a rod.

In some applications of the present invention, the method includes providing a tissue anchor coupled to the first coupling element, and providing a tissue-anchor-delivery tool coupled to the second element.

In some applications of the present invention, the tissue anchor includes a helical tissue anchor, and the tissue-anchor-delivery tool includes a torque-delivering tool configured to deliver torque to the tissue anchor to corkscrew the helical tissue anchor into tissue of a patient.

In some applications of the present invention, corkscrewing the helical tissue anchor includes rotating the first coupling element and the anchor about the first-coupling-element longitudinal axis, and rotating includes rotating the first coupling element and the anchor with respect to a connecting element coupled to an annular loop surrounding a proximal portion of the first coupling element.

In some applications of the present invention, rotating includes rotating the first coupling element and the anchor with respect to a flexible, longitudinal band coupled to the connecting element.

There is also provided, in accordance with some applications of the present invention, apparatus including:

a first tissue-engaging element:

at least one flexible longitudinal member coupled at a first end portion thereof to at least a portion of the first tissue-engaging element;

a second tissue-engaging element including a stent, the second tissue-engaging element being coupled to the first tissue-engaging element via the at least one flexible longitudinal member; and a flexible-longitudinal-member-adjustment mechanism coupled to the at least one flexible longitudinal member, the flexible-longitudinal-member-adjustment mechanism being configured to adjust a length of the selected flexible longitudinal member to draw the first and second tissue-engaging elements toward each other.

In some applications of the present invention, the flexible-longitudinal-member-adjustment mechanism includes a spool configured to adjust a length of the at least one flexible longitudinal member by winding a portion of the at least one flexible longitudinal member around the spool.

The present invention will be more fully understood from the following detailed description of applications thereof, taken together with the drawings, in which:

BRIEF DESCRIPTION OF THE DRAWINGS

FIGS. 3A-C are schematic illustrations of apparatus for reducing regurgitation of the heart valve which comprises a single stent, first and second tissue anchor, and first and second tensioning elements, in accordance with some applications of the present invention;

FIGS. 7A-D are schematic illustrations of a delivery system for a helical tissue anchor, in accordance with some applications of the present invention;

FIGS. 11A-C are schematic illustrations of another delivery system for a helical tissue anchor, in accordance with some applications of the present invention;

FIGS. 12A-C are schematic illustrations of the release of the tissue anchor from the delivery system of FIGS. 11A-C, in accordance with some applications of the present invention;

FIGS. 13A-C are schematic illustrations of a stent coupled to a helical anchor, in accordance with some applications of the present invention;

FIGS. 14A-C are schematic illustrations of another stent coupled to a helical anchor, in accordance with some applications of the present invention;

FIG. 19 is a schematic illustration of an endoluminal implant coupled to a helical anchor, in accordance with some applications of the present invention;

FIGS. 20-26 are schematic illustrations of apparatus for reducing regurgitation of a heart valve which comprises a stent, a tissue anchor, and first and second flexible longitudinal members that couple the stent and the tissue anchor using respective coupling elements, in accordance with some applications of the present invention;

FIGS. 34A-E are schematic illustrations of a method for deploying a system for repairing the tricuspid valve, in accordance with an application of the present invention;

FIGS. 35A-C are schematic illustrations of another configuration of the first flexible-longitudinal-member-coupling element of FIGS. 33A-B, coupled to the second flexible-longitudinal-member-coupling element of FIGS. 33A-B, in accordance with an application of the present invention;

FIGS. 36A-B are schematic illustrations of a link of the first flexible-longitudinal-member-coupling element of FIGS. 35A-C, in accordance with an application of the present invention;

FIGS. 37A-B and 38A-C are schematic illustrations of two respective configurations of another first flexible-longitudinal-member-coupling element, coupled to the second flexible-longitudinal-member-coupling element of FIGS. 33A-B, in accordance with respective applications of the present invention;

FIGS. 39A-B are schematic illustrations of another first flexible-longitudinal-member-coupling element and another second flexible-longitudinal-member-coupling element coupled thereto, in accordance with an application of the present invention; and FIGS. 40A-E are schematic illustrations of a method for deploying a system for repairing the tricuspid valve, in accordance with an application of the present invention.

DETAILED DESCRIPTION OF APPLICATIONS

Figure 1A:
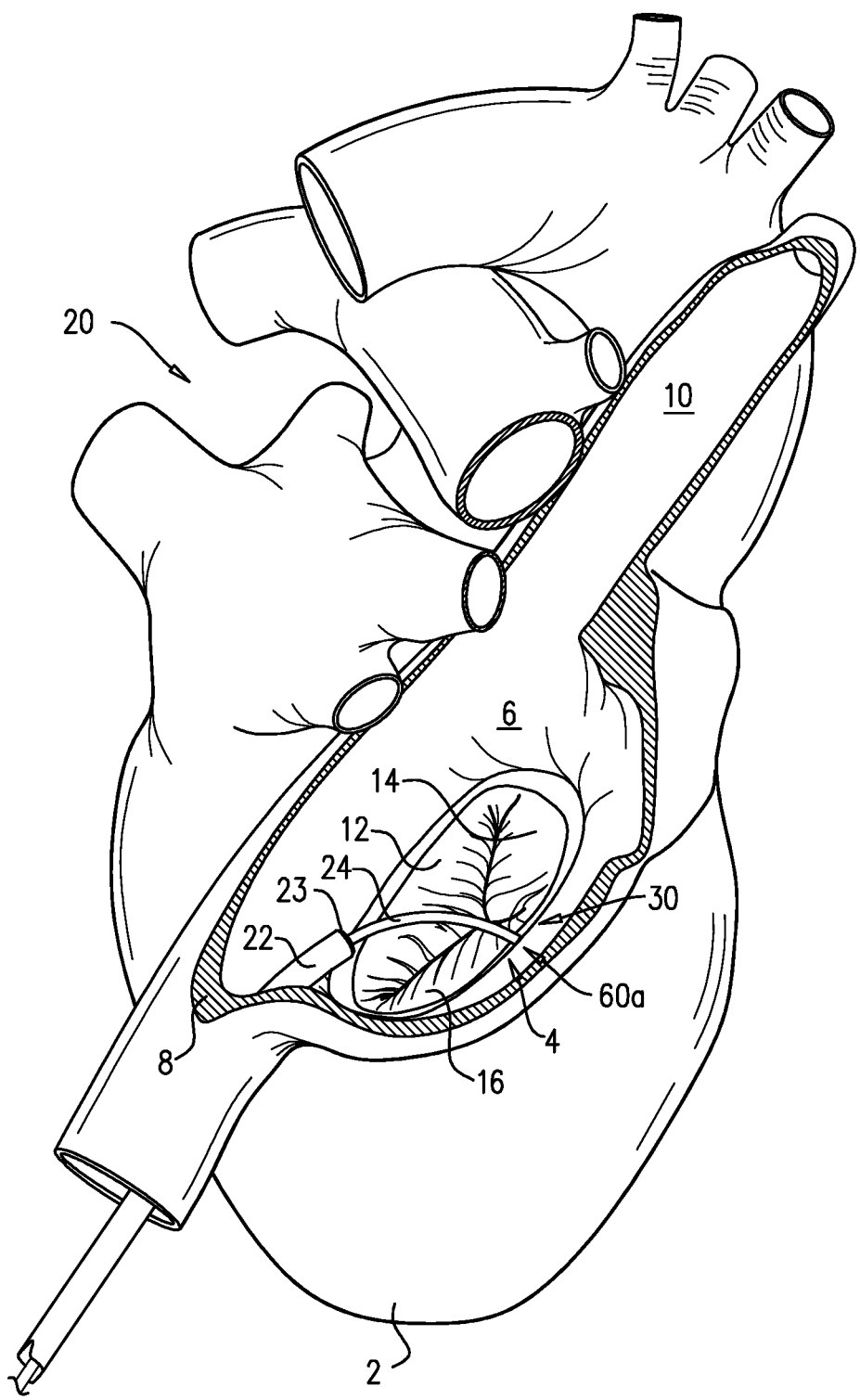
FIGS. 1A-D are schematic illustrations of apparatus for reducing regurgitation of a heart valve which comprises a stent, a tissue anchor, and a tensioning element that couples the stent and the tissue anchor, in accordance with some applications of the present invention.

Reference is now made to FIGS. 1A-D, which are schematic illustrations of a system 20 comprising a first tissue-engaging element 60a and a second tissue-engaging element 60b for repairing a tricuspid valve 4 of a heart 2 of a patient, in accordance with some applications of the present invention. First tissue-engaging element 60a comprises a tissue anchor 40 which is designated for implantation at least in part in cardiac tissue at a first implantation site 30. It is to be noted that tissue anchor 40 comprises a helical tissue anchor by way of illustration and not limitation and that tissue anchor 40 may comprise any tissue anchor for puncturing or clamping cardiac tissue, including, but not limited to, the tissue anchors described hereinbelow with reference to FIGS. 7A-D, 10A-D 11A-C, 12A-C, 13A-C, and 14A-C. Second tissue-engaging element 60b comprises a percutaneous implant, for example, an endoluminal implant, e.g., stent 50, which is designated for implantation in a portion of a blood vessel, e.g., a superior vena cava 10 (not shown) or an inferior vena cava 8 (such as shown in FIGS. 1A-D), at a second implantation site 52. First and second tissue-engaging elements 60a and 60b are coupled together by a flexible longitudinal member 42. Typically, a distance between first and second implantation sites 30 and 52 is adjusted by pulling to apply tension to or relaxing longitudinal member 42 and/or by applying tension to at least one of first and second tissue-engaging elements 60a and 60b. Responsively, a distance between the leaflets of tricuspid valve 4 is adjusted to reduce and eliminate regurgitation through and thereby repair tricuspid valve 4. For some applications, longitudinal member 42 is pulled or relaxed by manipulating second tissue-engaging element 60b, as is described hereinbelow.

Typically, longitudinal member 42 comprises a flexible biocompatible textile e.g. polyester, nylon, PTFE, ePTFE, PEEK, PEBAX™, and/or superelastic material, e.g., nitinol. Typically, longitudinal member 42 comprises a plurality of fibers which are aligned, e.g., woven or intertwined, to form a fabric band, as will be described hereinbelow with reference to FIGS. 11A-C, 13C, and 14C. In some applications of the present invention, longitudinal member 42 comprises a braided polyester suture (e.g., DACRON™). In other applications of the present invention, longitudinal member 42 is coated with polytetrafluoroethylene (PTFE). In some applications of the present invention, longitudinal member 42 comprises a plurality of wires that are intertwined to form a rope structure. For some applications, at least a part of longitudinal member 42 comprises a tension spring and/or a plurality of coils.

For some applications, first and second tissue-engaging elements 60*a* and 60*b* and longitudinal member 42 are fabricated from the same material, e.g., nitinol, from a single piece. That is, first and second tissue-engaging elements 60*a* and 60*b* and longitudinal member 42 define a single continuous implant unit. For some applications, at least second tissue-engaging element 60*b* and longitudinal member 42 are fabricated from a single piece.

For some applications, second tissue-engaging element 60*b* comprises a stent 50 which is advanced toward and expandable in a portion of inferior vena cava 8 (such as shown in FIGS. 1A-D) or superior vena cava 10 (not shown), i.e., a blood vessel that is in direct contact with a right atrium 6 of heart 2 of the patient. Second tissue-engaging element 60*b* is implanted at second implantation site 52. As shown, first implantation site comprises a portion of an annulus of tricuspid valve 4, specifically the antero-posterior commissure by way of illustration and not limitation. For some applications, implantation site 30 typically comprises a portion of the annulus of tricuspid valve 4 that is between (1) the middle of the junction between the annulus and anterior leaflet 14, and (2) the middle of the junction between the annulus and posterior leaflet 16, e.g., between the middle of the junction between the annulus and anterior leaflet 14 and the commissure between the anterior and posterior leaflets. That is, anchor 40 is coupled to, e.g., screwed into, the fibrous tissue of the tricuspid annulus close to the commissure in between anterior leaflet 14 and posterior leaflet 16. Implantation site 30 is typically close to the mural side of tricuspid valve 4. For such applications, the drawing together of first and second implantation sites 30 and 52 cinches tricuspid valve 4 and may create a bicuspidization of tricuspid valve 4, and thereby achieve stronger coaptation between anterior leaflet 14 and septal leaflet 12. During the bicuspidization, posterior leaflet 16 may be offset outside the plane of tricuspid valve 4.

For some applications, first implantation site 30 may include a portion of tissue of a wall defining right atrium 6 of heart 2, typically in a vicinity of the annulus of tricuspid valve 4, e.g., the anterior-posterior commissure, as shown. For other applications, first implantation site 30 may include a portion of a wall of a right ventricle of heart 2, a ventricular portion of the annulus of tricuspid valve 4, or a portion of a papillary muscle of the right ventricle of heart 2, as is shown hereinbelow in FIG. 6. First implantation site 30 is typically a distance away from, e.g., generally opposite, second implantation site 52 so that, following adjusting of longitudinal member 42, first and second implantation sites 30 and 52 are drawn together, and thereby at least first and second leaflets, e.g., all three leaflets, of tricuspid valve 4 are drawn toward each other. For applications in which first implantation site 30 includes a portion of tissue of the annulus, the adjusting of the distance between implantation sites 30 and 52 alters the geometry of (i.e., changes the configuration of) the annulus of tricuspid valve 4 and thereby draws together the leaflets of tricuspid valve 4. For applications in which first implantation site 30 includes tissue of a portion of a wall that defines atrium 6, the adjusting of the distance between implantation sites 30 and 52 alters the geometry of (i.e., changes the configuration of) the wall of atrium 6 and thereby draws together the leaflets of tricuspid valve 4.

FIG. 1A shows the advancement of a catheter 22 toward atrium 6 of the patient until a distal end 23 of the catheter is disposed within atrium 6, as shown. The procedure is typically performed with the aid of imaging, such as fluoroscopy, transesophageal echo, and/or echocardiography. For some applications, the procedure begins by advancing a semi-rigid guidewire into right atrium 6 of the patient. The guidewire provides a guide for the subsequent advancement of a catheter 22 therealong and into the right atrium. For some applications, once distal end 23 of catheter 22 has entered right atrium 6, the guidewire is retracted from the patient's body. Catheter 22 typically comprises a 14-20 F sheath, although the size may be selected as appropriate for a given patient. Catheter 22 is advanced through vasculature into right atrium 6 using a suitable point of origin typically determined for a given patient. For example:

catheter 22 may be introduced into the femoral vein of the patient, through inferior vena cava 8, and into right atrium 6;

catheter 22 may be introduced into the basilic vein, through the subclavian vein through superior vena cava 10, and into right atrium 6; or catheter 22 may be introduced into the external jugular vein, through the subclavian vein through superior vena cava 10, and into right atrium 6.

As shown in FIG. 1A, catheter 22 is advanced through inferior vena cava 8 of the patient and into right atrium 6 using a suitable point of origin typically determined for a given patient. Alternatively, catheter 22 is advanced through superior vena cava 10 of the patient and into right atrium 6 using a suitable point of origin typically determined for a given patient.

Once distal end 23 of catheter 22 is disposed within atrium 6, an anchor-deployment tube 24 is extended from within catheter 22 beyond distal end 23 thereof and toward first implantation site 30. Anchor-deployment tube 24 holds tissue anchor 40 and a distal portion of longitudinal member 42. For some applications, tube 24 is steerable, as is known in the catheter art, while for other applications, a separate steerable element may be coupled to anchor-deployment tube 24. Under the aid of imaging guidance, anchor-deployment tube 24 is advanced toward first implantation site 30 until a distal end thereof contacts cardiac tissue of heart 2 at first implantation site 30. Anchor-deployment tube 24 facilitates atraumatic advancement of first tissue-engaging element 60*a* toward first implantation site 30. For such applications in which anchor-deployment tube 24 is used, stent 50 is compressed within a portion of tube 24.

Figure 1B:
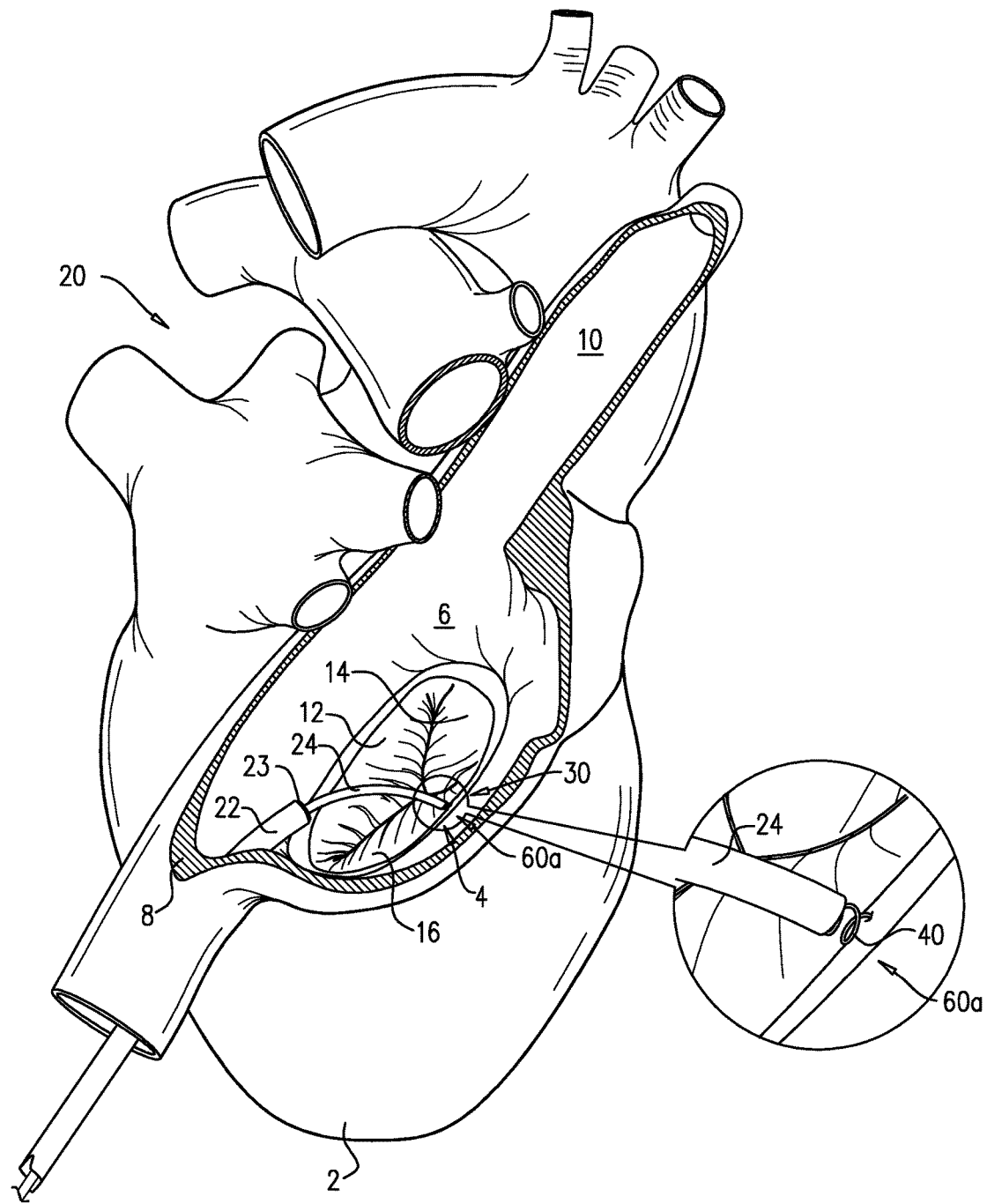

An anchor-manipulating tool (not shown for clarity of illustration), which is slidably disposed within anchor-deployment tube 24, is slid distally within tube 24 so as to push distally tissue anchor 40 of first tissue-engaging element 60*a* and expose tissue anchor 40 from within tube 24, as shown in FIG. 1B. For some applications of the present invention, the anchor-manipulating tool is reversibly coupled to anchor 40 and facilitates implantation of anchor 40 in the cardiac tissue. For applications in which anchor 40 comprises a helical tissue anchor, as shown, the operating physician rotates the anchor-manipulating tool from a site outside the body of the patient in order to rotate anchor 40 and thereby screw at least a portion of anchor 40 in the cardiac tissue.

Alternatively, system 20 is provided independently of the anchor-manipulating tool, and anchor-deployment tube 24 facilitates implantation of anchor 40 in the cardiac tissue. For applications in which anchor 40 comprises a helical tissue anchor, as shown, the operating physician rotates anchor-deployment tube 24 from a site outside the body of the patient in order to rotate anchor 40 and thereby screw at least a portion of anchor 40 in the cardiac tissue.

It is to be noted that for some applications of the present invention, anchor 40 comprises a clip, jaws, or a clamp which grips and squeezes a portion of cardiac tissue and does not puncture the cardiac tissue.

Figure 1C:
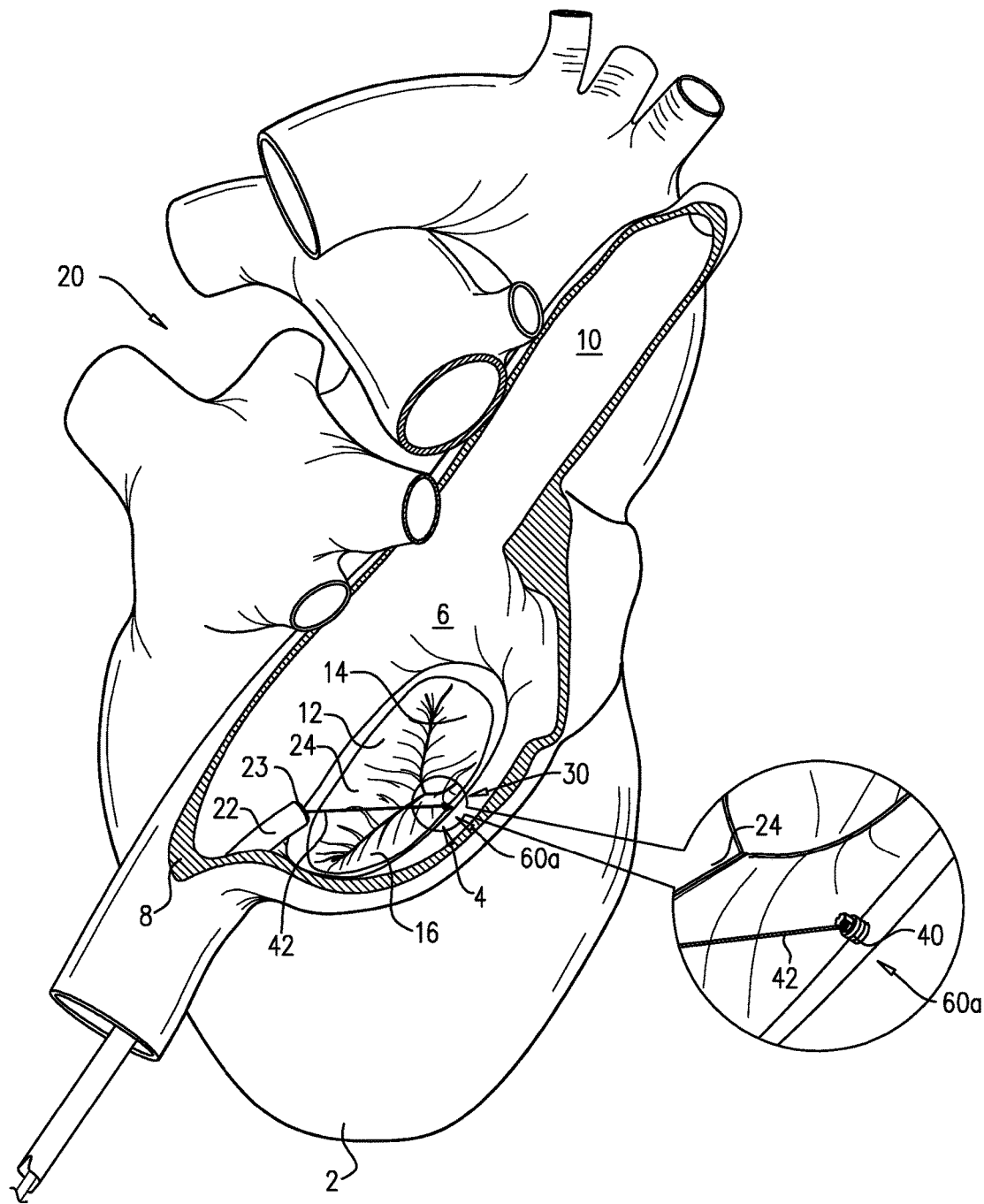

Following the implantation of anchor 40 at first implantation site 30, anchor-deployment tube 24 is retracted within catheter 22 in order to expose longitudinal member 42, as shown in FIG. 1C. Subsequently, longitudinal member 42 is pulled taut in order to repair tricuspid valve 4, as described hereinbelow.

For some applications, distal end 23 of catheter 22 is fixed in place with respect to longitudinal member 42. Fixing in place catheter 22 stabilizes catheter 22 as longitudinal member 42 is pulled. This enables distal end 23 to remain in place and not slide distally toward implantation site 30 during the adjusting of longitudinal member 42. For some applications of the present invention, a proximal portion of catheter 22 and/or a proximal handle portion coupled to catheter 22 is anchored or otherwise fixed in place at its access location, e.g., by taping or plastering. Alternatively or additionally, a distal portion of catheter 22 comprises an inflatable element coupled to an inflation conduit which runs the length of catheter 22 from the distal portion thereof to a site outside the body of the patient. Prior to the adjusting of longitudinal member 42, the inflatable element is inflated such that it contacts tissue of the vasculature through which catheter 22 is advanced, and thereby catheter 22 is fixed in place. Typically, the inflatable element comprises an annular inflatable element, such that when inflated, the annular inflatable element functions as a seal to hold in place the distal portion of catheter 22.

(In this context, in the specification and in the claims, "proximal" means closer to the orifice through which the implant (i.e., the prosthetic valve and the valve support) is originally placed into the body of the patient, along the path of delivery of the implant, and "distal" means further from this orifice along the path of delivery of the implant.)

Following the fixation of the mechanism that facilitates pulling of longitudinal member 42, the physician then pulls longitudinal member 42 and thereby draws together first and second implantation sites 30 and 52.

For some applications, catheter 22 is reversibly coupled to a proximal portion of longitudinal member 42 by being directly coupled to the proximal portion of member 42 and/or catheter 22 is reversibly coupled to second tissue-engaging element 60b. For example, catheter 22 may be reversibly coupled to stent 50 by the stent's application of a radial force against the inner wall of catheter 22 because of the tendency of stent 50 to expand radially. Following implantation of first tissue-engaging element 60a, catheter 22 (or an element disposed therein) is then pulled proximally to apply tension to longitudinal member 42, which, in such an application, functions as a tensioning element. For some applications, catheter 22 pulls on second tissue-engaging element 60b in order to pull longitudinal member 42. For other applications, catheter 22 pulls directly on longitudinal member 42. For yet other applications, a pulling mechanism pulls on longitudinal member 42, as is described hereinbelow with reference to FIGS. 7A-D.

Pulling longitudinal member 42 pulls taut the portion of longitudinal member 42 that is disposed between anchor 40 and distal end 23 of catheter 22. Additionally, longitudinal member 42 may be pulled or relaxed in order to adjust the distance between first and second implantation sites 30 and 52. Responsively to the pulling of longitudinal member 42, at least the anterior and septal leaflets of tricuspid valve 4 are drawn together because the geometry of the annulus and/or of the wall of atrium 6 is altered in accordance with the pulling of longitudinal member 42 and depending on the positioning of first tissue-engaging element 60a. For some applications, during the pulling of longitudinal member 42 by catheter 22, a level of regurgitation of tricuspid valve 4 is monitored and a parameter indicative of repair of tricuspid valve 4 is monitored. For example, leaflet anatomy during the opening and closing of tricuspid valve 4 is assessed using an imaging device such as intracardiac echocardiography, transthoracic echocardiography or transesophageal echocardiography. For some applications, during the monitoring, measurements used to assess the efficiency of the procedure are evaluated pre-, during-, and post-procedure. For example, these measurements could include, but not exclusively, measuring the echocardiographic distance between the anteroposterior commissure and the rim at the junction of the inferior vena cava and the right atrium, or measuring the echocardiographic regurgitant volume through tricuspid valve 4. Longitudinal member 42 is pulled until the regurgitation is reduced or ceases.

Once the physician determines that the regurgitation of tricuspid valve 4 is reduced or ceases, and tricuspid valve 4 has been repaired, the physician decouples catheter 22 from second tissue-engaging element 60b disposed therein and/or from longitudinal member 42, and then retracts catheter 22 in order to expose second tissue-engaging element 60b. i.e., stent 50. During the advancement of catheter 22 toward atrium 6, stent 50 is disposed within a distal portion of catheter 22 in a compressed state. Following initial retracting of catheter 22, stent 50 is exposed and is allowed to expand and contact a wall of inferior vena cava 8. Responsively to the expanding, stent 50 is implanted in second implantation site 52 and maintains the tension of longitudinal member 42 on anchor 40 and thereby on the portion of cardiac tissue to which anchor 40 is coupled.

Figure 5A:
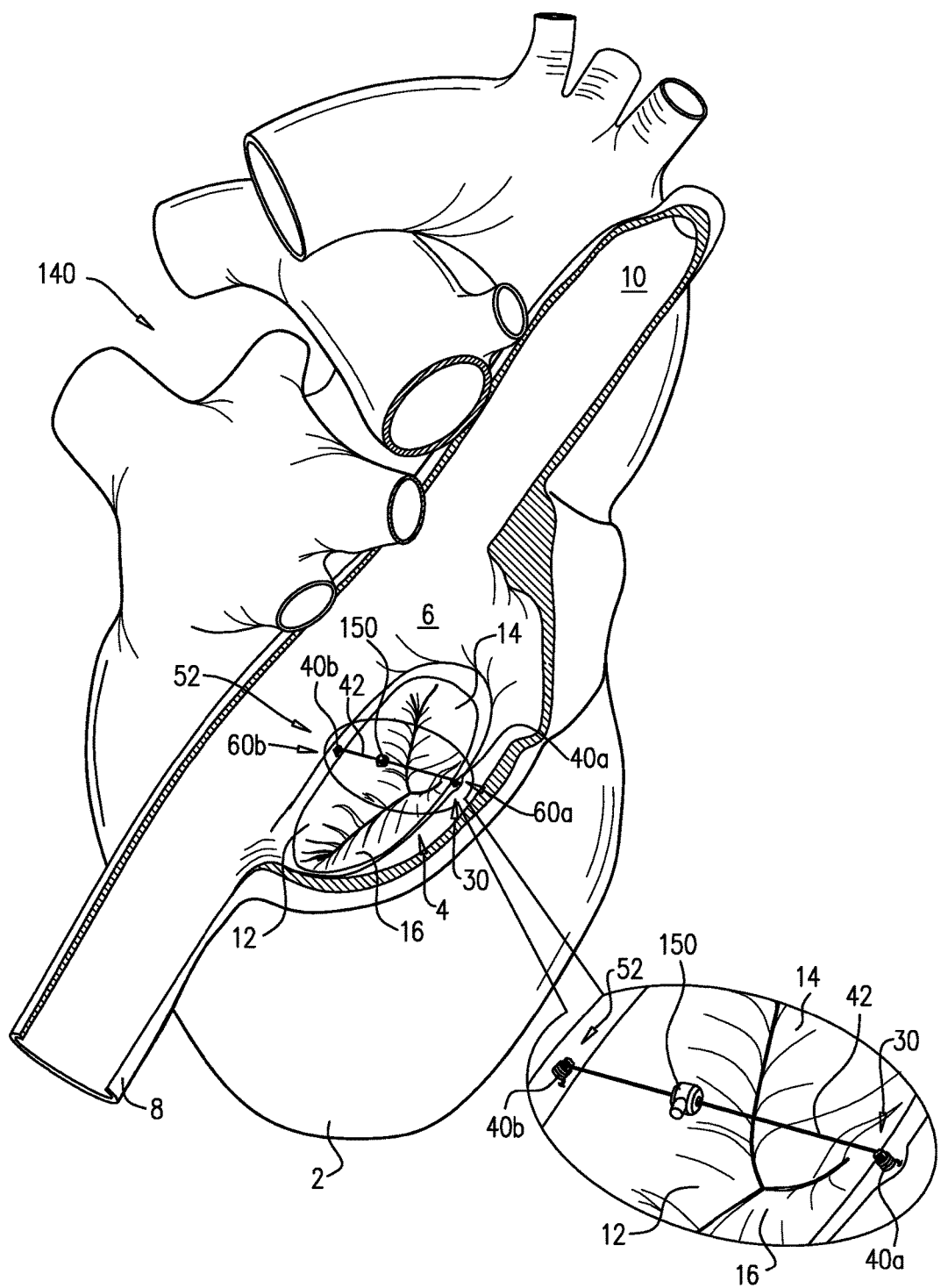
FIGS. 5A-B are schematic illustrations of apparatus for reducing regurgitation of the heart valve which comprises two or three tissue anchors and a tensioning element that couples the tissue anchors, in accordance with some applications of the present invention.
Figure 5B:
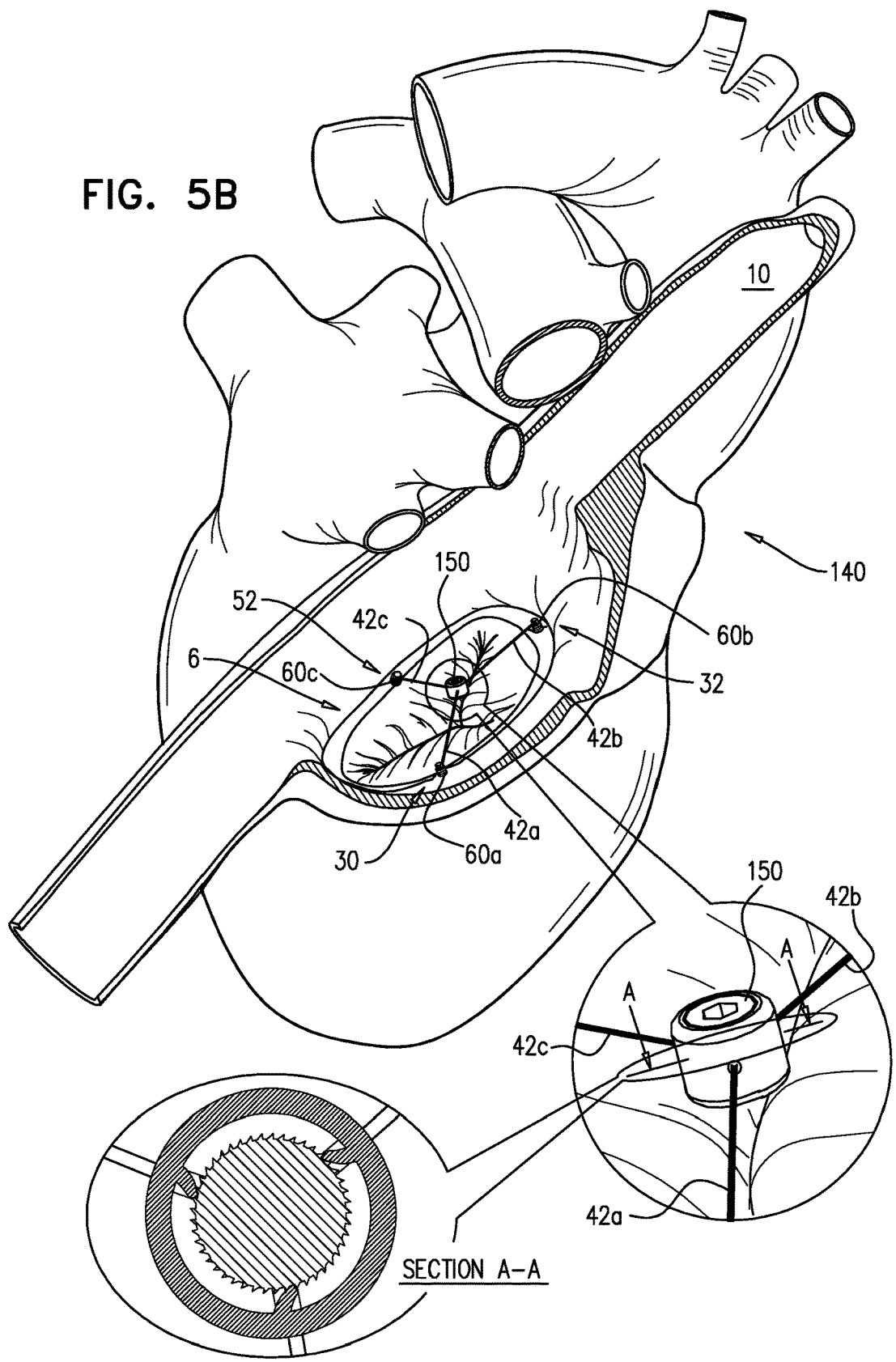

Reference is again made to FIGS. 1A-D. For some applications, following the implantation of first and second tissue-engaging elements 60a and 60b, a distance between first and second tissue-engaging elements 60a and 60b is adjusted by an adjustable mechanism, as described hereinbelow with reference to FIGS. 5A-B. In such applications, a length of longitudinal member 42 between first and second tissue-engaging elements 60a and 60b may be adjusted by an adjusting mechanism 150, as shown in FIGS. 5A-B. Adjusting mechanism 150 typically comprises a mechanical element which shortens a distance of longitudinal member 42 between first and second tissue-engaging elements 60a and 60b. For some applications, adjustable mechanism 150 may be permanently coupled to longitudinal member 42 (not shown) and comprises an adjusting element, e.g., a spool for looping portions of longitudinal member 42 therearound, a crimping bead for crimping and shortening a portion of longitudinal member 42, a ratchet element, or a deforming element which deforms a portion of longitudinal member 42 in order to shorten its length between first and second tissue-engaging elements 60a and 60b. A level of regurgitation of tricuspid valve 4 may be monitored during the adjusting of the distance between first and second tissue-engaging elements 60*a* and 60*b* by adjusting mechanism 150.

Figure 1D:
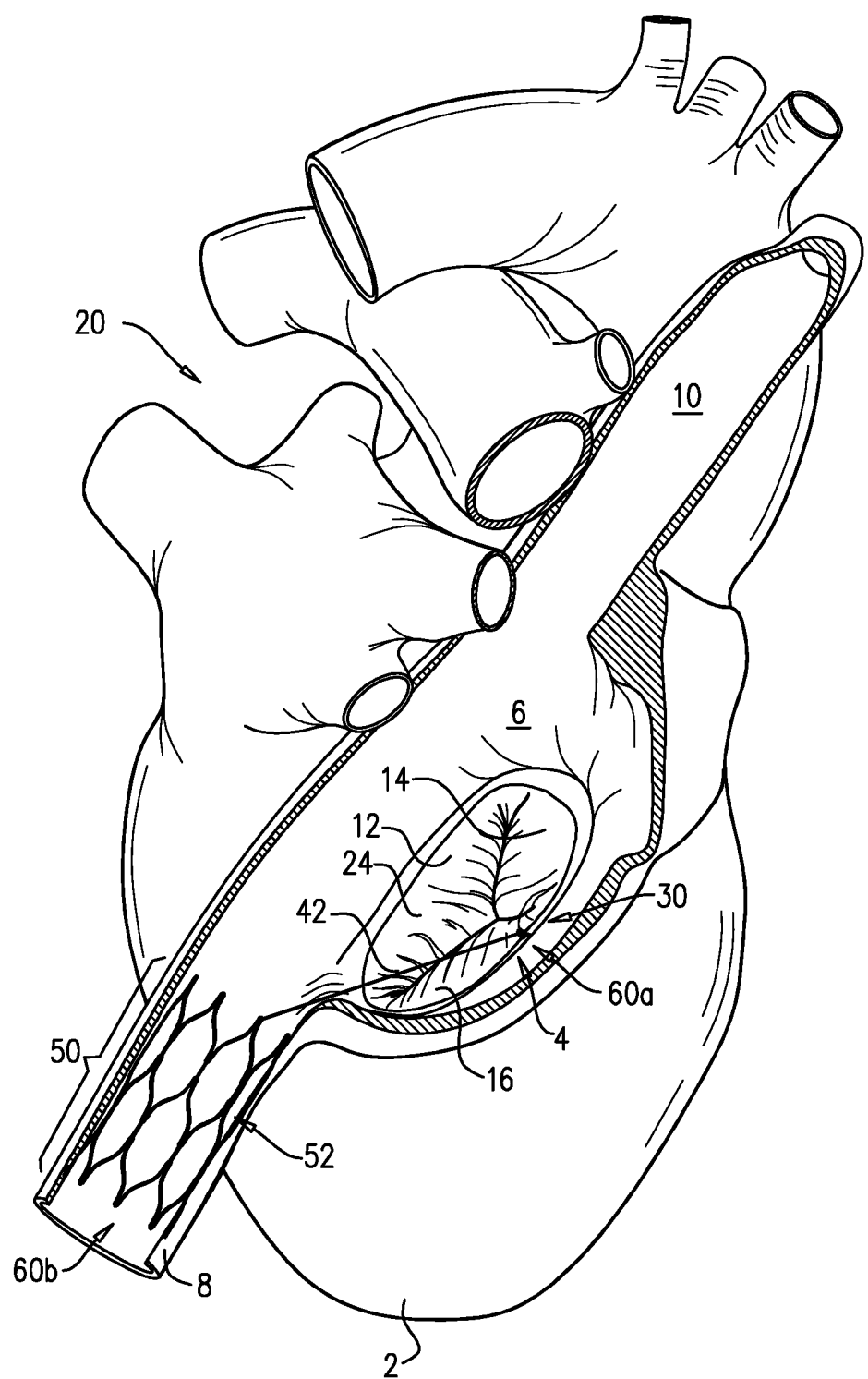

For some applications, such as shown in FIG. 1D, stent 50 comprises a plurality of interconnected superelastic metallic struts, arranged so as to allow crimping the stent into a relatively small diameter (typically less than 8 mm) catheter, while allowing deployment to a much larger diameter (typically more than 20 mm) in the vena cava, while still maintaining radial force against the vena cava tissue, in order to anchor stent 50 to the wall of the vena cava by friction.

For some applications, such as those described with reference to FIGS. 1A-D, longitudinal member 42 has a length of at least 10 mm, no more than 40 mm, and/or between 10 and 40 mm.

The configuration of stent 50 that is shown in FIG. 1D deployed in inferior vena cava 8 may instead be deployed in superior vena cava 10 (deployment not shown).

Reference is now made to FIGS. 7A-D, which are schematic illustrations of a delivery tool system 200 for implanting anchor 40, in accordance with some applications of the present invention. Delivery tool system 200 may be used, for example, to rotate and implant an anchor in combination with the applications described herein with reference to FIGS. 1A-D, 2A-B, 3A-C, 5A-B, 6, 8, 9, 13A-C, 14A-C, 15A-B, 16A-B, and 17. Although longitudinal member 42 is shown in FIGS. 7A-D as being fixed to stent 50, this is not necessarily the case, and tool system 200 thus may also be used in combination with the applications that do not utilize stent 50, such as those described herein with reference to FIGS. 3C and 5A-B.

Reference is now made to FIGS. 1A-D and 7A-D. It is to be noted that anchor 40 may be implanted using delivery tool system 200. FIG. 7A shows an exploded view of the components of delivery tool system 200 and its spatial orientation relative to stent 50, longitudinal member 42, and anchor 40. In such an application, a distal end of longitudinal member 42 comprises an annular loop 216, through which a portion of anchor 40 is coupled to the distal end of longitudinal member 42. For some such applications, stent 50, longitudinal member 42, and anchor 40 are not fabricated from the same piece, as described hereinabove, rather, only stent 50, longitudinal member 42, and annular loop 216 are typically fabricated from a single piece, and anchor 40 is coupled to longitudinal member 42 via annular loop 216. Alternatively, as mentioned above, longitudinal member 42 is not coupled to stent 50, such as for applications in which stent 50 is not provided.

System 200 typically comprises an adapter 218, which, for some applications, is shaped so as to define an annular proximal portion and a distal cylindrical portion having a distal end 220. During the manufacture of system 200, distal end 220 of the cylindrical portion of adapter 218 is slid through annular loop 218 at the distal end of longitudinal member 42, thereby coupling adapter 218 to the distal end of longitudinal member 42. Distal end 220 of adapter 218 is then welded or otherwise fixedly coupled to a proximal portion of an inner lumen of anchor 40, as shown in FIG. 7B. This coupling arrangement of anchor 40 to annular loop 216 and adapter 218 enables anchor 40 to rotate about a central longitudinal axis of delivery system 200, freely within annular loop 216. That is, delivery tool system 200 rotates anchor 40 without rotating longitudinal member 42 and stent 50 (if provided), as described hereinbelow.

Delivery tool system 200 comprises a delivery tool overtube 202 having a distal end thereof. For application in which stent 50 is provided, delivery tool overtube 202 is housed within catheter 22 such that a distal portion thereof passes in part through the lumen of stent 50 and a distal end 204 thereof extends toward tissue anchor 40. During delivery of tissue anchor 40 and stent 50 toward their respective implantation sites, deliver tool system 200 assumes the configuration shown in FIG. 7B. It is to be noted, however, that stent 50 is compressed around the portion of overtube 202 that extends through the lumen of stent 50 (not shown for clarity of illustration), and that catheter 22 (not shown for clarity of illustration) surrounds system 200 (and thereby compresses stent 50).

Reference is again made to FIG. 7A. Overtube 202 houses a torque-delivering and an anchor-pulling tube 208 and facilitates slidable coupling of tube 208 to overtube 202. A distal end of torque-delivering and anchor-pulling tube 208 is coupled to a manipulator 206 which is shaped so as to define a coupling 210 which couples manipulator 206 to adapter 218, and thereby, to anchor 40. In order to rotate anchor 40, torque-delivering and anchor-pulling tube 208 is rotated. As torque-delivering and anchor-pulling tube 208 is rotated, manipulator 206 is rotated in order to screw anchor 40 into the cardiac tissue of the patient. As adapter 218 rotates, the cylindrical portion thereof rotates freely within annular loop 216. This coupling arrangement of adapter 218 (and thereby anchor 40) to loop 216 (and thereby longitudinal member 42) enables the physician to rotate and implant anchor 40 without rotating longitudinal member 42 and stent 50 (if provided).

Following rotation of anchor 40, torque-delivering and anchor-pulling tube 208 is pulled by the physician in order to pull on anchor 40 and thereby on the portion of cardiac tissue to which anchor 40 is implanted at first implantation site 30. Tube 208 is typically coupled at a proximal end thereof to a mechanical element, e.g., a knob, at the handle portion outside the body of the patient. The physician pulls on tube 208 by actuating the mechanical element that is coupled to the proximal end of tube 208. This pulling of tube 208, and thereby of anchor 40 and of cardiac tissue at first implantation site 30, draws first implantation site toward second implantation site 52 and thereby draws at least anterior leaflet 14 toward septal leaflet 12 in order to achieve coaptation of the leaflets and reduce regurgitation through valve 4.

For some applications in which stent 50 is provided, following the pulling of anchor 40, stent 50 is positioned at second implantation site 52. Catheter 22 is then retracted slightly along tube 202 so as to pull taut longitudinal member 42 and to ensure that tension is maintained at first implantation site 30 and along longitudinal member 42. Stent 50 is then deployed when the physician holds torque-delivering and anchor-pulling tool 208 and then retracts proximally either (1) catheter 22 or (2) a sheath (i.e., that is disposed within catheter 22 and surrounds stent 50), around stent 50 so as to deploy stent 50 from within either (1) catheter 22 or (2) the sheath disposed within catheter 22.

It is to be noted that stent 50 is retrievable following at least partial deployment thereof, e.g., following deployment of up to ½ or up to ⅓ of stent 50. In such an application, following the initial retraction proximally of catheter 22 from around stent 50 in order to deploy at least a distal portion of stent 50, catheter 22 is advanceable distally so as to compress and retrieve the at least partially-deployed stent back into the distal end portion of catheter 22. Alternatively, catheter 22 houses a sheath which compresses stent 50 during delivery of stent to second implantation site 52. During the initial retracting of catheter 22 proximally, the sheath surrounding stent 50 is also retracted in conjunction with the retracting of catheter 22. Following the at least partial deployment of stent 50 in order to deploy at least a distal portion of stent 50, the sheath is advanceable distally (while catheter 22 remains in place) so as to compress and retrieve the at least partially-deployed stent back into the distal end portion of the sheath. The sheath is then retracted into catheter 22. For such applications of the present invention in which stent 50 is retrievable following at least partial deployment thereof, anchor 40 can then be unscrewed from first implantation site 30 and the entire implant system may be extracted from the body, or repositioned in the heart, depending on the need of a given patient.

For applications in which stent 50 is retrievable, in order to retrieve stent 50 (i.e., prior to the decoupling of manipulator 206 from adapter 218 and thereby from anchor 40), the physician holds torque-delivering and anchor-pulling tool 208 and then advances distally either (1) catheter 22 or (2) the sheath disposed within catheter 22, around stent 50 so as to compress stent 50 within either (1) catheter 22 or (2) the sheath disposed within catheter 22. Torque-delivering and anchor-pulling tool 208 may then be rotated in order to unscrew anchor 40 from the tissue, and the entire system may be extracted from the body, or repositioned in the heart, depending on the need of a given patient.

Reference is again made to FIGS. 7A-D. FIGS. 7C-D show the decoupling and release of torque-delivering and anchor-pulling tube 208 and manipulator 206 from adapter 218 and anchor 40. This release occurs typically following the deployment of stent 50 (if provided), as described hereinabove. As shown in FIG. 7A, system 200 comprises a releasable adapter holder 212 which is shaped so as to define arms 214 which have a tendency to expand radially. Holder 212 surrounds manipulator 206, as shown in FIG. 7C. During the delivery of anchor 40 toward implantation site 30 and the subsequent rotation of anchor 40 to screw anchor 40 into tissue at site 30, a distal end 204 of overtube 202 is disposed adjacently to loop 216 such that a distal end portion of overtube 202 surrounds and compresses arms 214 of holder 212 (as shown in FIG. 7B). Following the pulling of anchor 40 by torque-delivering and anchor-pulling tube 208, overtube 202 is retracted slightly in order to expose arms 214 of holder 212. Responsively, arms 214 expand radially (FIG. 7C) and release adapter 218 (and thereby anchor 40) from holder 212.

As shown in FIG. 7D, overtube 202 is held in place while the physician retracts tube 208 so as to collapse and draw arms 214 into the distal end portion of overtube 202. Overtube 202 is then slid proximally within catheter 22 leaving behind anchor 40, adapter 218 coupled to anchor 40, loop 216, longitudinal member 42, and stent 50 (if provided). Catheter 22, that houses overtube 202 and the components disposed therein, is extracted from the body of the patient.

For some applications, such as those described hereinabove with reference to FIGS. 7A-D, longitudinal member 42 has a length of at least 10 mm, no more than 40 mm, and/or between 10 and 40 mm.

Reference is again made to FIGS. 1A-D. It is to be noted that tissue-engaging elements 60*a* and 60*b* may be implanted at their respective implantation sites 30 and 50, as described hereinabove, by advancing catheter 22 and tissue-engaging elements 60*a* and 60*b* through superior vena cava 10, mutatis mutandis.

Figure 2A:
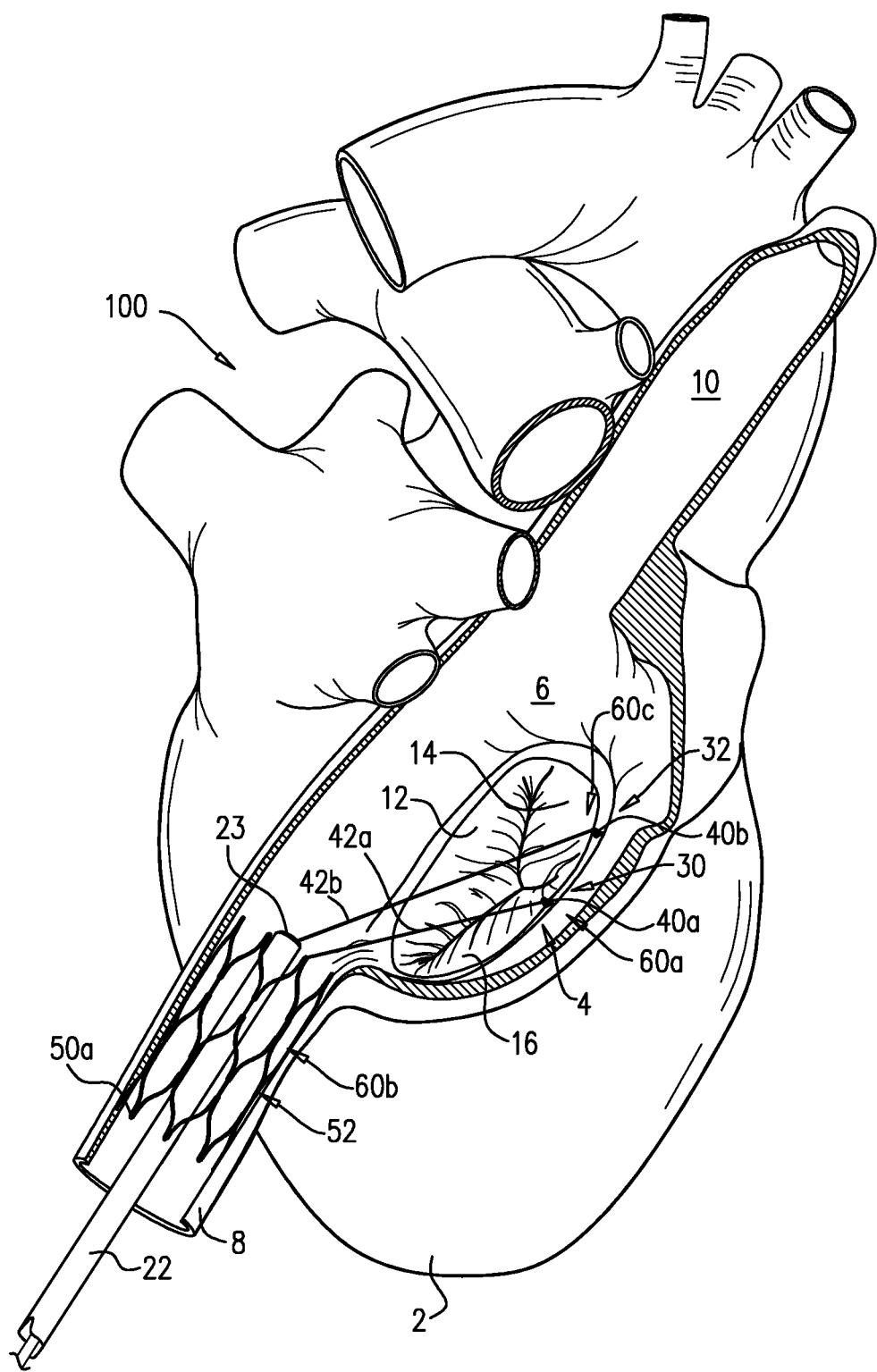
FIGS. 2A-B are schematic illustrations of apparatus for reducing regurgitation of the heart valve which comprises first and second stents, first and second tissue anchor, and first and second tensioning elements, in accordance with some applications of the present invention.
Figure 2B:
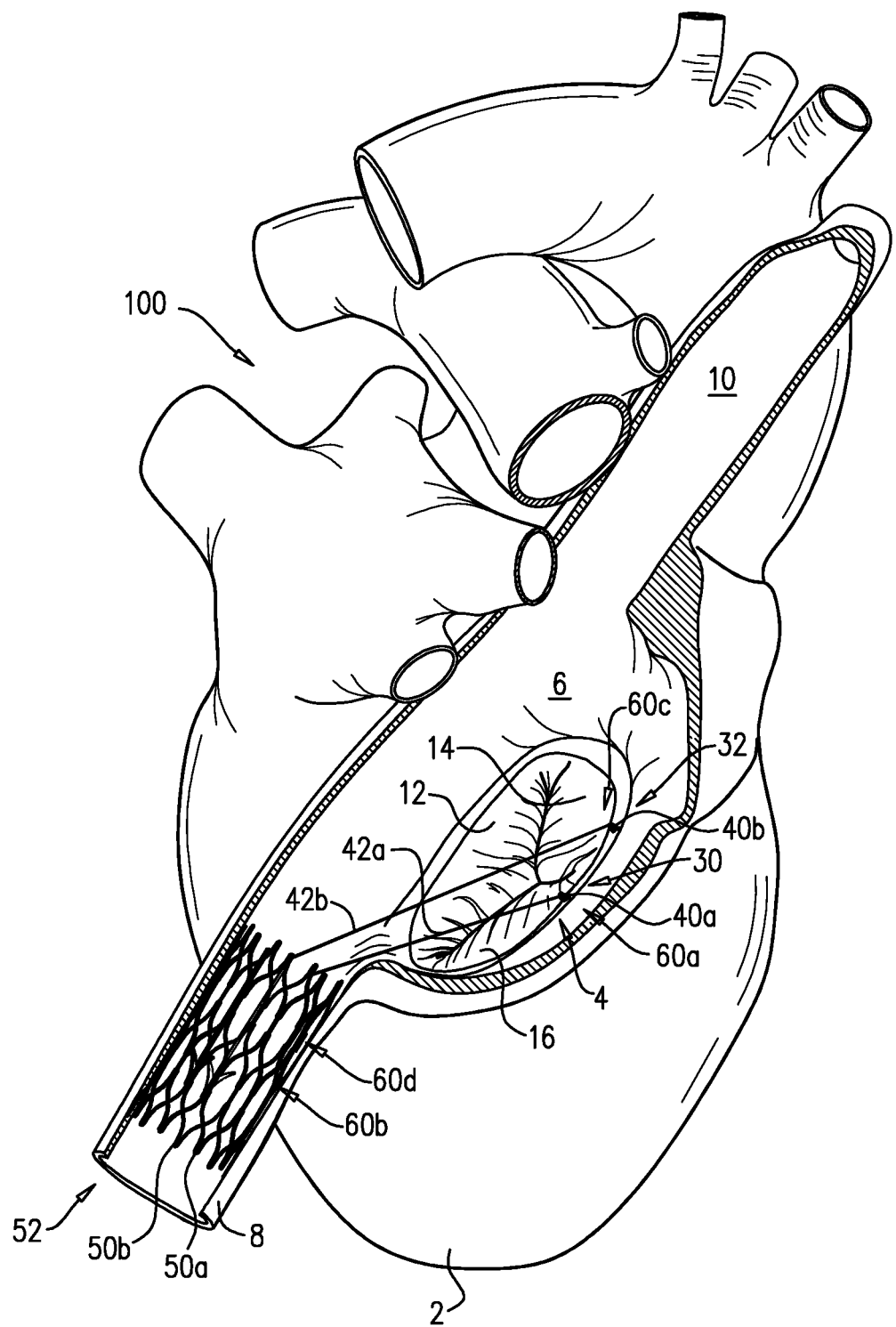

FIGS. 2A-B show a system 100 for repairing tricuspid valve 4 comprising first and second stents 50*a* and 50*b*, first and second longitudinal members 42*a* and 42*b*, and first and second tissue anchors 40*a* and 40*b*. First tissue anchor 40*a* defines first tissue-engaging element 60*a*. First stent 50*a* defines second tissue-engaging element 60*b*. Second tissue anchor 40*b* defines a third tissue-engaging element 60*c*. Second stent 50*b* defines a fourth tissue-engaging element 60*d*. For some applications of the present invention, following the implantation of first tissue-engaging element 60*a* and second tissue-engaging element 60*b*, such as described hereinabove with reference to FIGS. 1A-D, third and fourth tissue-engaging elements 60*c* and 60*d* are then implanted. As described hereinabove, first implantation site 30, as shown, comprises a portion of tissue that is in a vicinity of the commissure between anterior leaflet 14 and posterior leaflet 16. First implantation site 30 may comprise a portion of tissue that is between (1) the middle of the junction between the annulus and anterior leaflet 14, and (2) the middle of the junction between the annulus and posterior leaflet 16.

Following the implantation of first and second tissue-engaging elements 60*a* and 60*b*, catheter 22 is retracted from the body of the patient. Outside the body of the patient, catheter 22 is reloaded with third and fourth tissue-engaging elements 60*c* and 60*d*. Catheter 22 is then reintroduced within the body of the patient and is advanced toward right atrium 6, as shown in FIG. 2A, such that distal end 23 thereof passes through first stent 50*a* and toward atrium 6. It is to be noted that a proximal end portion of longitudinal member 42*a* is coupled to second tissue-engaging element 60*b* and is not disposed within catheter 22.

Subsequently, a second tissue anchor 40*b* (i.e., an anchor that is similar to tissue anchor 40*a*, as described hereinabove) is implanted at a second portion of cardiac tissue at a third implantation site 32. Third implantation site 32 includes a portion of cardiac tissue in the vicinity of tricuspid valve 4 (e.g., a second portion of tissue of the annulus of tricuspid valve 4, as shown). Third implantation site 32, as shown, comprises a portion of tissue that is between (1) the middle of the junction between the annulus and anterior leaflet 14, and (2) the middle of the junction between the annulus and posterior leaflet 16. For some applications, third implantation site 32 may comprise a second portion of the wall that defines right atrium 6. For other applications, third implantation site 32 may comprise a portion of cardiac tissue in the right ventricle, e.g., a portion of the wall that defines the right ventricle, a ventricular portion of the annulus of tricuspid valve 4, or a portion of a papillary muscle of the right ventricle.

Following implantation of third tissue-engaging element 60*c*, catheter 22 is retracted and tension is applied to third tissue-engaging element 60*c* in a manner as described hereinabove with reference to FIGS. 1C-D with regard to the application of tension to implantation site 30. Additionally, tension is applied to a second longitudinal member 42*b* which couples third and fourth tissue-engaging elements 60*c* and 60*d*, e.g., in a manner as described hereinabove with regard to the pulling of first longitudinal member 42*a*, with reference to FIG. 1C. As described herein, a level of regurgitation of tricuspid valve 4 may be monitored during the pulling tissue of third implantation site 32 toward second implantation site 52 and of second longitudinal member 42*b*.

Additionally, responsively to the pulling of tissue at first and third implantation sites 30 and 32 toward second implantation site 52, anterior leaflet 14 is drawn toward septal leaflet 12, and bicuspidization is achieved. Also, responsively to the pulling, a portion of tissue that is between first and third implantation sites 30 and 32 is cinched. Further, responsively to the pulling, posterior leaflet 16 is reduced and moved out of a plane of tricuspid valve 4 during the bicuspidization.

Reference is now made to FIG. 2B. Once the physician determines that the regurgitation of tricuspid valve 4 is reduced or ceases, and tricuspid valve 4 has been repaired, catheter 22 is decoupled from fourth tissue-engaging element 60*d* and/or from second longitudinal member 42*b*, and the physician retracts catheter 22 in order to expose fourth tissue-engaging element 60*d*. i.e., second stent 50*b*, as shown. During the advancement of catheter 22 toward atrium 6, second stent 50*b* is disposed within a distal portion of catheter 22 in a compressed state. Following initial retracting of catheter 22, second stent 50*b* is exposed and is allowed to expand within a lumen of first stent 50*a*, as shown, in order to contact a wall of inferior vena cava 8. Responsively to the expanding, second stent 50*b* is implanted in second implantation site 52 and maintains the tension of second longitudinal member 42*b* on second tissue anchor 40*b* and thereby on the portion of cardiac tissue to which anchor 40*b* is coupled.

It is to be noted that second stent 50*b* is implanted within the lumen of first stent 50*a* by way of illustration and not limitation, and that for some applications of the present invention, first and second stents 50*a* and 50*b* may be implanted coaxially at second implantation site 52.

It is to be noted that third and fourth tissue-engaging elements 60*c* and 60*d* and second longitudinal member 42*b* are typically fabricated from the same material, e.g., nitinol, from a single piece. That is, third and fourth tissue-engaging elements 60*c* and 60*d* and second longitudinal member 42*b* typically define a single continuous implant unit.

Figure 3A:
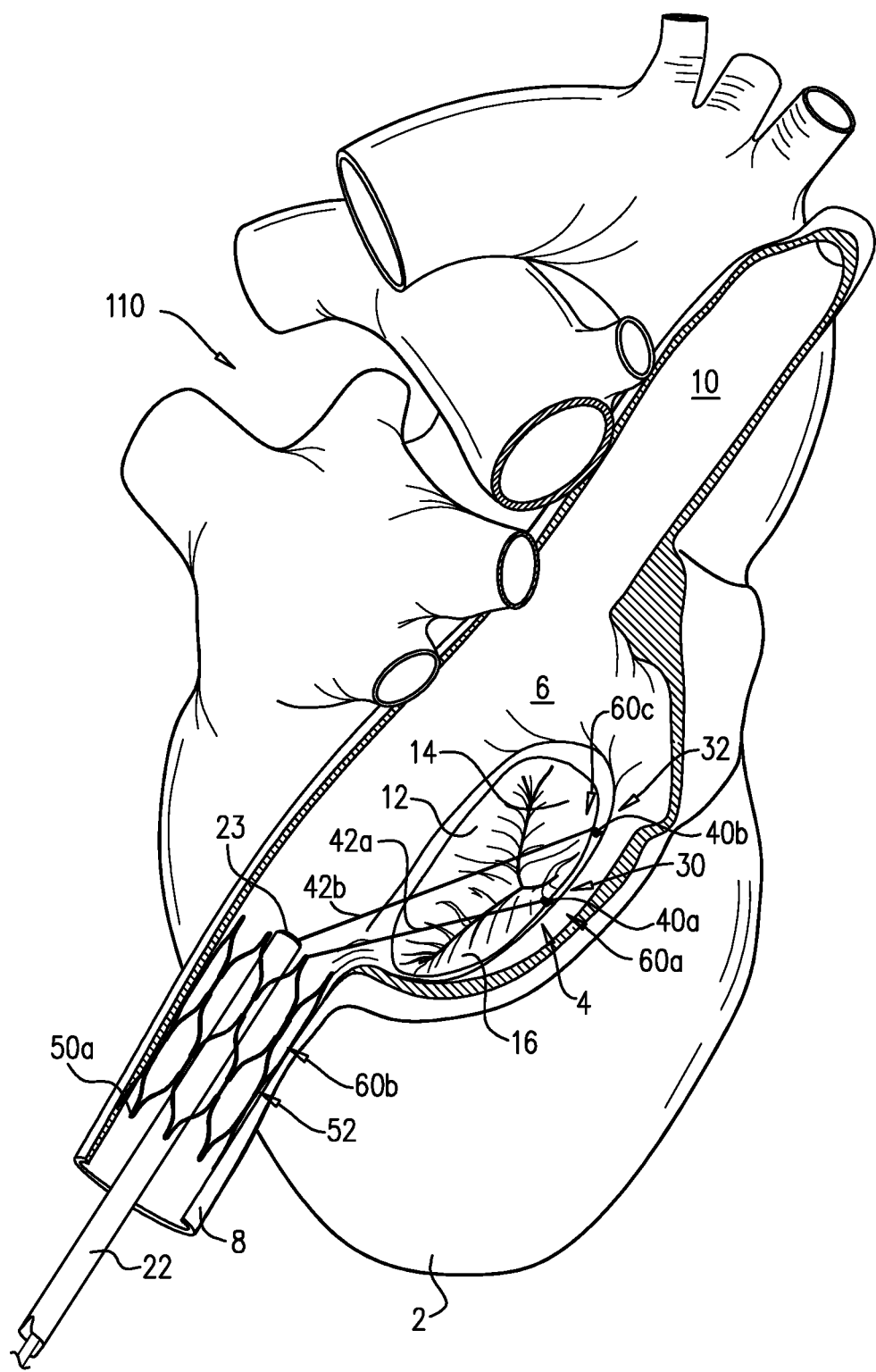
Figure 3B:
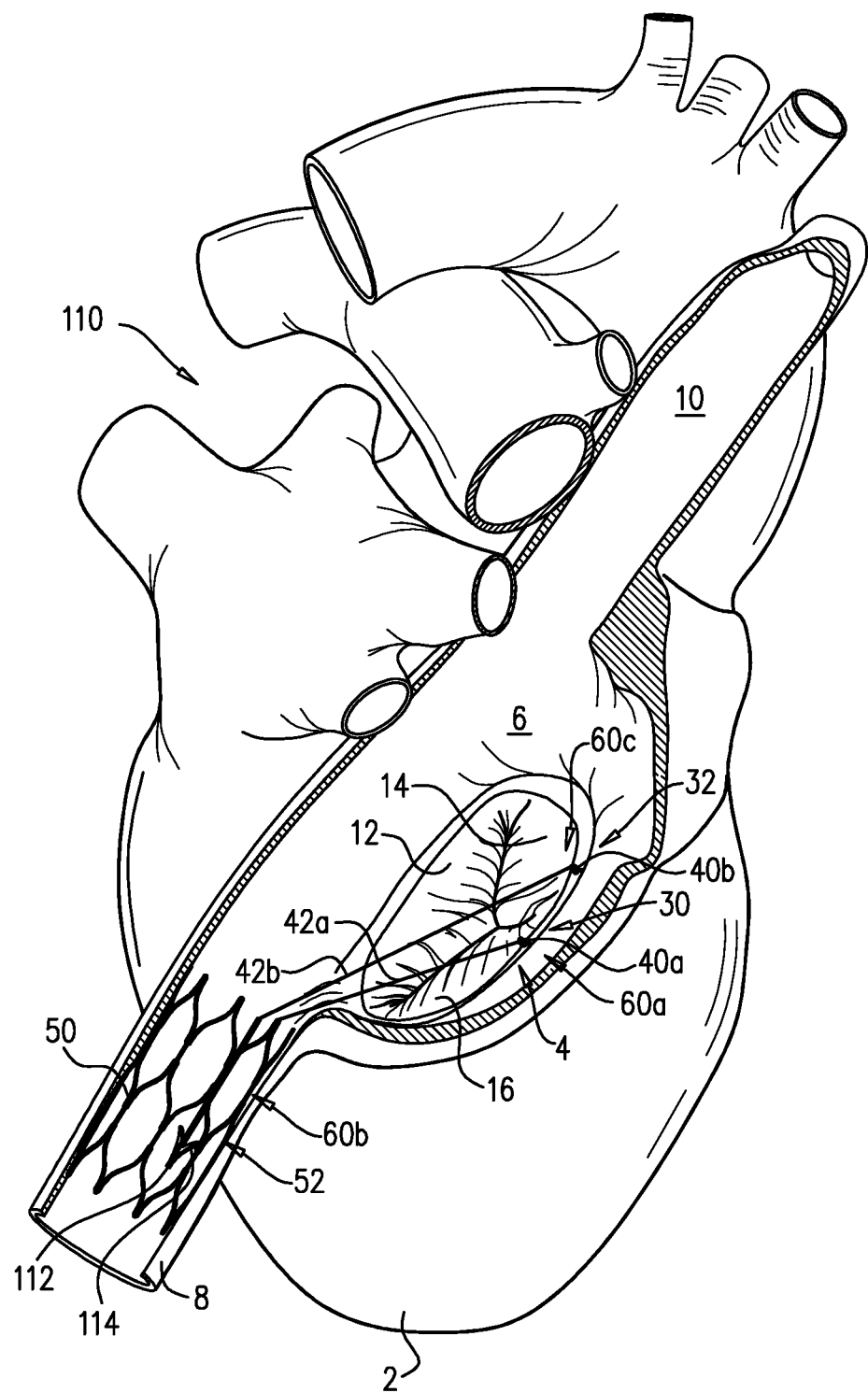

Reference is now made to FIGS. 3A-C, which are schematic illustrations of a system 110 for repairing tricuspid valve 4, which comprises first, second, and third tissue-engaging elements 60*a*, 60*b*, and 60*c*, and first and second longitudinal members 42*a* and 42*b*, in accordance with some applications of the present invention. System 110 is similar to system 100 described hereinabove with reference to FIGS. 2A-B, with the exception that system 110 does not comprise second stent 50*b*; rather, as shown in FIGS. 3B-C, a proximal end portion 112 of second longitudinal member 42*b* is shaped so as to define one or more engaging elements 114 (e.g., hooks or barbs, as shown). Following the implanting of third tissue-engaging element 60*c* and the subsequent pulling of second longitudinal member 42*b*, catheter 22 facilitates coupling of engaging elements 114 with the struts of stent 50 (as shown in FIG. 3C which is an enlarged image of stent 50 and the proximal portion of second longitudinal member 42*b* of FIG. 3B). The coupling of engaging elements 114 to stent 50 maintains the tension applied to longitudinal member 42, and thereby maintains the tension on third tissue-engaging element 60*c* in order to maintain the remodeled state of tricuspid valve 4.

It is to be noted that third tissue-engaging element 60*c*, second longitudinal member 42*b*, and engaging elements 114 and proximal end portion 112 of second longitudinal member 42*b* are typically fabricated from the same material, e.g., nitinol, from a single piece. That is, third tissue-engaging element 60*c*, second longitudinal member 42*b*, and engaging elements 114 and proximal end portion 112 of second longitudinal member 42*b* typically define a single continuous implant unit.

Reference is now made to FIGS. 2A-B and 3A-C. For some applications, following the implantation the tissue-engaging elements at their respective implantation sites, as described hereinabove, a length of each one of first and second longitudinal members 42*a* and 42*b* is adjusted by an adjustable mechanism, as described hereinbelow with reference to FIGS. 5A-B. Adjusting mechanism 150 typically comprises a mechanical element which shortens a length of each one of first and second longitudinal members 42*a* and 42*b*. For some applications, a respective adjustable mechanism 150 may be permanently coupled to each one of first and second longitudinal members 42*a* and 42*b* (not shown); each mechanism 150 comprises an adjusting element, e.g., a spool for looping respective portions of longitudinal members 42*a* and 42*b* therearound, a crimping bead for crimping and shortening respective portions of longitudinal members 42*a* and 42*b*, a ratchet element, or a deforming element which deforms respective portions of longitudinal members 42*a* and 42*b*. For other applications, the adjusting mechanism comprises only an adjusting tool which may comprise an adjusting element, e.g., a crimping bead for crimping and shortening respective portions of longitudinal members 42*a* and 42*b*, or a deforming element which deforms respective portions of longitudinal members 42*a* and 42*b*. In either application, a level of regurgitation of tricuspid valve 4 may be monitored during the adjusting of the respective lengths of first and second longitudinal members 42*a* and 42*b*.

Figure 4A:
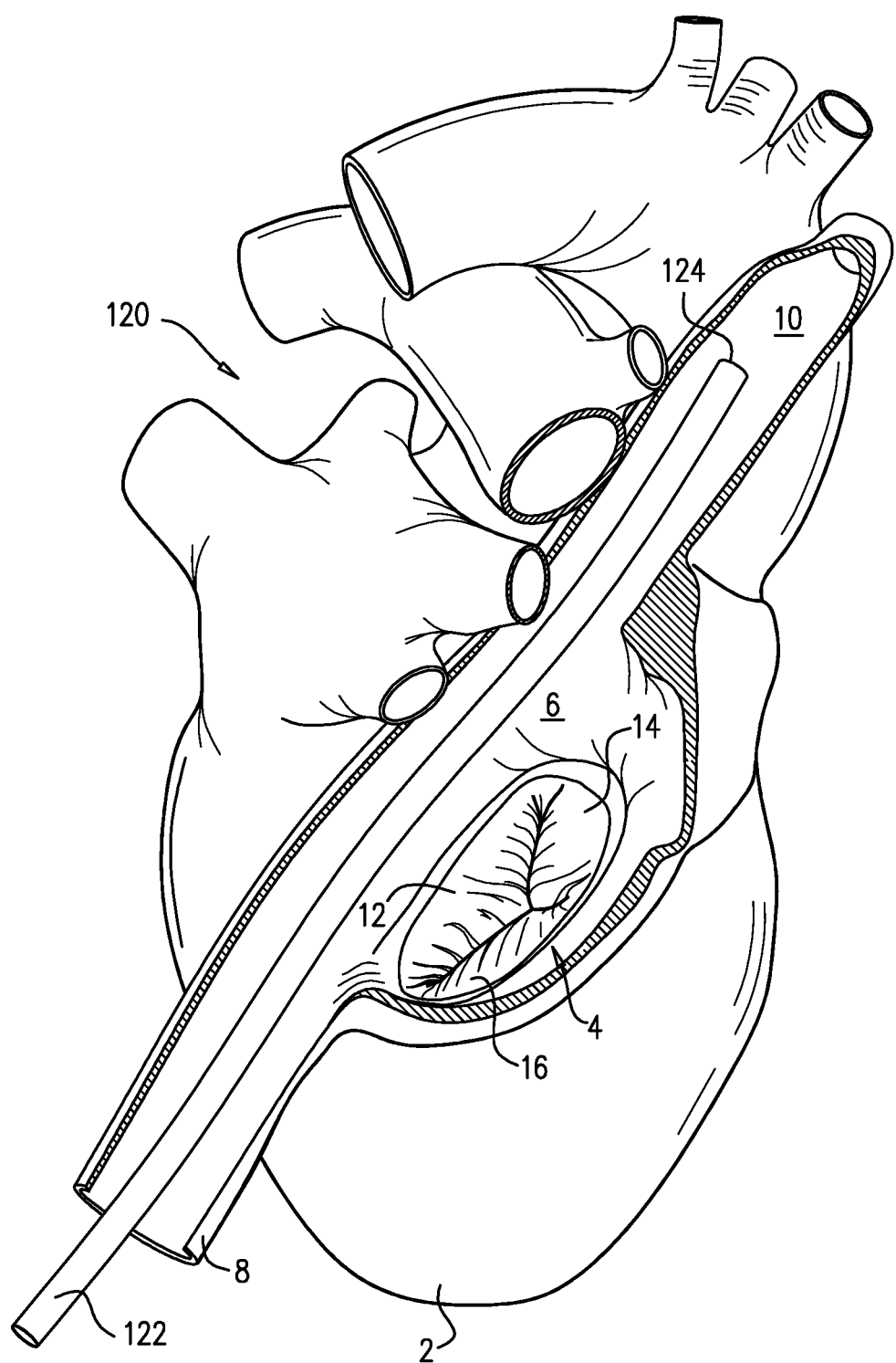
FIGS. 4A-C are schematic illustrations of apparatus for reducing regurgitation of a tricuspid valve which comprises first and second stents and first and a tensioning element that couples the first and second stents, in accordance with some applications of the present invention.
Figure 4B:
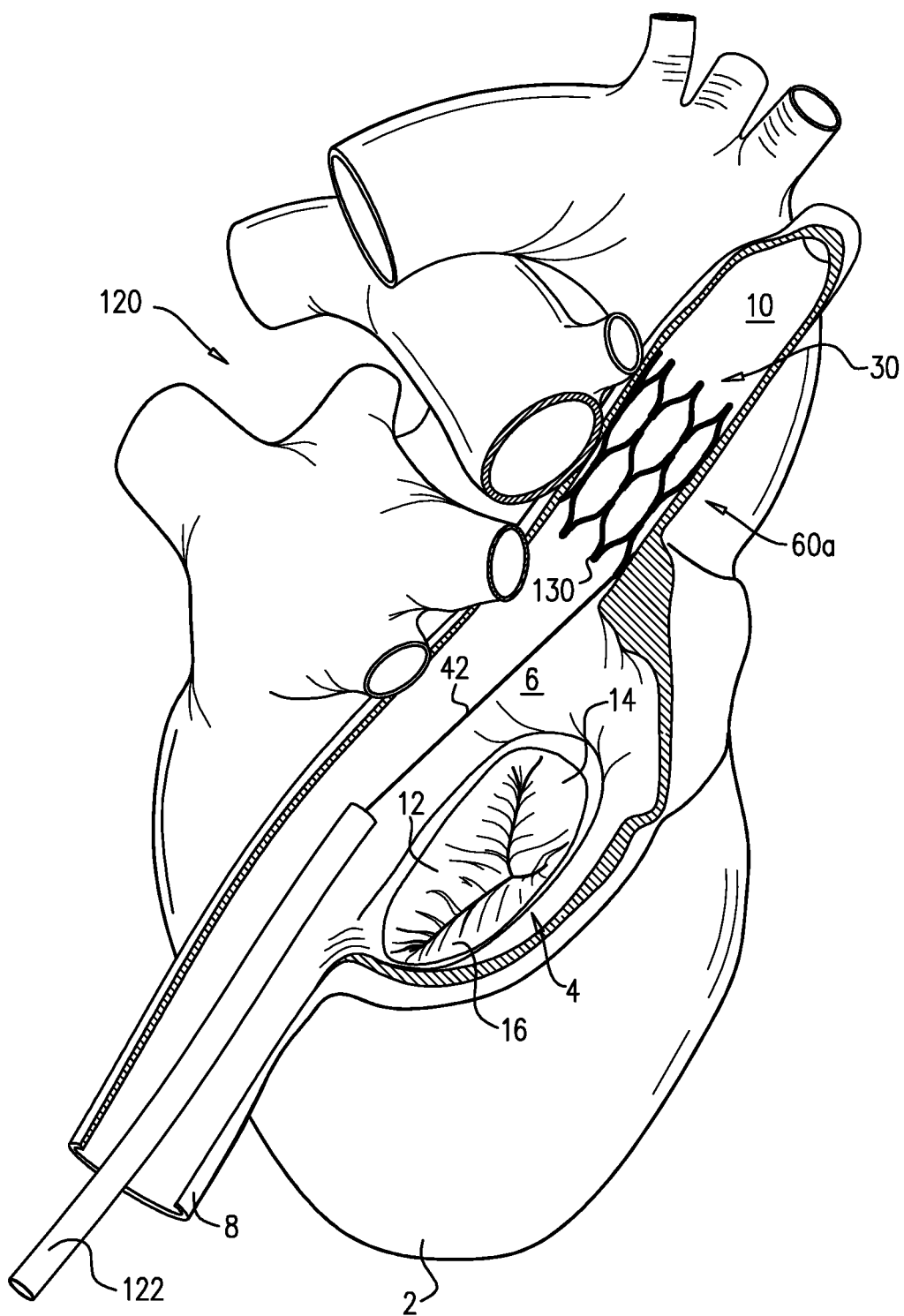
Figure 4C:
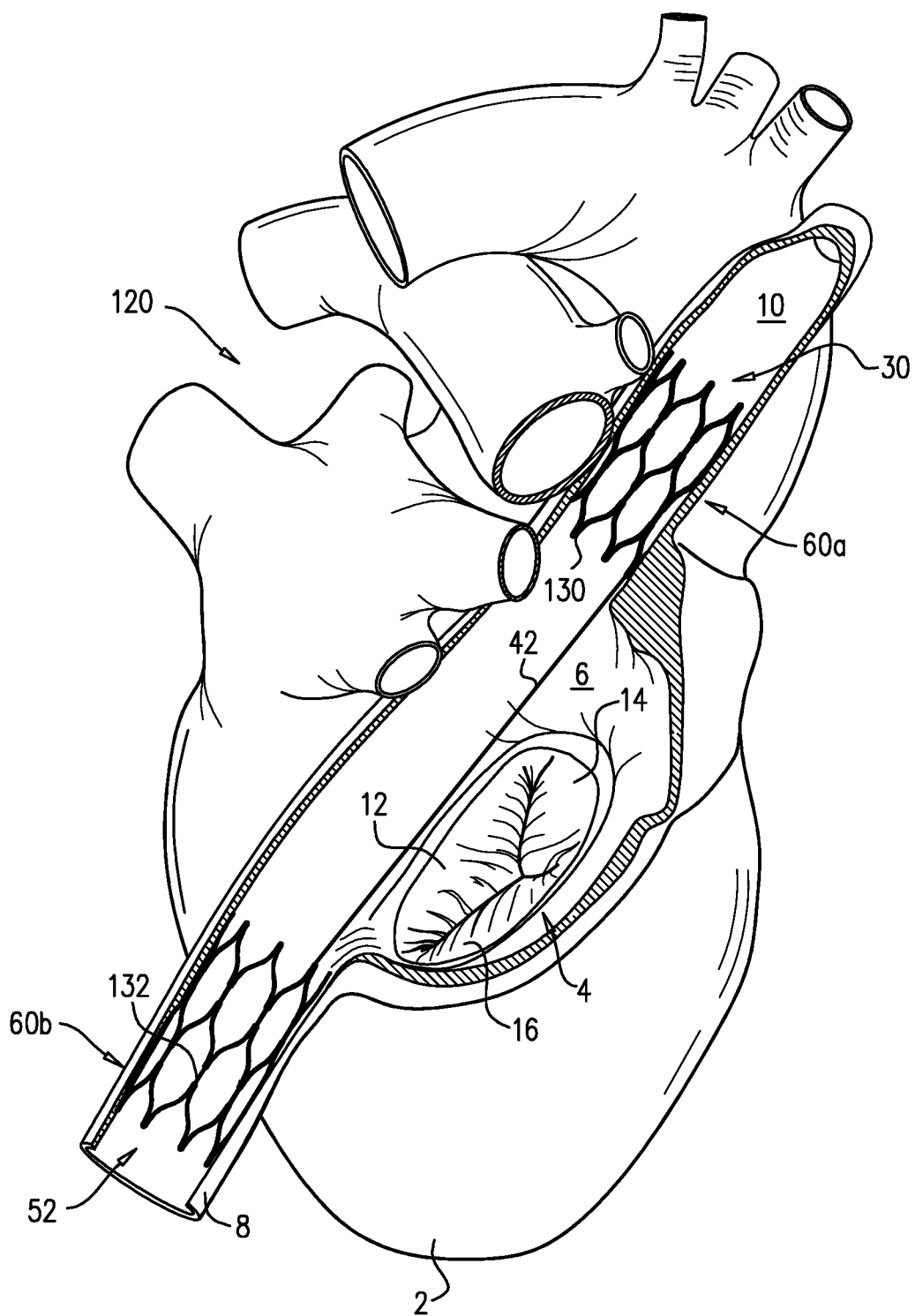

FIGS. 4A-C show a system 120 for repairing tricuspid valve 4 comprising first and second stents 130 and 132 implanted in superior vena cava 10 and inferior vena cava, respectively, in accordance with some applications of the present invention. A catheter 122 is advanced through vasculature of the patient such that a distal end 124 of catheter 122 toward superior vena cava 10, as shown in FIG. 4A. Catheter 122 is advanced from a suitable access location, e.g., catheter 122 may be introduced into the femoral vein of the patient, through inferior vena cava 8, and toward superior vena cava 10. During the advancement of catheter 122 toward superior vena cava 10 and inferior vena cava 8, stents 130 and 132 are disposed within a distal portion of catheter 122 in a compressed state.

In FIG. 4B, first stent 130 is deployed from within catheter 122 and expands to contact tissue of a wall of superior vena cava 10. This portion of the wall of the superior vena cava defines first implantation site 30 in such applications of the present invention. Additionally, first stent member 130 defines first tissue-engaging element 60*a* in such applications of the present invention. It is to be noted that the portion of superior vena cava 10 in which stent 130 is implanted defines a portion of tissue that is in the vicinity of tricuspid valve 4.

Catheter 122 is then retracted so as to pull and apply tension to longitudinal member 42. Longitudinal member 42 is pulled directly by catheter 122 and/or indirectly by pulling stent member 132 disposed within catheter 122. For some applications, during the pulling, a level of regurgitation of tricuspid valve 4 may be monitored, because responsively to the pulling, the geometry of the wall of atrium 6 is altered and the leaflets of tricuspid valve 4 are drawn together so as to reduce and eliminate regurgitation of tricuspid valve 4.

Once the physician determines that the regurgitation of tricuspid valve 4 is reduced or ceases, and tricuspid valve 4 has been repaired, the physician decouples catheter 122 from second stent member 132 disposed therein and/or from longitudinal member 42, and then retracts catheter 122 in order to expose second tissue-engaging element 60*b*, i.e., second stent member 132, as shown. Following initial retracting of catheter 122, second stent member 132 is exposed and is allowed to expand and contact a wall of inferior vena cava 8, as shown in FIG. 4C. Responsively to the expanding, second stent member 132 is implanted in second implantation site 52 and maintains the tension of longitudinal member 42 on first stent member 130 and thereby maintains the altered geometry of the wall of atrium 6 and of the leaflets of tricuspid valve 4.

Reference is again made to FIGS. 4A-C. For some applications, following the deploying of first and second tissue-engaging elements 60a and 60b (i.e., first and second stents 130 and 132, respectively), a distance between first and second tissue-engaging elements 60a and 60b is adjusted by an adjustable mechanism, as described hereinbelow with reference to FIGS. 5A-B. In such applications, a length of longitudinal member 42 between first and second stents 130 and 132 may be adjusted by an adjusting mechanism 150, as shown in FIGS. 5A-B. Adjusting mechanism 150 typically comprises a mechanical element which shortens a distance of longitudinal member 42 between first and second stents 130 and 132. For some applications, adjustable mechanism 150 may be permanently coupled to longitudinal member 42 (not shown) and comprises an adjusting element, e.g., a spool for looping portions of longitudinal member 42 therearound, a crimping bead for crimping and shortening a portion of longitudinal member 42, a ratchet element, or a deforming element which deforms a portion of longitudinal member 42 in order to shorten its length between first and second stents 130 and 132. A level of regurgitation and repair of tricuspid valve 4 may be monitored during the adjusting of the distance between first and second tissue-engaging elements 60a and 60b by adjusting mechanism 150.

It is to be noted that first and second stents 130 and 132 and longitudinal member 42 are typically fabricated from the same material, e.g., nitinol, from a single piece. That is, first and second stents 130 and 132 and longitudinal member 42 typically define a single continuous implant unit.

Reference is yet again made to FIGS. 4A-C. It is to be noted that distal end 124 of catheter 122 may first be advanced toward inferior vena cava, and not first toward superior vena cava, as shown in FIG. 4A. In such an embodiment, catheter 122 may be introduced into the external jugular vein, through the subclavian vein, through superior vena cava 10, and toward inferior vena cava 8. Alternatively, catheter 122 may be introduced into the basilic vein, through the subclavian vein, through superior vena cava 10 and toward inferior vena cava 8. It is to be noted that any suitable access location may be used to introduce catheter 122 into the vasculature of the patient.

Reference is still made to FIGS. 4A-C. For some applications, one or both of stents 130 and/or 132 comprise a plurality of interconnected superelastic metallic struts, such as described hereinabove with reference to FIG. 1D.

Reference is now made to FIGS. 5A-B, which are schematic illustrations of a system 140 for repairing tricuspid valve 4 comprising first and second tissue anchors 40a and 40b coupled together by longitudinal member 42, in accordance with some applications of the present invention. In such applications, first tissue anchor 40a defines first tissue-engaging element 60a, and second tissue anchor 40b defines second tissue-engaging element 60b. Tissue anchors 40a and 40b may comprise any suitable anchor for puncturing, squeezing, or otherwise engaging cardiac tissue of the patient. As shown by way of illustration and not limitation, tissue anchors 40a and 40b comprise helical tissue anchors which puncture and screw into the cardiac tissue. It is to be noted that first and second tissue-engaging elements 60a and 60b (i.e., first and second tissue anchors 40a and 40b) and longitudinal member 42 are fabricated from the same material, e.g., nitinol, from a single piece. That is, first and second tissue-engaging elements 60a and 60b and longitudinal member 42 define a single continuous implant unit.

A delivery catheter is advanced through vasculature of the patient, in manner as described hereinabove with regard to catheter 22 with reference to FIG. 1A. The catheter is advanced toward first implantation site 30 and facilitates implantation of first tissue anchor 40a in the cardiac tissue. As shown, first implantation site 30 includes a first portion of tissue of the annulus of tricuspid valve 4 at the mural side of tricuspid valve 4, by way of illustration and not limitation. For some applications, first implantation site 30 may include a first portion of the wall of atrium 6 of heart 2. As shown by way of illustration and not limitation, first implantation site 30 includes a portion of tissue of the annulus at the commissure between anterior leaflet 14 and posterior leaflet 16. It is to be noted that first implantation site 30 may be implanted at any suitable location along and in the vicinity of the annulus of tricuspid valve 4.

The delivery catheter is then advanced toward second implantation site 52 and facilitates implantation of second tissue anchor 40b in the cardiac tissue. For some applications, as the catheter is advanced toward second implantation site, longitudinal member 42 is pulled to draw together the leaflets of tricuspid valve 4, while a level of regurgitation of tricuspid valve 4 is monitored. As shown, second implantation site 52 includes a second portion of tissue of the annulus of tricuspid valve 4 at the septal side of tricuspid valve 4, by way of illustration and not limitation. For some applications, second implantation site 52 may include a second portion of the wall of atrium 6 of heart 2. As shown by way of illustration and not limitation, second implantation site 52 includes a portion of tissue of the annulus inferior of the middle of septal leaflet 12. It is to be noted that first implantation site 30 may be implanted at any suitable location along and in the vicinity of the annulus of tricuspid valve 4, e.g., at the commissure between posterior leaflet 16 and septal leaflet 12.

For such an application, by applying tension to longitudinal member 42, anterior leaflet 14 and septal leaflet 12 are drawn together, and bicuspidization of tricuspid valve 4 is achieved. For some applications, during the adjusting of mechanism 150, a retrievable stent may be deployed in inferior vena cava 8 so as to stabilize system 140 during the adjusting of adjusting mechanism 150. It is to be further noted that tissue-engaging elements 60a and 60b and the delivery catheter may be advanced toward atrium 6 through superior vena cava, mutatis mutandis.

For some applications of the present invention, system 140 comprises one or more anchor-manipulating tools (not shown for clarity of illustration), that is slidably disposed within the delivery catheter. The anchor-manipulating tool is slid distally with within the catheter so as to push distally tissue anchors 40a and 40b and expose tissue anchors 40a and 40b from within the catheter. For some applications of the present invention, the anchor-manipulating tool(s) is/are reversibly couplable to anchors 40a and 40b, and facilitate(s) implantation of anchors 40a and 40b in the cardiac tissue. For applications in which anchors 40a and 40b comprises respective helical tissue anchor, as shown, the operating physician rotates the anchor-manipulating tool(s) from a site outside the body of the patient in order to rotate anchors 40a and 40b, and thereby screw at least respective distal portions of anchors 40a and 40b in the cardiac tissue.

Reference is again made to FIGS. 5A-B. It is to be noted that first and second implantation sites 30 and 52 include cardiac tissue that is upstream of tricuspid valve 4 by way of illustration and not limitation, and that either or both first and second implantation sites may include cardiac tissue that is downstream of tricuspid valve 4.

Typically, following implantation of first and second tissue anchors 40a and 40b, a length of longitudinal member 42, that is disposed between first and second tissue anchors 40a and 40b, is adjusted by adjusting mechanism 150. Adjusting mechanism 150 typically comprises a mechanical element which shortens a distance of longitudinal member 42 between first and second tissue-engaging elements 60a and 60b. For some applications, adjustable mechanism 150 may be permanently coupled to longitudinal member 42 (as shown in FIG. 5B) and comprises an adjusting element, e.g., a spool for looping portions of longitudinal member 42 therearound, a crimping bead for crimping and shortening a portion of longitudinal member 42, a ratchet element, or a deforming element which deforms a portion of longitudinal member 42 in order to shorten its length between first and second tissue-engaging elements 60a and 60b.

For other applications, system 140 comprises only an adjusting tool (which functions as an adjusting mechanism) and not adjusting mechanism 150. In such applications, the adjusting tool may comprise an adjusting element, e.g., a crimping bead for crimping and shortening a portion of longitudinal member 42, or a deforming element which deforms a portion of longitudinal member 42 in order to shorten its length between first and second tissue-engaging elements 60a and 60b.

In either application, a level of regurgitation of tricuspid valve 4 may be monitored during the adjusting of the distance between first and second tissue-engaging elements 60a and 60b by adjusting mechanism 150.

Following the adjusting of the distance between first and second implantation sites 30 and 52, the adjusting tool and the delivery catheter are decoupled from longitudinal member 42 and are extracted from the body of the patient.

Reference is now made to FIG. 5B, which is a schematic illustration of another configuration of system 140, in accordance with some applications of the present invention. This configuration of system 140 is generally similar to the configuration described above with reference to FIG. 5A, except that the system comprises a third tissue-engaging element 60c (i.e., a third tissue anchor), in addition to first and second tissue-engaging elements 60a and 60b. Third tissue-engaging element 60c is implanted at third implantation site 32, such as using the techniques described hereinabove with reference to FIG. 5A. For some applications, third implantation site 32 may include a third portion of the wall of atrium 6. By way of illustration and not limitation, the three implantation sites may include portions of tissue of the annulus of the three leaflets of the valve, such as at the middle of the leaflets.

Tissue-engaging elements 60a, 60b, and 60c are coupled to longitudinal members 42a, 42b, and 42c, respectively. The longitudinal members are coupled together by adjusting mechanism 150. For some applications, adjusting mechanism 150 comprises a spool for looping portions of the longitudinal members therearound, and a ratchet element which allows the spool to rotate in only one direction. Rotation of the spool loops the longitudinal member therearound, thereby shortening the effective lengths of the members and applying tension thereto, to draw the leaflets toward one another, such as described hereinabove with reference to FIG. 5A. As a result, a geometry of the wall of the right atrium may be altered.

Figure 6:
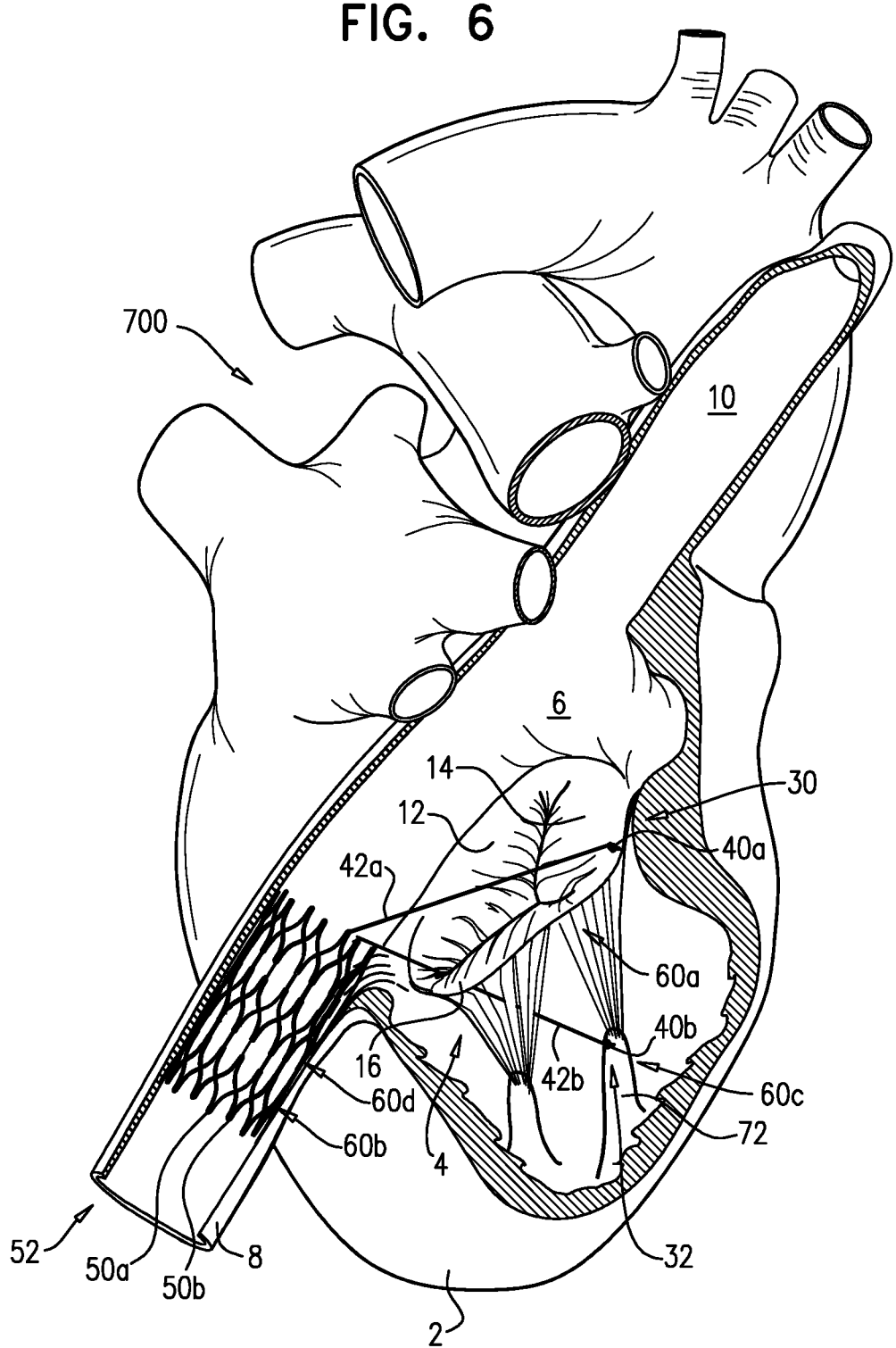
FIG. 6 is a schematic illustration of apparatus for reducing regurgitation of the heart valve which comprises a first anchoring system in the inferior vena cava, a first tissue anchor implanted at the valve, and a second tissue anchor implanted in the papillary muscle.

Reference is now made to FIG. 6 which is a schematic illustration of a system 700 for repairing tricuspid valve 4 comprising first tissue-engaging element 60a implanted at a portion of the annulus of tricuspid valve 4 and a third tissue-engaging element 60c implanted at a portion of a papillary muscle 72 in the right ventricle of the patient, in accordance with some applications of the present invention. It is to be noted that third implantation site 32 comprises papillary muscle 72 by way of illustration and not limitation, and that third implantation site 32 may comprise any potion of a wall of the right ventricle (e.g., a portion of tissue of the annulus at the ventricular surface of tricuspid valve 4, a portion of the wall of the ventricle in the vicinity of tricuspid valve 4, a portion of tissue in the vicinity of the apex of heart 2, or any other suitable portion of the wall of the ventricle).

Reference is now made to FIGS. 2A-B and 6. First, second, and third tissue-engaging elements 60a-c of FIG. 6 are implanted in cardiac tissue in a manner as described hereinabove with reference to FIGS. 2A-B, with the exception that, in order to implant third tissue-engaging element 60c, catheter 22 passes through the leaflets of tricuspid valve 4 into the right ventricle and implants third tissue-engaging element 60c in tissue of the ventricle. Following coupled of third tissue-engaging element 60c in FIG. 6, second stent 50b is deployed in second implantation site 52 in inferior vena cava 8, as described hereinabove with reference to FIG. 2B.

Reference is now made to FIGS. 3A-C and 6. It is to be noted, that for some applications, second longitudinal member 42b is coupled at a proximal end thereof to one or more barbs 114 (i.e., and is not connected to second stent 50, as shown). Barbs 114 enable second longitudinal member 42b to be coupled to stent 50 that is in connection with first longitudinal member 42a, and thereby maintain tension on third implantation site 32 and maintain coaptation of at least anterior leaflet 14 and septal leaflet 12.

Reference is again made to FIG. 6. Such an application of at least one tissue-engaging element 60 in a portion of tissue of the ventricle of heart 2, in some applications, facilitates independent adjustment of tricuspid valve 4 and a portion of the ventricle wall of heart 2. That is, for some application, geometric adjustment of the right ventricle to improve its function is achieved.

For some applications, following the deploying of first, second, third, and fourth tissue-engaging elements 60a-d (i.e., first and second anchors 40a and 40b, and first and second stents 50a and 50b), (1) a distance between first and second tissue-engaging elements 60a and 60b is adjustable by first adjustable mechanism, and (2) a distance between third and fourth tissue-engaging elements 60c and 60d is adjustable by a second adjustable mechanism, as described hereinbelow with reference to FIG. 5A. In such applications. (1) a length of first longitudinal member 42a between first and second tissue-engaging elements 60a and 60b may be adjusted by a first adjusting mechanism 150, as shown in FIG. 5A, and (2) a length of second longitudinal member 42b between third and fourth tissue-engaging elements 60c and 60d may be adjusted by a second adjusting mechanism 150, as shown in FIG. 5A or 5B.

Adjusting mechanisms 150 typically each comprise a mechanical element which shortens a distance of respective longitudinal members 42a and 42b. For some applications, adjustable mechanisms 150 may be permanently coupled to respective longitudinal members 42a and 42b (not shown) and each comprise an adjusting element, e.g., a spool for looping portions of longitudinal members 42a and 42b therearound, a crimping bead for crimping and shortening respective portions of longitudinal members 42a and 42b, a ratchet element, or a deforming element which deforms respective portions of longitudinal members 42a and 42b in order to shorten its length between the respective tissue-engaging elements 60. For other applications, system 700 comprises an adjusting mechanism comprising only an adjusting tool (not shown). In such applications, the adjusting tool may comprise an adjusting element, e.g., a crimping bead for crimping and shortening respective portions of longitudinal members 42a and 42b, or a deforming element which deforms respective portions of longitudinal members 42a and 42b. In either application, a level of regurgitation of tricuspid valve 4 may be monitored and the adjustment of the geometry of the right ventricle is monitored during (1) the adjusting of the distance between first and second implantation sites 30 and 52, and (2) the adjusting of the distance between third and second implantation sites 32 and 52, respectively.

Figure 8:
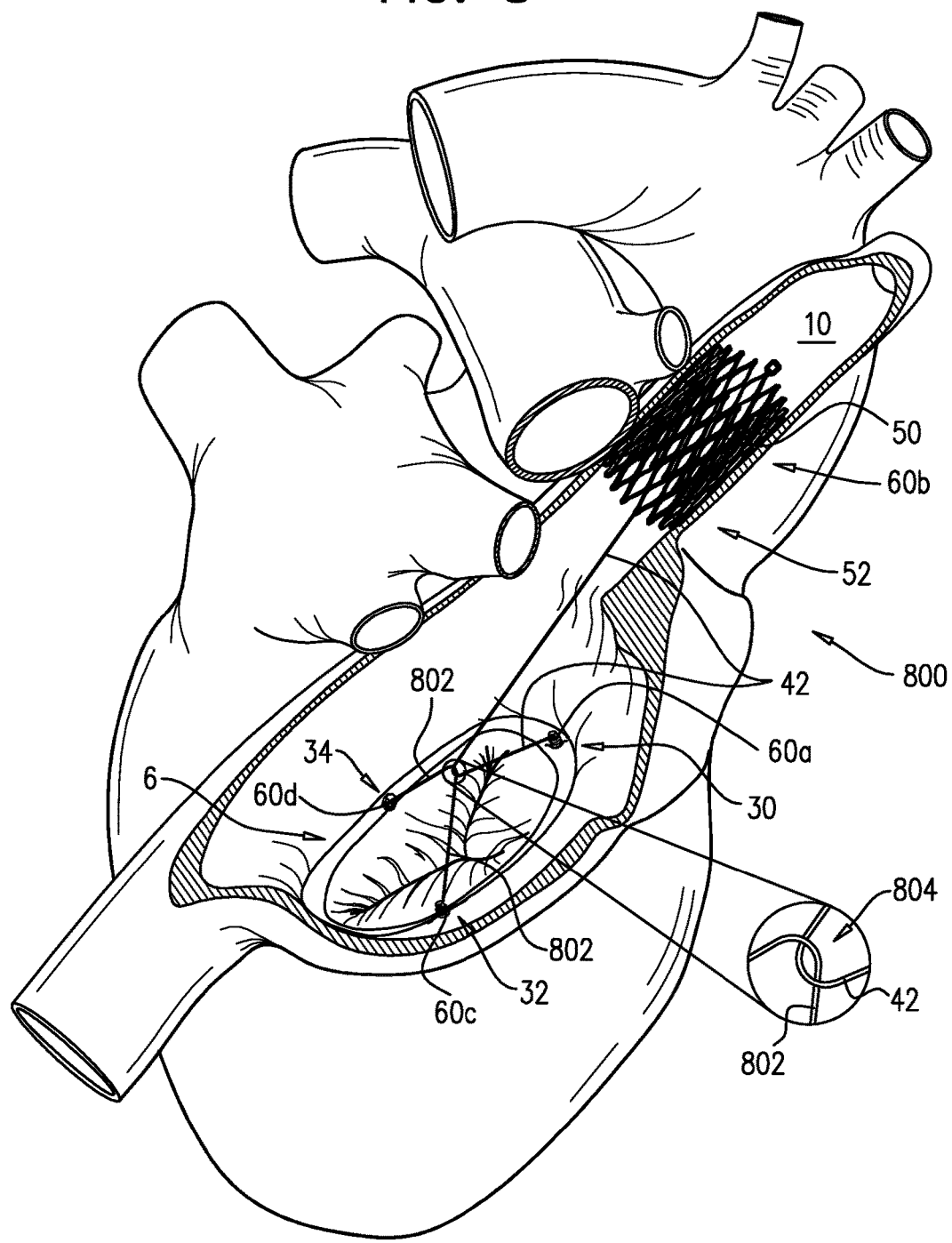
FIGS. 8 and 9 are schematic illustrations of a system for repairing a tricuspid valve, using a superior vena cava approach and an inferior vena cava approach, respectively, in accordance with respective applications of the present invention.
Figure 9:
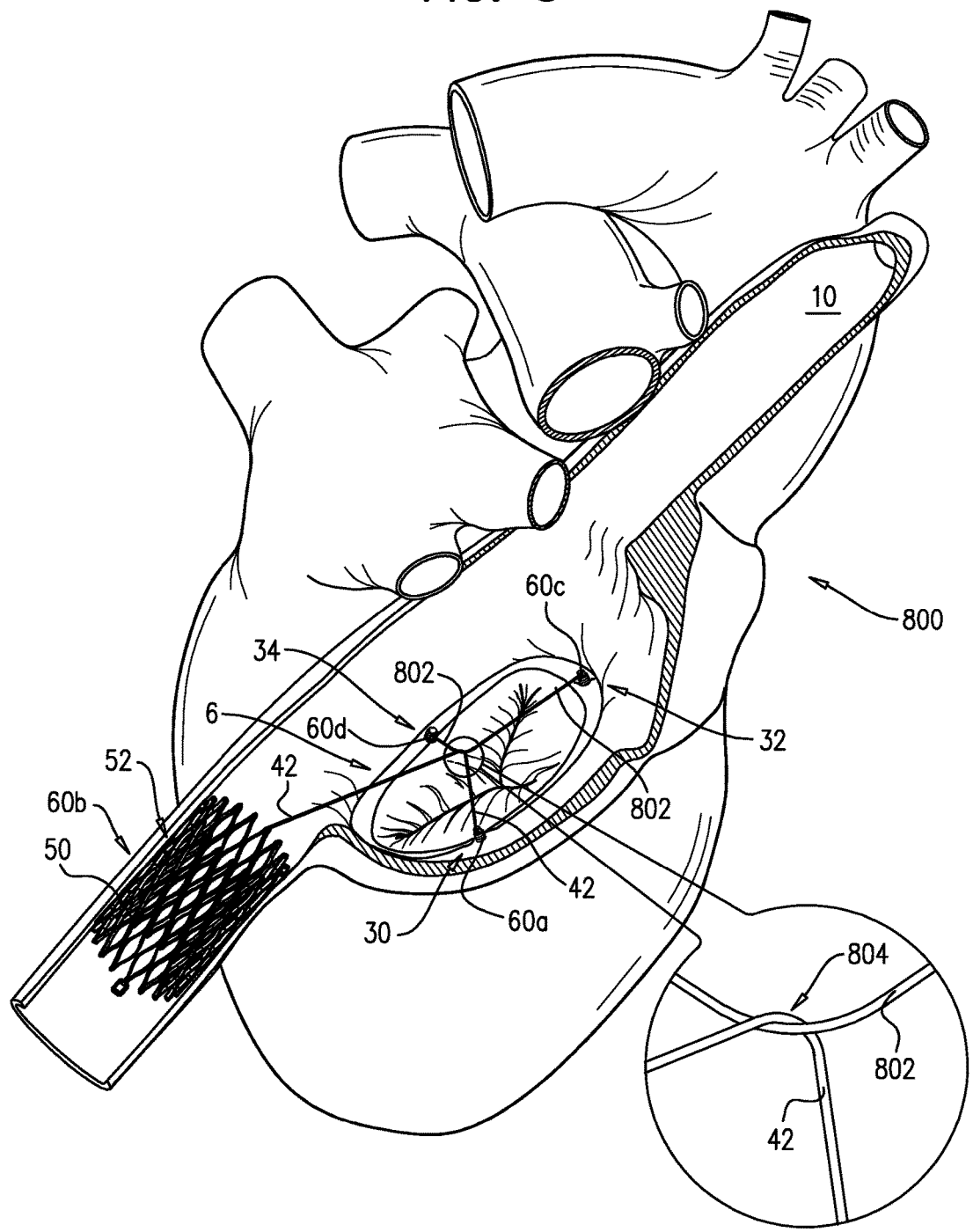

Reference is now made to FIGS. 8 and 9, which are schematic illustrations of a system 800 for repairing tricuspid valve 4, in accordance with respective applications of the present invention. As shown in FIGS. 8 and 9, system 800 comprises first, second, third, and fourth tissue-engaging elements 60a, 60b, 60c, and 60d. System 800 is similar in some respects to system 110 described hereinabove with reference to FIGS. 3A-B, with the exception that system 800 typically comprises only exactly one longitudinal member 42. Typically, longitudinal member 42 is directly coupled to first tissue-engaging element 60a, and indirectly coupled to tissue-engaging elements 60c and 60d by a longitudinal sub-member 802. Typically, one end of longitudinal sub-member 802 is coupled to tissue-engaging element 60c, and the other end of the sub-member is coupled to tissue-engaging element 60d. For some applications, as shown, longitudinal member 42 is not fixed to longitudinal sub-member 802; instead, longitudinal sub-member 802 engages, e.g., is hooked on or looped over, longitudinal member 42, at a junction 804 during deployment of the longitudinal sub-member. Alternatively, a ring is provided that couples the longitudinal sub-member to the longitudinal member (configuration not shown).

For some applications, as shown in FIG. 8, a superior vena cava approach is used to implant system 800, in which tissue-engaging elements 60a, 60c, and 60d are advanced into atrium 6 via superior vena cava 10, and tissue-engaging element 60b is deployed in the superior vena cava. FIG. 9 illustrates an inferior vena cava approach, in which tissue-engaging elements 60a, 60c, and 60d are advanced into atrium 6 via inferior vena cava 8, and tissue-engaging element 60b is deployed in the inferior vena cava. Typically, one of tissue-engaging elements 60a. 60c, and 60d is deployed at the septal side of tricuspid valve 4 in the caudal part of the base of the septal leaflet, and the other two of tissue-engaging elements 60a, 60c, and 60d are deployed at the mural side of the valve, dividing the entire mural side in three equal spaces, generally at the middle of anterior leaflet and the commissure between the anterior and posterior leaflets. For some applications, yet another tissue-engaging element is deployed at the mural side of the valve (configuration not shown).

An anchor-deployment tube is deployed into atrium 6, for example, using techniques described hereinabove with reference to FIG. 1A. First tissue-engaging element 60a is deployed at first implantation site 30, such as using anchoring techniques described herein. First implantation site 30 includes a portion of cardiac tissue in the vicinity of tricuspid valve 4 (e.g., a first portion of tissue of the annulus of tricuspid valve 4, as shown). For example, in the approach shown in FIG. 8, first implantation site 30 may be on the mural side of the annulus of the valve (e.g., at anterior leaflet 14), approximately centered between two of the commissures of the valve. In the approach shown in FIG. 9, first implantation site 30 may be on the mural side of the annulus (e.g., at posterior leaflet 16), approximately centered between two of the commissures of the valve. Alternatively, although typically less desirable, first implantation site 30 may be approximately at a commissure of the valve.

During the implantation using system 800, the distal end of the anchor-deployment tube is advanced to third implantation site 32. Third tissue-engaging element 60c is deployed at third implantation site 32, such as using anchoring techniques described herein. Third implantation site 32 includes a portion of cardiac tissue in the vicinity of tricuspid valve 4 (e.g., a second portion of tissue of the annulus of tricuspid valve 4, as shown). For example, in the approach shown in FIG. 8, third implantation site 32 may be on the mural side of the annulus of the valve (e.g., at posterior leaflet 16), approximately centered between two of the commissures of the valve. In the approach shown in FIG. 9, third implantation site 32 may be on the mural side of the annulus of the valve (e.g., at anterior leaflet 14), approximately centered between two of the commissures of the valve. Alternatively, although typically less desirable, third implantation site 32 may be approximately at a commissure of the valve.

Subsequently to implantation at third implantation site, the distal end of the anchor-deployment tube is advanced to a fourth implantation site 34. As mentioned above, longitudinal sub-member 802 extends between tissue-engaging elements 60c and 60d. As fourth tissue-engaging element 60d is brought to fourth implantation site 34, longitudinal sub-member 802 engages, e.g., becomes hooked on or looped over, longitudinal member 42 at junction 804. Fourth tissue-engaging element 60d is deployed at fourth implantation site 34, such as using anchoring techniques described herein. Fourth implantation site 34 includes a portion of cardiac tissue in the vicinity of tricuspid valve 4 (e.g., a second portion of tissue of the annulus of tricuspid valve 4, as shown). For example, in the approaches shown in FIGS. 8 and 9, fourth implantation site 34 may be on septal side of the annulus of the valve (e.g., at the caudal part of the base of septal leaflet 12, approximately centered between two of the commissures of the valve. Alternatively, although typically less desirable, fourth implantation site 34 may be approximately at a commissure of the valve.

Following implantation at fourth implantation site 34, the anchor-deployment tube is withdrawn into the vena cava. Second tissue-engaging element 60b (stent 50) pulls on longitudinal member 42, which directly pulls on first tissue-engaging element 60a, and indirectly pulls on tissue-engaging elements 60c and 60d via longitudinal sub-member 802. Responsively, a distance between the leaflets of tricuspid valve 4 is adjusted to reduce and eliminate regurgitation through and thereby repair tricuspid valve 4. For some applications, during the pulling of longitudinal member 42, a level of regurgitation of tricuspid valve 4 is monitored. Longitudinal member 42 is pulled until the regurgitation is reduced or ceases. Once the physician determines that the regurgitation of tricuspid valve 4 is reduced or ceases, and tricuspid valve 4 has been repaired, second tissue-engaging element 60b (e.g., stent 50) is deployed from the anchor-deployment tube in the vena cava, such as described hereinabove, thereby implanting the tissue-engaging element at second implantation site 52, as shown in FIGS. 8 and 9.

For some applications, stent 50 comprises a plurality of interconnected superelastic metallic struts, such as described hereinabove with reference to FIG. 1D.

For some applications, following the implantation the tissue-engaging elements at their respective implantation sites, as described hereinabove, a length of longitudinal member 42 is adjusted by an adjustable mechanism, as described hereinabove with reference to FIG. 5A or 5B. Adjusting mechanism 150 typically comprises a mechanical element which shortens a length of longitudinal member 42. For some applications, adjustable mechanism 150 may be permanently coupled to longitudinal member 42; mechanism 150 comprises an adjusting element, e.g., a spool for looping a portion of longitudinal member 42 therearound, a crimping bead for crimping and shortening the portion of longitudinal member 42, a ratchet element, or a deforming element which deforms the portion of longitudinal member 42. For other applications, system 800 comprises an adjusting mechanism comprising only an adjusting tool. In such applications, the adjusting tool may comprise an adjusting element, e.g., a crimping bead for crimping and shortening the portion of longitudinal member 42, or a deforming element which deforms the portion of longitudinal member 42. In either application, a level of regurgitation of tricuspid valve 4 may be monitored during the adjusting of the length of longitudinal member 42.

Reference is now made to FIGS. 10A-D, which are schematic illustrations of tissue anchors 40, in accordance with respective applications of the present invention. One or more of these anchors may be used as anchors 40 in the applications described hereinabove with reference to FIGS. 1A-D, 2A-B, 3A-C, 5A-B, 6, 8, 9, 11A-C, 12A-C, 13C, and/or 14C.

Figure 10A:
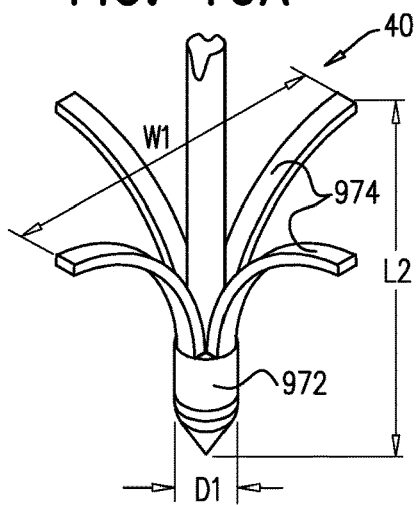
FIGS. 10A-D are schematic illustrations of tissue anchors, in accordance with respective applications of the present invention.

In the configuration shown in FIG. 10A, anchor 40 comprises a distal tissue-piercing tip 972 fixed to a plurality of arms 974, which extend from tip 972 in respective generally distal and radially-outward directions. The arms are inserted entirely into the tissue, thereby helping to couple the anchor to the tissue. For some applications, a greatest width W1 of anchor 40 is at least 6.5 mm, no more than 39 mm, and/or between 6.5 and 39 mm, such as 13 mm. For some applications, a length L2 of anchor 40, measured along an axis of the anchor from tips of arms 974 to the end of tip 972 of the anchor, is at least 5 mm, no more than 30 mm, and/or between 5 and 30 mm, such as 10 mm. For some applications, a greatest diameter D1 of tip 972 is at least 1 mm, no more than 6 mm, and/or between 1 and 6 mm, such as 2 mm.

Figure 10B:
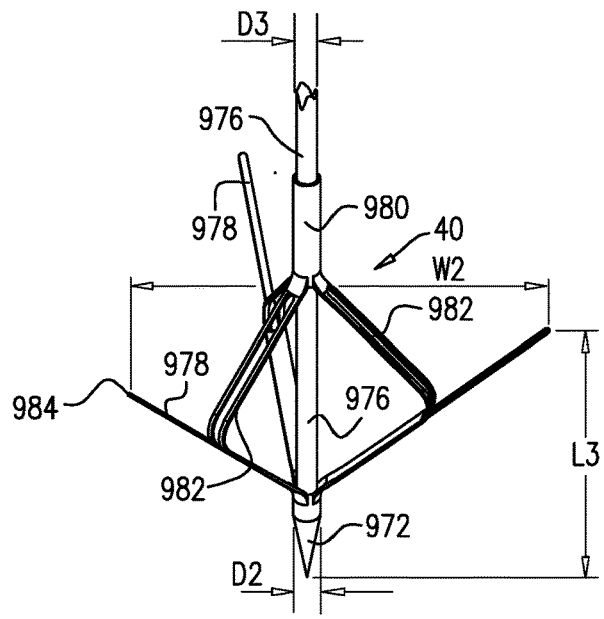
Figure 10C:
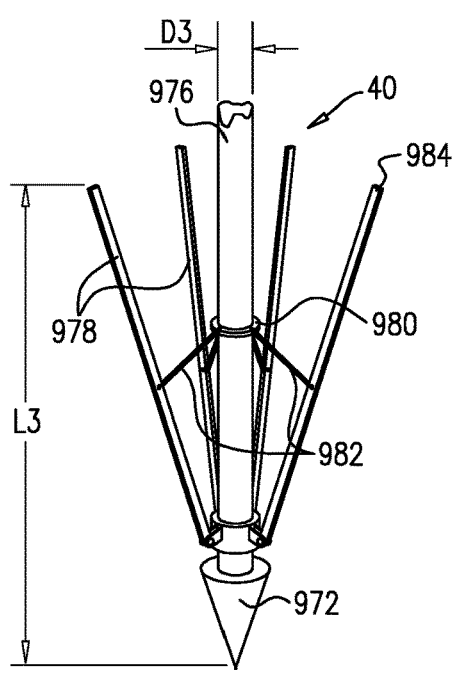

In the configurations shown in FIGS. 10B and 10C, anchor 40 is configured to radially contract and expand in a manner generally similar to that of an umbrella (but without the umbrella cloth). The anchor is inserted into the tissue in a radially-contracted (closed) state, and is transitioned to a radially-expanded (open) state, either automatically or by the surgeon, in order to fix the anchor within the tissue. For some applications, such as shown in FIG. 10B, the anchor is configured to assume the radially-expanded state when resting; the anchor is held in a radially-contracted state during deployment, and transitions to the radially-expanded state upon being released. For other applications, such as shown in FIG. 10C, the anchor is configured to assume the radially-contracted state when resting; the anchor is deployed in the radially-contracted state, and is actively transitioned to the radially-expanded state by the surgeon after being inserted into the tissue.

Anchor 40 comprises distal tissue-piercing tip 972, which is fixed at a distal end of a post 976 (which typically comprises a tube). The anchor further comprises a plurality of ribs 978 (e.g., three or four). Ribs 978 are coupled to the anchor near distal tip 972, such that the ribs can articulate with post 796, thereby changing respective angles between the ribs and the post. The anchor further comprises a runner 980 (which typically comprises a tube), which is slidably coupled to post 976, such that the runner can slide along the post. A plurality of stretchers 982 are coupled to runner 980 and respective ones of the ribs, such that stretchers can articulate with the runner and the respective ribs. Each of the stretchers may comprise one or more elongated elements; by way of example, each of the stretchers is shown comprising two elongated elements. Typically, tips 984 of ribs 978 (i.e., at the ends not coupled to the anchor) are blunt.

For some applications, such as the configuration shown in FIG. 10B, the anchor at least partially comprises a shape-memory alloy (e.g., nitinol), and the anchor's natural, resting state is the radially-expanded (open) state. The anchor is crimped inside a catheter so that it remains radially-contracted (closed) until deployed. Once deployed into the tissue, the catheter is pulled back and the anchor is allowed to open (i.e., automatically transition to the radially-expanded state).

For some applications, in order to allow retraction of the anchor (such as if the anchor has been improperly positioned, or needs to be removed for another reason), the proximal end of runner 980 (i.e., the end farther from tip 972) is removably coupled to an inner tube positioned within the catheter. For example, an outer surface of the proximal end of runner 980 and an inner surface of the inner tube near a distal end thereof may be threaded, to enable the removable coupling. Runner 980 thus remains coupled to the inner tube until released, such as by rotating the inner tube with respect to the runner (the tissue prevents the runner from also rotating). In order to retract the anchor, post 976 is pushed in a distal direction while the runner is still coupled to the inner tube, thereby moving post 976 with respect to runner 980 and transitioning the anchor back to its radially-contracted (closed) state. The anchor can thus be withdrawn into the catheter, repositioned, and deployed again at a different location. The surgeon rotates the inner tube to decouple the anchor once the location of the anchor has been finalized.

For some applications, in the configuration shown in FIG. 10C, anchor 40 further comprises a tube positioned around post 976, proximal to runner 980 (i.e., farther from tip 972). The tube is used to push runner 980 in a distal direction (toward the tip), in order to open the umbrella.

For some applications, a greatest width W2 of anchor 40, when radially expanded, is at least 6.5 mm, no more than 39 mm, and/or between 6.5 and 39 mm, such as 13 mm. For some applications, a length L3 of anchor 40, measured along an axis of the anchor from tips 984 of ribs 978 to the end of tip 972 of the anchor when the anchor is radially expanded, is at least 5 mm, no more than 30 mm, and/or between 5 and 30 mm, such as 10 mm. For some applications, a greatest diameter D2 of tip 972 is at least 0.4 mm, no more than 2.4 mm, and/or between 0.4 and 2.4 mm, such as 0.8 mm. For some applications, a greatest diameter D3 of post 976 is at least 0.3 mm, no more than 1.8 mm, and/or between 0.3 and 1.8 mm, such as 0.6 mm. For some applications, each of ribs 978 has a length of at least 6 mm, no more than 20 mm, and/or between 6 and 20 mm, such as 10 mm.

Figure 10D:
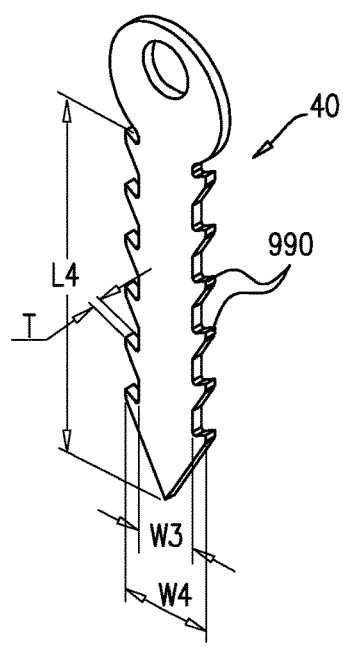

In the configuration shown in FIG. 10D, anchor 40 is barbed. For example, the anchor may be generally flat, and is shaped so as to define one or more barbs 990, which typically extend from both sides of the anchor. The barbs help couple the anchor to the tissue. For some applications, a greatest width W3 of anchor 40, excluding barbs 990, is at least 0.85 mm, no more than 5.1 mm, and/or between 0.85 and 5.1 mm, such as 1.7 mm. For some applications, a greatest width W4 of anchor 40, including barbs 990, is at least 1.25 mm, no more than 7.5 mm, and/or between 1.25 and 7.5 mm, such as 2.5 mm. For some applications, a length L4 of anchor 40, measured along an axis of the anchor from a distal end of the barbed portion to the proximal tip of the anchor, is at least 5 mm, no more than 30 mm, and/or between 5 and 30 mm, such as 9.5 mm. For some applications, a greatest thickness T of anchor 40 is at least 0.1 mm, no more than 0.6 mm, and/or between 0.1 and 0.6 mm, such as 0.2 mm.

Figure 11C:
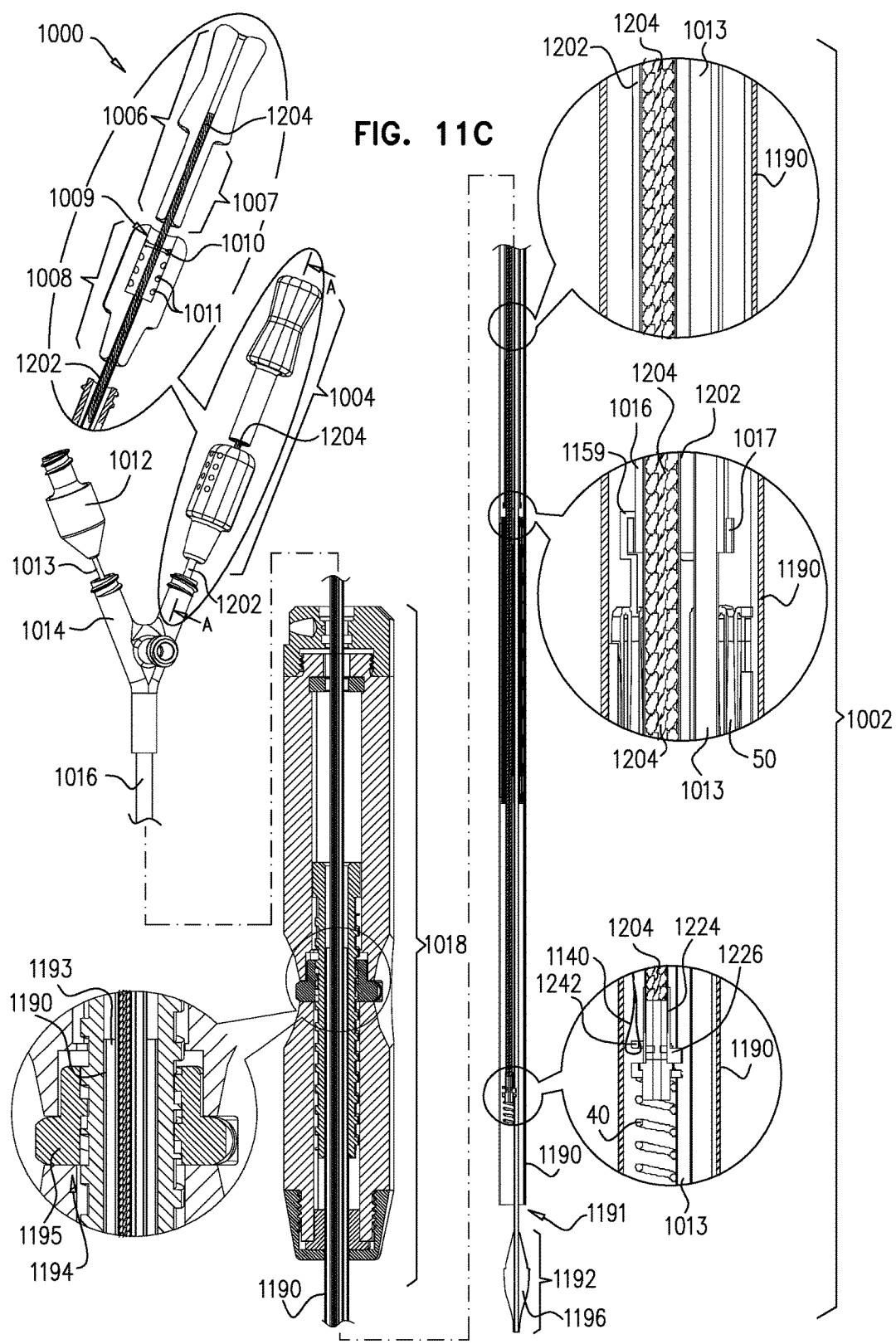

Reference is now made to FIGS. 11A-C, which are schematic illustrations of a delivery tool system 1000 for implanting anchor 40, in accordance with some applications of the present invention. Delivery tool system 1000 may be used, for example, to rotate, locate, place, and implant an anchor in combination with the applications described herein with reference to FIGS. 1A-D, 2A-B, 3A-C, 5A-B. 6, 8, 9, 13A-C, 14A-C, 15A-B, 16A-B, and 17. Although longitudinal member 42 is shown in FIGS. 11A-C as being fixed to stent 50, this is not necessarily the case, and tool system 200 thus may also be used in combination with the applications that do not utilize stent 50, such as those described herein with reference to FIGS. 3C and 5A-B.

FIG. 11A shows an exploded view of some of the components of delivery tool system 1000 and its spatial orientation relative to stent 50, longitudinal member 42, and anchor 40. In such an application, longitudinal member 42 comprises a plurality of fibers aligned so as to form a band 1140. Band 1140 is coupled at a first portion 1141 thereof (e.g., a proximal portion, as shown) to a portion of stent 50. Stent 50 comprises a plurality of mechanical structural elements 1651 arranged so as to form a tubular structure of stent 50 in a radially-expanded state of stent 50. First portion 1141 of band 1140 is coupled to the portion of stent 50 via a tension-distributing element 1160, as will be described hereinbelow with reference to FIGS. 13A-C, 14A-C, and 15A-B.

A second portion 1143 of band 1140 is coupled to tissue anchor 40 via a connecting element 1240 that is coupled to a proximal portion of anchor 40 via an adapter head 1230. Tissue anchor 40 comprises a helical tissue anchor having a central lumen about a longitudinal axis 1155. Connecting element 1240 is shaped so as to define a flexible-longitudinal-member-coupler 1242 at a proximal portion of connecting element 1240. Flexible-longitudinal-member-coupler 1242 is shaped so as to define an opening 1244 configured for coupling of second portion 1143 of band 1140 to connecting element 1240. Typically second portion 1143 of band 1140 is coupled to connecting element 1240 by threading it through opening 1244 and forming a distal loop 1142.

Connecting element 1240 is shaped so as to provide an annular loop 1246 at a portion of element 1240 that is distal to opening 1244 and flexible-longitudinal-member-coupler 1242. Annular loop 1246 has an inner diameter that is larger than an outer diameter of the anchor 40. Annular loop 1246 surrounds the proximal-most coil in a manner which facilitates rotation of anchor 40 about axis 1155 freely by facilitating rotation of the proximal-most loop of anchor 40 freely about axis 1155. For some applications loop 1246 rotates around the proximal portion of anchor 40.

Adapter head 1230 is shaped so as to define a distal tissue-anchor coupling element 1233 which has an outer diameter that is equal to or less than a diameter of the lumen of anchor 40 in a manner in which tissue-anchor coupling element 1233 fits within the lumen of anchor 40 and is welded to a proximal portion of anchor 40 in order to couple adapter head 1230 to anchor 40 (as shown hereinbelow with reference to FIGS. 12A-C). Adapter head 1230 is shaped so as to define an annular element 1234 which has an outer diameter that is larger than a diameter of an opening provided by annular loop 1246. Thus, adapter head 1230 prevents decoupling of connecting element 1240 from anchor 40 since connecting element 1240 is not welded to anchor 40.

System 1000 comprises a torque-delivering tool comprising a torque-delivering cable 1204 that is slidably disposed within a lumen of a tube 1202. Torque-delivering cable 1204 is welded at a distal end thereof to a first coupling 1220 shaped so as to define a male coupling element 1222. Adapter head 1230 is shaped so as to provide a second coupling 1232 shaped so as to define a female coupling element configured to fit the male coupling element 1222. When coupled together, as will be described hereinbelow with reference to FIGS. 12A-C, first and second couplings 1220 and 1232, respectively, couple torque-delivering cable 1204 to tissue anchor 40. Torque-delivering cable 1204 is rotated in order to rotate first coupling 1220 and second coupling 1232 of adapter head 1230, and thereby tissue anchor 40.

Since adapter head 1230, having second coupling 1232, is welded to a proximal portion of anchor 40, when adapter head 1230 is rotated, anchor 40 is rotated. As anchor 40 is rotated, the proximal-most coil of anchor 40 rotates freely within annular loop 1246, and anchor 40 rotates with respect to annular loop 1246.

As shown, the proximal portion of connecting element 1240 comprising flexible-longitudinal-member-coupler 1242, shaped so as to define opening 1244, is generally crescent-shaped. A portion of tube 1202 in a vicinity of distal end 1205 of tube 1202 is coupled to an anti-entanglement device 1224 which is shaped so as to define a distal element 1226 that is generally crescent-shaped. Distal element 1226 is disposed alongside the proximal portion of connecting element 1240 in a manner in which the crescent shaped are aligned, as shown in FIG. 11B. In such a configuration, during rotation of torque-delivering cable 1204 to rotate anchor 40, tube 1202 is not rotated around cable 1204, but is held in place, which (1) keeps anti-entanglement device 1224 maintained in a relative position with reference to connecting element 1240, and thereby (2) connecting element 1240 is not rotated as anchor 40 is rotated, and flexible member 42 (or band 1140, in this application) is not rotated when anchor is rotated. In such a manner, as anchor 40 rotates with respect to annular loop 1246, anchor 40 rotates with respect to flexible member 42, thus anti-entanglement device 1224 prevents band 1140 from entangling during rotation of anchor 40.

As shown in FIG. 11B, tissue anchor 40 defines first tissue-engaging element 60a, and stent 50 defines second tissue-engaging element 60b.

Reference is now made to FIG. 11C which shows a tool 1002 for facilitating implanting of tissue anchor 40 and expansion of stent 50 within the blood vessel of the patient. Tool 1002 comprises a proximal handle portion 1004 which is coupled to a proximal portion of a first shaft 1016. As shown in the enlarged cross-sectional image on the middle-right of FIG. 11C, stent 50 crimped within a sheath 1190. A proximal portion of stent 50 is shaped so as to define two or more delivery-tool couplers 1159. A distal end of first shaft 1016 is shaped so as to provide one or more stent-couplers 1017. A respective delivery tool coupler 1159 is coupled to shaft 1016 by being coupled to a respective stent coupler 1017. When sheath 1190 surrounds stent 50, stent 50 is maintained in a crimped state and couplers 1159 remain coupled to couplers 1017. As shown, tube 1202 and torque-delivering cable 1204 pass through a lumen of stent 50 in its crimped, or radially-compressed state.

As described hereinabove, tissue anchor 40 defines first tissue-engaging element 60a and stent 50 defines second tissue-engaging element 60b. As described hereinabove, tissue anchor 40 is implanted in tissue of the patient prior to positioning stent 50 in the blood vessel of the patient. That is, tissue anchor 40 is exposed from within sheath 1190 and implanted in tissue of the patient while stent 50 remains crimped within sheath 1190. Since torque-delivering cable 1204 and tube 1202 pass through the lumen of stent 50, during rotation of anchor 40, anchor 40 rotates with respect to stent 50 while stent remains static.

Tool 1002 comprises a "Y"-shaped connector 1014 coupled to a proximal end of shaft 1016. A first arm of connector 1014 provides a lumen for passage of a guidewire tube 1013 that is configured to hold a guidewire (not shown). A second arm of connector 1014 provides a lumen for passage of tube 1202 that surrounds torque-delivering cable 1204. As shown in the cross-sectional image on the top-right, tube 1202 surrounding cable 1204 passes alongside guidewire tube 1013. Guidewire tube 1013 extends through tool 1002 and through a lumen provided by a distal atraumatic tip 1192. For such an application, tip comprises a symmetrical tip 1196. Tip 1192 enables atraumatic advancement the shafts of tool 1002 through vasculature of the patient. Tip 1192 comprises a flexible biocompatible material, e.g., polyurethane, and a radiopacity-enhancing material such as an embedded marker made from a radiopaque substance such as Pt—Ir, or alternatively by adding BaSO4 to the biocompatible material.

Figure 18A:
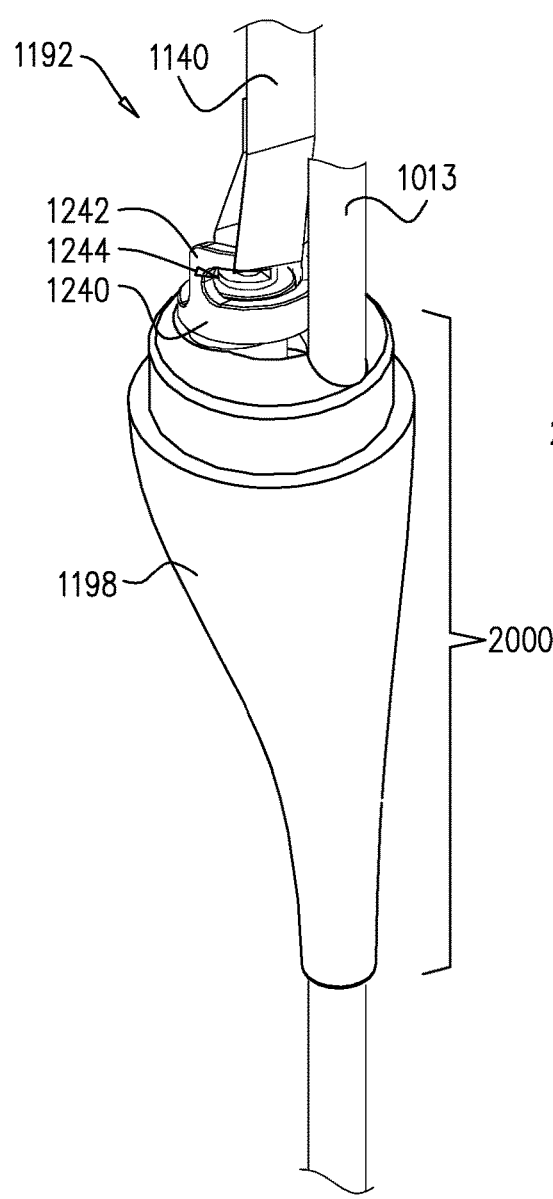
FIGS. 18A-B are schematic illustrations of an alternative portion of the delivery system of FIGS. 11A-C, in accordance with some applications of the present invention.
Figure 18B:
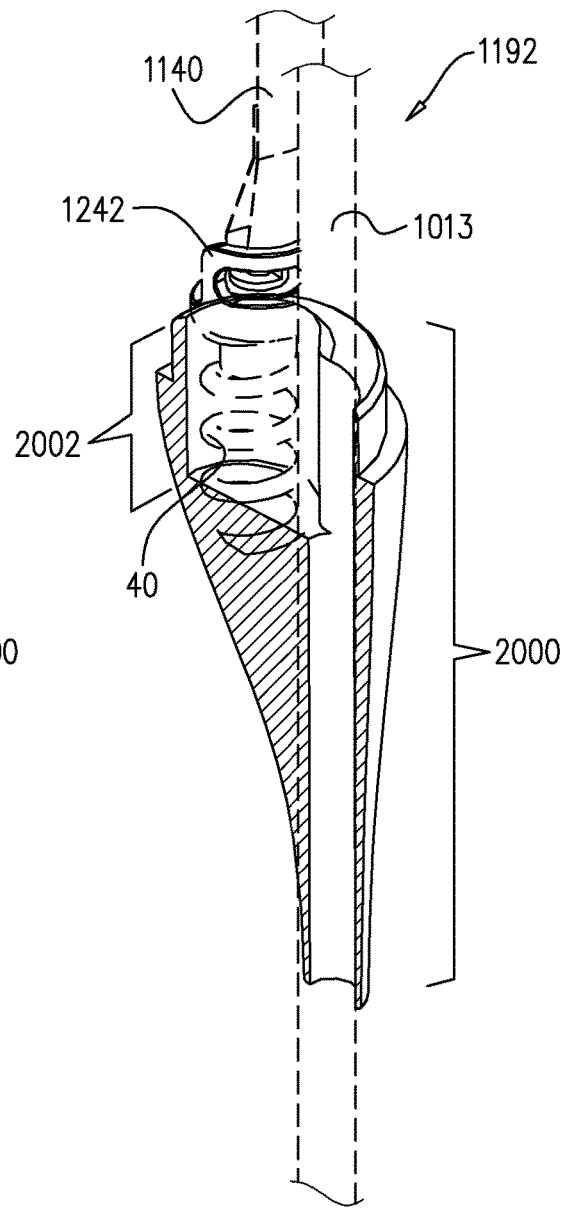

Reference is now made to FIGS. 18A-B, which are schematic illustrations of atraumatic tip 1192 comprising an asymmetrical atraumatic tip 2000 having an asymmetrical body 1198, in accordance with some applications of the present invention. As shown, tip 2000 is shaped so as to provide a lumen for passage therethrough of guidewire tube 1013. Tip 2000 is shaped so as to define a recess 2002 for housing anchor 40 during the advancement of the shafts of tool 1002 through the vasculature of the patient. Anchor 40, flexible-longitudinal-member-coupler 1242, band 1140, and guidewire tube 1013 are shown in phantom to indicate their positioning relative to tip 2000. Once the physician wishes to release anchor 40 from within recess 2002, the physician pushes on guidewire tube 1013 so as to disengage tip 2000 from distal end 1191 of sheath 1190 (shown in FIG. 11C) and distance tip 2000 and anchor 40 from distal end 1191. The physician then pulls proximally on cable 1204 so as to retract anchor 40 from within recess 2002. Once anchor 40 is exposed from within recess 2002, anchor 40 may be rotated, as described hereinabove with reference to FIGS. 11C and 12A, and may be disengaged from first coupling 1220, as described hereinabove with reference to FIGS. 11C and 12B-C.

Reference is again made to FIG. 11C. The shafts of tool 1002 are guided along the guidewire (not shown for clarity of illustration) to the respective implantation sites of anchor 40 and stent 50. During the advancement of the shafts through the vasculature, tip 1192 is coupled to a distal end 1191 of sheath 1190 (e.g., by having a proximal portion of tip 1192 disposed within a lumen of sheath 1190 at distal end 1191 thereof. Prior to deployment and implantation of anchor 40 from within sheath 1190, tip 1192 is pushed distally so as to decouple tip 1192 from distal end 1191 of sheath 1190. Tip 1192, for some applications comprises symmetrical tip 1196. Symmetrical tip 1196 facilitates recoupling of tip 1192 to distal end 1191 of sheath 1190 following the decoupling of tip 1192 from sheath 1190.

Reference is now made to FIGS. 12A-C, which are schematic illustrations of first and second couplings 1220 and 1232, respectively, in their locked state (FIG. 12A) and their unlocked state (FIG. 12C), in accordance with some applications of the present invention. As described hereinabove, first coupling 1220 matingly engages second coupling 1232 when a distal end 1205 of tube 1202 surrounding torque-delivering cable 1204 is disposed distally. When distal end 1205 is disposed distally, as shown in FIG. 12A, a distal portion of tube 1202 surrounds first and second couplings 1220 and 1232, respectively, in a manner which keeps first and second couplings 1220 and 1232, respectively, coupled together. As shown in FIG. 12A, and as described hereinabove, the distal portion of tube 1202 is coupled to anti-entanglement device 1224. As shown in the cross-sectional images of FIGS. 12A-C, distal element 1226 of anti-entanglement device 1224 is disposed behind flexible-longitudinal-member-coupler 1242 at the proximal portion of connecting element 1240.

Reference is now made to FIGS. 11C and 12A. As shown in FIG. 11C, tool 1002 comprises a steering mechanism 1018 that surrounds shaft 1016 and is coupled to a proximal end 1193 of sheath 1190. Steering mechanism 1018 facilitates proximal and distal movement of a steering wire (not shown for clarity) with respect to mechanism 1018, tube 1202, and guidewire tube 1013. Steering mechanism 1018 comprises a user-engaging element 1195 which enables the physician to facilitate steering of sheath 1190. Steering mechanism 1018 comprises an actuating mechanism 1194 comprising a plurality of teeth which facilitate proximal and distal movement of the steering wire when user-engaging element 1195 is actuated by the physician using system 1000.

When the physician wishes to expose anchor 40 from within sheath 1190, the physician slides the cable 1204 and tube 1202 together so as to expose anchor 40. For some applications, cable 1204 and tube 1202 are slid when the physician pushes at least handle portion 1004 so as to push tube 1202 (and cable 1204 disposed therein) distally in order to push anchor 40 distally within sheath 1190 and expose anchor 40 from within sheath 1190. During the sliding, mechanism 1018 is held in place so as to prevent distal sliding of sheath 1190 during the distal sliding of anchor 40. (When the physician desires to deploy stent 50, the physician slides sheath 1190 proximally by sliding mechanism 1018 with respect to shaft 1016 so as to expose stent 50. For such applications, stent 50 is exposed from within sheath 1190 and is allowed to expand radially and disengage delivery-tool couplers 1159 of stent 50 from stent-couplers 1017 of tool 1002).

When the physician wishes to position anchor 40 into the correct anatomical place such as the anteroposterior commissure, the physician actuates user-engaging element 1195 to actuate steering mechanism 1018 which pulls the steering cable, causing steering of sheath 1190 in order to deflect sheath 1190 in one direction. The physician may then rotate the handle portion of mechanism 1018 to change the deflection direction and reach the correct anatomical positioning of anchor 40.

As shown in FIG. 11C, proximal handle portion 1004 comprises an anchor-deployment actuator 1006 and a holder 1008. Actuator 1006, as shown in the cross-sectional image, is coupled to torque-delivering cable 1204 such that when first and second couplings 1220 and 1232, respectively, are coupled together (as shown in FIG. 12A), rotation of actuator 1006 rotates torque-delivering cable 1204 in order to rotate anchor 40. Typically, anchor 40 is rotated once anchor 40 is exposed from within sheath 1190, as described hereinabove, in order to screw anchor 40 into tissue of the patient.

Holder 1008 is coupled to a proximal portion of tube 1202 that surrounds cable 1204. Holder 1008 is shaped so as to define a proximal recess 1009, with transverse holes 1011. Actuator 1006 is shaped so as to define a distal protrusion 1007 which is shaped so as to fit within recess 1009 of holder 1008.

As shown in FIGS. 11C and 12A, the distal portion of tube 1202 disposed around first and second couplings 1220 and 1232, respectively. In such a configuration, protrusion 1007 of actuator 1006 is disposed proximally to holder 1008. Furthermore, holder 1008 comprises a safety 1010 (e.g., a suture which extends transverse to the longitudinal lumen of recess 1009 through holes 1011) which prevents protrusion 1007 from sliding within recess 1009 of holder 1008.

When the physician desires to disengage first and second couplings 1220 and 1232, respectively, the physician releases safety 1010 (e.g., by cutting the suture) and pushes actuator 1006 distally so that protrusion 1007 of actuator 1006 slides within recess 1009 of holder 1008. During the pushing of actuator 1006, the physician holds holder 1008. Responsively, since actuator 1006 is coupled to cable 1204, cable 1204 is slid distally (in the direction as indicated by arrow 2) so that first and second couplings 1220 and 1232, respectively, are exposed from within the distal portion of tube 1202. Additionally, since tissue anchor 40 is implanted in tissue of the patient, the tissue exerts a force on tube 1202 which pushes tube 1202 proximally, in the direction as indicated by arrow 1. Consequently, first and second couplings 1220 and 1232, respectively, are exposed from within the distal portion of tube 1202, as shown in FIG. 12B.

As shown in FIG. 12C, the physician tilts tube 1202 (e.g., clockwise, as shown) in order to disengage male coupling element 1222 of first coupling 1220 from the female coupling element of second coupling 1232. Thereby, tool 1002 is disengaged from anchor 40. Following the disengaging of tool 1002 from anchor 40, anchor 40, adapter head 1230, and connecting element 1240 remain implanted at the implantation site.

Following the implantation of tissue anchor 40 at first implantation site 30, sheath 1190 is retracted proximally by pulling proximally mechanism 1018 so as to expose band 1140 coupled to tissue anchor 40. Sheath 1190 is navigated by mechanism 1194 such that distal end 1191 of sheath 1190 is positioned in second implantation site 52. As tool 1002 is navigated, tension is applied to band 1140 in order to draw together first and second implantation sites 30 and 52, respectively, and repair tricuspid valve 4, in a manner as described hereinabove with reference to FIGS. 1A-D.

For some applications, during the pulling of band 1140 by tool 1002, a level of regurgitation of tricuspid valve 4 is monitored and a parameter indicative of repair of tricuspid valve 4 is monitored. For example, leaflet anatomy during the opening and closing of tricuspid valve 4 is assessed using an imaging device such as intracardiac echocardiography, transthoracic echocardiography or transesophageal echocardiography. For some applications, during the monitoring, measurements used to assess the efficiency of the procedure are evaluated pre-, during, and post-procedure. For example, these measurements could include, but not exclusively, measuring the echocardiographic distance between the anteroposterior commissure and the rim at the junction of the inferior vena cava and the right atrium, or measuring the echocardiographic regurgitant volume through tricuspid valve 4. Band 1140 is pulled until the regurgitation is reduced or ceases.

Once the physician determines that the regurgitation of tricuspid valve 4 is reduced or ceases, and tricuspid valve 4 has been repaired, sheath 1190 is retracted proximally as described hereinabove with reference to FIG. 11C by pulling proximally on sheath 1190, which is done by pulling proximally on mechanism 1018, so as to expose stent 50 from within sheath 1190. As stent 50 expands radially, delivery-tool couplers 1159 of stent 50 expand away and disengage from stent-couplers 1017 of tool 1002, thereby disengaging stent 50 from tool 1002. Following the disengaging of tool 1002 from stent 50, tool 1002 is extracted from the body of the patient.

Reference is now made to FIGS. 13A-C, which are schematic illustrations of a stent 1150 comprising a proximal portion 1156 and a distal portion 1157, each of portions 1156 and 1157 comprising a plurality of mechanical structural elements 1651 shaped so as to define a plurality of peaks 1152, a plurality of valleys 1154, and a plurality of interconnectors 1158, in accordance with some applications of the present invention. FIG. 13A shows stent 1150 in an assembled state, and FIG. 13B shows stent 1150 in a flattened state in which stent 1150 is cut longitudinally and flattened, for clarity of illustration. It is to be noted, however, that the configuration shown in FIG. 13A defines the configuration of stent 1150 in a radially-expanded state.

The structural configuration of stent 1150 provided by mechanical structural elements 1651 may be formed by expanding a laser-slotted metallic tube, or may be chemically etched from a flat sheet and welded to a tube, or may be formed from a single wire, or may be formed by assembling individual wire elements, or by any other method of construction known to those skilled in the art. The design of stent 1150 can be laser cut from a small diameter tube, expanded to the final diameter, or may be cut from a large diameter tube, which is equal to the final diameter of a fully expanded stent or which may be further expanded to an even larger diameter.

Stent 1150 is shaped so as to provide a plurality of coaxially-disposed annular ring portions 1151. Each ring portion 1151 is shaped so as to define a plurality of peaks 1152 and a plurality of valleys 1154. As shown, each of the plurality of interconnectors 1158 is oriented vertically. As shown in exemplary ring portions 1151a and 1151b, the ring portions are aligned in a manner in which peaks 1152 and 1154 are in phase. Thus, interconnectors 1158 are vertically disposed between respective valleys 1154 of respective ring portions 1151.

Such a configuration of mechanical structural elements 1651 provides stent 1150 with a property of generally maintaining its longitudinal length L5 measured along longitudinal axis 1155, during radial expansion of stent 1150 from a radially-compressed state of stent 1150. Additionally, such a configuration of mechanical structural elements 1651 in distal portion 1157 of stent 1150 facilitates partial compressibility retrievability/retractability into sheath 1190 (as described hereinabove with reference to FIG. 11C) of distal portion 1157 following radial expansion of distal portion 1157. That is, sheath 1190 is slidable proximally to expose distal portion 1157 from within the sheath and allow distal portion 1157 to radially expand while proximal portion 1156 remains disposed radially-compressed within sheath 1190. Since (1) peaks 1152 of distal portion 1157 all point distally, and (2) interconnectors 1158 connect valleys 1154 of distal portion 1157, there is no portion of distal portion 1157 which protrudes from the tubular structure of stent 1150, which would otherwise interfere with distal sliding of sheath 1190 to compress and retrieve/retract distal portion 1157 within sheath 1190. Therefore, distal portion 1157 is retrievable/retractable within sheath 1190. As such stent 1150 is retrievable up to ½ deployment, as shown.

Each annular ring portion 1151 comprises a plurality of struts 1153. Each strut has a width W7 of between 50 and 1000 micron, e.g., between 100 and 500 micron, for example, 200 micron. Each interconnector 1158 has a width W6 of between 50 and 500 micron e.g., 200 micron.

Stent 1150 is shaped so as to provide a plurality of delivery-tool couplers 1159 at a proximal end 1300 thereof, as described hereinabove with reference to FIG. 11C. Couplers 1159 are shaped so as to surround and engage a plurality of tabs, which may function as pawls, provided on shaft 1016 of tool 1002.

As shown in FIG. 13C, stent 1150 is coupled to flexible band 1140 at a first portion thereof, i.e., a proximal portion thereof. Flexible band 1140, in turn, is coupled at a second portion (i.e., a distal portion thereof) to tissue anchor 40. As described hereinabove with reference to FIGS. 1A-D, tissue anchor 40 is implanted in tissue of tricuspid valve 4, then stent 50 is pulled in order to apply tension to flexible member 42 in order to adjust the relative positioning of the leaflets of tricuspid valve 4, and then stent 50 is deployed in the blood vessel. Following the deploying of stent 50 in the blood vessel, flexible member 42 exerts tension force on stent 50. In order to distribute tension along the length of stent 1150, stent 1150 is shaped so as to define a tension-distributing element 1160.

Tension-distributing element 1160 has a width W5 of between 1 and 4 mm, e.g., 2.6 mm. Tension-distributing element 1160 has a longitudinal length L6 measured along longitudinal axis 1155 that is generally equal to longitudinal length L5 of stent 1150, as shown by way of illustration and not limitation. Thus, tension-distributing element 1160, as shown in FIGS. 13A-C, comprises an elongate tension-distributing element 1161. That is, each one of lengths L5 and L6 of stent 1150 and tension-distributing element 1160, respectively, is between 20 and 120 mm, e.g., 70 mm. It is to be noted that lengths L5 and L6 are shown as being generally equal by way of illustration and not limitation, and that length L6 tension-distributing element 1160 may be smaller than the longitudinal length of the stent, as shown hereinbelow with reference to FIGS. 15A-B, for example. That is, the longitudinal length of tension-distributing element 1160 is at least 15% of longitudinal length L5 of stent 1150.

Typically, a width of a widest mechanical structural element 1651 is between 100 and 500 micron, and width W5 of tension-distributing element 1160 is between 1 and 4 mm. For some applications, width W5 of tension-distributing element 1160 is at least 13 times the width of the widest mechanical structural element 1651.

Tension-distributing element 1160 is shaped so as to provide a plurality of eyelets 1170 (FIGS. 13A-B). As shown in FIG. 13C, the proximal portion of flexible member 42 (or band 1140, as shown) is threaded through eyelets 1170 of tension-distributing element 1160. By threading the proximal portion of band 1140 through tension-distributing element 1160, tension applied from anchor 40 and band 1140 is distributed along the length of stent 1150.

It is to be noted that tension-distributing element 1160 and mechanical structural elements 1651 are typically fabricated from a single piece of tubular alloy, typically superelastic, e.g., nitinol. For some applications tension-distributing element 1160 and mechanical structural elements 1651 are modularly assembled.

As shown in FIG. 13C, tissue anchor 40 defines first tissue-engaging element 60a, and stent 1150 defines second tissue-engaging element 60b.

Figure 14C:
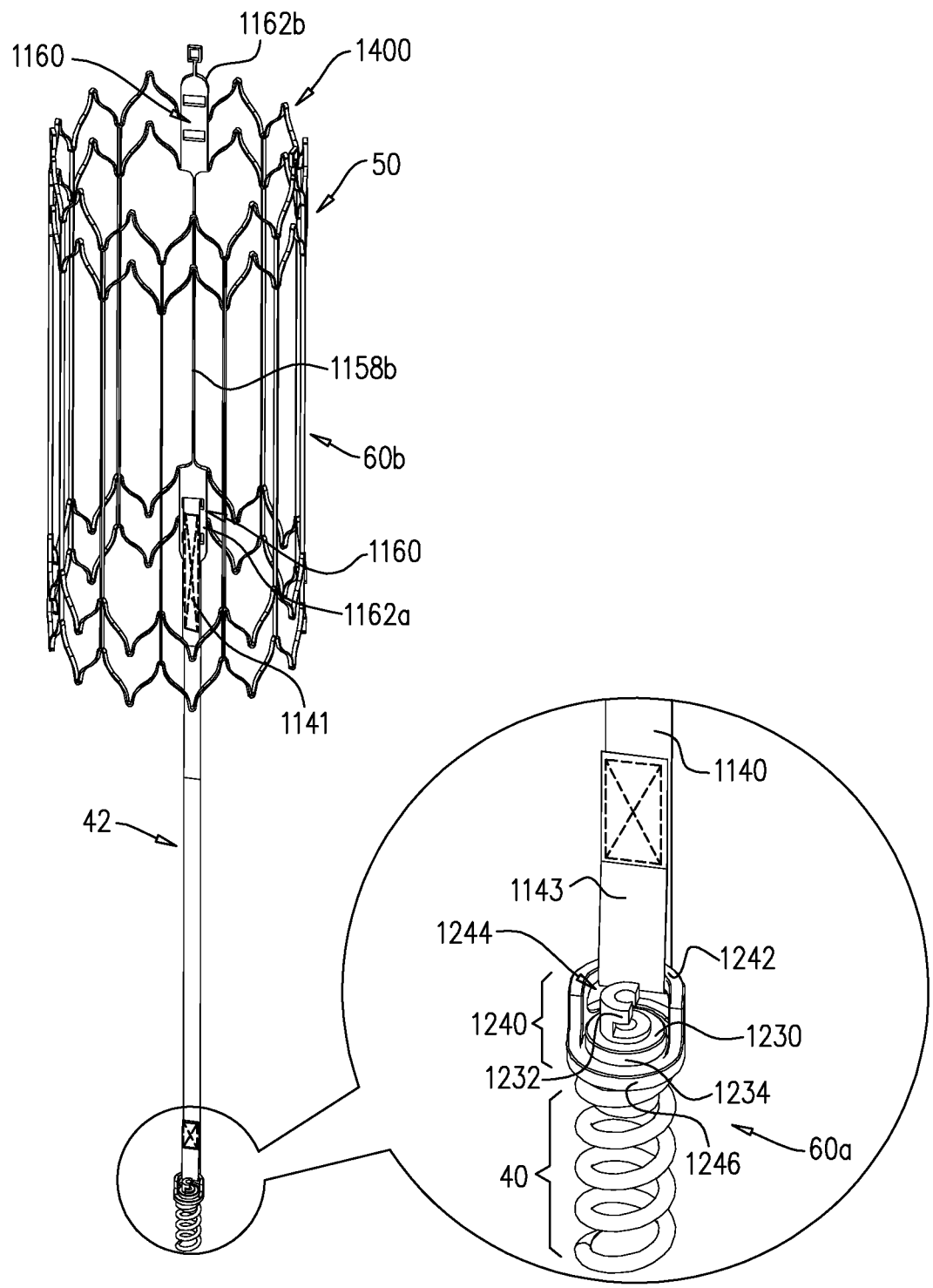

Reference is now made to FIGS. 14A-C, which are schematic illustrations of a stent 1400 comprising one or more (e.g., two, as shown) first portions 1402 and one or more (e.g., one, as shown) second portion 1404, each of portions 1402 and 1404 comprising a plurality of mechanical structural elements 1651, in accordance with some applications of the present invention. FIG. 14A shows stent 1400 in an assembled state, and FIG. 14B shows stent 1400 in a flattened state in which stent 1400 is cut longitudinally and flattened, for clarity of illustration. It is to be noted, however, that the configuration shown in FIG. 14A defines the configuration of stent 1400 in a radially-expanded state.

The structural configuration of stent 1400 provided by mechanical structural elements 1651 may be formed by expanding a laser-slotted metallic tube, or may be chemically etched from a flat sheet and welded to a tube, or may be formed from a single wire, or may be formed by assembling individual wire elements, or by any other method of construction known to those skilled in the art. The design of stent 1400 can be laser cut from a small diameter tube, expanded to the final diameter, or may be cut from a large diameter tube, which is equal to the final diameter of a fully expanded stent or which may be further expanded to an even larger diameter.

Portions 1402 of stent 1400 are each shaped so as to provide a plurality (e.g., two, as shown) of coaxially-disposed annular ring portions 1151. Each ring portion 1151 is shaped so as to define a plurality of peaks 1152 and a plurality of valleys 1154. Stent 1400 comprises a plurality of interconnectors 1158 (e.g., vertical interconnectors, as shown). As shown in exemplary ring portions 1151a and 1151b, the ring portions are aligned in a manner in which peaks 1152 and 1154 are in phase. Thus, interconnectors 1158 are vertically disposed between respective valleys 1154 of respective ring portions 1151.

Portions 1402 have interconnectors 1158a having a length of between 4 and 25 mm, e.g., 9 mm. Portion 1404 is shaped so as to provide a plurality of elongate interconnectors 1158b which connect portions 1402. Interconnectors 1158b have a length of between 20 and 80 mm, e.g., 50 mm. Taken together, peaks 1152, valleys 1154, and interconnectors 1158a of portions 1402 impart a greater radial force on surrounding tissue in a radially-expanded state of stent 1400 than portion 1404 of stent 1400, because portion 1404 comprises only elongate interconnectors 1158b. Such a configuration of stent 1400 provides an endoluminal implant which has a portion that exerts less radial force on surrounding tissues; thus, stent 1400 is configured to be placed in a blood vessel (e.g., the inferior vena cava) that is surrounded by organs. For applications in which stent 1400 is placed within the blood vessel that is surrounded by organs, portion 1404 of stent 1400 exerts less radial force on the surrounding organs than portions 1402.

Such a configuration of mechanical structural elements 1651 provides stent 1400 with a property of generally maintaining its longitudinal length L5 measured along longitudinal axis 1155, during radial expansion of stent 1400 from a radially-compressed state of stent 1400.

Each annular ring portion 1151 comprises a plurality of struts 1153. Each strut has a width W7 of between 50 and 1000 micron, e.g., between 100 and 500 micron, for example, 200 micron. Each interconnector 1158 has a width W6 of between 50 and 500 micron e.g., 200 micron.

Stent 1400 is shaped so as to provide a plurality of delivery-tool couplers 1159 at a proximal end 1300 thereof, as described hereinabove with reference to FIG. 11C. Couplers 1159 are shaped so as to surround and engage a plurality of tabs, which may function as pawls, provided on shaft 1016 of tool 1002.

As shown in FIG. 14C, stent 1400 is coupled to flexible band 1140 at a first portion thereof, i.e., a proximal portion thereof. Flexible band 1140, in turn, is coupled at a second portion (i.e., a distal portion thereof) to tissue anchor 40. As described hereinabove with reference to FIGS. 1A-D, tissue anchor 40 is implanted in tissue of tricuspid valve 4 (e.g., in the anteroposterior commissure), then stent 50 is pulled in order to apply tension to flexible member 42 (or band 1140) in order to adjust the relative positioning of the leaflets of tricuspid valve 4, and then stent 50 is deployed in the blood vessel. Following the deploying of stent 50 in the blood vessel, flexible member 42 exerts tension force on stent 50. In order to distribute tension along the length of stent 1400, stent 1400 is shaped so as to define tension-distributing element 1160.

As shown in FIG. 14B, tension-distributing element 1160 comprises a modular tension-distributing element having a distal tension-distributing element 1162a and a proximal tension-distributing element 1162b. Distal tension-distributing element 1162a and proximal tension-distributing element 1162b are coupled together by an interconnector 1158b. Distal tension-distributing element 1162a and proximal tension-distributing element 1162b, together with interconnector 1158, assume length L6 of tension-distributing element 1160 that is generally equal to longitudinal length L5 of stent 1400, as shown by way of illustration and not limitation. Each one of lengths L5 and L6, respectively, is between 20 and 120 mm, e.g., 70 mm. It is to be noted that lengths L5 and L6 are shown as being generally equal by way of illustration and not limitation, and that length L6 tension-distributing element 1160 may be smaller than the longitudinal length of the stent, as shown hereinbelow with reference to FIGS. 15A-B, for example. That is, the longitudinal length of tension-distributing element 1160 is at least 15% of longitudinal length L5 of stent 1400.

Each one of distal tension-distributing element 1162a and proximal tension-distributing element 1162b has a longitudinal length L7 of between 5 and 25 mm.

As shown in FIG. 14C, first portion 1143 of band 1140 is coupled to distal tension-distributing element 1162a by being threaded through eyelet 1170 of element 1162a. It is to be noted, however, that portion 1143 of band 1140 may be coupled to both distal tension-distributing element 1162a and proximal tension-distributing element 1162b by extending along the longitudinal length of stent 1400. It is to be noted that longer the portion of band 1140 coupled along the longitudinal length of stent 1400, the more force is distributed along the longitudinal length of stent 1400.

It is to be noted that tension-distributing elements 162a and 1162b and mechanical structural elements 1651 are fabricated from a single piece of tubular alloy, typically superelastic, e.g., nitinol. For some applications tension-distributing elements 1162a and 1162b and mechanical structural elements 1651 are modularly assembled.

As shown in FIG. 14C, tissue anchor 40 defines first tissue-engaging element 60a, and stent 1400 defines second tissue-engaging element 60b.

Figures 15A, 15B:
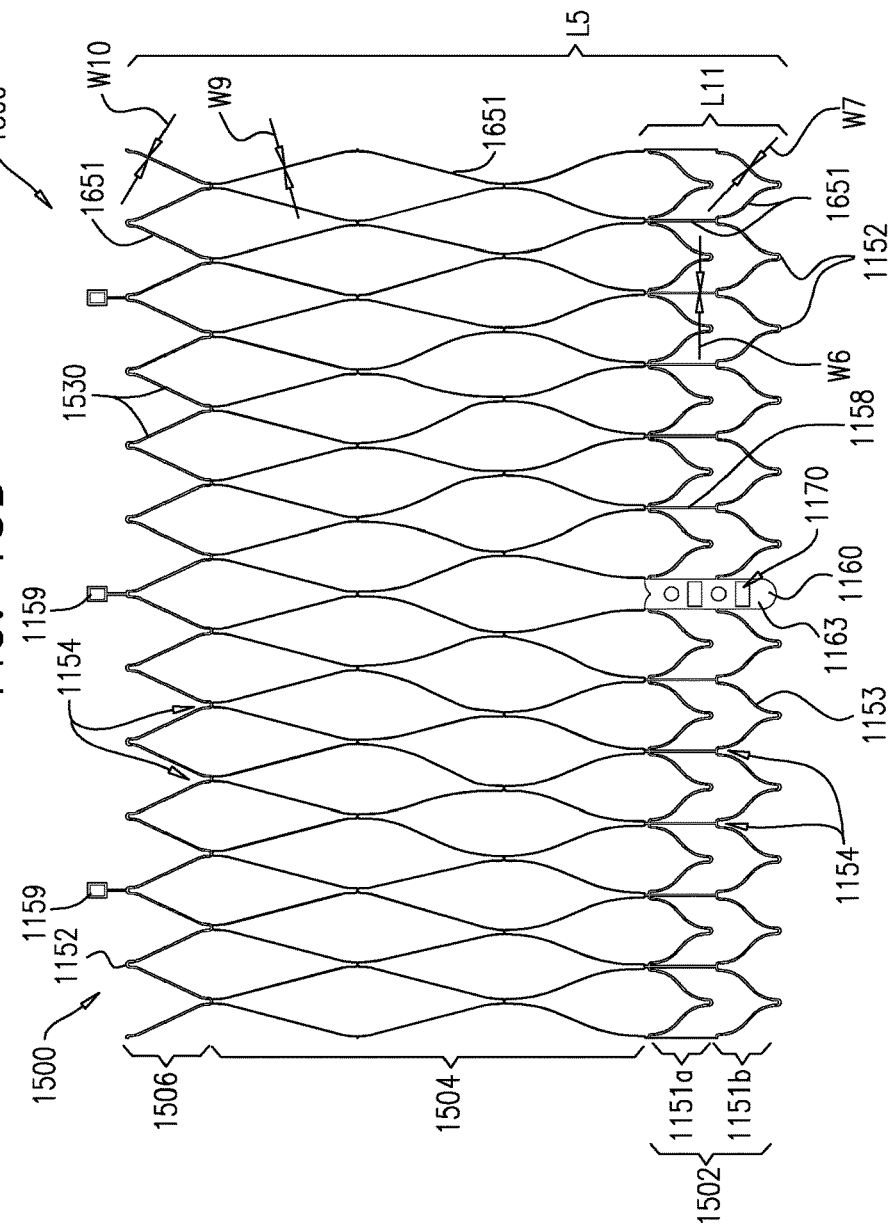
FIGS. 15A-B are schematic illustrations of yet another stent coupled to a helical anchor, in accordance with some applications of the present invention.

Reference is now made to FIGS. 15A-B, which are schematic illustrations of a stent 1500 comprising a first portion 1502, a second portion 1504, and a third portion 1506, each of portions 1502, 1504, and 1506 comprising a plurality of mechanical structural elements 1651, in accordance with some applications of the present invention. FIG. 15A shows stent 1500 in an assembled state, and FIG. 15B shows stent 1500 in a flattened state in which stent 1500 is cut longitudinally and flattened, for clarity of illustration. It is to be noted, however, that the configuration shown in FIG. 15A defines the configuration of stent 1500 in a radially-expanded state.

The structural configuration of stent 1500 provided by mechanical structural elements 1651 may be formed by expanding a laser-slotted metallic tube, or may be chemically etched from a flat sheet and welded to a tube, or may be formed from a single wire, or may be formed by assembling individual wire elements, or by any other method of construction known to those skilled in the art. The design of stent 1500 can be laser cut from a small diameter tube, expanded to the final diameter, or may be cut from a large diameter tube, which is equal to the final diameter of a fully expanded stent or which may be further expanded to an even larger diameter.

Portion 1504 comprises a plurality of struts 1520 each having a width W9 of between 25 and 250 micron, e.g., 100 micron. Struts 1520 are spatially arranged so as to form a plurality of quadrilateral-shaped openings 1522, e.g., diamond-shaped openings.

Portion 1506 comprises a plurality of struts 1530 each having a width W10 of between 50 and 500 micron, e.g., 200 micron. Struts 1530 are spatially arranged so as to form a plurality of peaks 1152 and valleys 1154.

Struts 1520 of portion 1504 are longer and thinner than struts 1530 of portion 1506. Thus, portion 1506 exerts a greater radial force on surrounding tissue in a radially-expanded state of stent 1500 than portion 1504 of stent 1500. Additionally, the relative spatial arrangement of struts 1530 of portion 1506 (as compared with the relative spatial arrangement of struts 1520 of portion 1504) enables portion 1506 to exert a greater radial force on surrounding tissue than portion 1504.

Portion 1502 of stent 1500 is shaped so as to provide a plurality (e.g., two, as shown) of coaxially-disposed annular ring portions 1151. Each ring portion 1151 is shaped so as to define a plurality of peaks 1152 and a plurality of valleys 1154. Stent 1400) comprises a plurality of interconnectors 1158 (e.g., vertical interconnectors, as shown). As shown in exemplary ring portions 1151a and 11516b, the ring portions are aligned in a manner in which peaks 1152 and 1154 are in phase. Thus, interconnectors 1158 are vertically disposed between respective valleys 1154 of respective ring portions 1151.

Each one of interconnectors 1158 of portion 1502 has a length of between 4 and 25 mm, e.g., 9 mm. Taken together, peaks 1152, valleys 1154, and interconnectors 1158 of portions 1502 impart a greater radial force on surrounding tissue in a radially-expanded state of stent 1500 than portions 1504 and 1506 of stent 1500. Such a configuration of stent 1500 provides an endoluminal implant which has one or more portions (e.g., portions 1504 and 1506) that exert less radial force on surrounding tissues than portion 1502; thus, stent 1500 is configured to be placed in a blood vessel (e.g., the inferior vena cava) that is surrounded by organs. For applications in which stent 1500 is placed within the blood vessel that is surrounded by organs, portion 1504 of stent 1500 exerts less radial force on the surrounding organs than portion 1502.

Such a configuration of mechanical structural elements 1651 provides stent 1500 with a property of generally maintaining its longitudinal length L5 measured along longitudinal axis 1155, during radial expansion of stent 1500 from a radially-compressed state of stent 1500.

Each annular ring portion 1151 comprises a plurality of struts 1153. Each strut has a width W7 of between 50 and 1000 micron, e.g., between 100 and 500 micron, for example, 200 micron. Each interconnector 1158 has a width W6 of between 50 and 500 micron e.g., 200 micron.

Stent 1500 is shaped so as to provide a plurality of delivery-tool couplers 1159 at a proximal end 1300 thereof, as described hereinabove with reference to FIG. 11C. Couplers 1159 are shaped so as to surround and engage a plurality of tabs, which may function as pawls, provided on shaft 1016 of tool 1002.

Stent 1500 is couplable to flexible band 1140 in a manner as described hereinabove with reference to FIGS. 13A-C and 14A-C. Flexible band 1140, in turn, is coupled at a second portion (i.e., a distal portion thereof) to tissue anchor 40. As described hereinabove with reference to FIGS. 1A-D, tissue anchor 40 is implanted in tissue of tricuspid valve 4 (e.g., in the anteroposterior commissure), then stent 50 is pulled in order to apply tension to flexible member 42 (e.g., band 1140) in order to adjust the relative positioning of the leaflets of tricuspid valve 4, and then stent 50 is deployed in the blood vessel. Following the deploying of stent 50 in the blood vessel, flexible member 42 exerts tension force on stent 50. In order to distribute tension along the length of stent 1500, stent 1500 is shaped so as to define tension-distributing element 1160.

As shown in FIG. 15B, tension-distributing element 1160 comprises a distal tension-distributing element 1163. Distal tension-distributing element 1163 has a longitudinal length L1 of between 10 and 60 mm. That is, the longitudinal length of tension-distributing element 1160 is at least 15% of longitudinal length L5 of stent 1500.

A first portion of band 1140 is coupled to distal tension-distributing element 1163 is configured to be threaded through eyelet 1170 of element 1163.

It is to be noted that tension-distributing element 1163 and mechanical structural elements 1651 may be fabricated from a single piece of tubular alloy, typically superelastic, e.g., nitinol. For some applications tension-distributing element 1163 and mechanical structural elements 1651 are modularly assembled.

Stent 1500 defines second tissue-engaging element 60b.

The structural configuration of stent 1500 provided by mechanical structural elements 1651 may be formed by expanding a laser-slotted metallic tube, or may be chemically etched from a flat sheet and welded to a tube, or may be formed from a single wire, or may be formed by assembling individual wire elements, or by any other method of construction known to those skilled in the art. The design of stent 1500 can be laser cut from a small diameter tube, expanded to the final diameter, or may be cut from a large diameter tube, which is equal to the final diameter of a fully expanded stent or which may be further expanded to an even larger diameter.

Figure 16A:
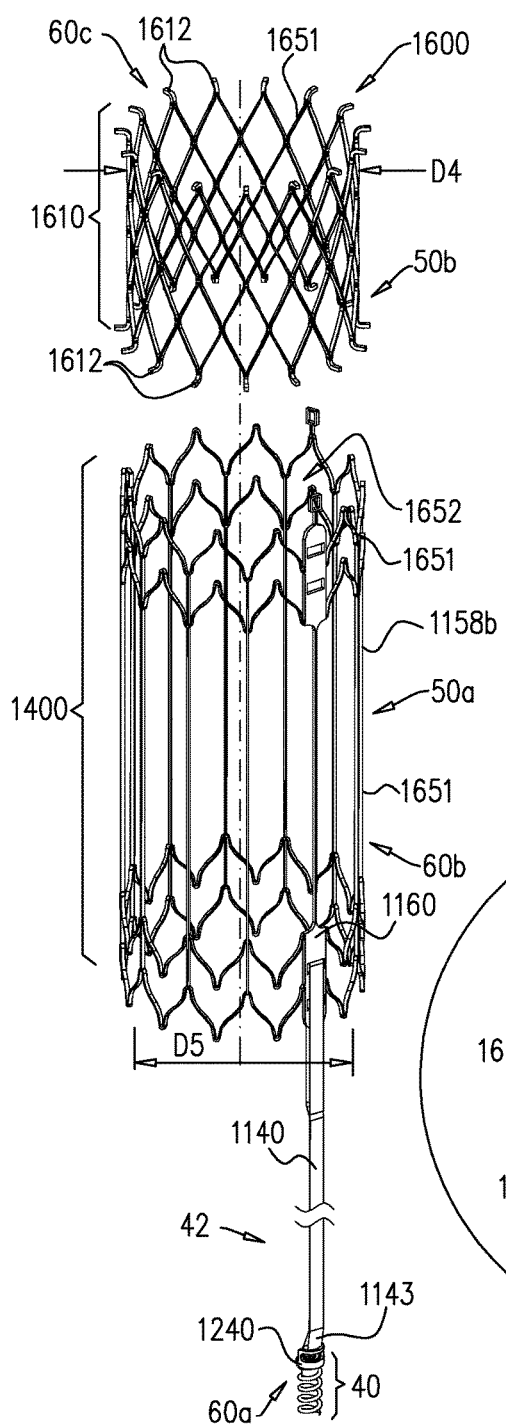
FIGS. 16A-B are schematic illustrations of a first and a second stent configured to be disposed concentrically, in accordance with some applications of the present invention.
Figure 16B:
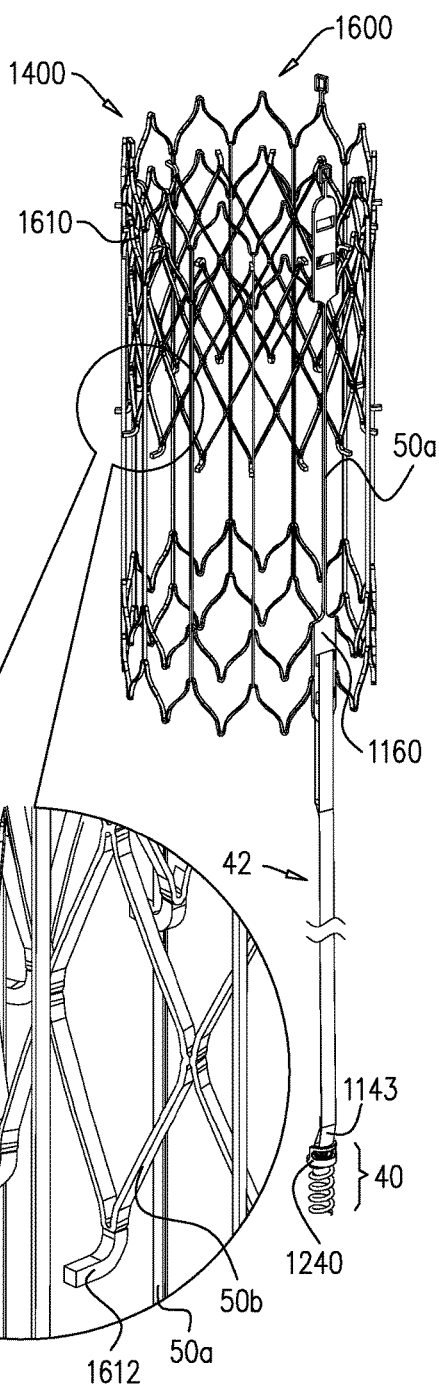

Reference is now made to FIGS. 16A-B, which are schematic illustrations of a stent system 1600 comprising a first stent 50a and a second stent 50b shaped so as to be concentrically disposed within a lumen of stent 50a and facilitate anchoring of stent 50a in the blood vessel, in accordance with some applications of the present invention. Stent 50a, as shown in FIGS. 16A-B comprises stent 1400 as described hereinabove with reference to FIGS. 14A-C. It is to be noted, however, that stent 50a may comprise any one of the stents shown in FIGS. 1D, 13A-C, 14A-C, and 15A-B. It is to be noted that stents 50a and 50b define respective radially-expandable percutaneous, e.g., endoluminal, implants.

Stent 50a comprises a plurality of mechanical structural elements 1651 that are arranged so as to form a first tubular structure having a lumen 1652 in a radially-expanded state of stent 50a that has an inner diameter D5 of between 18 and 45 mm, e.g., 24 mm, 28 mm, or 32 mm.

Stent 50b comprises a radially-expandable implant 1610 that comprises a plurality of mechanical structural elements 1651 that are arranged so as to form a second tubular structure. Implant 1610 is shaped so as to provide a plurality of tissue-engaging structures 1612 which protrude from the generally-tubular structure of implant 1610. For example, structures 1612 comprise barbs. Implant 1610 has an outer diameter D4 in a radially-expanded state of implant 1610, excluding tissue-engaging structures 1612, of between 18 and 45 mm, e.g., 24 mm, 28 mm, or 32 mm. Diameter D4 enables implant 1610 to expand at least as large as the inner diameter D5 of lumen 1652 of stent 50b. When implant 1610 expands to assume its expanded state within lumen 1652, as shown in FIG. 16B, tissue-engaging structures 1612 extend between mechanical structural elements 1651 of stent 50a in order to engage and be anchored to tissue of the blood vessel. Since structures 1612 extend between mechanical structural elements 1651 of stent 50a, stent 50b of implant 1610 facilitates anchoring of stent 50a in the blood vessel.

Tissue anchor 40 defines first tissue-engaging element 60a, stent 50a defines second tissue-engaging element 60b, and stent 50b defines third tissue-engaging element 60c.

As described hereinabove, tissue anchor 40 is implanted in first implantation site 30, and then stent 50b is deployed in the blood vessel. Following the deploying of stent 50b in the blood vessel, implant 1610 is position and deployed within lumen 1652 of stent 50a.

As described hereinabove, following implantation of stent 50a in the blood vessel, tension is applied to stent 50a by flexible member 42 (e.g., band 1140), which may cause migration of stent 50a within the blood vessel. By deploying stent 50b within lumen 1652 of stent 50a, tissue-engaging structures 1612 expand between mechanical structural elements 1651 of stent 50a in order to engage tissue of the blood vessel and anchor stent 50a to the blood vessel. Additionally, the expanding of stent 50b within lumen 1652 of stent 50a provides additional radial force of stent 50b in its expanded state against stent 50b, in order to apply additional radial force of stent 50a against the blood vessel.

The structural configuration of implant 1610 provided by mechanical structural elements 1651 may be formed by expanding a laser-slotted metallic tube, or may be chemically etched from a flat sheet and welded to a tube, or may be formed from a single wire, or may be formed by assembling individual wire elements, or by any other method of construction known to those skilled in the art. The design of implant 1610 can be laser cut from a small diameter tube, expanded to the final diameter, or may be cut from a large diameter tube, which is equal to the final diameter of a fully expanded stent or which may be further expanded to an even larger diameter. It is to be noted that mechanical structural elements 1651 may be arranged in a relative spatial orientation that is different from the orientation shown in FIG. 16A.

Figure 17:
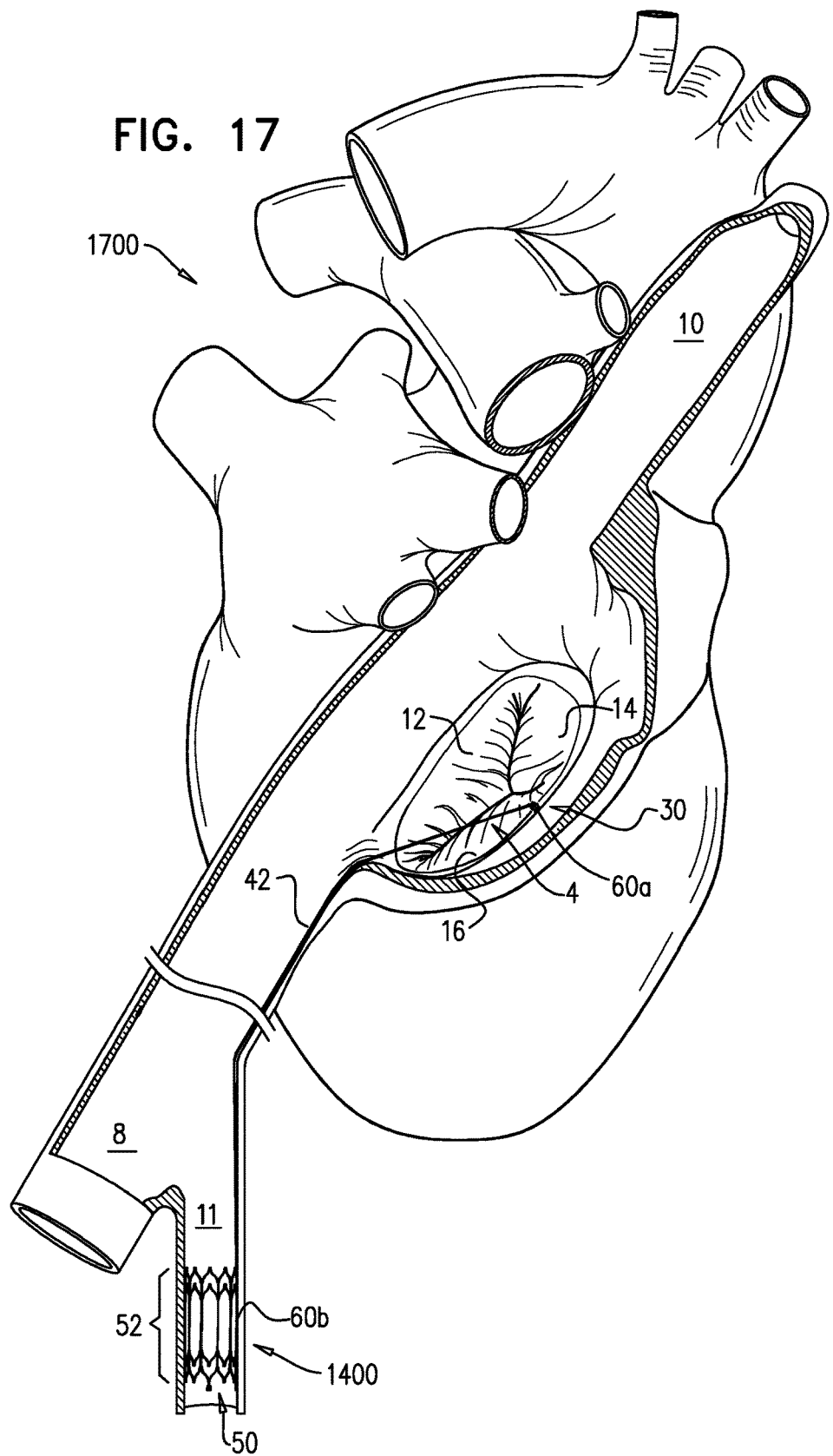
FIG. 17 is a schematic illustration of apparatus for reducing regurgitation of a heart valve which comprises a stent, a tissue anchor, and a tensioning element that couples the stent and the tissue anchor, in accordance with some applications of the present invention.

FIG. 17 shows a system 1700 for implanting second tissue-engaging element 60b in a blood vessel other than inferior vena cava 8 and superior vena cava 10, e.g., left hepatic vein 11, as shown, in accordance with some applications of the present invention. It is to be noted that second tissue-engaging element 60b comprises stent 1400 as described hereinabove with reference to FIGS. 14A-C, by way of illustration and not limitation. It is to be noted that second tissue-engaging element 60b may comprise any one of the stents or endoluminal implants shown in FIGS. 1D, 13A-C, 14A-C, 15A-B, and 16A-B. First and second tissue-engaging elements 60a and 60b are implanted at first and second implantation sites 30 and 52, in a manner as described hereinabove with reference to FIGS. 1A-D, 7A-D, 11A-C, and 12A-C. It is to be noted that for applications in which second tissue-engaging element 60b is implanted in the hepatic vein, element 60b in an expanded state thereof has an outer diameter of between 8.5 and 12 mm, and has a length of between 17 and 36 mm.

For some applications, flexible member 42 comprises band 1140, as described hereinabove.

For applications in which second implantation site 52 includes left hepatic vein 11, flexible member 42 has a length of between 150 and 300 mm. e.g., 200 mm.

It is to be noted that although implantation site 52 includes a portion of left hepatic vein 11, implantation site 52 may be a portion of a right hepatic vein or a middle hepatic vein.

Reference is made to FIGS. 1A-D. For applications in which second implantation site 52 includes inferior vena cava 8 or superior vena cava 10, flexible member 42 has a length of between 20 and 80 mm, e.g., between 40 and 60 mm.

It is to be noted that the scope of the present invention includes implanting second tissue-engaging element 60b in a coronary sinus of the patient. For such an application, flexible member has a length of between 10 and 40 mm, e.g., 20 mm.

Reference is now made to FIGS. 13A-C, 14A-C. 15A-B, and 16A-B. It is to be noted that any suitable configuration of tension-distributing element 1160 shown in any of FIGS. 13A-C, 14A-C, 15A-B, and 16A-B may be part of any of stents 1150, 1400, or 1500 shown in FIGS. 13A-C, 14A-C, 15A-B, and 16A-B.

FIG. 19 shows a system 2500 comprising an endoluminal percutaneous implant 2504 comprising two or more radially-expandable rings 2502a and 2502b which define second tissue-engaging element 60b, in accordance with some applications of the present invention. Rings 2502a and 2502b are shown as being elliptical by way of illustration and not limitation, and that rings 2502a and 2502b may be circular. Implant 2504 is coupled to a portion of longitudinal member 42 at a junction between rings 2502a and 2502b, by way of illustration and not limitation.

First and second elements 60a and 60b are implanted in manner as described hereinabove with reference to FIGS. 1A-D, 7A-D, 11A-C, and 12A-C. During the advancement of implant 2504, implant 2504 is crimped and radially-compressed within a sheath. For example, implant 2504 may be advanced within sheath 1190, as described hereinabove with reference to FIGS. 11A-C and 12A-C.

Implant 2504 exerts a strong radial force on tissue of the blood vessel while defining a low profile volume of mechanical structural elements.

It is to be noted that although second implantation site 52 includes a portion of inferior vena cava 8, second implantation site may include a portion of superior vena cava 10, hepatic vein 11, or any other suitable blood vessel.

Figure 23:
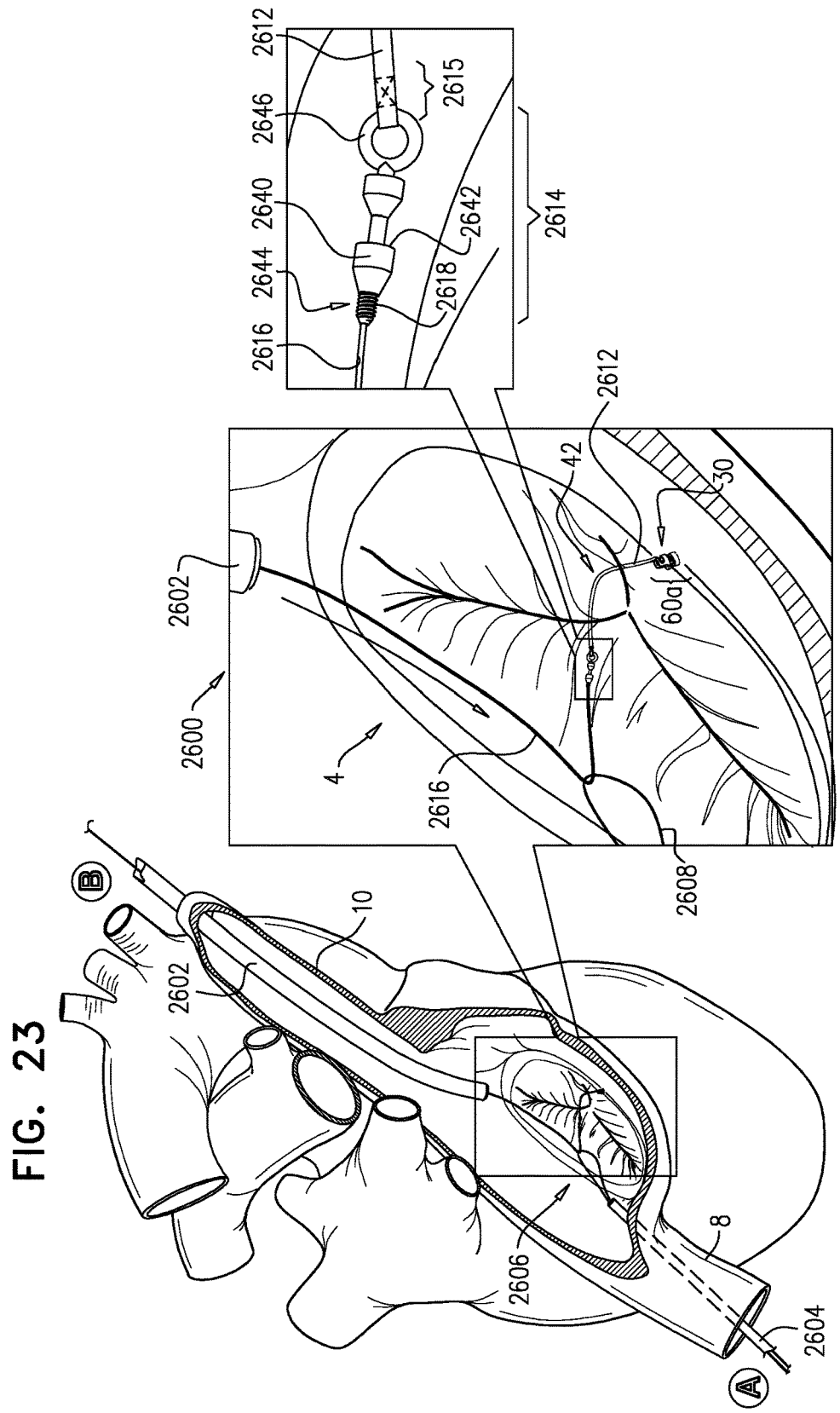
Figure 24:
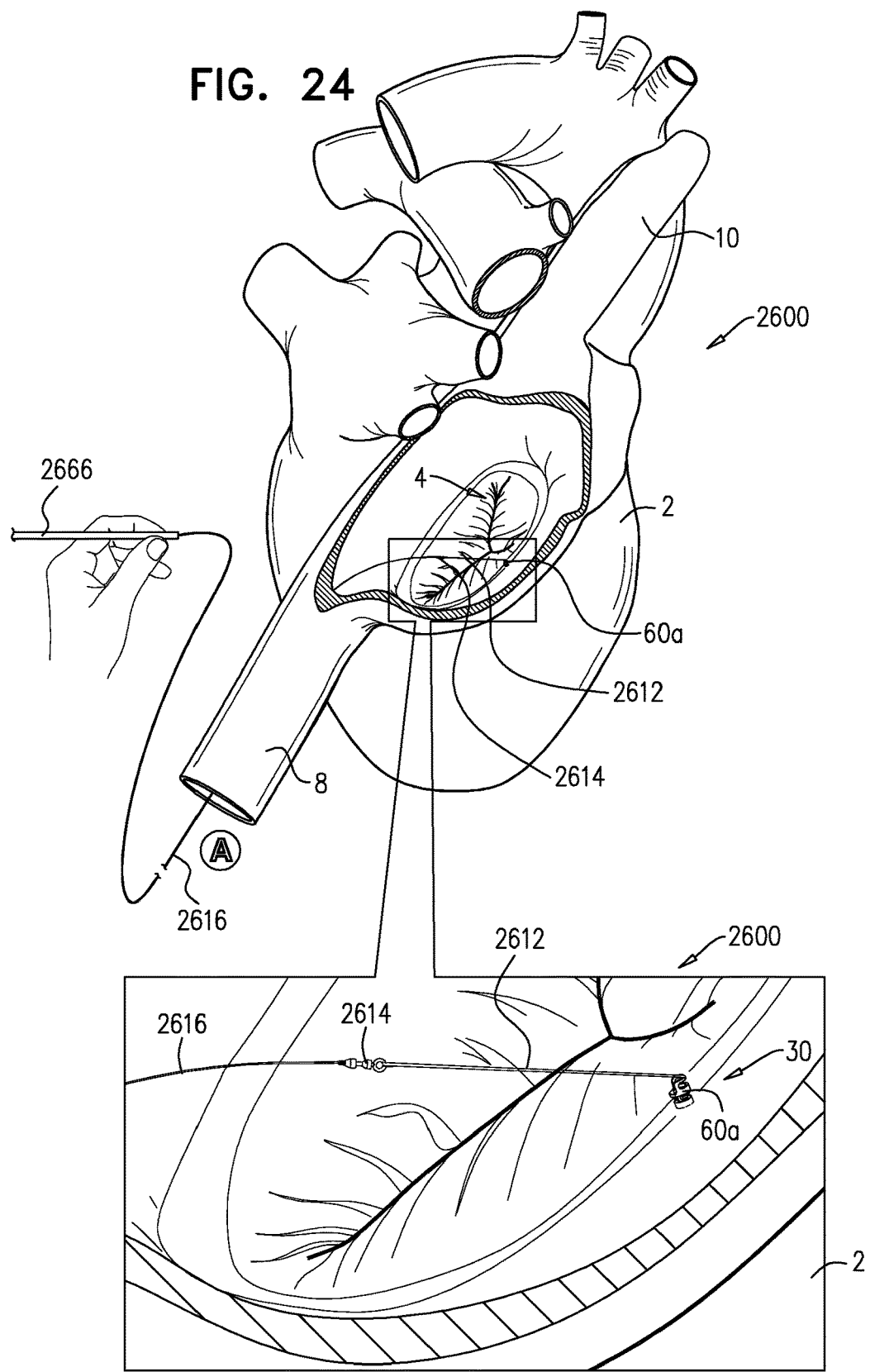
Figure 25:
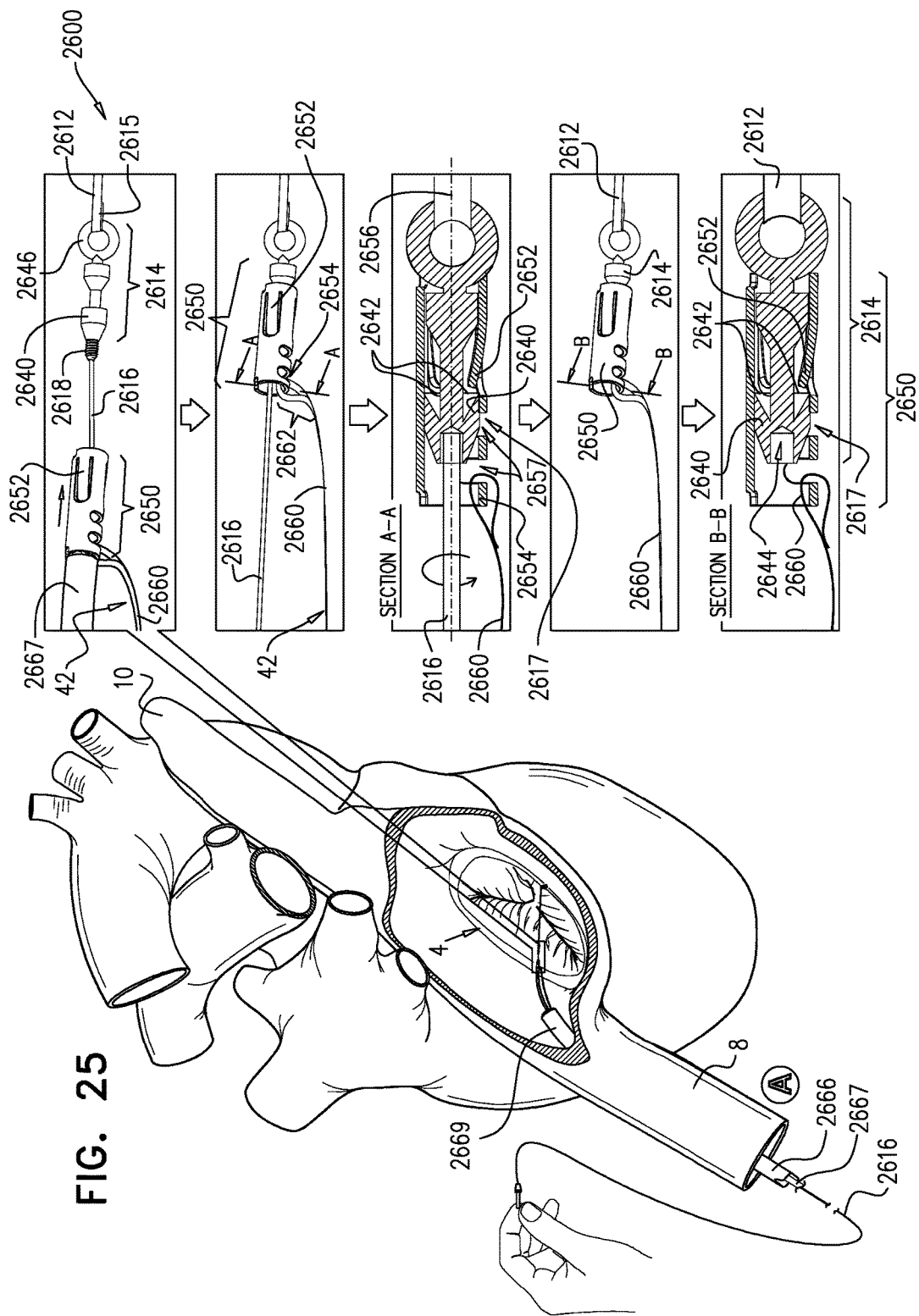
Figure 26:
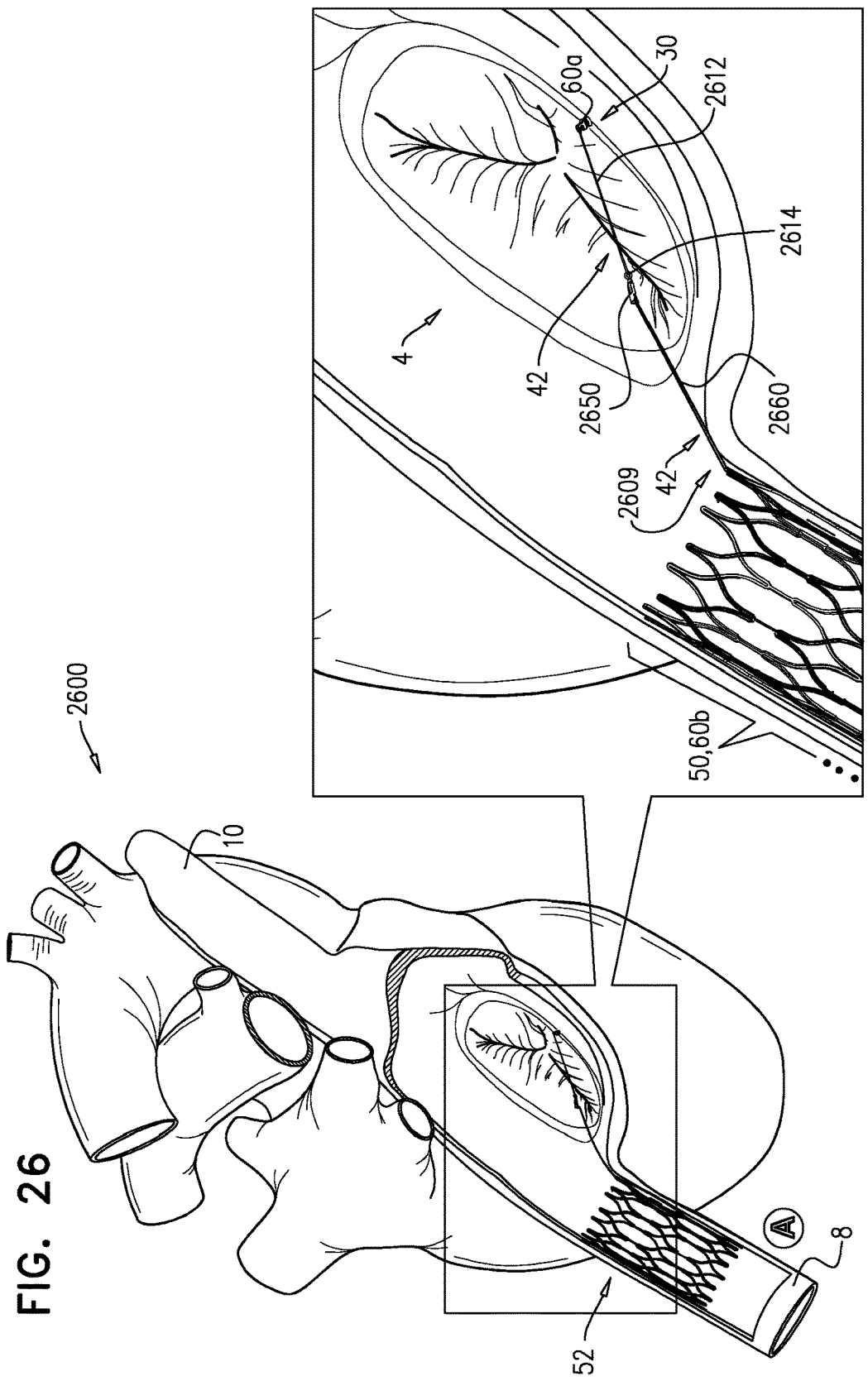

Reference is now made to FIGS. 20-26, which are schematic illustrations of a system 2600 comprising a first tissue-engaging element 60a coupled to a first flexible longitudinal member 2612 at a distal first end portion 2613 of first flexible longitudinal member 2612, and a second tissue-engaging element 60b coupled to a second flexible longitudinal member 2660 at a proximal first end portion 2609 of second flexible longitudinal member 2660, for repairing tricuspid valve 4 of heart 2 of a patient, in accordance with some applications of the present invention. Second flexible longitudinal member 2660 is coupled at a distal second end portion 2662 thereof to a proximal portion of a second flexible-longitudinal-member-coupling element 2650, e.g., by being looped around a portion of second flexible-longitudinal-member-coupling element 2650, as shown. Typically, as shown in FIGS. 25 and 26, second flexible-longitudinal-member-coupling element 2650 is shaped so as to define a coupling interface that is not coaxial with the second flexible-longitudinal-member-coupling element, and second flexible longitudinal member 2660 is fixed to the coupling interface. First and second end portions 2609 and 2662 of second flexible longitudinal member 2660 are disposed at opposite longitudinal ends of the second flexible longitudinal member.

System 2600 further comprises a first delivery tool 2602 and a second delivery tool 2666, as described hereinbelow.

First tissue-engaging element 60a comprises a tissue anchor 40 which is designated for implantation at least in part in cardiac tissue at a first implantation site 30, such as tissue of an annulus of an atrioventricular valve, or tissue of a wall of the atrium adjacent the atrioventricular valve, as mentioned above. It is to be noted that tissue anchor 40 comprises a helical tissue anchor by way of illustration and not limitation and that tissue anchor 40 may comprise any tissue anchor for puncturing or clamping cardiac tissue, including, but not limited to, the tissue anchors described hereinabove with reference to FIGS. 7A-D, 10A-D 11A-C, 12A-C, 13A-C, and 14A-C. Second tissue-engaging element 60b comprises a percutaneous implant, for example, an endoluminal implant, e.g., stent 50, which is designated for implantation in a portion of a blood vessel, e.g., inferior vena cava 8 (such as shown in FIG. 26) or superior vena cava 10 (not shown), at second implantation site 52. Except as described hereinbelow, system 2600 is similar to system 20 described hereinabove with reference to FIGS. 1A-D. System 2600 comprises one or more longitudinal members 42, which couple together first and second tissue-engaging elements 60a and 60b, as described hereinabove. For such applications, system 2600 comprises (1) first flexible longitudinal member 2612 (which defines a first of the one or more longitudinal members 42) coupled at a first portion thereof to first tissue-engaging element 60a, and (2) second flexible longitudinal member 2660 (which defines a second of the one or more longitudinal members 42) coupled at a first portion thereof to second tissue-engaging element 60b.

Typically, first and second flexible longitudinal members 2612 and 2660 comprise a flexible biocompatible textile e.g. polyester, nylon. PTFE, ePTFE. PEEK. PEBAX™, and/or superelastic material, e.g., nitinol. Typically, first and second flexible longitudinal members 2612 and 2660 comprise a plurality of fibers which are aligned, e.g., woven or intertwined, to form a fabric band, as is described hereinabove with reference to FIGS. 11A-C, 13C, and 14C. In some applications of the present invention, first and second flexible longitudinal members 2612 and 2660 each comprise a braided polyester suture (e.g., DACRON™). In other applications of the present invention, first and second flexible longitudinal members 2612 and 1660 are coated with polytetrafluoroethylene (PTFE). In some applications of the present invention, first and second flexible longitudinal members 2612 and 2660 each comprise a plurality of wires that are intertwined to form a rope structure. For some applications, at least a part of each of first and second flexible longitudinal members 2612 and 2660 comprises a tension spring and/or a plurality of coils.

Figure 20:
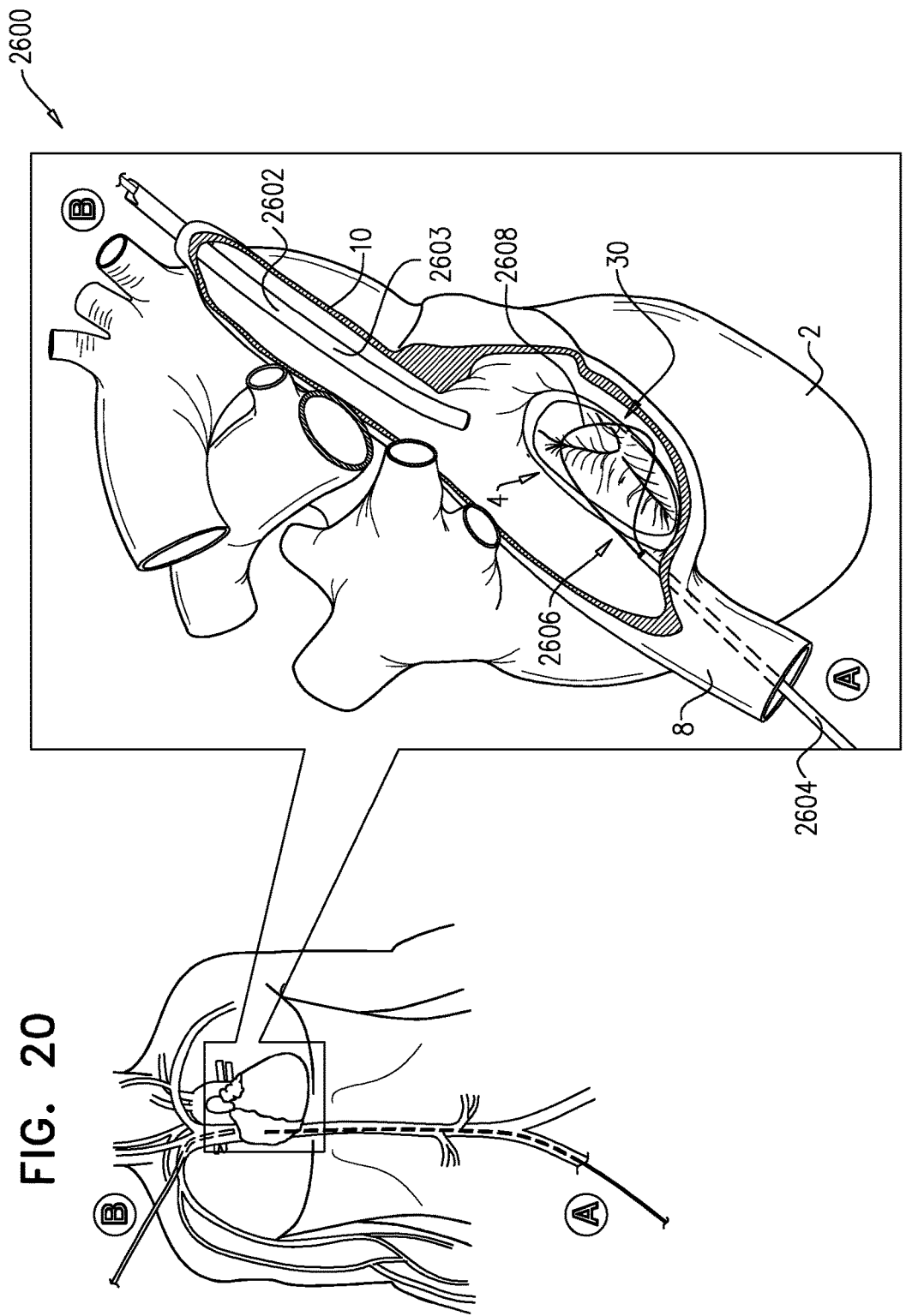

FIG. 20 shows first delivery tool 2602 being advanced toward first implantation site 30 at tricuspid valve 4 through superior vena cava 10 from a suitable point of entry, in a direction from B to A. As can be seen in FIG. 20, first delivery tool 2602 comprises a catheter tube 2603, which is sized and configured to be introduced percutaneously. Additionally, a snare 2606 shaped to define a loop 2608 is advanced by a snare delivery tool 2604 toward first implantation site 30 at tricuspid valve 4 through inferior vena cava 8 from a suitable point of entry, in a direction from A to B. It is to be noted that system 2600 can be advanced in opposite direction to the one as shown in FIGS. 20-26. That is, first-tissue-engaging-element tool 2602 may be advanced through inferior vena cava 8 in the direction from A to B, while snare delivery tool 2604 may be advanced through superior vena cava 10 in the direction from B to A.

FIGS. 21 and 22A-D show a delivery system to implant first tissue-engaging element 60*a* in tissue of the annulus of tricuspid valve 4 or of the wall of atrium above the annulus. Tissue anchor 60*a* is described hereinabove with reference to FIGS. 1A-D and 11A-C. Distal first end portion 2613 of first flexible longitudinal member 2612 is looped around flexible-longitudinal-member-coupler 1242, and within a portion of opening 1244 of connecting element 1240. As described hereinabove with reference to FIG. 11A, adapter head 1230 is coupled to a proximal portion of anchor 40 via annular loop 1246. As anchor 40 is rotated, the proximal-most coil of anchor 40 rotates freely within annular loop 1246, and anchor 40 rotates with respect to annular loop 1246.

Anchor 40 is rotated by the torque-delivering tool comprising torque-delivering cable 1204. As described hereinabove, torque-delivering cable 1204 is welded at a distal end thereof to first coupling 1220, which defines a first coupling element. As shown in FIG. 22D, the first coupling element has a first-coupling-element longitudinal axis along an axis 2611. First coupling 1220 is shaped so as to define a first-coupling-element main body portion 2620 shaped so as to define a first-coupling-element-main-body passage 2621. First coupling 1220 is shaped so as to define a first-coupling-element secondary body portion 2622 coaxial with main body portion 2620. First-coupling element secondary body portion 2622 is shaped so as to define a first-coupling-element-secondary-body-portion passage 2623 that is coaxial with first-coupling-element-main-body passage 2621. First coupling 1220 is shaped so as to define a connecting element 2624 that connects first-coupling-element secondary body portion 2622 to first-coupling-element main body portion 2620. First coupling 1220 is shaped so as to define a first-coupling-element space 2625 between main body portion 2620 and secondary body portion 2622.

As shown in FIG. 22D, adapter head 1230 defines a second coupling element having a longitudinal axis along axis 2611 (FIGS. 22C-D). Head 1230 is shaped so as to define a second-coupling-element main body portion 2630 shaped so as to define a second-coupling-element-main-body passage 2631. Head 1230 is shaped so as to define a second-coupling-element secondary body portion 2632 coaxial with main body portion 2630. The second-coupling element secondary body portion 2632 is shaped so as to define a second-coupling-element-secondary-body-portion passage 2633 that is coaxial with second-coupling-element-main-body passage 2631. Head 1230 is shaped so as to define a connecting element 2634 that connects second-coupling-element secondary body portion 2632 to second-coupling-element main body portion 2630. Head 1230 is shaped so as to define a second-coupling-element space 2635 between main body portion 2630 and secondary body portion 2632.

Figure 21:
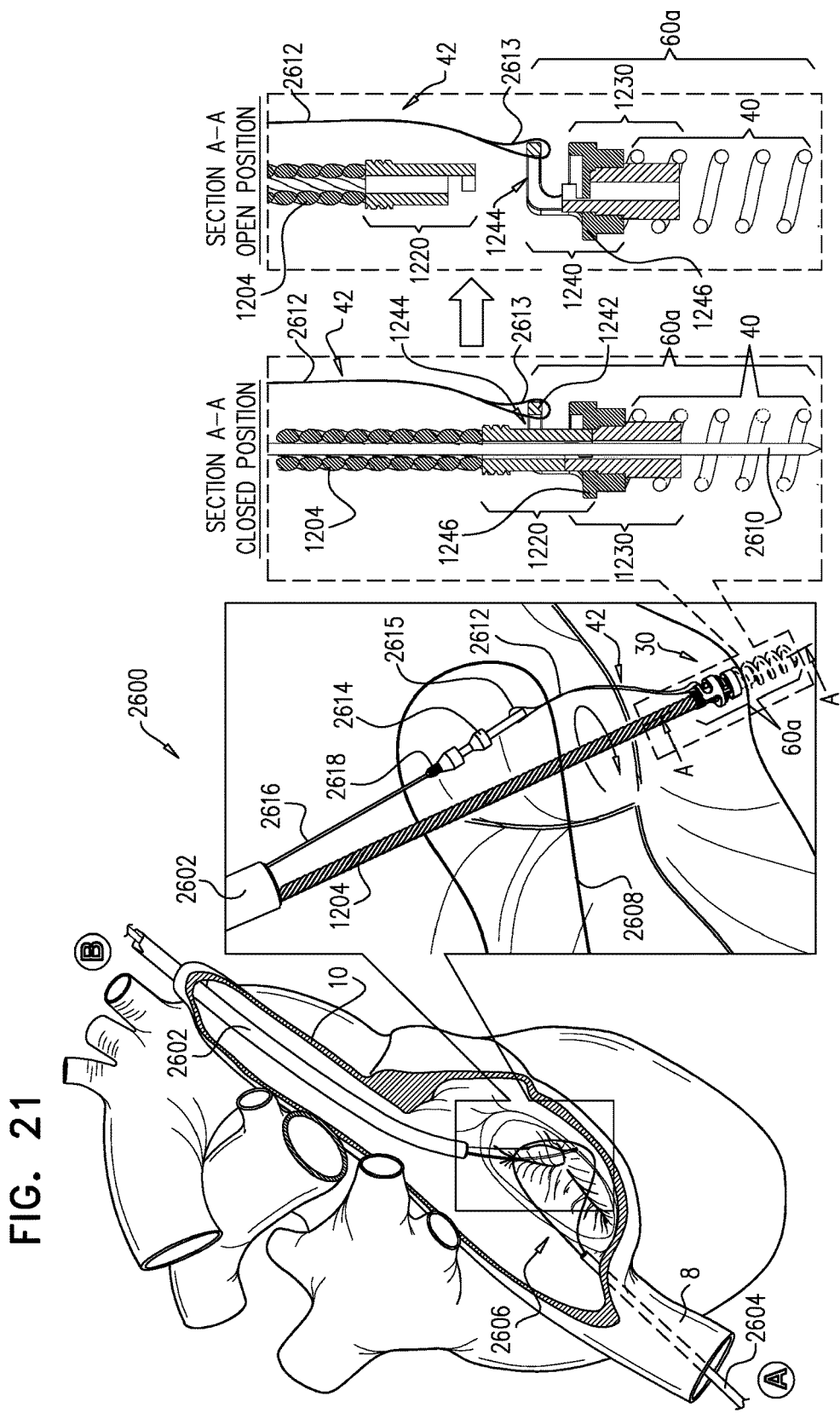

As shown in FIG. 21 (section A-A, closed position) and in FIGS. 22A-B, first coupling 1220 and head 1230 are coupled together in order to reversibly couple torque-delivering cable 1204 to anchor 40. In such a closed position, (1) first-coupling-element secondary body portion 2622 fits within second-coupling-element space 2635 of head 1230, and (2) second-coupling-element secondary body portion 2632 fits within first-coupling-element space 2625 of first coupling 1220. In such a manner of these fittings, first-coupling-element-main-body passage 2621, first-coupling-element-secondary-body-portion passage 2623, second-coupling-element-main-body passage 2631, and second-coupling-element-secondary-body-portion passage 2633 are aligned along axis 2611.

In order to maintain such coupling of first coupling 1220 and head 1320, an elongate longitudinal element 2610 (e.g., a rod) is reversibly disposed within first-coupling-element-main-body passage 2621, first-coupling-element-secondary-body-portion passage 2623, second-coupling-element-main-body passage 2631, and second-coupling-element-secondary-body-portion passage 2633.

As shown in FIG. 22C, elongate longitudinal element 2610 is removed from within the passages of coupling 1220 and of head 1230 in order to facilitate decoupling of coupling 1220 from head 1230.

FIG. 21 (section A-A, open position) and FIGS. 22C-D show coupling 1220 and head 1230 decoupled from each other. This is accomplished when (1) first-coupling-element secondary body portion 2622 is removed from second-coupling-element space 2635 of head 1230, and (2) second-coupling-element secondary body portion 2632 is removed from first-coupling-element space 2625 of coupling 1220. This decoupling may be accomplished by tilting cable 1204 away from axis 2611.

Reference is again made to FIG. 21. A proximal second end portion 2615 of first flexible longitudinal member 2612 is coupled to (e.g., by being looped around) a portion of a first flexible-longitudinal-member-coupling element 2614. A proximal end of first flexible-longitudinal-member-coupling element 2614 is reversibly coupled to a distal end of a flexible longitudinal guide member 2616. For some applications, in order to enable such coupling, the proximal end of first flexible-longitudinal-member-coupling element 2614 is shaped so as to define a threaded coupling 2644 for receiving a screw 2618 that is coupled to the distal end of flexible longitudinal guide member 2616, as shown. For other applications, the proximal end of first flexible-longitudinal-member-coupling element 2614 is reversibly coupled to the distal end of flexible longitudinal guide member 2616 using the techniques described hereinabove with reference to FIGS. 21 and 22A-D for reversibly coupling torque-delivering cable 1204 to distal tissue-anchor coupling element 1233 of anchor 40, mutatis mutandis. First and second end portions 2613 and 2615 of first flexible longitudinal member 2612 are disposed at opposite longitudinal ends of the first flexible longitudinal member.

When in the closed position (shown in FIG. 21, Section A-A), cable 1204 is coupled to anchor 40 and facilitates advancement of anchor 40 toward first implantation site 30. As the physician advances tool 2602, the physician also advances snare 2606. Under imaging guidance, torque-delivering cable 1204 and anchor 40 are advanced through loop 2608 of snare 2606, in order to create a coupling between snare 2606 and guide member 2616.

As shown in FIG. 21, torque-delivering cable 1204 is advanced within a lumen of tool 2602 alongside first flexible longitudinal member 2612 and guide member 2616. Torque-delivering cable 1204 is then rotated in order to implant anchor 40 in cardiac tissue at implantation site 30. As described hereinabove annular loop 1246 (shown in section A-A) facilitates rotation of anchor 40 with respect to (and not facilitating rotation of) connecting element 1240, first flexible longitudinal member 2612, first flexible-longitudinal-member-coupling element 2614, and guide member 2616.

Following implantation of anchor 40 at site 30, cable 1204 is decoupled from anchor 40, as described hereinabove, such that the open position is assumed (section A-A, FIG. 21). Torque-delivering cable 1204 is then retracted through delivery tool 2602. Alternatively, cable 1204 is retracted at a later stage together with delivery tool 2602.

FIG. 23 shows snare 2606, via loop 2608, pulling guide member 2616 in direction A toward inferior vena cava 8. As guide member 2616 is pulled, the proximal portion of guide member 2616 slides in direction A out of delivery tool 2602.

As shown in the enlarged image of FIG. 23, first flexible-longitudinal-member-coupling element 2614 is shaped so as to define a loop 2646 through which proximal second end portion 2615 of first flexible longitudinal member 2612 is looped, thereby first flexible longitudinal member 2612 to first flexible-longitudinal-member-coupling element 2614. Proximal second end portion 2615 is sewn to itself to maintain the looped coupling. As shown, first flexible-longitudinal-member-coupling element 2614 is shaped so as to define a male coupling 2617 shaped so as to provide one or more protrusions 2640 (e.g., an annular protrusion, as shown). Protrusion 2640 is shaped so as to provide a distal shelf 2642 (e.g., an annular shelf), which is described hereinbelow.

For some applications (configuration not shown), the distal end of guide member 2616 may be coupled to first coupling 1220 (described hereinabove with reference to FIGS. 21 and 22A-D), and a proximal end of first flexible-longitudinal-member-coupling element 2614 may be coupled to adapter head 1230 (described hereinabove with reference to FIGS. 21 and 22A-D; configuration not shown, but shown in FIG. 28). For such applications, reversible coupling of guide member 2616 to first flexible-longitudinal-member-coupling element 2614 is accomplished via coupling of coupling 1220 to head 1230. As described hereinabove, the coupling of coupling 1220 and head 1230 is maintained by elongate longitudinal element 2610 (described hereinabove with reference to FIGS. 21 and 22A-D).

FIG. 24 shows guide member 2616 disposed within inferior vena cava 8 following the pulling of member 2616 therethrough via snare 2606.

As shown in FIG. 25, second delivery tool 2666 is then threaded over a proximal portion of guide member 2616 in order to advance second tissue-engaging element 60b, second flexible longitudinal member 2660, and second flexible-longitudinal-member-coupling element 2650 toward tricuspid valve 4 from direction A. Second delivery tool 2666 is advanced through inferior vena cava 8. As shown in FIG. 25, second delivery tool 2666 comprises a catheter tube 2669, which is sized and configured to be introduced percutaneously. An advancement tube 2667 of second delivery tool 2666 is advanced through a lumen of tool 2666 and is reversibly coupled at a distal end thereof to second flexible-longitudinal-member-coupling element 2650, or is pushed against second flexible-longitudinal-member-coupling element 2650 without being coupled thereto. Second flexible-longitudinal-member-coupling element 2650 defines a female coupling that is shaped so as to define a cylindrical element, in such applications, which receives male coupling 2617 of first flexible-longitudinal-member-coupling element 2614. Second flexible-longitudinal-member-coupling element 2650 and tube 2667 slide along guide member 2616 in order to couple together second flexible-longitudinal-member-coupling element 2650 and first flexible-longitudinal-member-coupling element 2614. In order to allow such sliding, second flexible-longitudinal-member-coupling element 2650 is typically shaped so as to define a lumen therethrough, through which guide member 2616 passes. Typically, to couple together the first and the second flexible-longitudinal-member-coupling elements, the operator pulls guide member 2616 and/or pushes second flexible-longitudinal-member-coupling element 2650. Guide member 2616 and second delivery tool 2666 thus allow the operator to remotely and percutaneously control the coupling and tensioning of first and second flexible-longitudinal-member-coupling elements 2614 and 2650, including remotely and percutaneously inserting male coupling 2617 into the female coupling. These techniques also allow separate delivery of the tissue-engaging elements, using two separate delivery tools 2602 and 2666. Such separate delivery simplifies the procedure for the operator as well as allowing approaches via two or more different blood vessels, such as transfemoral, transjugular, transradial, and/or or transapical approaches, whichever may provide simpler access to the anchoring point.

As shown in FIGS. 25 and 26, first and second flexible longitudinal members 2612 and 2660 are two separate flexible longitudinal members, rather than integral longitudinal portions of a single flexible longitudinal member. Respective second end portions 2615 and 2662 of first and second flexible longitudinal member 2612 and 2660 are coupled together via first and second flexible-longitudinal-member-coupling elements 2614 and 2650. Respective first end portions 2613 and 2609 of first and second flexible-longitudinal-member-coupling elements 2614 and 2650 are not coupled together; typically, no portions of first and second flexible longitudinal members 2612 and 2660, other than respective second end portions 2615 and 2662, are coupled together. Typically, first and second flexible longitudinal members 2612 and 2660 are coupled together only by first and second flexible-longitudinal-member-coupling elements 2614 and 2650.

For some applications, as shown in FIG. 25, the female coupling of second flexible-longitudinal-member-coupling element 2650 comprises a hollow cylinder configured to receive male coupling 2617. Second flexible-longitudinal-member-coupling element 2650 is shaped so as to define one or more tabs 2652, which may function as pawls, biased to flex toward a longitudinal axis 2656 of the cylinder of second flexible-longitudinal-member-coupling element 2650. As second flexible-longitudinal-member-coupling element 2650 slides over male coupling 2617 of first flexible-longitudinal-member-coupling element 2614, the protrusion 2640 of male coupling 2617 of first flexible-longitudinal-member-coupling element 2614 is advanceable with respect to the one or more tabs 2652 in a first direction (e.g., a proximal direction) to push tab 2652 away from longitudinal axis 2656. First flexible-longitudinal-member-coupling element 2614 is shaped so as to define a section distal to protrusion 2640 that is narrower than protrusion 2640. After protrusion 2640 advances beyond tab 2652, tab 2652 assumes its resting position in which it flexes toward axis 2656 and closes around the narrower portion distal to protrusion 2640, as shown in Section A-A. Shelf 2642 of protrusion 2640 has a dimension that is larger than a dimension of tab 2652 in its resting state and restricts advancement of male coupling 2617 of first flexible-longitudinal-member-coupling element 2614 in a second direction (e.g., a distal direction). In such a manner, tabs 2652, protrusion 2640, and shelf 2642 lock first flexible-longitudinal-member-coupling element 2614 with respect to second flexible-longitudinal-member-coupling element 2650. For some applications, the hollow cylinder of second flexible-longitudinal-member-coupling element 2650 is circular, as shown, while for other applications, the hollow cylinder has a different shape.

For some applications, a greatest outer diameter of first flexible-longitudinal-member-coupling element 2614 is at least 1 mm, no more than 6 mm, and/or between 1 and 6 mm, inter alia in order to allow passage of element 2614 through catheter tube 2603 of first delivery tool 2602. For some applications, a greatest outer diameter of second flexible-longitudinal-member-coupling element 2650 is at least 1 mm, no more than 6 mm, and/or between 1 and 6 mm, inter alia in order to allow passage of element 2650 through catheter tube 2669 of second delivery tool 2666.

For some applications, as shown, second flexible-longitudinal-member-coupling element 2650 is shaped so as to define one or more slots 2657. For some applications, protrusion 2640 fits within the one or more slots 2657 in order to couple together second and first flexible-longitudinal-member-coupling elements 2650 and 2614. As shown, distal second end portion 2662 of second flexible longitudinal member 2660 is looped around a looping portion 2654 of second flexible-longitudinal-member-coupling element 2650. For some applications, male coupling 2617 is shaped so as to define one or more internal ridges, such as described hereinbelow with reference to FIG. 33A, mutatis mutandis. The internal ridges engage tabs 2652 when the tabs enter the male coupling, thereby help prevent angular rotation of first flexible-longitudinal-member-coupling element 2614 with respect to second flexible-longitudinal-member-coupling element 2650 as guide member 2616 is unscrewed from threaded coupling 2644, as described hereinbelow.

Following the coupling of second and first flexible-longitudinal-member-coupling elements 2650 and 2614, tube 2667 is decoupled or simply proximally withdrawn from second flexible-longitudinal-member-coupling element 2650. Additionally, guide member 2616 is decoupled from first flexible-longitudinal-member-coupling element 2614, such as by unscrewing screw 2618 from threaded coupling 2644 of first flexible-longitudinal-member-coupling element 2614 (as shown by the arrow in section A-A), or, for applications in which the proximal end of first flexible-longitudinal-member-coupling element 2614 is reversibly coupled to the distal end of flexible longitudinal guide member 2616 using the techniques described hereinabove with reference to FIGS. 21 and 22A-D, using the decoupling techniques described hereinabove with reference to FIGS. 21 and 22A-D, mutatis mutandis. Thus the operator remotely and percutaneously decouples guide member 2616 from first flexible-longitudinal-member-coupling element 2614. These techniques also allow separate delivery of the tissue-engaging elements, using two separate delivery tools 2602 and 2666. Such separate delivery simplifies the procedure for the operator as well as allowing approaches via two or more different blood vessels, such as transfemoral, transjugular, transradial, and/or or transapical approaches, whichever may provide simpler access to the anchoring point.

Following decoupling of guide member 2616, first and second flexible-longitudinal-member-coupling elements 2614 and 2650 remain coupled together and thereby couple together first and second flexible longitudinal members 2612 and 2660.

After first and second flexible-longitudinal-member-coupling elements 2614 and 2650 are coupled together, tool 2666 is retracted through inferior vena cava 8 in order apply tension to first and second flexible longitudinal members 2612 and 2660 and thereby to first tissue-engaging element 60a, as described hereinabove, in order to adjust a distance between the leaflets of tricuspid valve 4 to reduce and eliminate regurgitation through and thereby repair tricuspid valve 4.

In FIG. 26, second tissue-engaging element 60b comprising stent 50 is then deployed in inferior vena cava 8 so as to ensure that tension is maintained at first implantation site 30 and along first and second flexible longitudinal members 2612 and 2660 (i.e., longitudinal members 42). Stent 50 is coupled to a proximal portion of second flexible longitudinal member 2660. The positioning of stent 50 along inferior vena cava 8 depends on the desired degree of tension of first and second flexible longitudinal members 2612 and 2660 and on site 30 and of the desired degree of repair of tricuspid valve 4.

It is to be noted that any one of stents 1150, 1400, and 1500 described hereinabove may be used in place of any one of stents 50.

Reference is now made to FIGS. 20-26. It is to be noted that the direction of implantation of elements 60a and 60b may be opposite to those as shown in FIGS. 20-26. For example, element 60a may be implanted in tissue of tricuspid valve 4 by being advanced through inferior vena cava 8, and element 60b may be implanted in superior vena cava 10.

Figure 27:
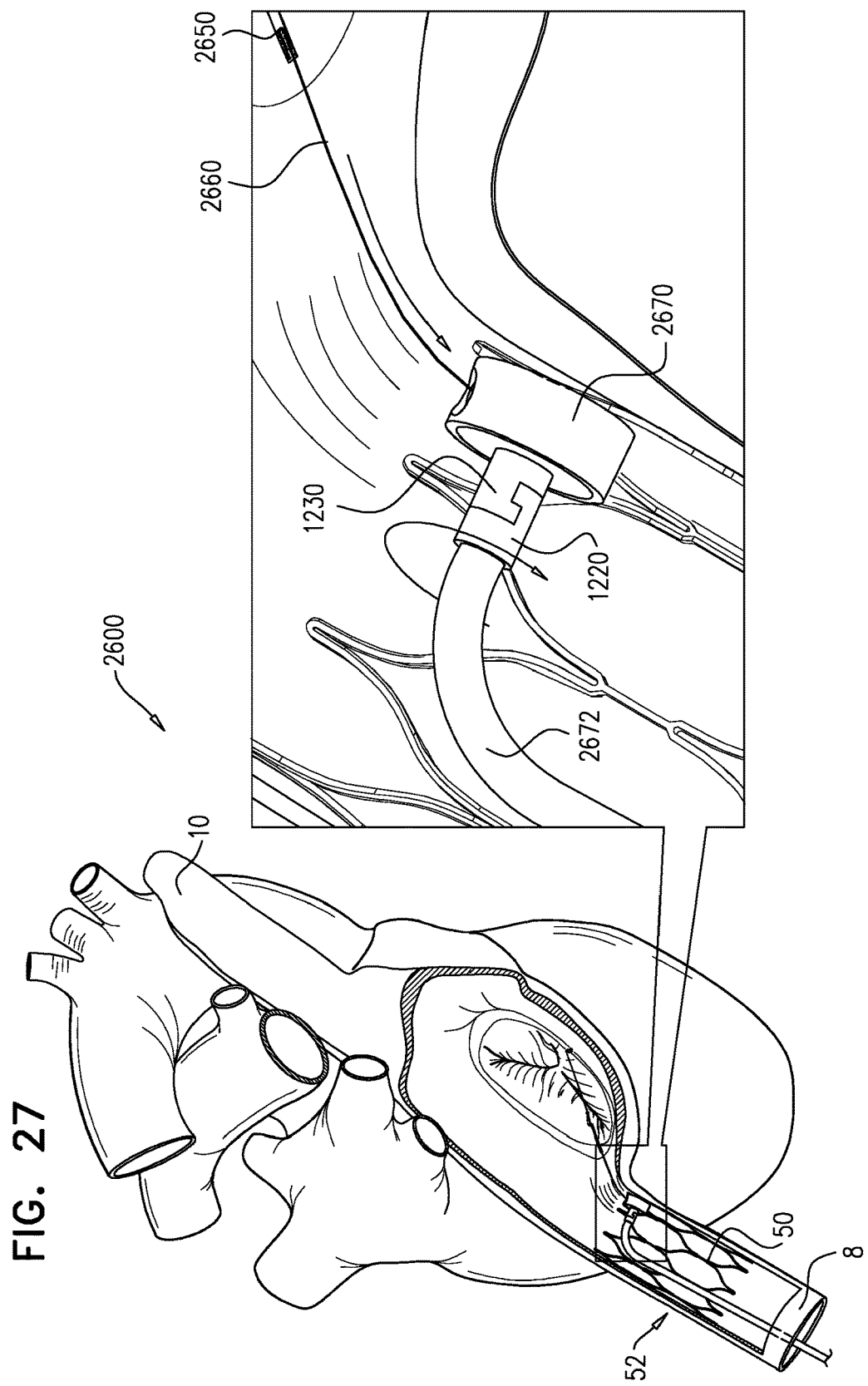
FIG. 27 is a schematic illustration of a flexible-longitudinal-member-adjustment mechanism for adjusting a length of at least one of the first and second flexible longitudinal members of FIGS. 20-26, in accordance with some applications of the present invention.

Reference is now made to FIG. 27, which is a schematic illustration of a flexible-longitudinal-member-adjustment mechanism 2670 which is coupled to flexible longitudinal member 2660 in order to adjust a length and/or degree of tension of member 2660, in accordance with some applications of the present invention. For some applications, mechanism 2670 comprises a spool (not shown) configured to adjust the length/tension of member 2660 by winding a portion of member 2660 around the spool. For some applications, adjustment mechanism 2670 is coupled to first flexible longitudinal member 2612.

An adjustment-mechanism tool 2672 is reversibly coupled to mechanism 2670. As shown, tool 2672 is coupled at a distal end thereof to first coupling 1220 (described hereinabove with reference to FIGS. 21 and 22A-D), and adjustment mechanism 2670 is coupled to adapter head 1230 (described hereinabove with reference to FIGS. 21 and 22A-D). For such applications, reversible coupling of tool 2672 to mechanism 2670 is accomplished via coupling of coupling 1220 to head 1230. As described hereinabove, the coupling of coupling 1220 and head 1230 is maintained by elongate longitudinal element 2610 (described hereinabove with reference to FIGS. 21 and 22A-D).

Flexible-longitudinal-member-adjustment mechanism 2670 may be used in combination with system 2600 described herein with reference to FIGS. 20-26 and 28-32. Additionally, mechanism 2670 may be used in combination with systems 20, 100, 110, 120, 140, 200, 700, 800, 1000, and/or 2500.

Figure 28:
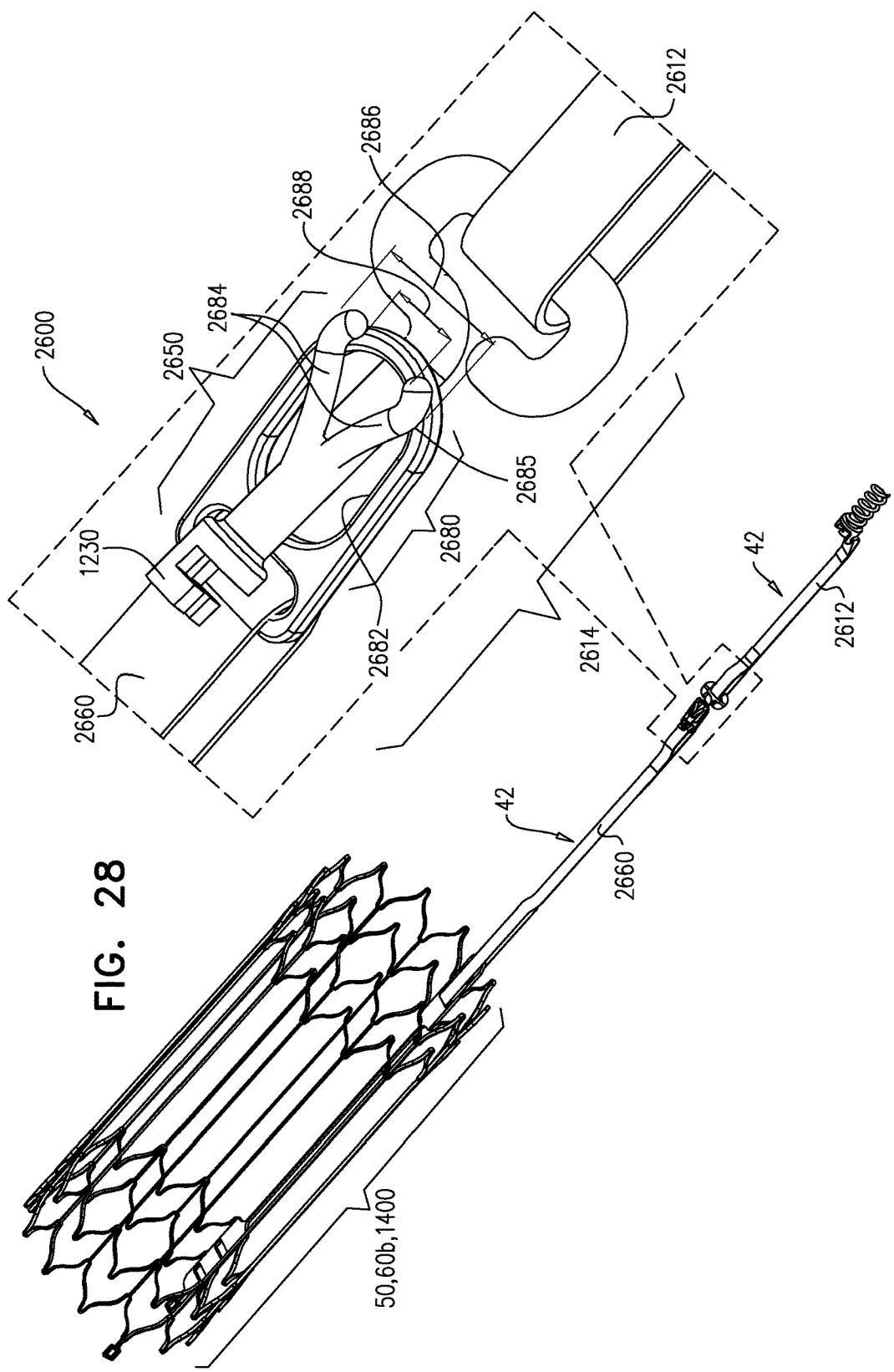
FIG. 28 is a schematic illustration of respective coupling elements of the first and second flexible longitudinal members of FIGS. 20-26, in accordance with another application of the present invention.

Reference is now made to FIG. 28, which is a schematic illustration of (1) first flexible-longitudinal-member-coupling element 2614 comprising one or more (e.g., two, as shown) radially-displaceable arms 2684, and (2) second flexible-longitudinal-member-coupling second flexible-longitudinal-member-coupling element 2650 having one or more walls 2682 shaped so as to define an opening 2680, in accordance with some applications of the present invention. Opening 2680 has a dimension 2688.

A proximal end of first flexible-longitudinal-member-coupling element 2614 is coupled to adapter head 1230 (described hereinabove with reference to FIGS. 21 and 22A-D), or a longitudinal-guide-member-coupling element. For such applications, guide member 2616 (not shown) is coupled at a distal end thereof to first coupling 1220 (described hereinabove with reference to FIGS. 21 and 22A-D) and is coupled to first flexible-longitudinal-member-coupling element 2614 via couplings 1220 and head 1230. It is to be noted that guide member 2616 may also be coupled to first flexible-longitudinal-member-coupling element 2614 by being screwed into a threaded coupling 2644 of first flexible-longitudinal-member-coupling element 2614, as described hereinabove with reference to FIGS. 21, 23, and 25.

In either embodiment, second flexible-longitudinal-member-coupling element 2650 is slid over the guide member until opening 2680 is aligned with arms 2684 of first flexible-longitudinal-member-coupling element 2614. Second flexible-longitudinal-member-coupling element 2650 is further slid distally along first flexible-longitudinal-member-coupling element 2614 such that wall 2682 compresses arms 2684 through opening 2680. Once second flexible-longitudinal-member-coupling element 2650 is slid further, arms 2684 are exposed from within opening 2680 and expand to a position that is above opening 2680. Arms 2684 expand to a dimension 2686 that is larger than dimension 2688 of opening 2680. Arms 2684 expand to a position in which at least a portion of respective outer surfaces 2685 of arms 2684 is beyond and above wall 2682. In such a manner, arms 2684 lock first flexible-longitudinal-member-coupling element 2614 to second flexible-longitudinal-member-coupling element 2650, and thereby maintain coupling of first and second flexible longitudinal members 2612 and 2660.

Reference is now made to FIGS. 29 and 30A-D, which are schematic illustrations of (1) first flexible-longitudinal-member-coupling element 2614 comprising one or more radially-displaceable legs 2694 (e.g., two, as shown), and (2) second flexible-longitudinal-member-coupling element 2650 having one or more walls 2691 (FIG. 30A) shaped so as to define an opening 2693 and one or more shelves 2692 (e.g., an annular shelf), in accordance with some applications of the present invention.

In such applications, the female coupling is coupled to first flexible longitudinal member 2612, and the coupling 2617 is coupled to second flexible longitudinal member 2660.

As shown in FIGS. 30A-B, guide member 2616 is coupled at a distal end thereof to a guide-member-coupling element 2690 (e.g., a disc, as shown). At a first stage, element 2690 is restricted from movement in a proximal direction by shelf 2692 of element 2560. In such a manner, guide member 2616 is reversibly coupled to second flexible-longitudinal-member-coupling element 2650.

Figure 29:
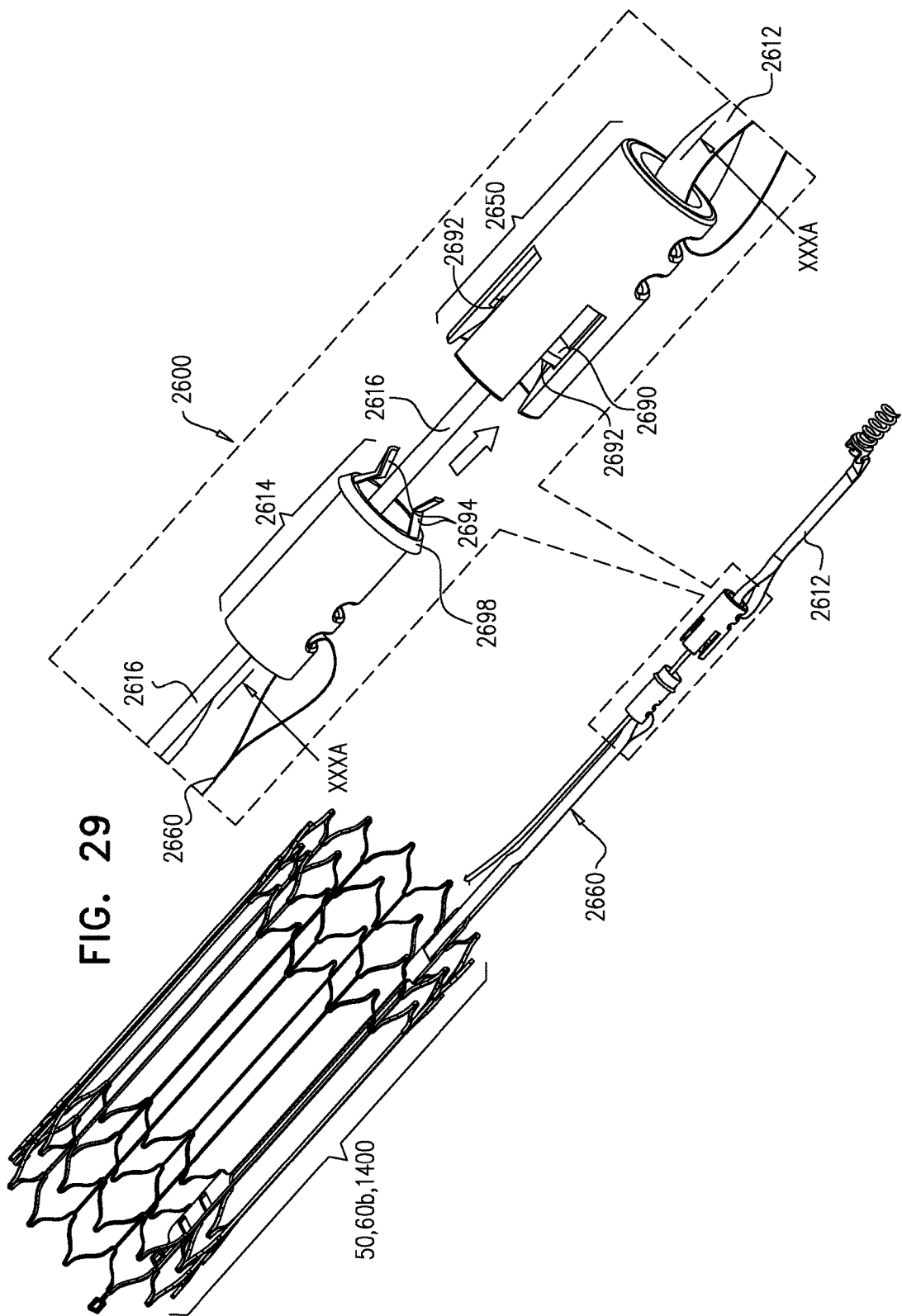
FIGS. 29 and 30A-D are schematic illustrations of respective coupling elements of the first and second flexible longitudinal members of FIGS. 20-26, in accordance with yet another application of the present invention.
Figure 30:
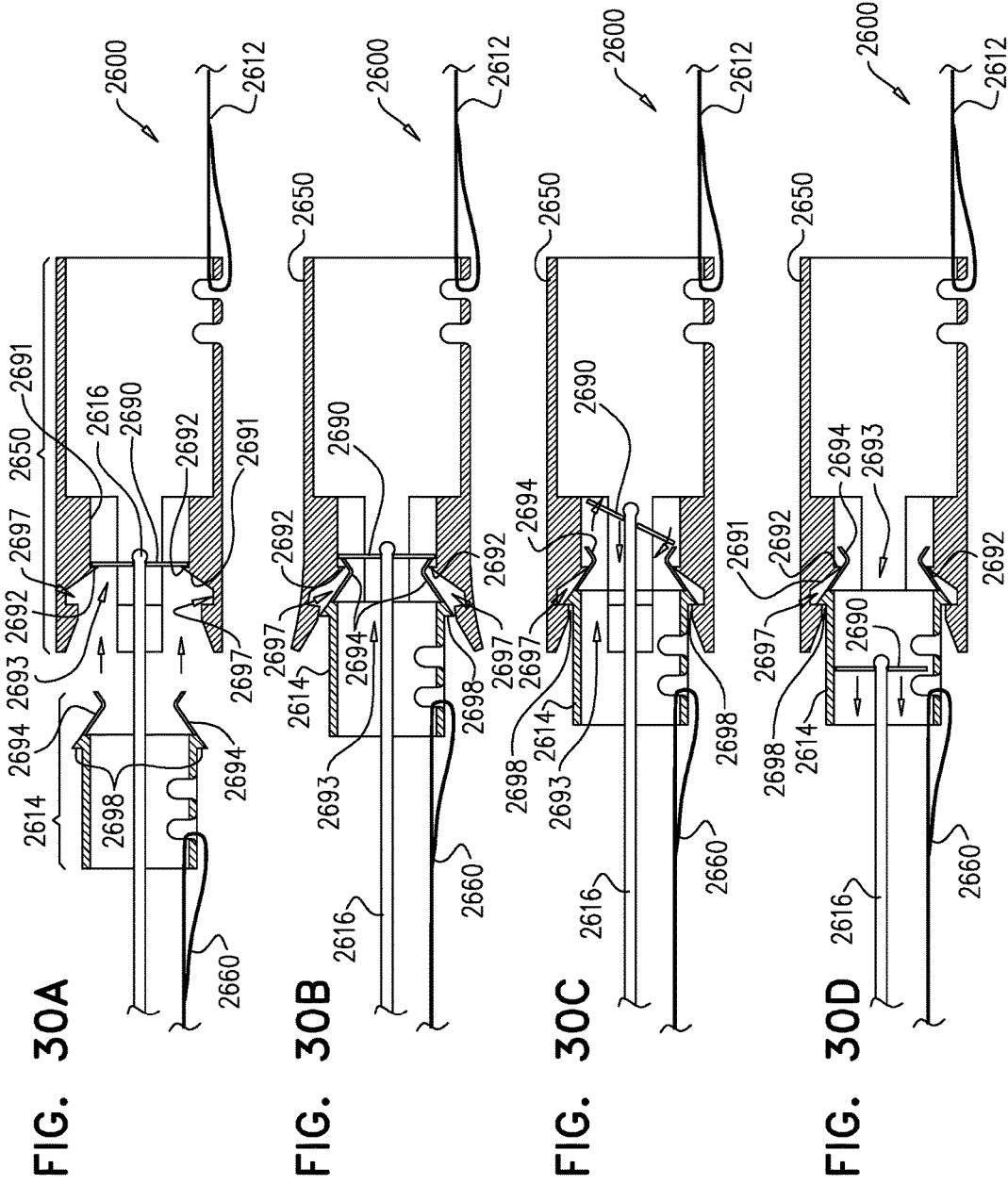

As shown in FIGS. 29 and 30A, first flexible-longitudinal-member-coupling element 2614 is shaped so as to define a hollow cylinder having a lumen, and is guided along guide member 2616 toward first flexible-longitudinal-member-coupling element 2614. For some applications, the hollow cylinder of first flexible-longitudinal-member-coupling element 2614 is circular, as shown, while for other applications, the hollow cylinder has a different shape.

In FIG. 30B a distal end of first flexible-longitudinal-member-coupling element 2614 and legs 2694 are advanced in a first direction (e.g., a distal direction) within a lumen of second flexible-longitudinal-member-coupling element 2650, and legs 2694 approach opening 2693. As they approach opening 2693, legs 2694 are compressed by wall 2691 and by shelf 2692. Following the advancement of legs 2694 beyond shelf 2692 in the first advancement direction, legs 2694 are expandable to lock first flexible-longitudinal-member-coupling element 2614 to second flexible-longitudinal-member-coupling element 2650. Additionally, following the expanding of legs 2694, shelf 2692 restricts advancement of legs 2694 in a second advancement direction (e.g., a proximal direction) since legs 2694 expand to a dimension larger than a dimension of shelf 2692.

Additionally, the positioning of legs 2694 beyond shelf 2692 displaces guide-member-coupling element 2690, as shown in FIG. 30C. The displacement of element 2690 shifts the relative position of element 2690 with respect to shelf 2692 of second flexible-longitudinal-member-coupling element 2650, and element 269 may be advanced in the second direction (e.g., the proximal direction) through and beyond opening 2693.

FIG. 30D shows the decoupling of element 2690 and guide member 2616 from second flexible-longitudinal-member-coupling element 2650 and subsequently, from first flexible-longitudinal-member-coupling element 2614. As shown, first and second flexible-longitudinal-member-coupling elements 2614 and 2650 are locked together by the positioning of the distal portion of legs 2694 distally to shelf 2692.

Wall 2691 of second flexible-longitudinal-member-coupling element 2650 is shaped so as to define at least one groove 2697. As shown in FIG. 29, first flexible-longitudinal-member-coupling element 2614 is shaped so as to define at least one protrusion 2698 (e.g., an annular protrusion, as shown), which is shaped so as to fit within the at least one groove 2697. The positioning of protrusion 2698 within groove 2697, as shown in FIGS. 30C-D, further locks first and second flexible-longitudinal-member-coupling elements 2614 and 2650.

Figure 31:
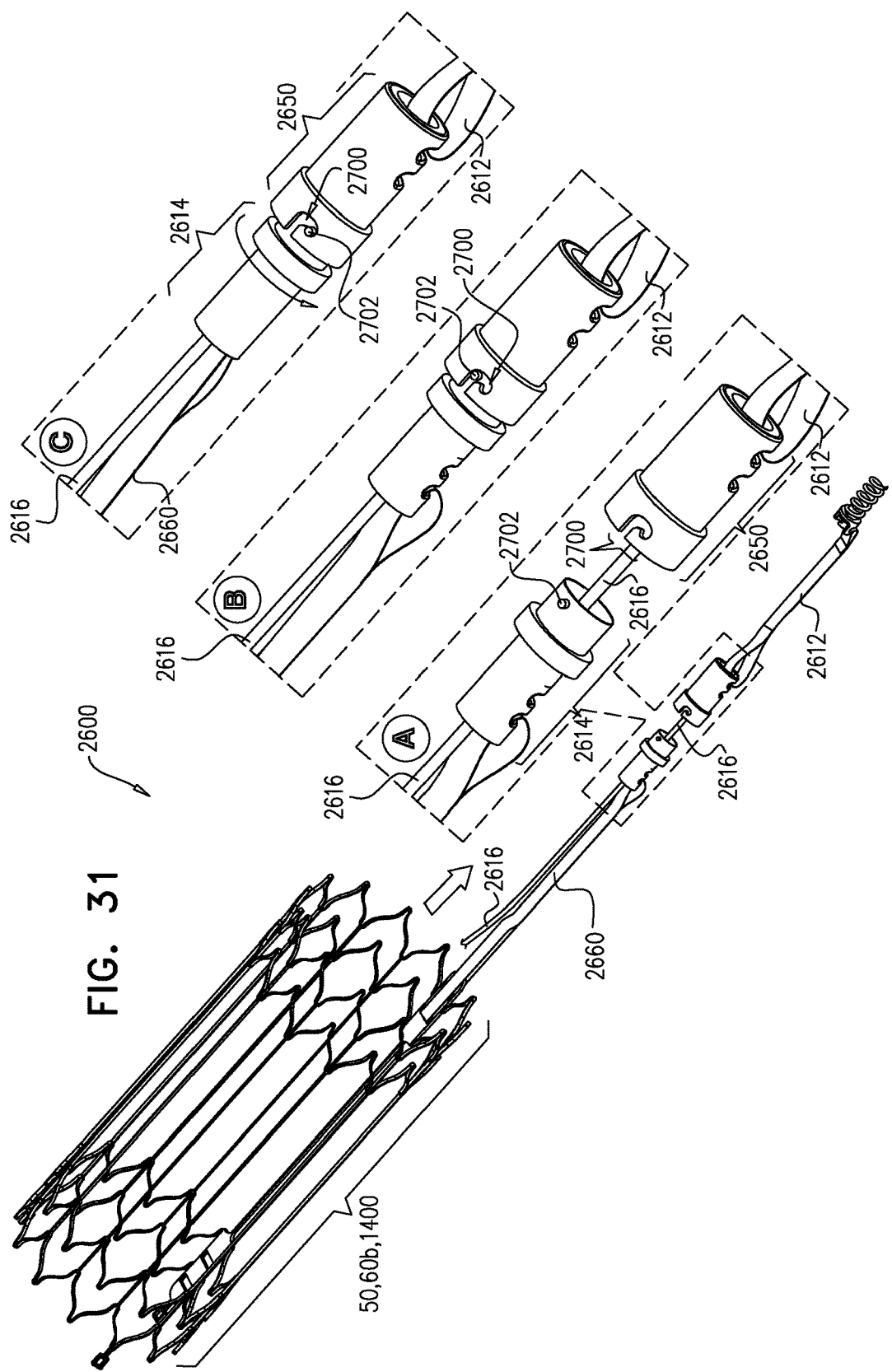
FIG. 31 is a schematic illustration of respective coupling elements of the first and second flexible longitudinal members of FIGS. 20-26, in accordance with still yet another application of the present invention.

Reference is now made to FIG. 31, which is a schematic illustration of (1) first flexible-longitudinal-member-coupling element 2614 comprising one or more protrusions 2702, and (2) second flexible-longitudinal-member-coupling element 2650 being shaped so as to define one or curved grooves 2700, in accordance with some applications of the present invention. Guide member 2616 is reversibly coupled to second flexible-longitudinal-member-coupling element 2650 using any of the coupling apparatus described herein with reference to FIGS. 21, 22A-C, 23, 25, 28, 29, 30A-D, and 32.

As shown in view A, first flexible-longitudinal-member-coupling element 2614 is advanced along guide member 2616 toward second flexible-longitudinal-member-coupling element 2650. In view B, protrusion 2702 of first flexible-longitudinal-member-coupling element 2614 is positioned within a portion of curved groove 2700. In view C, first flexible-longitudinal-member-coupling element 2614 is rotated in order to position and lock protrusion 2702 within groove 2700 at an end of groove 2700. In such a manner, first flexible-longitudinal-member-coupling element 2614 is locked to second flexible-longitudinal-member-coupling element 2650. Following the locking of first and second flexible-longitudinal-member-coupling elements 2614 and 2650, guide member 2616 is decoupled from second flexible-longitudinal-member-coupling element 2650.

Figure 32:
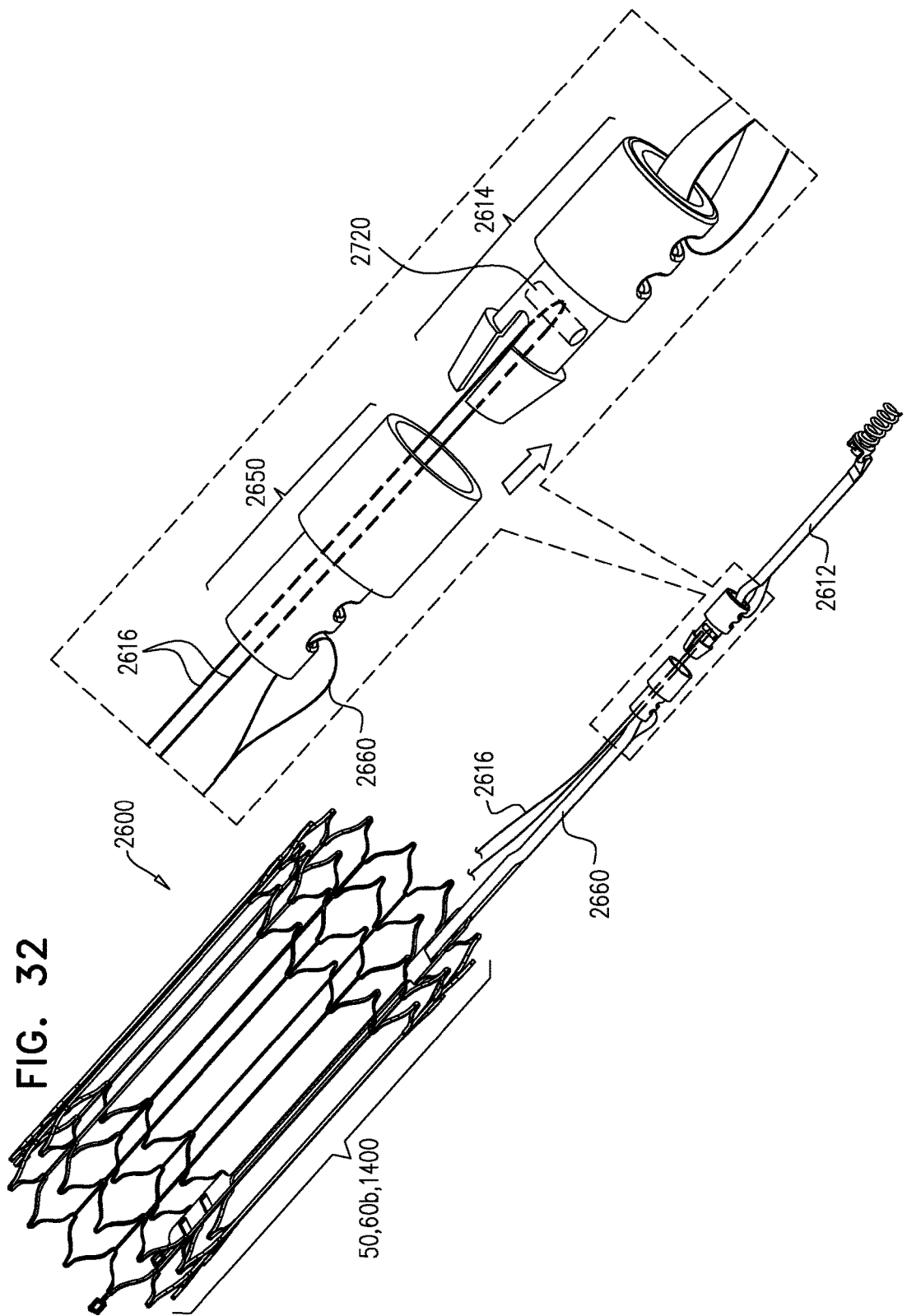
FIG. 32 is a schematic illustration of a flexible longitudinal guide member reversibly coupled to one of the coupling elements of FIGS. 20-31, in accordance with some applications of the present invention.

FIG. 32 shows guide member 2616 being coupled to first flexible-longitudinal-member-coupling element 2614 by bring looped around a bar 2720 coupled to first flexible-longitudinal-member-coupling element 2614, in accordance with some applications of the present invention. In such an application, second flexible-longitudinal-member-coupling element 2650 defines the female coupling which is advanced along guide member 2616 toward first flexible-longitudinal-member-coupling element 2614, which defines male coupling 2617. Once second flexible-longitudinal-member-coupling element 2650 is coupled to first flexible-longitudinal-member-coupling element 2614, a first end of looped guide member 2616 is released, and the second end of guide member 2616 is pulled in order to unloop guide member 2616 from around bar 2720, and thereby to decouple guide member 2616 from first flexible-longitudinal-member-coupling element 2614.

Reference is now made to FIGS. 28, 29, 31, and 32. It is to be noted that although stent 50 is shown as comprising stent 1400, any one of stents 1150 and 1500 may be used in place of any one of stents 1400.

Reference is now made to FIGS. 20-32. The scope of the present invention includes coupling of first flexible-longitudinal-member-coupling element 2614 to either of first and second longitudinal members 2612 and 2660 and coupling of second flexible-longitudinal-member-coupling element 2650 to either of longitudinal members 2612 and 2660.

Figures 33A, 33B:
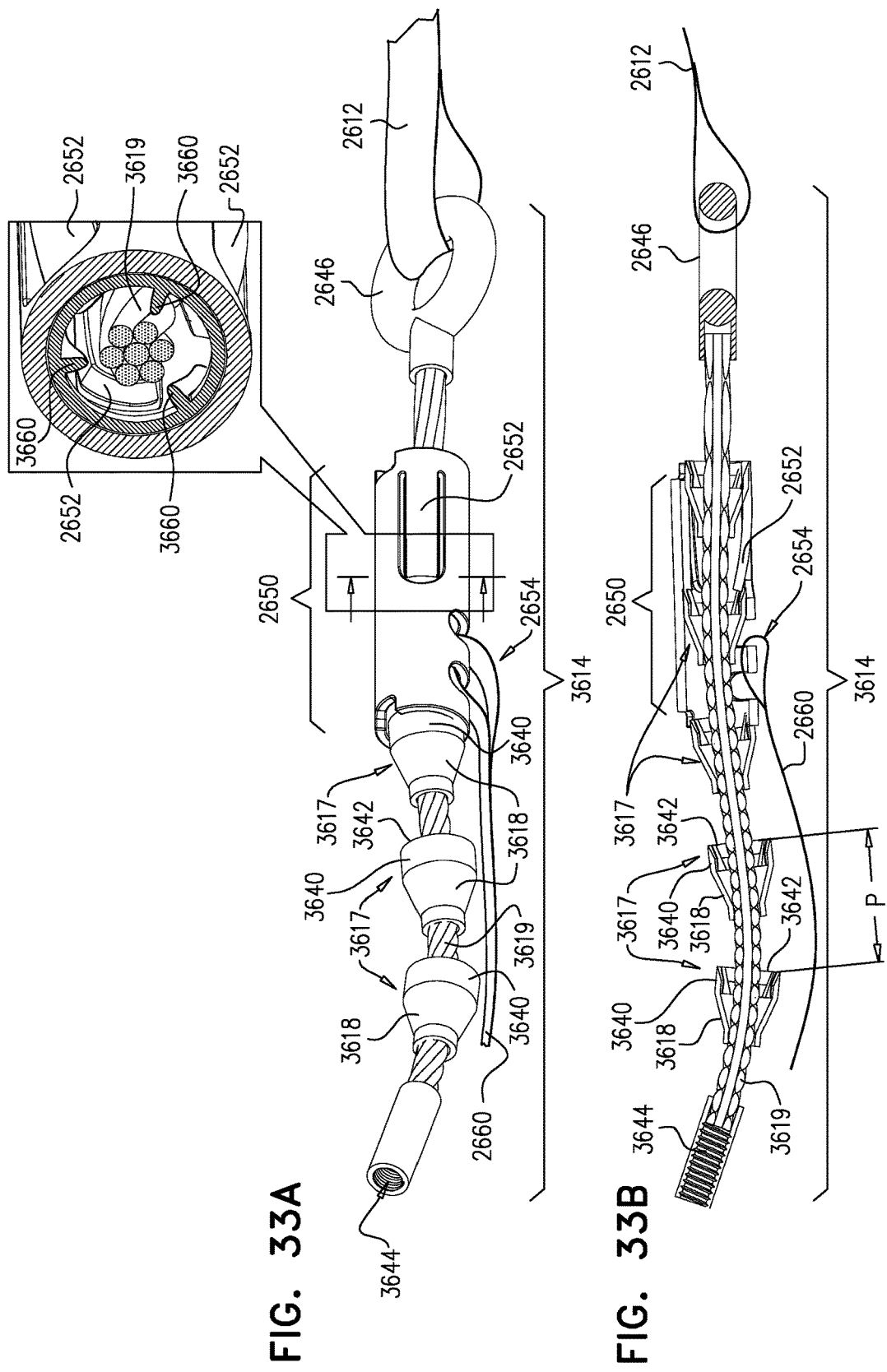
FIGS. 33A-B are schematic illustrations of a first flexible-longitudinal-member-coupling element coupled to a second flexible-longitudinal-member-coupling element, in accordance with an application of the present invention.

Reference is now made to FIGS. 33A-B, which are schematic illustrations of a first flexible-longitudinal-member-coupling element 3614 coupled to second flexible-longitudinal-member-coupling element 2650, in accordance with an application of the present invention. First flexible-longitudinal-member-coupling element 3614 is an alternative configuration of first flexible-longitudinal-member-coupling element 2614, described hereinabove with reference to FIGS. 25-26, and may be implemented in combination with techniques described hereinabove with reference to FIGS. 20-26, mutatis mutandis.

First flexible-longitudinal-member-coupling element 3614 comprises a plurality of male couplings 3617, disposed along the first flexible-longitudinal-member-coupling element at respective, different longitudinal sites. For some applications, first flexible-longitudinal-member-coupling element 3614 further comprises a flexible cable 3619, to which the male couplings 3617 are fixed at respective, different longitudinal sites. The male couplings typically surround an entire circumference of the cable. The female coupling of second flexible-longitudinal-member-coupling element 2650 is configured to receive male couplings 3617, allow advancement of male couplings 3617 through the female coupling in a first direction, and restrict (e.g., prevent) advancement of male couplings 3617 through the female coupling in a second direction opposite the first direction. The first direction is proximal (i.e., to the left in FIGS. 33A-B), and the second direction is distal (i.e., to the right in FIGS. 33A-B). Because of this unidirectional advancement, the coupling between first and second flexible-longitudinal-member-couplings element 3614 and 2650 functions as a ratchet mechanism. Typically, flexible cable 3619 is free to bend. For some applications, flexible cable 3619 is substantially not twistable. In other words, torque applied to any longitudinal site of the flexible cable causes rotation of the entire flexible cable, rather than twisting of the cable to absorb the torque. For example, flexible cable 3619 may comprise metal, polymer, or textile fibers.

For some applications, male couplings 3617 have respective conical features 3618. Typically, the plurality of male couplings 3617 comprises no more than 20 male couplings. Typically, the male couplings are disposed along first flexible-longitudinal-member-coupling element 3614 at an average pitch P of at least 1 mm, no more than 12 mm, and/or between 1 and 12 mm. Typically, each of male couplings 3617 has a length of at least 4 mm, no more than 10 mm, and/or between 4 and 10 mm.

As mentioned above with reference to FIG. 25, for some applications the female coupling of second flexible-longitudinal-member-coupling element 2650 comprises a hollow cylinder. The hollow cylinder is configured to receive male couplings 3617, and is shaped so as to define one or more tabs 2652, which may functions as pawls, biased to flex toward a central longitudinal axis of the cylinder. For these applications, male couplings 3617 are shaped so as to define respective protrusions 3640, and the protrusions and the one or more tabs are shaped and sized (a) to allow advancement of first flexible-longitudinal-member-coupling element 3614 through the hollow cylinder in a proximal direction (to the left in FIGS. 33A-B), by pushing the one or more tabs away from the longitudinal axis, and (b) to restrict advancement of first flexible-longitudinal-member-coupling element 3614 in a distal direction opposite the proximal direction (to the right in FIGS. 33A-B). For some applications, protrusions 3640 are shaped so as to define respective edges 3642, and the one or more tabs 2652 are configured to flex toward the longitudinal axis after the advancement of the edge of the male couplings beyond the one or more tabs 2652, so as to restrict advancement of the male couplings with respect to the one or more tabs 2652 in the distal direction.

For some applications, each of male couplings 3617 is shaped so as to define one or more internal ridges 3660, which help prevent angular rotation of first flexible-longitudinal-member-coupling element 3614 with respect to second flexible-longitudinal-member-coupling element 2650 as guide member 2616 is unscrewed from threaded coupling 3644, as described hereinbelow with reference to Blow-ups C and D of FIG. 34D. As shown in the blow-up in 33A, internal ridges 3660 engage tabs 2652 when the tabs enter one of the male couplings, as show in FIG. 33B.

For some applications, a greatest outer diameter of first flexible-longitudinal-member-coupling element 3614 is at least 1 mm, no more than 6 mm, and/or between 1 and 6 mm, inter alia in order to allow passage of element 3614 through catheter tube 2603 of first delivery tool 2602. For some applications, a greatest outer diameter of second flexible-longitudinal-member-coupling element 2650 is at least 1 mm, no more than 6 mm, and/or between 1 and 6 mm, inter alia in order to allow passage of element 2650 through catheter tube 2669 of second delivery tool 2666.

Reference is now made to FIGS. 34A-E, which are schematic illustrations of a method for deploying a system 3600 for repairing tricuspid valve 4, in accordance with an application of the present invention. System 3600 comprises (a) first tissue-engaging element 60a coupled to distal first end portion 2613 of first flexible longitudinal member 2612, and (b) second tissue-engaging element 60b coupled to proximal first end portion 2609 of second flexible longitudinal member 2660. System 3600 further comprises first and second delivery tools 2602 and 2666.

Figure 34A:
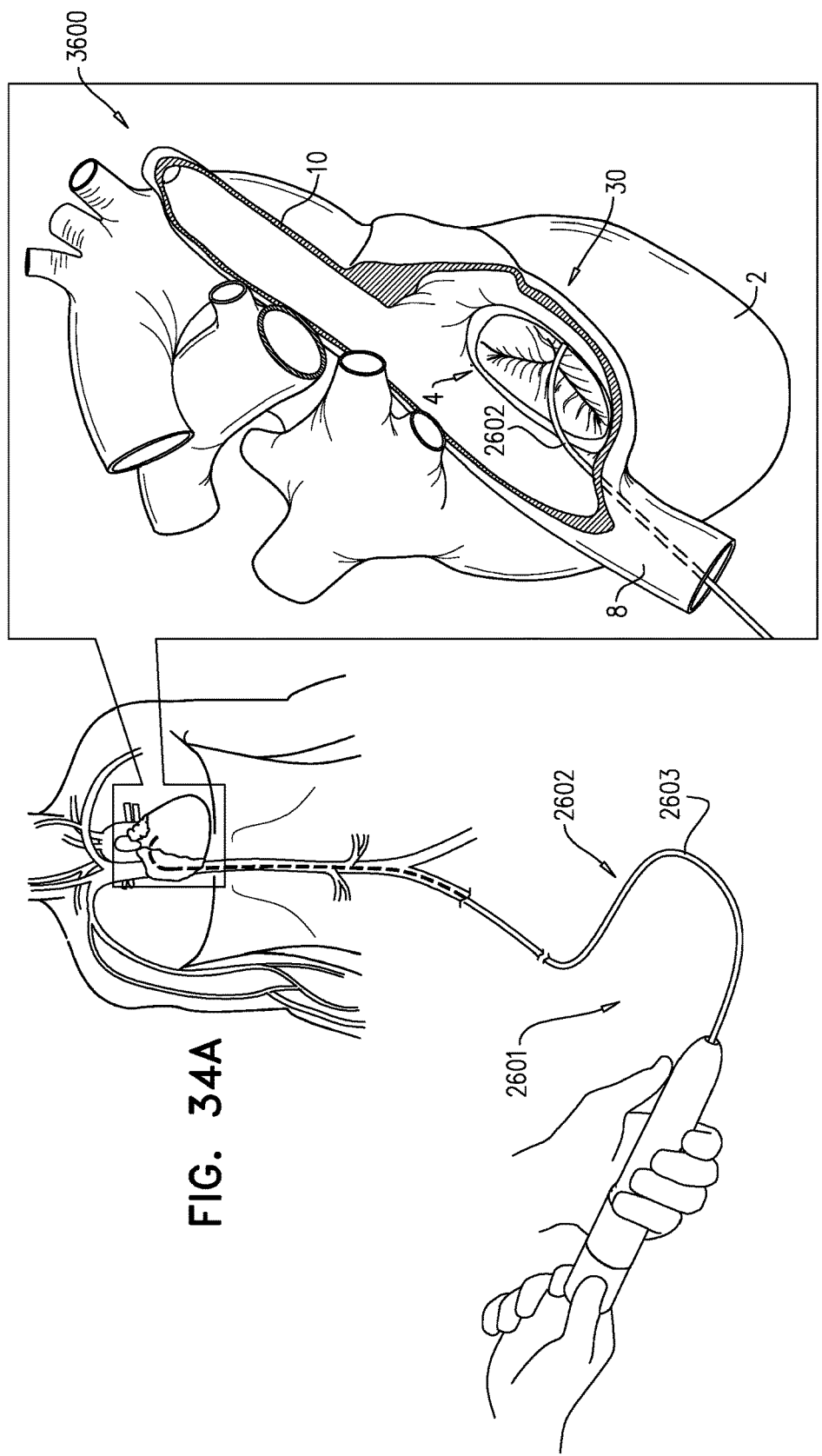

As shown in FIG. 34A, first delivery tool 2602 is advanced toward first implantation site 30 at tricuspid valve 4 through interior vena cava 8 from a suitable point of entry. Alternatively, the delivery tool may be advanced through superior vena cava 10.

Figure 34B:
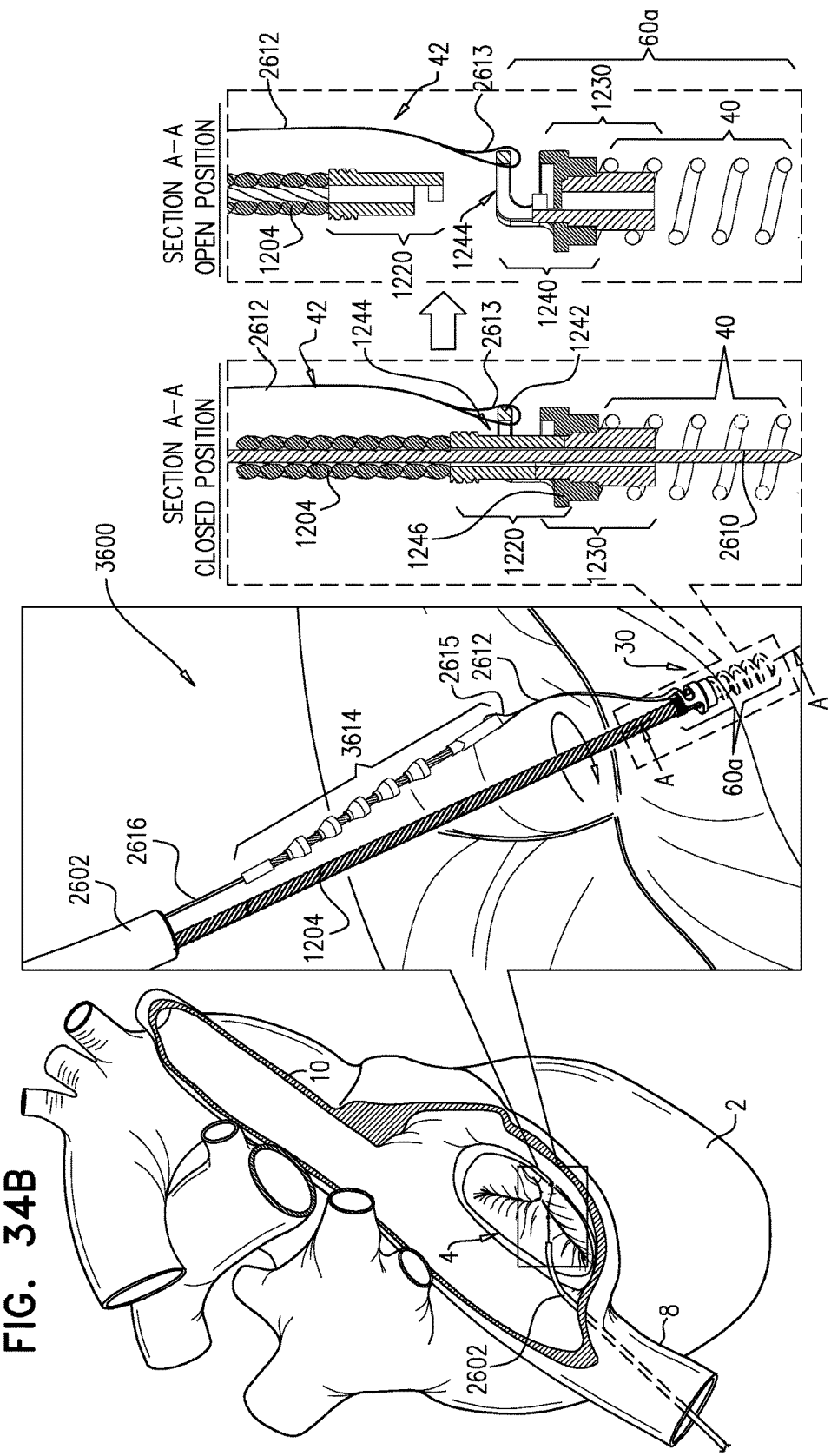

As shown in FIG. 34B, first tissue-engaging element 60a is implanted in tissue of the annulus of tricuspid valve 4, as described hereinabove with reference to FIGS. 21 and 22A-D. Alternatively, first tissue-engaging element 60a is implanted in tissue of a wall of the atrium above the annulus. Anchor 40 of first tissue-engaging element 60a is rotated by the torque-delivering tool comprising torque-delivering cable 1204, as described hereinabove with reference to FIGS. 21 and 22A-D. Optionally, torque-delivering cable 1204 is decoupled from first tissue-engaging element 60a using the techniques described hereinabove with reference to FIGS. 22A-D.

Proximal second end portion 2615 of first longitudinal member 2612 is coupled to (e.g., by being looped around) a portion of first flexible-longitudinal-member-coupling element 3614. A proximal end of first flexible-longitudinal-member-coupling element 3614 is reversibly coupled to a distal end of flexible longitudinal guide member 2616. For some applications, in order to enable such coupling, the proximal end of first flexible-longitudinal-member-coupling element 3614 is shaped so as to define threaded coupling 3644 for receiving screw 2618 that is coupled to a distal end of flexible longitudinal guide member 2616, as shown. For other applications, the proximal end of first flexible-longitudinal-member-coupling element 3614 is reversibly coupled to the distal end of flexible longitudinal guide member 2616 using the techniques described hereinabove with reference to FIGS. 21 and 22A-D for reversibly coupling torque-delivering cable 1204 to distal tissue-anchor coupling element 1233 of anchor 40, mutatis mutandis. First and second end portions 2613 and 2615 of first flexible longitudinal member 2612 are disposed at opposite longitudinal ends of the first flexible longitudinal member.

As shown in FIG. 34C, first tissue-engaging element 60a, first flexible longitudinal member 2612, first flexible-longitudinal-member-coupling element 3614, and flexible longitudinal guide member 2616 have been deployed in the atrium. At this stage of the deployment procedure, flexible longitudinal guide member 2616 is still removably coupled to the proximal end of first flexible-longitudinal-member-coupling element 3614.

Figure 34D:
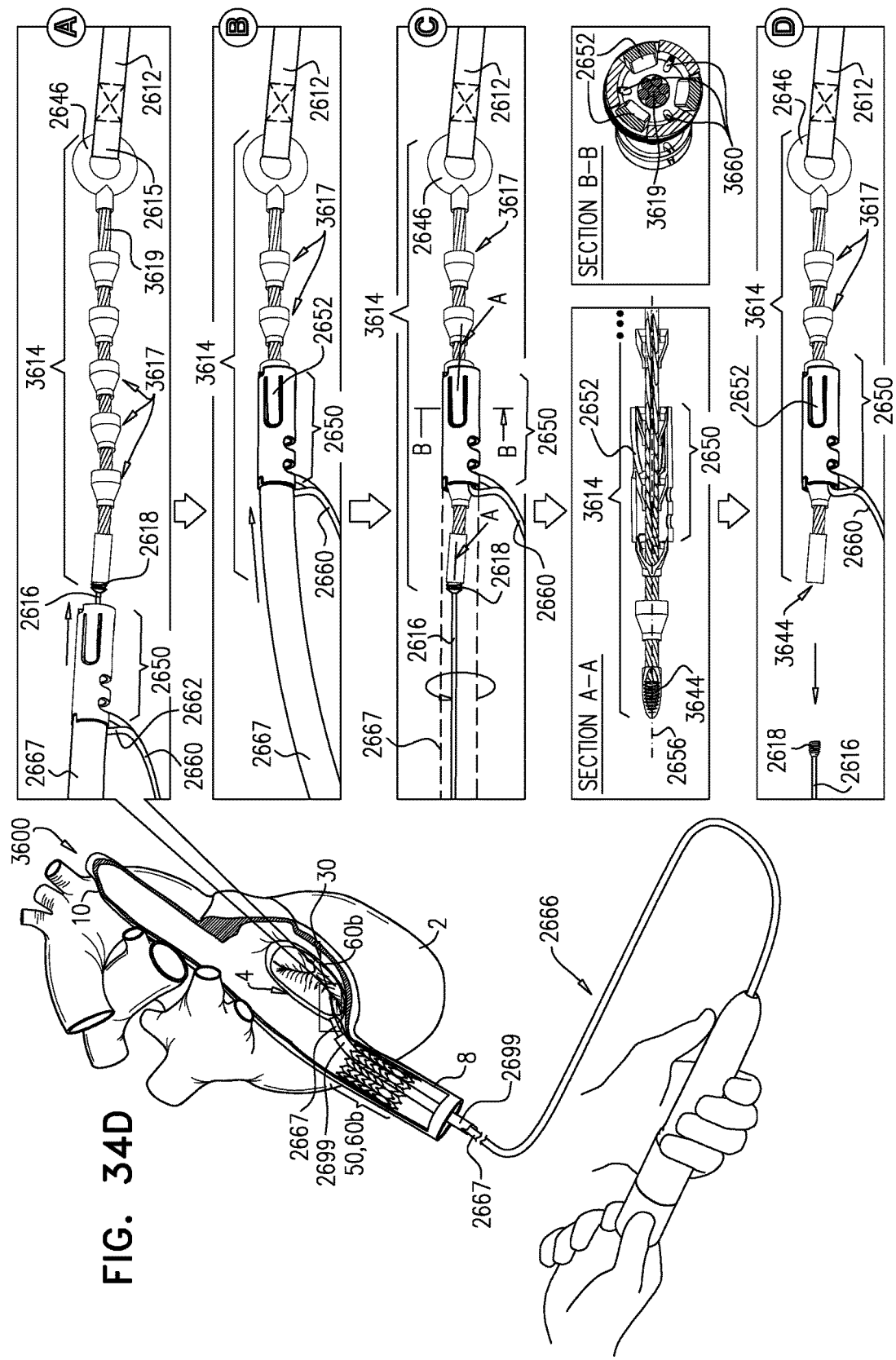

As shown in FIG. 34D, second tissue-engaging element 60b is deployed in inferior vena cava 8, typically using second delivery tool 2666. Alternatively, the second tissue-engaging element is deployed in superior vena cava 10, or in a coronary sinus. For some applications, the second tissue-engaging element is deployed in the same vein through which first delivery tool 2602 was advanced earlier in the procedure, as shown in FIG. 34A.

Also as shown in FIG. 34D, second delivery tool 2666, including catheter tube 2669 thereof, is threaded over a proximal portion of guide member 2616 in order to advance second flexible longitudinal member 2660 and a second flexible-longitudinal-member-coupling element 2650 toward tricuspid valve 4. In the configuration shown in FIG. 34D, second delivery tool 2666 is advanced through inferior vena cava 8. Alternatively, the second delivery tool is advanced through superior vena cava 10. For some applications, second delivery tool 2666 is advanced through the same vein through which first delivery tool 2602 was advanced earlier in the procedure, as shown in FIG. 34A. Alternatively, second delivery tool 2666 is advanced through a different vein from that through which first delivery tool 2602 was advanced earlier in the procedure, such as shown in FIG. 25, mutatis mutandis; for example, one of first and second delivery tools 2602 and 2666 may be advanced through superior vena cava 10, and the other through inferior vena cava 8. Thus, second delivery tool 2666 is configured to deliver second flexible longitudinal member 2660 and second flexible-longitudinal-member-coupling element 2650 after deployment of second tissue-engaging element 60b.

For some applications in which second tissue-engaging element 60b comprises radially-expandable stent 50, such as described hereinabove with reference to FIGS. 1A-D, second delivery tool 2666 is configured and sized to pass through stent 50 when the stent is in a radially-expanded state.

As shown in Blow-up A of FIG. 34D, advancement tube 2667 of second delivery tool 2666 is advanced through a lumen of catheter tube 2669 of tool 2666 and is reversibly coupled at a distal end thereof to second flexible-longitudinal-member-coupling element 2650, or is pushed against second flexible-longitudinal-member-coupling element 2650 without being coupled thereto. The operator slides second flexible-longitudinal-member-coupling element 2650 and tube 2667 along guide member 2616, in order to couple second flexible-longitudinal-member-coupling element 2650 to first flexible-longitudinal-member-coupling element 3614. In order to allow such sliding, second flexible-longitudinal-member-coupling element 2650 is typically shaped so as to define a lumen therethrough, through which guide member 2616 passes. A leading (proximal-most) one of male couplings 3617 may help direct second flexible-longitudinal-member-coupling element 2650 onto first flexible-longitudinal-member-coupling element 3614. Guide member 2616 and second delivery tool 2666 thus allow the operator to remotely and percutaneously control the coupling and tensioning of first and second flexible-longitudinal-member-coupling elements 3614 and 2650, including remotely and percutaneously inserting the leading male coupling 3617 into the female coupling. These techniques also allow separate delivery of the tissue-engaging elements, using two separate delivery tools 2602 and 2666. Such separate delivery simplifies the procedure for the operator as well as allowing approaches via two or more different blood vessels, such as transfemoral, transjugular, transradial, and/or or transapical approaches, whichever may provide simpler access to the anchoring point.

As shown in Blow-up B of FIG. 34D, for some applications, the female coupling comprises a hollow cylinder configured to receive the male couplings. During the coupling of first and second flexible-longitudinal-member-coupling elements 3614 and 2650, the operator tensions first and second flexible longitudinal members 2612 and 2660 by pulling one or more of male couplings 3617 into the female coupling. The operator pulls the one or more male couplings into the female coupling by pulling flexible longitudinal guide member 2616 and/or pushing second flexible-longitudinal-member-coupling element 2650 with tube 2667. The tensioning of first and second flexible longitudinal members 2612 and 2660 applies a force to first tissue-engaging element 60a, in order to adjust a distance between the leaflets of tricuspid valve 4 to reduce and eliminate regurgitation through and thereby repair tricuspid valve 4. Guide member 2616 and second delivery tool 2666 thus allow the operator to remotely and percutaneously control the applied tension by remotely and percutaneously pulling one or more male couplings 3617 through the female coupling.

This providing of an adjustable length between first and second tissue-engaging elements 60a and 60b allows fine-tuning of the tension by the operator, both during and after implantation of both tissue-engaging elements, and even after formation of neointima on the tissue-engaging elements. These techniques also allow separate delivery of the tissue-engaging elements, using two separate delivery tools 2602 and 2666. Such separate delivery simplifies the procedure for the operator as well as allowing approaches via two or more different blood vessels, such as transfemoral, transjugular, transradial, and/or or transapical approaches, which may provide simpler access to the anchoring point.

As shown in Blow-up C of FIG. 34D, a desired amount of tension is applied to first and second flexible longitudinal members 2612 and 2660.

As shown in Blow-ups C and D of FIG. 34D, guide member 2616 is decoupled from first flexible-longitudinal-member-coupling element 3614. For some applications, the decoupling comprises unscrewing screw 2618 thereof from threaded coupling 3644 of first flexible-longitudinal-member-coupling element 3614 (as indicated by the arrow in Blow-up D). Typically, while unscrewing screw 2618, tube 2267 is held rotationally stationary in order to hold second flexible-longitudinal-member-coupling element 2650, and thus first flexible-longitudinal-member-coupling element 3614, rotationally stationary. Tube 2667 is then decoupled or simply proximally withdrawn from second flexible-longitudinal-member-coupling element 2650. Alternatively, for applications in which the proximal end of first flexible-longitudinal-member-coupling element 3614 is reversibly coupled to the distal end of flexible longitudinal guide member 2616 using the techniques described hereinabove with reference to FIGS. 21 and 22A-D, guide member 2616 is decoupled from first flexible-longitudinal-member-coupling element 3614 using the decoupling techniques described hereinabove with reference to FIGS. 21 and 22A-D, mutatis mutandis. For these applications, tube 2667 may be decoupled or simply proximally withdrawn from second flexible-longitudinal-member-coupling element 2650 before or after decoupling guide member 2616 from first flexible-longitudinal-member-coupling element 3614. In any case, the operator remotely and percutaneously decouples guide member 2616 from first flexible-longitudinal-member-coupling element 3614.

Figure 34E:
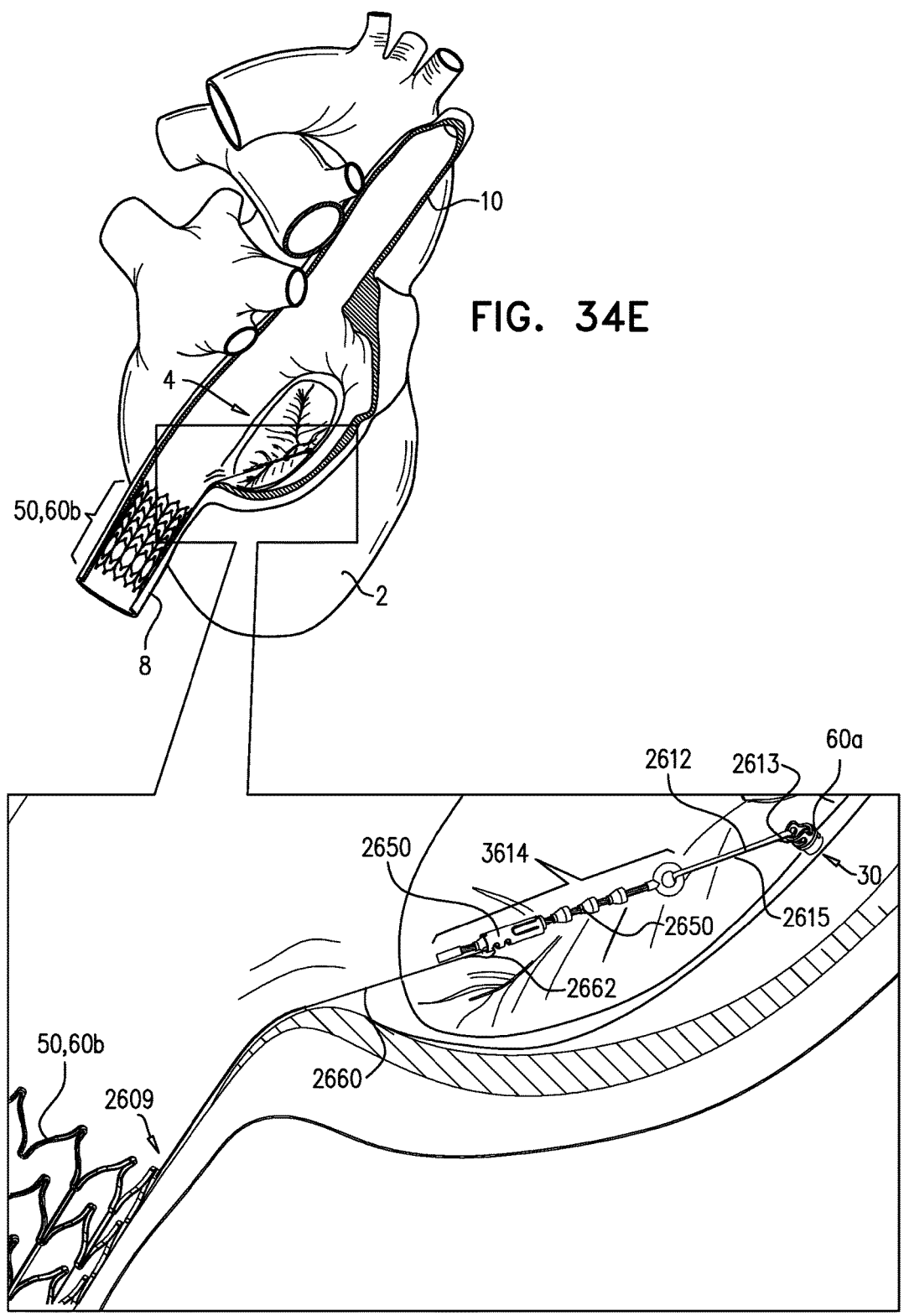

As shown in Blow-up D of FIG. 34D and in FIG. 34E, following decoupling of guide member 2616, first and second flexible-longitudinal-member-coupling elements 3614 and 2650 remain coupled together and thereby couple together first and second flexible longitudinal members 2612 and 2660. These techniques allow separate delivery of the tissue-engaging elements, using two separate delivery tools 2602 and 2666. Such separate delivery simplifies the procedure for the operator as well as allowing approaches via two or more different blood vessels, such as transfemoral, transjugular, transradial, and/or or transapical approaches, which may provide simpler access to the anchoring point.

As shown in FIGS. 34A, 34D, and 34E, first and second flexible longitudinal members 2612 and 2660 are two separate flexible longitudinal members, rather than integral longitudinal portions of a single flexible longitudinal member. Respective second end portions 2615 and 2662 of first and second flexible longitudinal member 2612 and 2660 are coupled together via first and second flexible-longitudinal-member-coupling elements 3614 and 2650. Respective first end portions 2613 and 2609 of first and second flexible-longitudinal-member-coupling elements 3614 and 2650 are not coupled together; typically, no portions of first and second flexible longitudinal members 2612 and 2660, other than respective second end portions 2615 and 2662, are coupled together. Typically, first and second flexible longitudinal members 2612 and 2660 are coupled together only by first and second flexible-longitudinal-member-coupling elements 3614 and 2650.

Reference is now made to FIGS. 35A-C, which are schematic illustrations of another configuration of first flexible-longitudinal-member-coupling element 3614, coupled to second flexible-longitudinal-member-coupling element 2650, in accordance with an application of the present invention. Except as described below, first flexible-longitudinal-member-coupling element 3614 may incorporate any of the features described hereinabove with reference to FIGS. 33A-34E, and is typically deployed using the techniques of FIGS. 34A-E, mutatis mutandis.

In this configuration, first flexible-longitudinal-member-coupling element 3614 comprises a flexible chain 3700 of interconnected links 3702, which are shaped so as to define respective male couplings 3617. For some applications, male couplings 3617 have respective conical features 3618. Typically, links 3702 comprise no more than 20 links. Typically, each of links 3702 has a length of at least 4 mm, no more than 18 mm, and/or between 4 and 18 mm.

Reference is still made to FIGS. 35A-C, as well as to FIGS. 36A-B, which are schematic illustrations of a single one of links 3702, in accordance with an application of the present invention. In this configuration, each of links 3702 is shaped so as to define a spherical head 3710 at a proximal end 3712 of the link (typically, proximal to male coupling 3617), and a spherical receptacle 3714 at a distal end 3713 of the link 3716 (typically, distal to male coupling 3617). Each of the spherical receptacles is shaped and sized so as to couplingly receive the spherical head of a distally-adjacent link, so that the two distally-adjacent links can articulate with respect to each other. To this end, an opening 3718 through a distal end of the spherical receptacle is sized so as to receive the spherical head of a distally-adjacent link. The opening is large enough for passage therethrough of a neck 3720 of the adjacent spherical head, but not large enough for passage of the adjacent spherical head 3710. Neck 3720 is narrower than spherical head 3710. For some applications, a short rod 3730 connects a housing 3732 of spherical receptacle 3714 to spherical head 3710 of the adjacent link 3702.

Reference is now made to FIGS. 37A-B and 38A-C, which are schematic illustrations of two respective configurations of another first flexible-longitudinal-member-coupling element 4614, coupled to second flexible-longitudinal-member-coupling element 2650, in accordance with respective applications of the present invention. Except as described below, first flexible-longitudinal-member-coupling element 4614 may incorporate any of the features described hereinabove with reference to FIGS. 33A-34E, and is typically deployed using the techniques of FIGS. 34A-E, mutatis mutandis.

In this configuration, first flexible-longitudinal-member-coupling element 4614 comprises a flexible cable 4616, and second flexible-longitudinal-member-coupling element 2650 comprises a female coupling. The female coupling (a) comprises a hollow cylinder configured to receive cable 4616, and (b) is shaped so as to define one or more tabs 2652, which may function as pawls, biased to flex toward a central longitudinal axis of the cylinder. Cable 4616 and the one or more tabs 2652 are shaped and sized to allow advancement of first flexible-longitudinal-member-coupling element 4614 through the hollow cylinder in a proximal direction, and to restrict, by friction, advancement of first flexible-longitudinal-member-coupling element 4614 in a distal (loosening) direction. The tabs apply more friction to the cable in the direction of loosening (relaxing) than in the direction of tightening (tensioning).

In order to couple together first and second flexible-longitudinal-member-coupling elements 4614 and 2650, the first and the second flexible longitudinal members are tensioned by pulling the flexible longitudinal guide member, and/or pushing second flexible-longitudinal-member-coupling element 2650, such as using tube 2667. For some applications, the hollow cylinder of second flexible-longitudinal-member-coupling element 2650 is circular, as shown, while for other applications, the hollow cylinder has a different shape. For example, cable 4616 may comprise metal, polymer, or textile fibers.

In the configuration shown in FIGS. 37A-B, a diameter of cable 4616 equals between 20% and 100% of an inner diameter of the cylinder of the female coupling of second flexible-longitudinal-member-coupling element 2650, excluding tabs 2652. Tabs 2652 are biased to flex toward longitudinal axis 2656 of the cylinder, thereby contacting cable 4616.

In the configuration shown in FIGS. 38A-C, a diameter of cable 4616 equals between 20% and 50% of the inner diameter of the cylinder of the female coupling of second flexible-longitudinal-member-coupling element 2650, excluding tabs 2652. Tabs 2652 are biased to flex toward longitudinal axis 2656 of the cylinder, thereby contacting cable 4616. In the configuration shown in FIGS. 38A-C, tabs 2652 are disposed at respective, different longitudinal sites along the cylinder, e.g., cascading, in order to apply more friction to cable 4616 by forcing it to go through a tortuous path inside the female coupling.

For some applications, a greatest outer diameter of second flexible-longitudinal-member-coupling element 2650 is at least 1 mm, no more than 6 mm, and/or between 1 and 6 mm, inter alia in order to allow passage of element 2650 through catheter tube 2669 of second delivery tool 2666.

Reference is now made to FIGS. 39A-B, which are schematic illustrations of another first flexible-longitudinal-member-coupling element 5614 and another second flexible-longitudinal-member-coupling element 5650 coupled thereto, in accordance with an application of the present invention. Except as described below, first flexible-longitudinal-member-coupling element 5614 may incorporate any of the features of first flexible-longitudinal-member-coupling element 2614, described hereinabove with reference to FIGS. 25-26, and/or of first flexible-longitudinal-member-coupling element 3614, described hereinabove with reference to FIGS. 33A-34E. Similarly, except as described below, second flexible-longitudinal-member-coupling element 5650 may incorporate any of the features of second flexible-longitudinal-member-coupling element 2650, described hereinabove with reference to FIGS. 25-26 and/or FIGS. 33A-34E. Other elements of this configuration typically have the features of these element described hereinabove, such as with reference to FIGS. 20-26 and/or 33A-34E.

In this configuration, a threaded mechanism, rather than the ratchet mechanisms described hereinabove with reference to FIGS. 33A-38C, is used to couple first and second longitudinal members 2612 and 2660. The threaded mechanism allows percutaneous and remote (through a catheter) insertion, coupling, and both linear tensioning and relaxing of the longitudinal members 2612 and 2660.

First flexible-longitudinal-member-coupling element 5614 is coupled to second end portion 2615 of first longitudinal member 2612. First flexible-longitudinal-member-coupling element 5614 comprises a cable 5619, which is configured to be flexible and substantially not twistable (e.g., the cable does not twist more than 90 degrees over its entire length. First flexible-longitudinal-member-coupling element 5614 further comprises a wire 5620, which is helically wound around cable 5619, typically at an average pitch P equal to at least one times a diameter, no more than four times a diameter, and/or between one and four times a diameter of cable 5619. Typically, the wire is fixed to the cable, typically along the entire length of the wire; for example, the wire may be welded to the cable, or otherwise woven, braided or glued to the cable. First flexible-longitudinal-member-coupling element 5614 is thus male. First and second end portions 2613 and 2615 of first flexible longitudinal member 2612 are disposed at opposite longitudinal ends of the first flexible longitudinal member.

Second flexible-longitudinal-member-coupling element 5650 is coupled to second end portion 2662 of second flexible longitudinal member 2660. Second flexible-longitudinal-member-coupling element 5650 comprises a female coupling, which (a) comprises a hollow cylinder 5670 configured to receive first flexible-longitudinal-member-coupling element 5614, and (b) is shaped so as to define an internal thread 5652 shaped and sized so as to correspond with helically-wound wire 5620, so as to couple together first and second flexible-longitudinal-member-coupling elements 5614 and 5650. First and second end portions 2609 and 2662 of second flexible longitudinal member 2660 are disposed at opposite longitudinal ends of second flexible longitudinal member 2660. Hollow cylinder 5670 is shaped so as to define a lumen therethrough, and is configured to slide along flexible longitudinal guide member 2616 when the flexible longitudinal guide member passes through the lumen.

A distal end of flexible longitudinal guide member 2616 is reversibly coupled to a proximal end of first flexible-longitudinal-member-coupling element 5614. For some applications, this reversible coupling is performed using the techniques described hereinabove with reference to FIGS. 21 and 22A-D for reversibly coupling torque-delivering cable 1204 to distal tissue-anchor coupling element 1233 of anchor 40, mutatis mutandis. Among other features of these techniques, the distal end of flexible longitudinal guide member 2616 comprises a first coupling 5720, similar to first coupling 1220 of torque-delivering cable 1204, and the proximal end of first flexible-longitudinal-member-coupling element 5614 comprises a distal coupling element 5733, similar to distal tissue-anchor coupling element 1233. In order to maintain the coupling of first coupling 5720 and distal coupling element 5733, an elongate longitudinal element 5710 (e.g., a rod), similar to elongate longitudinal element 2610, is reversibly disposed within a first-coupling-element-body passage 5721, and a second-coupling-element-body passage 2731. Alternatively, the reversible coupling is performed using other coupling techniques.

During an implantation procedure, such as described hereinbelow with reference to FIG. 40D, a rotation-stabilization tube 5667 of second delivery tool 2666 is advanced over flexible longitudinal guide member 2616 until tube 5667 reversibly engages and rotationally locks with a proximal end of second flexible-longitudinal-member-coupling element 5650. For example, tube 5667 may define one or more protrusions 5668 that engage respective slots 5669 defined by the proximal end of second flexible-longitudinal-member-coupling element 5650. While tube 5667 is held rotationally stationary, the operator remotely (i.e., through a catheter) and percutaneously rotates flexible longitudinal guide member 2616, which rotates male first flexible-longitudinal-member-coupling element 5614 with respect to female second flexible-longitudinal-member-coupling element 5650. For some applications, such as described hereinabove with reference to FIGS. 7A-D and 11A-B, tissue-engaging element 66a is configured such that the flexible longitudinal member connected thereto can rotate with respect to helical anchor 40; such rotation prevents twisting of first flexible longitudinal member 2612 and second flexible longitudinal member 2660 as male first flexible-longitudinal-member-coupling element 5614 is rotated. Rotation of flexible longitudinal guide member 2616 in a first direction tightens the threaded coupling between the coupling elements, thereby tensioning first and second longitudinal members 2612 and 2660. Rotation in the opposite direction loosens the coupling, thereby relaxing the first and the second longitudinal members. These techniques thus allow remote tightening (tensioning) and relaxing (tension reduction) of the first and the second longitudinal members. The operator may monitor a parameter indicative of regurgitation of the tricuspid valve during the tightening and relaxing, in order to apply the optimal level of tension.

Alternatively, the operator remotely and percutaneously rotates tube 5667 while holding rotationally stationary flexible longitudinal guide member 2616, and thus first flexible-longitudinal-member-coupling element 5614.

For some applications, a greatest outer diameter of first flexible-longitudinal-member-coupling element 5614 is at least 1 mm, no more than 6 mm, and/or between 1 and 6 mm, inter alia in order to allow passage of element 5614 through catheter tube 2603 of first delivery tool 2602. For some applications, a length of first flexible-longitudinal-member-coupling element 5614 is at least 5 mm, no more than 40 mm, and/or between 5 and 40 mm. For some applications, a greatest outer diameter of second flexible-longitudinal-member-coupling element 5650 is at least 1 mm, no more than 6 mm, and/or between 1 and 6 mm, inter alia in order to allow passage of element 5650 through catheter tube 2669 of second delivery tool 2666.

For some applications, second flexible-longitudinal-member-coupling element 5650 is shaped so as to define a coupling interface that is not coaxial with second flexible-longitudinal-member-coupling element 5650, and second flexible longitudinal member 2660 is fixed to the coupling interface.

Reference is now made to FIGS. 40A-E, which are schematic illustrations of a method for deploying a system 5600 for repairing tricuspid valve 4, in accordance with an application of the present invention. System 5600 comprises (a) first tissue-engaging element 60a coupled to distal first end portion 2613 of first flexible longitudinal member 2612, and (b) second tissue-engaging element 60b coupled to proximal first end portion 2609 of second flexible longitudinal member 2660. System 3600 further comprises first and second delivery tools 2602 and 2666. The elements of system 3600 typically have the features of these elements described hereinabove, such as with reference to FIGS. 20-26 and/or 33A-34E.

Figure 40A:
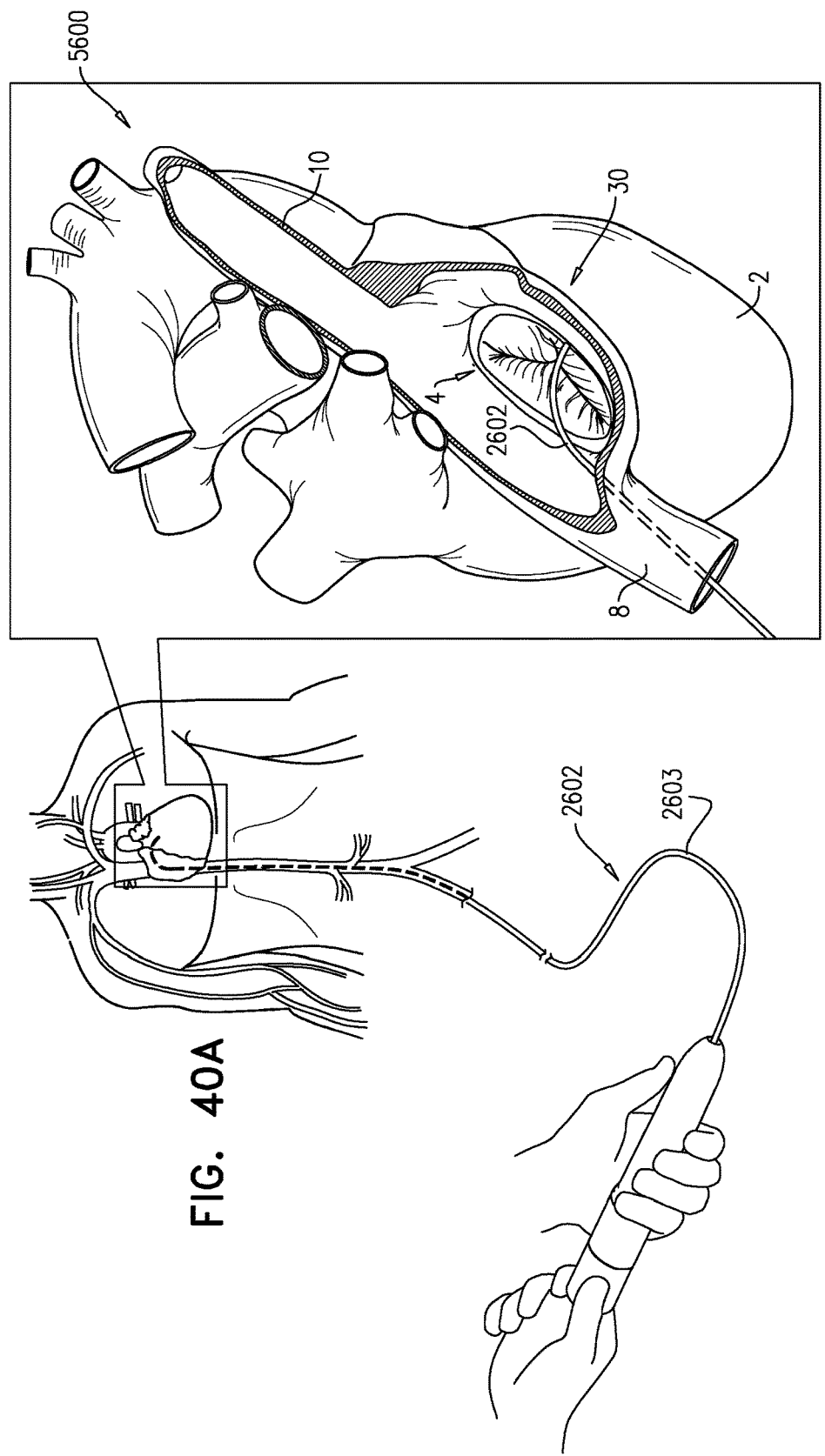

As shown in FIG. 40A, first delivery tool 2602 is advanced toward first implantation site 30 at tricuspid valve 4 through interior vena cava 8 from a suitable point of entry. Alternatively, the delivery tool may be advanced through superior vena cava 10.

Figure 40B:
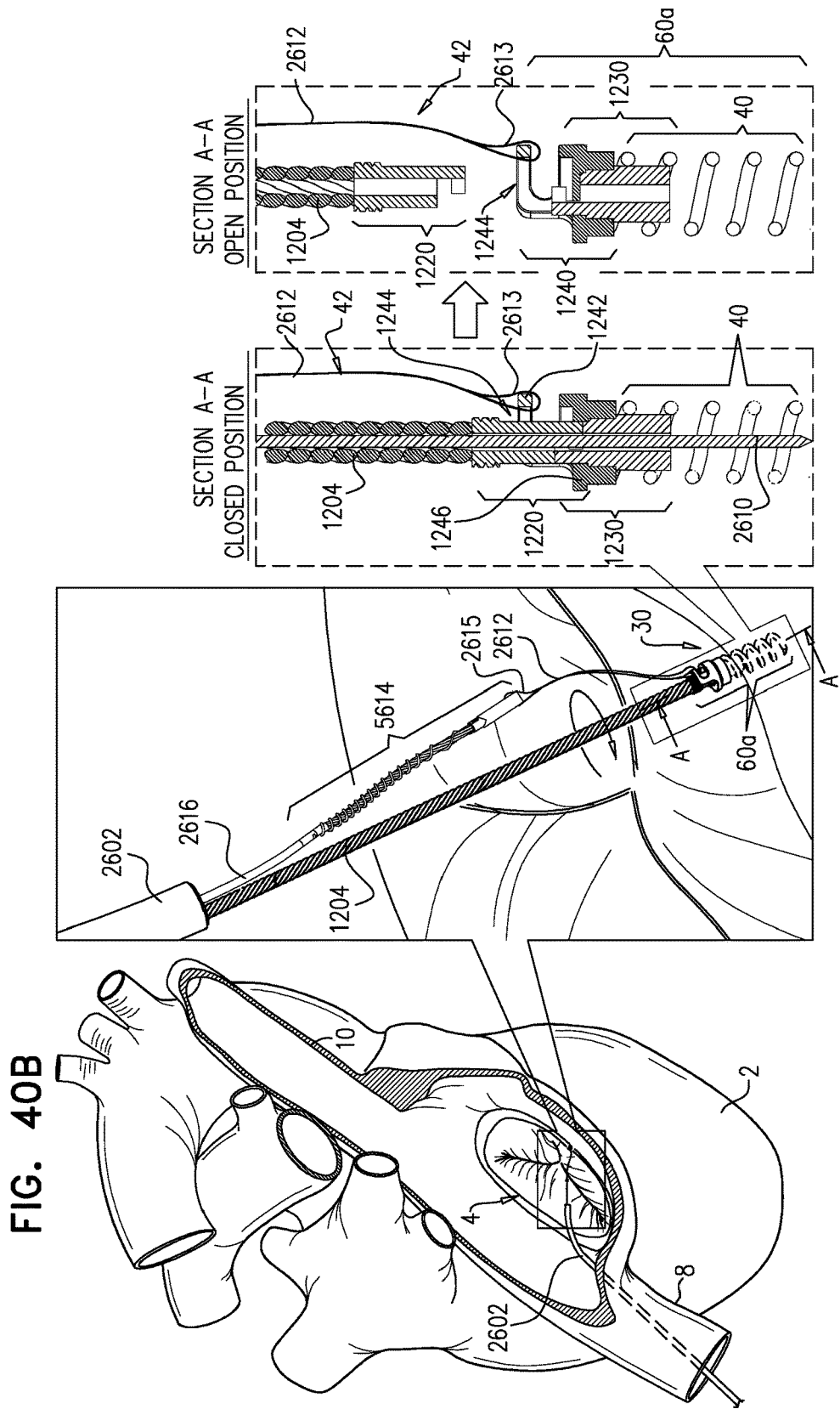

As shown in FIG. 40B, first tissue-engaging element 60a is implanted in tissue of the annulus of tricuspid valve 4, as described hereinabove with reference to FIGS. 21 and 22A-D. Alternatively, first tissue-engaging element 60a is implanted in tissue of a wall of the atrium above the annulus. Anchor 40 of first tissue-engaging element 60a is rotated by the torque-delivering tool comprising torque-delivering cable 1204, as described hereinabove with reference to FIGS. 21 and 22A-D. Optionally, torque-delivering cable 1204 is decoupled from first tissue-engaging element 60a using the techniques described hereinabove with reference to FIGS. 22A-D.

Proximal second end portion 2615 of first longitudinal member 2612 is coupled to (e.g., by being looped around) a portion of first flexible-longitudinal-member-coupling element 5614. A proximal end of first flexible-longitudinal-member-coupling element 5614 is reversibly coupled to a distal end of a flexible longitudinal guide member 2616. For some applications, in order to enable such coupling, the proximal end of first flexible-longitudinal-member-coupling element 5614 is reversibly coupled to the distal end of flexible longitudinal guide member 2616 using the techniques described hereinabove with reference to FIGS. 21 and 22A-D for reversibly coupling torque-delivering cable 1204 to distal tissue-anchor coupling element 1233 of anchor 40, mutatis mutandis. First and second end portions 2613 and 2615 of first flexible longitudinal member 2612 are disposed at opposite longitudinal ends of the first flexible longitudinal member.

As shown in FIG. 40C, first tissue-engaging element 60a, first flexible longitudinal member 2612, first flexible-longitudinal-member-coupling element 5614, and flexible longitudinal guide member 2616 have been deployed in the atrium. At this stage of the deployment procedure, flexible longitudinal guide member 2616 is still removably coupled to the proximal end of first flexible-longitudinal-member-coupling element 5614.

Figure 40D:
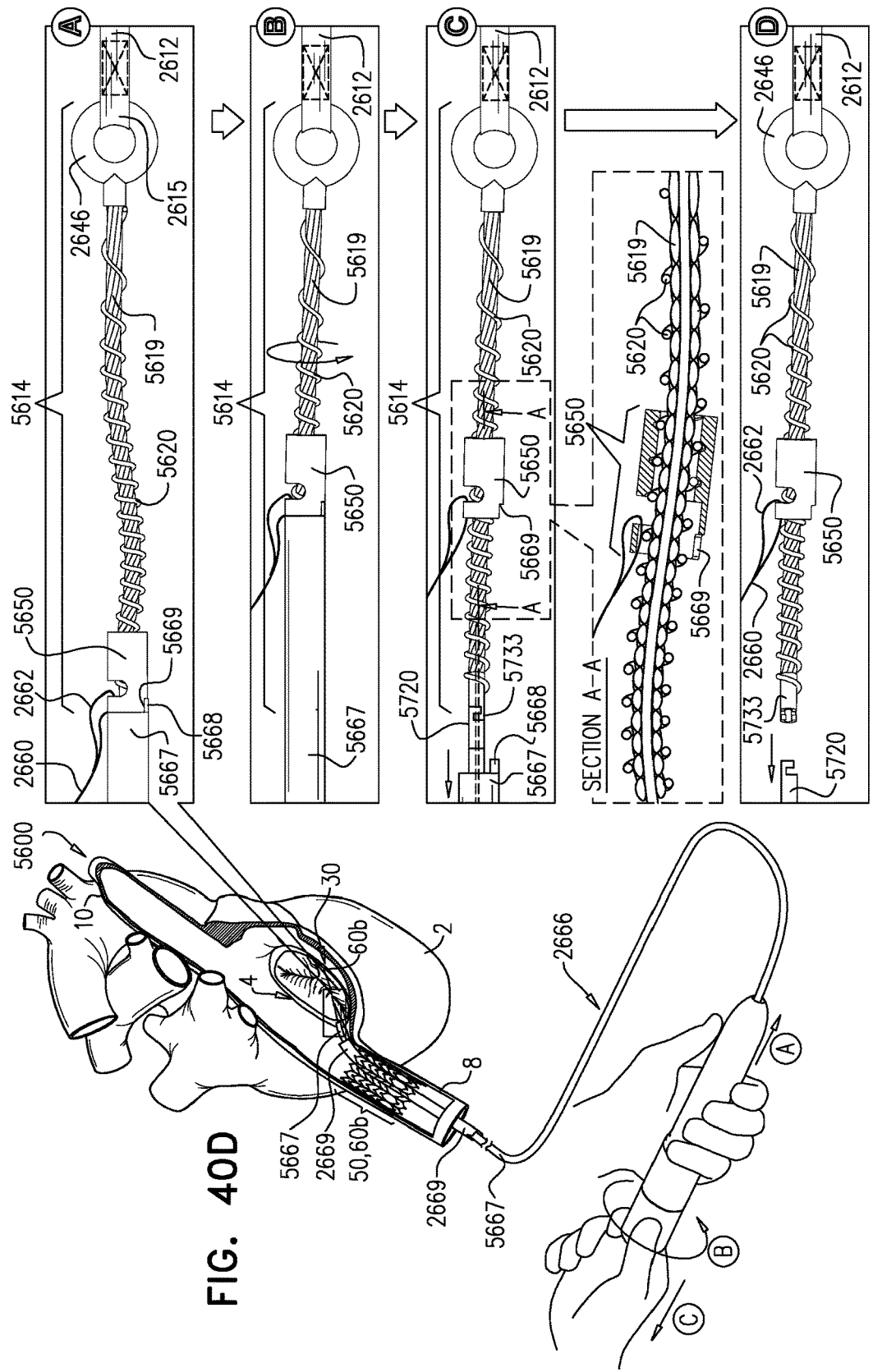

As shown in FIG. 40D, second tissue-engaging element 60b is deployed in inferior vena cava 8, typically using second delivery tool 2666. Alternatively, the second tissue-engaging element is deployed in superior vena cava 10, or in a coronary sinus. For some applications, the second tissue-engaging element is deployed in the same vein through which first delivery tool 2602 was advanced earlier in the procedure, as shown in FIG. 40A.

Also as shown in FIG. 40D, second delivery tool 2666, including catheter tube 2669 thereof, is threaded over a proximal portion of guide member 2616 in order to advance second flexible longitudinal member 2660 and a second flexible-longitudinal-member-coupling element 5650 toward tricuspid valve 4. In the configuration shown in FIG. 40D, second delivery tool 2666 is advanced through inferior vena cava 8. Alternatively, the second delivery tool is advanced through superior vena cava 10. For some applications, second delivery tool 2666 is advanced through the same vein through which first delivery tool 2602 was advanced earlier in the procedure, as shown in FIG. 40A. Alternatively, second delivery tool 2666 is advanced through a different vein from that through which first delivery tool 2602 was advanced earlier in the procedure, such as shown in FIG. 25, mutatis mutandis; for example, one of first and second delivery tools 2602 and 2666 may be advanced through superior vena cava 10, and the other through inferior vena cava 8. Thus, second delivery tool 2666 is configured to deliver second flexible longitudinal member 2660 and second flexible-longitudinal-member-coupling element 5650 after deployment of second tissue-engaging element 60b.

For some applications in which second tissue-engaging element 60b comprises radially-expandable stent 50, such as described hereinabove with reference to FIGS. 1A-D, second delivery tool 2666 is configured and sized to pass through stent 50 when the stent is in a radially-expanded state.

Second delivery tool 2666 of system 5600 typically comprises rotation-stabilization tube 5667, rather than advancement tube 2667 (described hereinabove with reference to FIG. 40D). As shown in Blow-up A of FIG. 40D, rotation-stabilization tube 5667 of second delivery tool 2666 is advanced through a lumen of catheter tube 2669 of tool 2666 until tube 5667 reversibly engages and rotationally locks with a proximal end of second flexible-longitudinal-member-coupling element 5650. The operator slides second flexible-longitudinal-member-coupling element 5650 and tube 5667 along guide member 2616, in order to couple second flexible-longitudinal-member-coupling element 5650 to first flexible-longitudinal-member-coupling element 5614. In order to allow such sliding, second flexible-longitudinal-member-coupling element 5650 is typically shaped so as to define a lumen therethrough, through which guide member 2616 passes. Guide member 2616 and second delivery tool 2666 thus allow the operator to remotely and percutaneously control the coupling and tensioning of first and second flexible-longitudinal-member-coupling elements 5614 and 5650, including remotely and percutaneously inserting the leading (proximal) end of first flexible-longitudinal-member-coupling elements 5614 into female second flexible-longitudinal-member-coupling elements 5650.

As shown in Blow-up B of FIG. 40D, during the coupling of first and second flexible-longitudinal-member-coupling elements 5614 and 5650, the operator tensions first and second flexible longitudinal members 2612 and 2660 by pulling one or more of male couplings 3617 into the female coupling. While tube 5667 is held rotationally stationary, the operator remotely (i.e., through catheter tube 2669) and percutaneously rotates flexible longitudinal guide member 2616, which rotates male first flexible-longitudinal-member-coupling element 5614 with respect to female second flexible-longitudinal-member-coupling element 5650. Rotation of flexible longitudinal guide member 2616 in a first direction tightens the threaded coupling between the coupling elements, thereby tensioning first and second longitudinal members 2612 and 2660. Rotation in the opposite direction, which is also performed by the operator remotely and percutaneously, loosens the coupling, thereby relaxing the first and the second longitudinal members.

The tensioning of first and second flexible longitudinal members 2612 and 2660 applies a force to first tissue-engaging element 60a, in order to adjust a distance between the leaflets of tricuspid valve 4 to reduce and eliminate regurgitation through and thereby repair tricuspid valve 4. Guide member 2616 and second delivery tool 2666 thus allow the operator to remotely and percutaneously control the applied tension by remotely and percutaneously rotating first and second flexible-longitudinal-member-coupling elements 5614 and 5650 with respect to each other.

This providing of an adjustable length between first and second tissue-engaging elements 60a and 60b allows fine-tuning of the tension by the operator, both during and after implantation of both tissue-engaging elements, and even after formation of neointima on the tissue-engaging elements. These techniques also allow separate delivery of the tissue-engaging elements, using two separate delivery tools 2602 and 2666. Such separate delivery simplifies the procedure for the operator as well as allowing approaches via two or more different blood vessels, such as transfemoral, transjugular, transradial, and/or or transapical approaches, which may provide simpler access to the anchoring point.

As shown in Blow-up C of FIG. 40D, once a desired amount of tension has been applied to first and second flexible longitudinal members 2612 and 2660, tube 5667 is decoupled and proximally withdrawn from second flexible-longitudinal-member-coupling element 5650.

As shown in Blow-ups C and D of FIG. 40D, guide member 2616 is remotely and percutaneously decoupled from first flexible-longitudinal-member-coupling element 5614, such as using the decoupling techniques described hereinabove with reference to FIGS. 21 and 22A-D, mutatis mutandis.

Figure 40E:
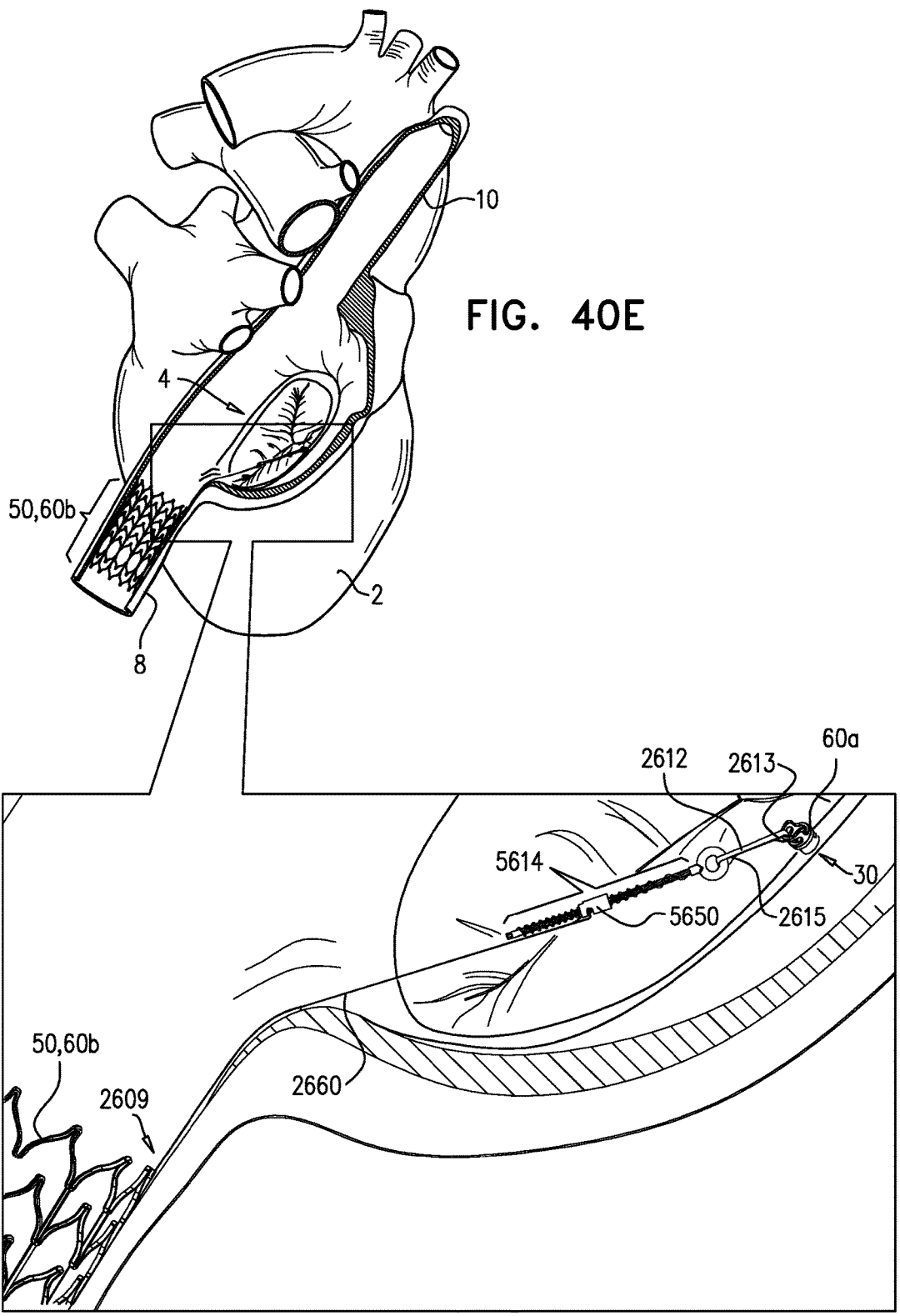

As shown in Blow-up D of FIG. 40D and in FIG. 40E, following decoupling of guide member 2616, first and second flexible-longitudinal-member-coupling elements 5614 and 5650 remain coupled together and thereby couple together first and second flexible longitudinal members 2612 and 2660.

As shown in FIGS. 40A, 40D, and 40E, first and second flexible longitudinal members 2612 and 2660 are two separate flexible longitudinal members, rather than integral longitudinal portions of a single flexible longitudinal member. Respective second end portions 2615 and 2662 of first and second flexible longitudinal member 2612 and 2660 are coupled together via first and second flexible-longitudinal-member-coupling elements 5614 and 5650. Respective first end portions 2613 and 2609 of first and second flexible-longitudinal-member-coupling elements 5614 and 5650 are not coupled together; typically, no portions of first and second flexible longitudinal members 2612 and 2660, other than respective second end portions 2615 and 2662, are coupled together. Typically, first and second flexible longitudinal members 2612 and 2660 are coupled together only by first and second flexible-longitudinal-member-coupling elements 5614 and 5650.

Reference is now made to FIGS. 1A-D, 2A-B, 3A-C, 4A-C, 5A-B, 6, 7A-D, 8, 9, 10A-D, 11A-C, 12A-C, 13A-C, 14A-C. 15A-B, 16A-B, 17, 18A-B, 19-32, 33A-34E, 35A-36B, 37A-38C, 39A-B, and 40A-E. It is to be noted that apparatus and methods described herein for repairing tricuspid valve 4 may also be applied to repair any other heart valve of the patient, e.g., a mitral valve, a pulmonary valve, or an aortic valve. For such applications, second implantation site 52 may include a portion of a blood vessel that is in contact with the left atrium of the patient, e.g., a pulmonary vein, a portion of the wall of the left atrium, a portion of the annulus of the mitral valve, or a portion of the left ventricle of the heart of the patient, and first implantation site 30 may include a portion of the wall of the left atrium, a portion of the annulus of the mitral valve, or a portion of the left ventricle of the heart of the patient.

Reference is again made to FIGS. 1A-D, 2A-B, 3A-C, 4A-C, 5A-B, 6, 7A-D, 8, 9, 10A-D, 11A-C, 12A-C, 13A-C, 14A-C, 15A-B, 16A-B, 17, 18A-B, 19-32, 33A-34E, 35A-36B, 37A-38C. 39A-B, and 40A-E. It is to be noted that any one of stents 1150, 1400, and 1500 may be used in place of any one of stents 50 shown in FIGS. 1D, 2A-B, 3A-C, 4B-C, 6, 7A-D, 8, 9, 16A-B, 17, 34D-E, and 40D-E. It is to be further noted that system 1000 shown in FIGS. 11A-C and 12A-C may be used to implant any tissue anchor 40 described herein and stent 50 described herein. Specifically, system 1000 shown in FIGS. 11A-C and 12A-C may be used in place of system 200, as described hereinabove with reference to FIGS. 7A-D.

Reference is yet again made to FIGS. 1A-D, 2A-B, 3A-C, 4A-C, 5A-B, 6, 7A-D, 8, 9, 10A-D, 11A-C, 12A-C, 13A-C, 14A-C, 15A-B, 16A-B. 17, 18A-B. 19-32, 33A-34E, 35A-36B, 37A-38C, 39A-B, and 40A-E. It is to be noted that any suitable number of tissue-engaging elements 60 may be implanted in and/or grasp cardiac tissue, depending on the needs of a given patient. Typically, one or more tissue-engaging elements 60 is/are implanted in cardiac tissue (e.g., tissue of the annulus, tissue of the wall of the atrium adjacent the valve, or tissue of the wall of the ventricle adjacent the valve) in a vicinity of the valve that is between the middle of the anterior leaflet and the middle of the posterior leaflet, e.g., at the commissure between the middle of the anterior leaflet and the middle of the posterior leaflet. For such an application, pulling together implantation sites 30 and 52 pulls anterior leaflet 14 toward septal leaflet 12 and thereby achieves bicuspidization of tricuspid valve 4. It is to be noted, however, that tissue-engaging elements 60 may be implanted in portions of tissue in the vicinity of any portion of the annulus of valve 4.

Reference is still yet again made to FIGS. 1A-D, 2A-B, 3A-C, 4A-C, and 5A-B, 6, 7A-D, 8, 9, 10A-D, 11A-C, 12A-C, 13A-C, 14A-C, 15A-B, 16A-B, 17, 18A-B, 19-32, 33A-34E, 35A-36B, 37A-38C, 39A-B, and 40A-E. It is to be noted that the adjustment of the distance between the respective implantation sites of the tissue-engaging elements 60 is facilitated by adjusting mechanism 150 following initial implantation of the tissue-engaging elements 60 and the repair of the valve and/or the adjustment of the heart wall geometry.

The scope of the present invention includes embodiments described in the following applications, which are assigned to the assignee of the present application and are incorporated herein by reference. In an embodiment, techniques and apparatus described in one or more of the following patent applications are combined with techniques and apparatus described herein:

U.S. Pat. No. 8,475,525 to Maisano et al.
US Patent Application Publication 2012/0035712
US Patent Application Publication 2013/0325115
US Patent Application Publication 2013/0046380
PCT Publication WO 2013/179295

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
    a torque-delivering cable, which comprises a first coupling, wherein the torque-delivering cable and the first coupling are shaped so as to collectively define a first passage therethrough;
    a tissue anchor, which comprises a tissue-engaging element and a second coupling, which second coupling is shaped so as to define a second passage therethrough open to a space surrounded by the tissue-engaging element, wherein the first and the second couplings are interlockingly coupleable to each other; and
    an elongate longitudinal locking element, which is configured to be advanceable into the space surrounded by the tissue-engaging element, and which:
        when reversibly disposed in the first and the second passages, maintains coupling together of the first and the second couplings, and
        when withdrawn from the second passage, allows decoupling of the first and the second couplings from each another,
    wherein the torque-delivering cable is configured such that rotation thereof, when the first and the second couplings are coupled together, rotates the first and the second couplings, and thereby the tissue anchor.

2. The apparatus according to claim 1, wherein the elongate longitudinal locking element comprises a rod.

3. The apparatus according to claim 1, wherein the tissue-engaging element is helical.

4. The apparatus according to claim 1, further comprising a flexible longitudinal member, which is fixed to the tissue anchor.

5. The apparatus according to claim 1, wherein the elongate longitudinal locking element is shaped so as to define a sharp tip.

6. A method comprising:
    advancing a tissue anchor toward an implantation site using a torque-delivering cable, which comprises a first coupling, wherein (a) the torque-delivering cable and the first coupling are shaped so as to collectively define a first passage therethrough, (b) the tissue anchor comprises a tissue-engaging element and a second coupling, which second coupling is shaped so as to define a second passage therethrough open to a space surrounded by the tissue-engaging element, and (c) the first and the second couplings are interlockingly coupled to each other by an elongate longitudinal locking element, which is (i) reversibly disposed in the first and the second passages so as to maintain coupling together of the first and the second couplings and (ii) advanced into the space surrounded by the tissue-engaging element;
    implanting the tissue-engaging element in tissue at the implantation site by screwing the tissue-engaging element into the tissue by rotating the torque-delivering cable, when the first and the second couplings are coupled together, thereby rotating the first and the second couplings and thus rotating the tissue anchor;
    thereafter, withdrawing the elongate longitudinal locking element from the second passage to facilitate decoupling of the first and the second couplings from each another;
    thereafter, decoupling the first and the second couplings from each other; and
    thereafter, withdrawing the torque-delivering tool.

7. The method according to claim 6, wherein the elongate longitudinal locking element comprises a rod.

8. The method according to claim 6, wherein the tissue-engaging element is helical.

9. The method according to claim 6, further comprising applying tension to the tissue anchor using a flexible longitudinal member that is fixed to the tissue anchor.

10. The method according to claim 6, wherein implanting the tissue-engaging element in the issue comprises advancing the sharp tip of the elongate longitudinal locking member to the tissue such that the sharp tip punctures the tissue, and thereafter screwing the tissue-engaging element into the tissue.

11. The method according to claim 6, wherein the elongate longitudinal locking element is shaped so as to define a sharp tip.

* * * * *